United States Patent
Bensi et al.

(10) Patent No.: US 7,754,228 B2
(45) Date of Patent: Jul. 13, 2010

(54) CYTOTOXIC T-CELL EPITOPES FROM CHLAMYDIA

(75) Inventors: Giuliano Bensi, Siena (IT); Guido Grandi, Siena (IT); Sergio Abrignani, Siena (IT)

(73) Assignee: Novartis Vaccines and Diagnostics, Srl, Siena (IT)

( * ) Notice: Subject to any disclaimer, the term of this patent is extended or adjusted under 35 U.S.C. 154(b) by 1041 days.

(21) Appl. No.: 10/503,135

(22) PCT Filed: Feb. 13, 2003

(86) PCT No.: PCT/IB03/01161

§ 371 (c)(1),
(2), (4) Date: Aug. 11, 2004

(87) PCT Pub. No.: WO03/068811

PCT Pub. Date: Aug. 21, 2003

(65) Prior Publication Data

US 2005/0152926 A1    Jul. 14, 2005

(30) Foreign Application Priority Data

Feb. 13, 2002   (GB) ................... 0203403.1

(51) Int. Cl.
- A61K 39/118   (2006.01)
- C07K 14/425   (2006.01)
- C07H 21/04    (2006.01)
- C12P 21/04    (2006.01)
- C12N 1/21     (2006.01)

(52) U.S. Cl. ............... 424/263.1; 424/184.1; 424/190.1; 530/300; 530/350; 435/69.1; 435/69.7; 435/252.3; 435/320.1; 536/23.7

(58) Field of Classification Search ........................ None
See application file for complete search history.

(56) References Cited

U.S. PATENT DOCUMENTS 6,822,071 B1 * 11/2004 Stephens et al. ............ 530/300

FOREIGN PATENT DOCUMENTS

| WO | WO 99/27105 | 6/1999 |
|----|-------------|--------|
| WO | WO 99/28475 | 6/1999 |
| WO | WO 99/51745 | 10/1999 |
| WO | WO 00/11183 | 3/2000 |
| WO | WO 00/27994 | 5/2000 |
| WO | WO 00/34483 | 6/2000 |
| WO | WO 01/40474 | 6/2001 |
| WO | WO 01/81379 | 11/2001 |
| WO | WO0181379 A2 * | 11/2001 |
| WO | WO 02/02606 | 1/2002 |
| WO | WO 02/08267 | 1/2002 |
| WO | WO 03/041560 | 5/2003 |

OTHER PUBLICATIONS

J. Gen. Microbiol. 137, 465-475, 1991 (sequence indicated in the action).*
Infect. Immun. 60, 5319-5323, 1992(sequence indicated in the action).*
Nature Genet. 21, 385-389, 1999(sequence indicated in the action).*
Houghten et al. (Vaccines, 1986, Edited by Fred Brown: Cold Spring Harbor Laboratory).*
Holmes, Exp. Opin.Invest. Drugs, 2001, 10(3):511-519).*
Greenspan et al (Nature Biotechnology, 1999, 7:936-937).*
Anonymous Third party observations filed under Article 115 EPC for European Patent Applications 99939279.8; 99939280.6; 99951023.3; 99954126.1; 99958455.0; 99960752.6; 99963037.9; 00901235.2; 00908862.6; 00925004.4; 00962125.1; 00962134.3; 00984741.9; 01928775.4; 01931274.3; 01954278.6; and 01959114.8, dated Mar. 23, 2006.
Halme S et al "Characterization Od Chlamydia pneumoniae Antigens Using Human T Cell Clones" Scandinavian Journal of Immunology, Blackwell Science Publ., Oxford, GB, vol. 45, No. 4, Apr. 1, 1997, pp. 378-384 XP002057609 ISSN: 0300-9475.
Stephens RS et al: : Genome sequence of an obligate intracellular pathogen of humans: Chlamydia trachomatis "see comments!" Science, American Association for the Advancement of Science., US, vol. 282, No. 5389, Oct. 23, 1998, pp. 754-759, XP002104802 ISSN: 0036-8075.
Database embl Online YOPS translocation protein U 1 Nov. 1998 XP002248308 accession no. EBI Database accession No. 084093.
Knight S C et al: "A Peptide of Chlamydia trachomatis Shown to Be a Primary T-Cell Epitope In Vitro Induces Cell-Mediated Immunity In Vivo" Immunology, Blackwell Scientific Publications, GB, vol. 85, No. 1, May 1, 1995, pp. 8-15, XP000502790 ISSN: 0019-2805.
Saren Anne et al: "Identification of Chlamydia pneumoniae-derived mouse CD8 epitopes." Infection and immunity, vol. 70, No. 7, Jul. 2002, pp. 3336-3343, XP002248307 ISSN: 0019-9567.
Stephens et al., "Genome sequence of an obligate intracellular pathogen of humans: Chlamydia trachomatis," Science 282(5389), 1998, pp. 754-759.
Kalman et al., "Comparative Genomes of Chlamydia pneumoniae and C. trachomatis," Nature Genetics, 21(4), 1999, pp. 385-389.
Capo et al., "Chlamydia pneumoniae genome sequence analysis and identification of HLA-A2-restricted CD8+ T cell epitopes recognized by infection-primed T cells," Vaccine 23, 50288-37, 2005.

(Continued)

Primary Examiner—Robert B Mondesi
Assistant Examiner—Padma V Baskar
(74) Attorney, Agent, or Firm—Novartis Vaccines and Diagnostics, Srl; Silvia Brazzini

(57) ABSTRACT

Cytotoxic T-cell epitopes from C.pneumoniae proteins have been empirically determined. The epitopes from corresponding C.trachomatis proteins have also been identified, and some of these are identical to those from C.pneumoniae. The empirical method showed that algorithmic prediction was inadequate. The epitopes are useful for immunisation and/or diagnosis.

4 Claims, 27 Drawing Sheets

OTHER PUBLICATIONS

Kim et al., "Induction of HLA class I-restricted CD8+ CTLs specific for the major outer membrane protein of *Chlamydia trachomatis* in human genital tract infections," *J. Immunol.* 162, 6855-66, Jun. 1, 1999.

Kim et al., "Epitope clusters in the major outer membrane protein of *Chlamydia trachomatis*," *Curr. Opin. Immunol.* 13, 429-36, Aug. 1, 2001.

Ortiz et al., "*Chlamydia trachomatis* major outer membrane protein (MOMP) epitopes that activate HLA class II-restricted T cells from infected humans," *J. Immunol.* 157, 4554-67, Nov. 15, 1996.

European search report for EP application 03 73 9628, Nov. 9, 2005.

* cited by examiner

FIGURE 1
FIGURE 1(i)
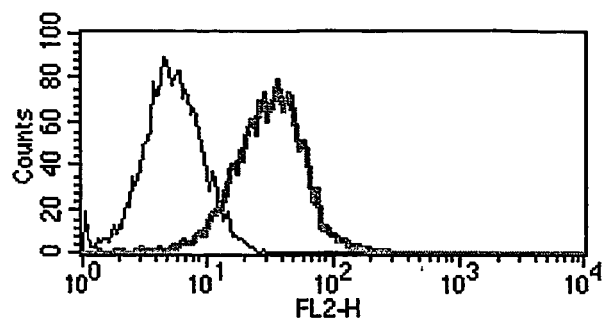
FIGURE 1(ii)
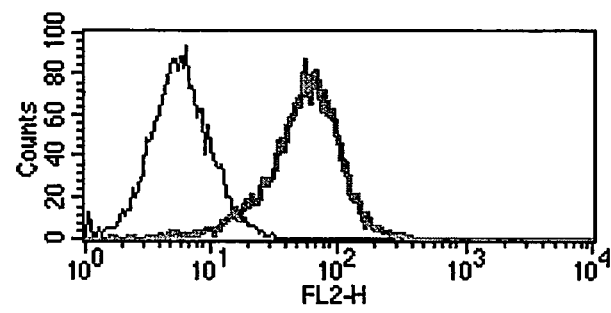
FIGURE 1(iii)
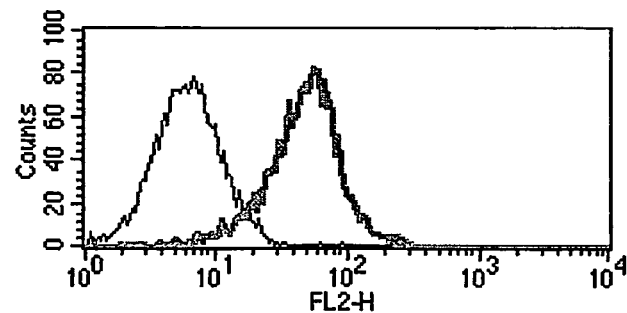
FIGURE 1(iv)
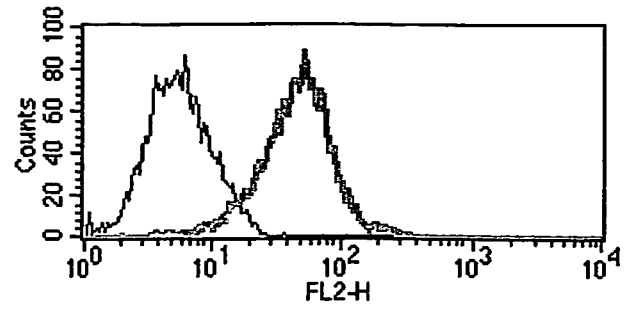

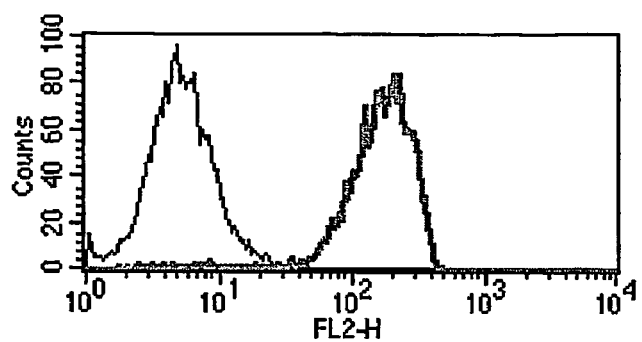
FIGURE 1(v)
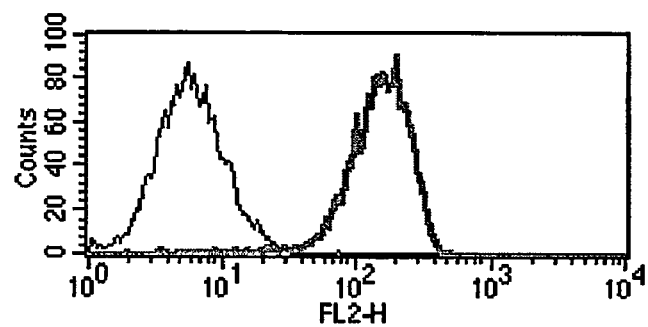
FIGURE 1(vi)
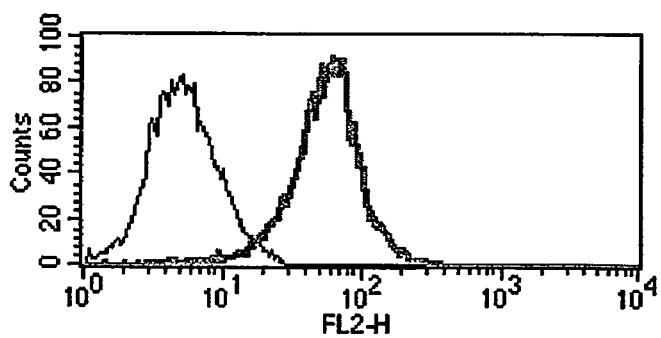
FIGURE 1(vii)
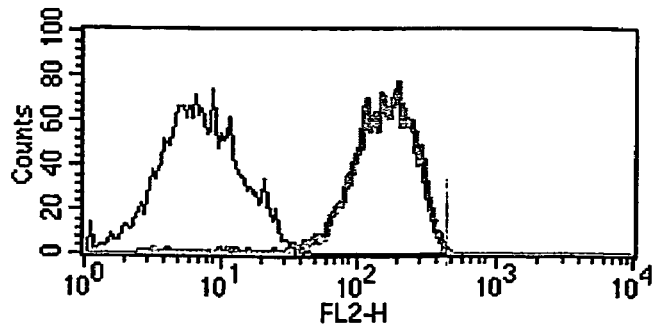
FIGURE 1(viii)

FIGURE 1(xii)
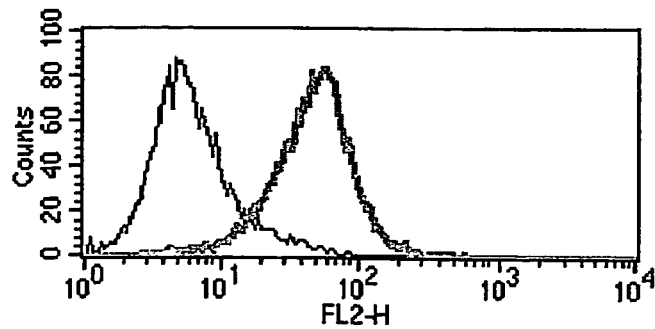

FIGURE 1(xiii)
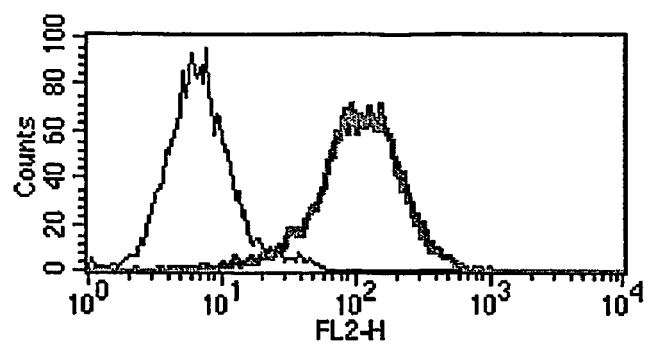
FIGURE 1(xiv)
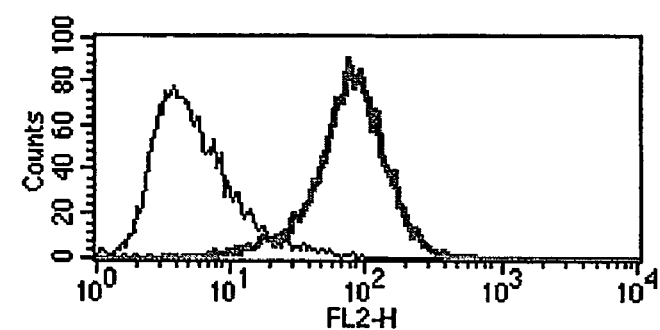
FIGURE 1(xv)
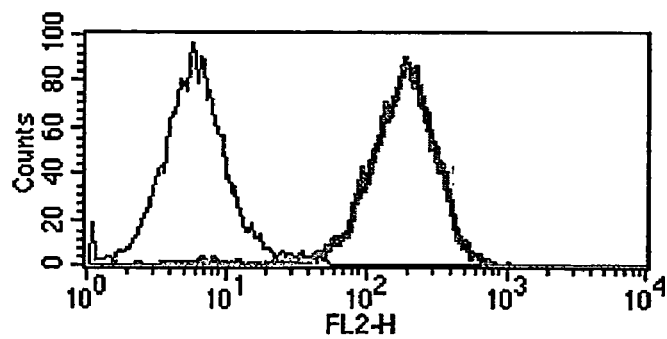
FIGURE 1(xvi)
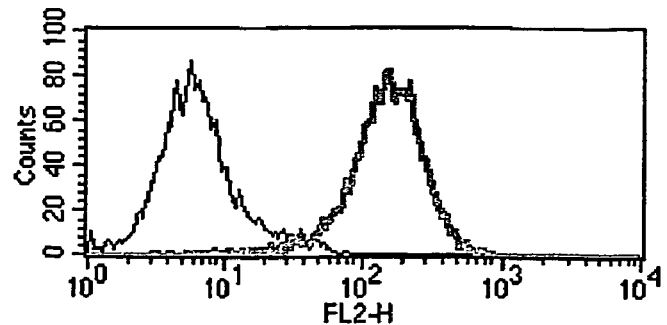

FIGURE 1(xvii)
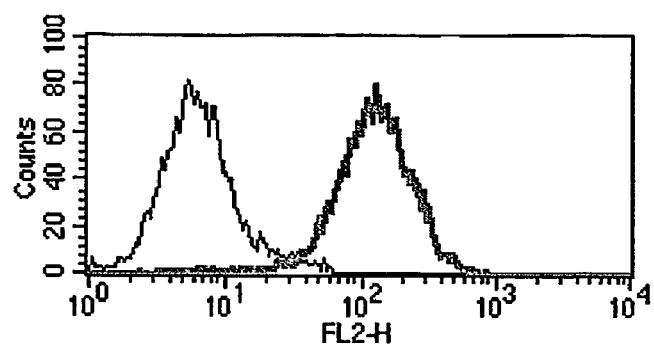
FIGURE 1(xviii)
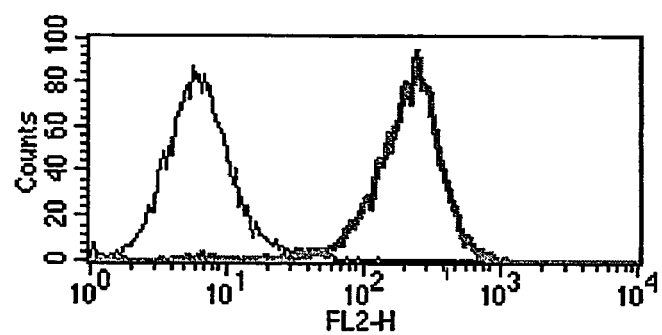
FIGURE 1(xix)
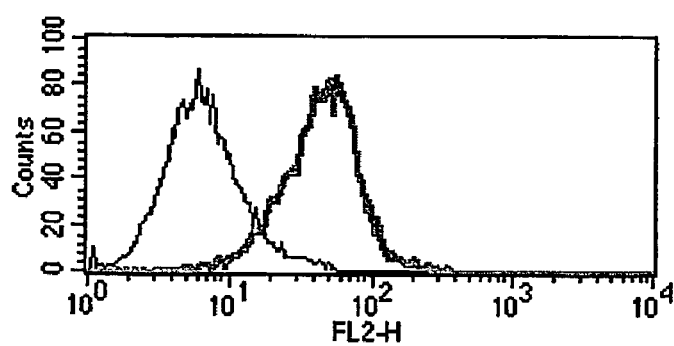
FIGURE 1(xx)
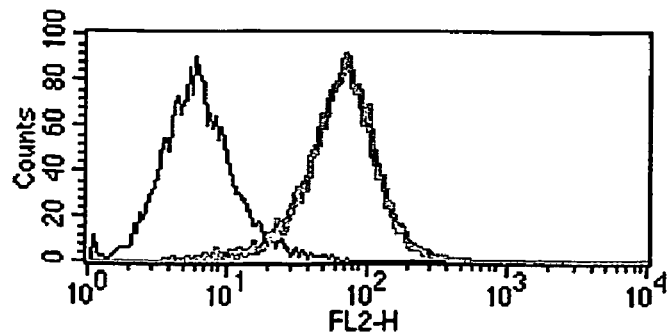

FIGURE 1(xxi)
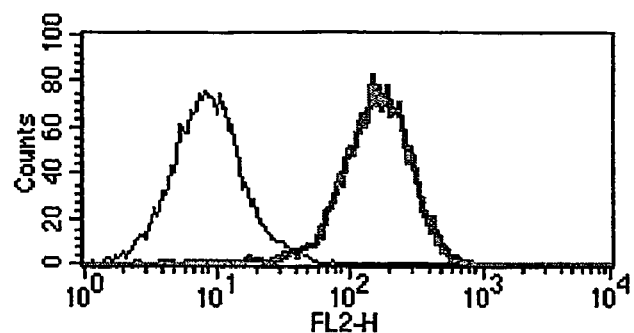
FIGURE 1(xxii)
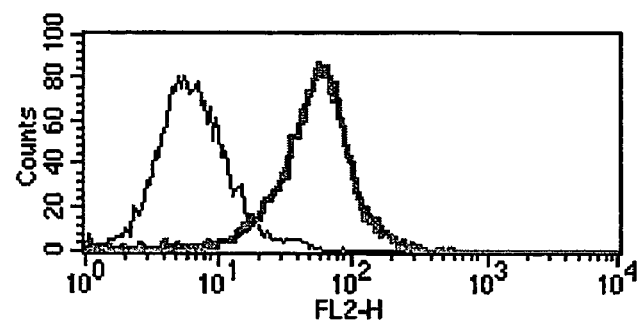
FIGURE 1(xxiii)
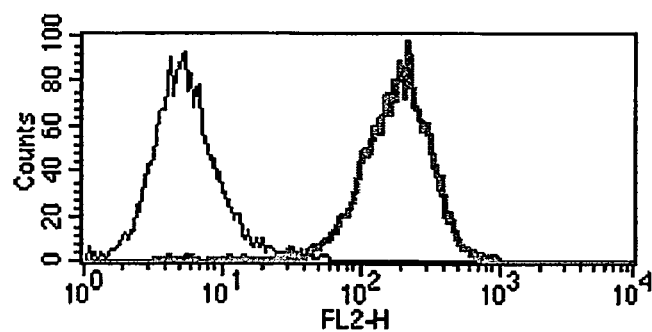
FIGURE 1(xxiv)
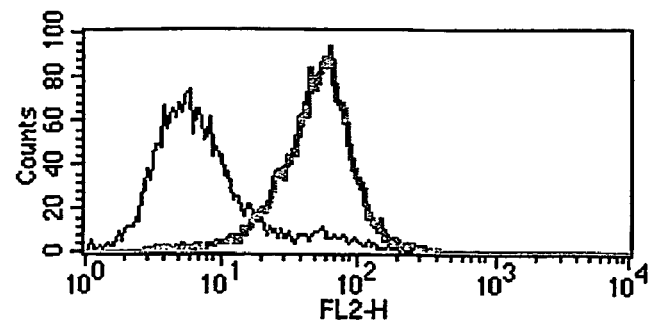

FIGURE 1(xxv)
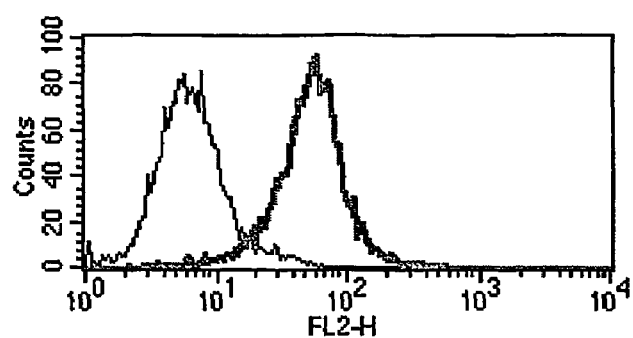
FIGURE 1(xxvi)
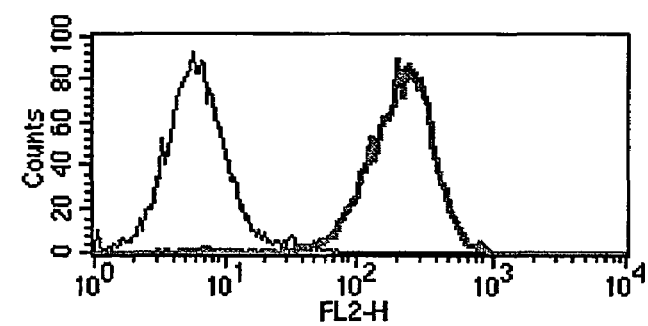
FIGURE 1(xxvii)
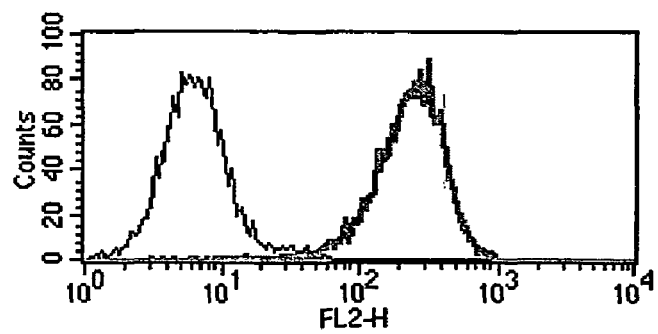
FIGURE 1(xxviii)
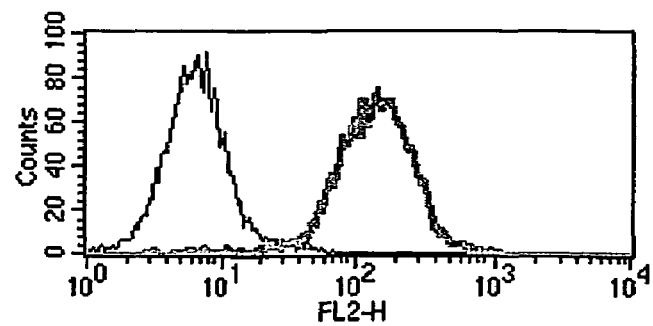

FIGURE 1(xxix)
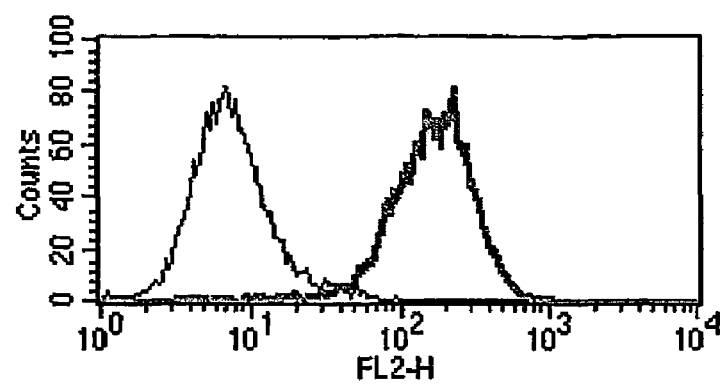

FIGURE 2
FIGURE 2(i)
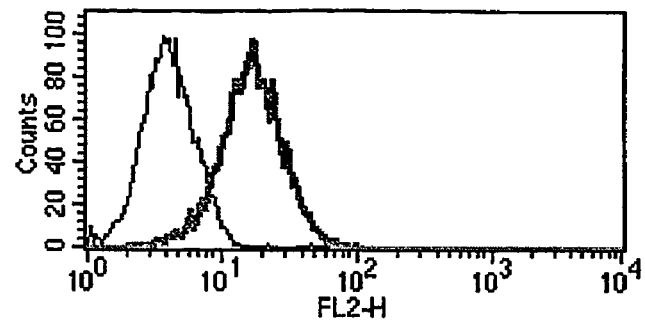
FIGURE 2(ii)
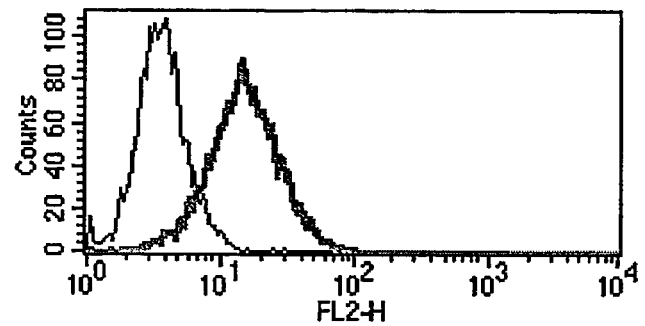
FIGURE 2(iii)
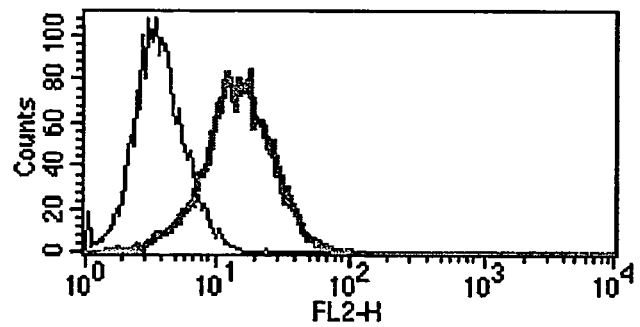
FIGURE 2(iv)
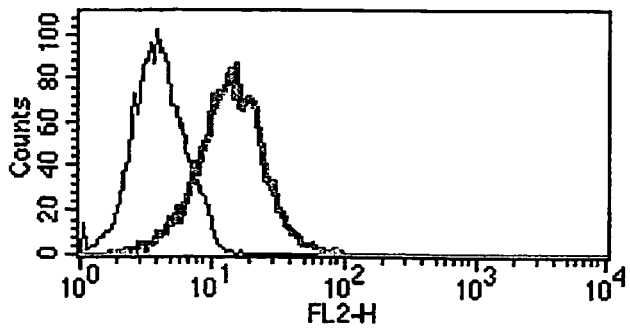

FIGURE 2(vii)
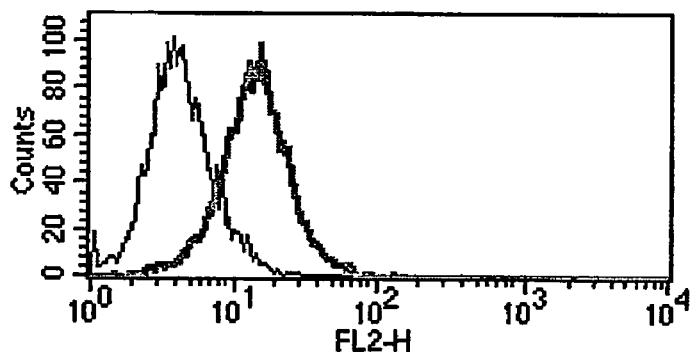
FIGURE 2(viii)
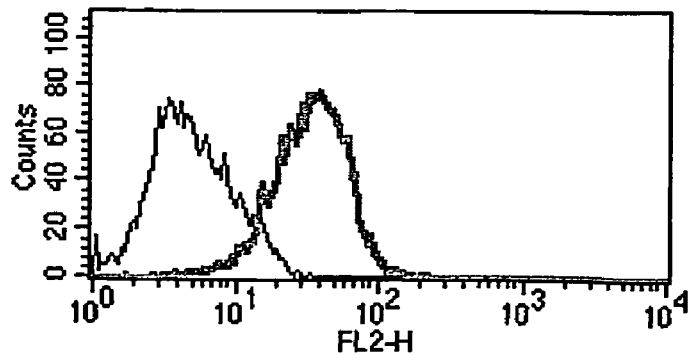

FIGURE 2(xii)
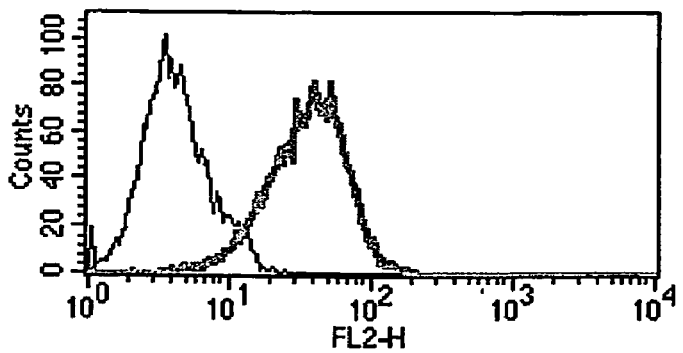

FIGURE 2(xiii)
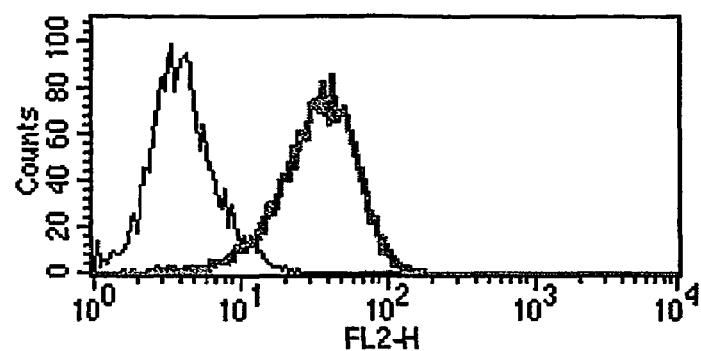
FIGURE 2(xiv)
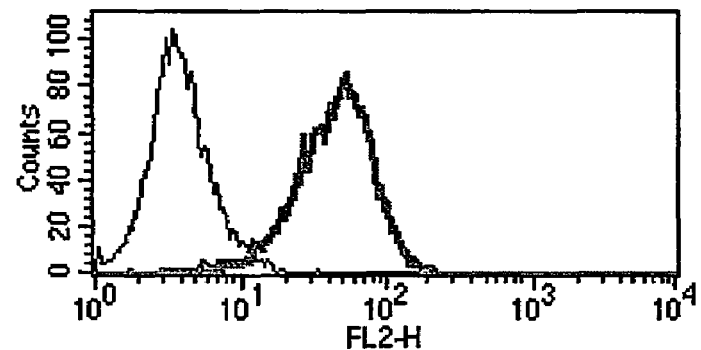
FIGURE 2(xv)
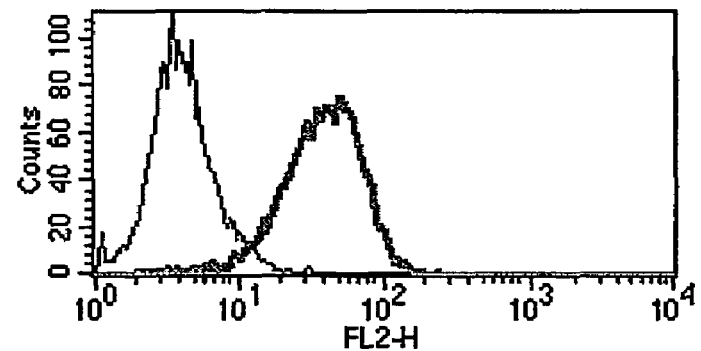
FIGURE 2(xvi)
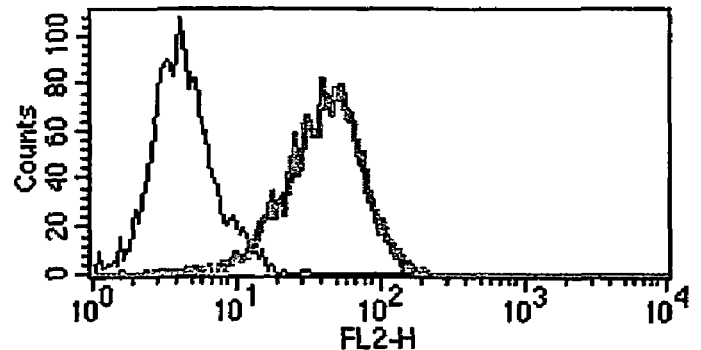

FIGURE 2(xvii)
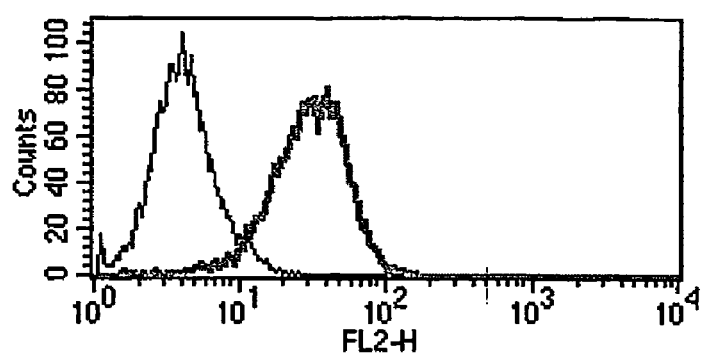
FIGURE 2(xviii)
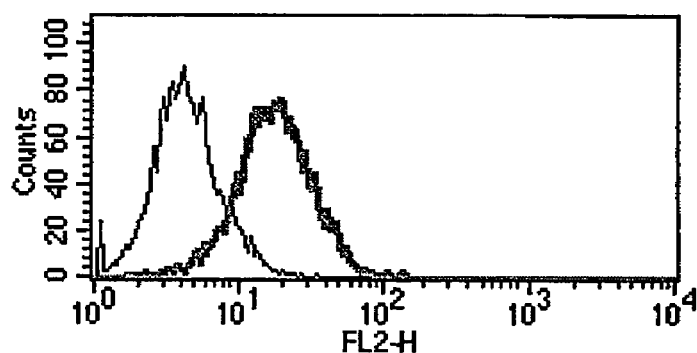
FIGURE 2(xix)
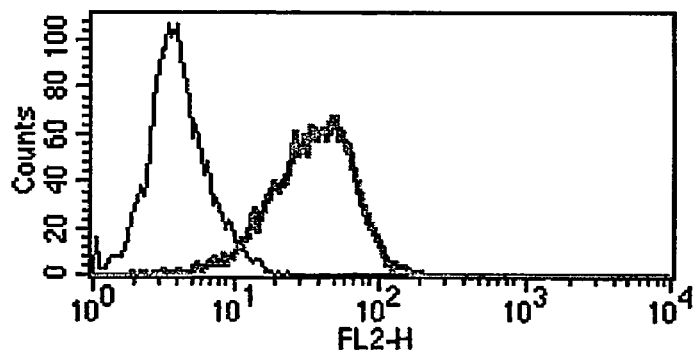
FIGURE 2(xx)
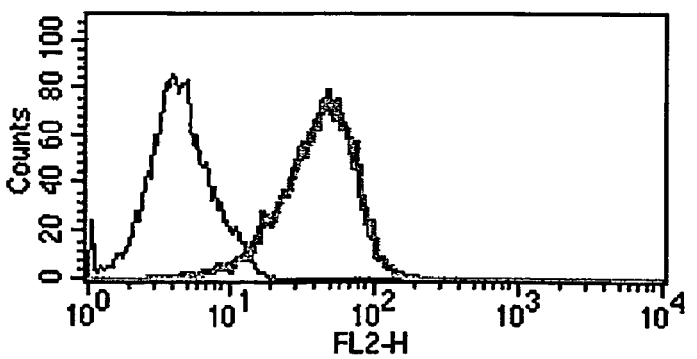

FIGURE 2(xxi) 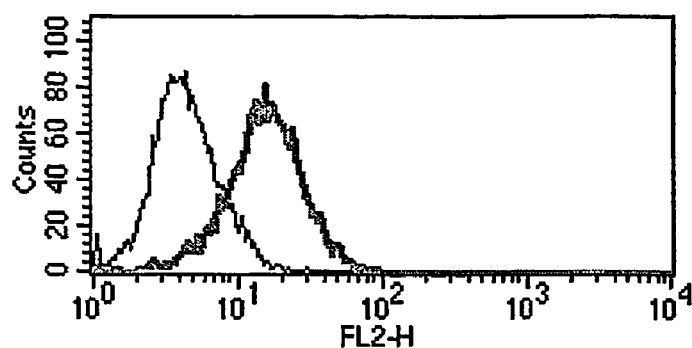
FIGURE 2(xxii) 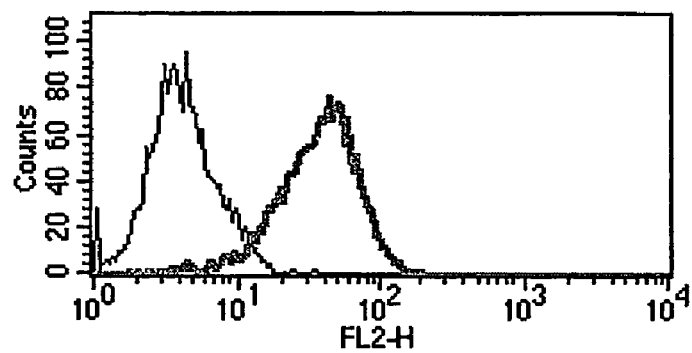
FIGURE 2(xxiii) 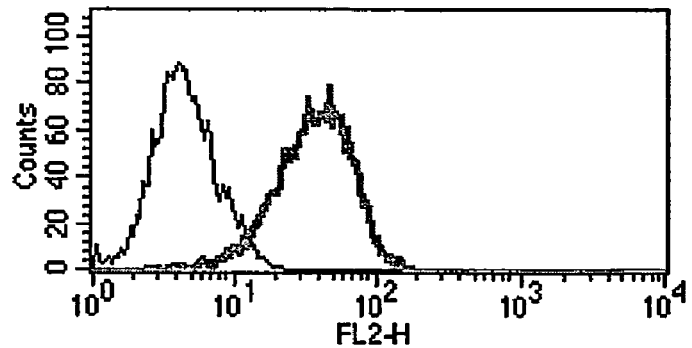
FIGURE 2(xxiv) 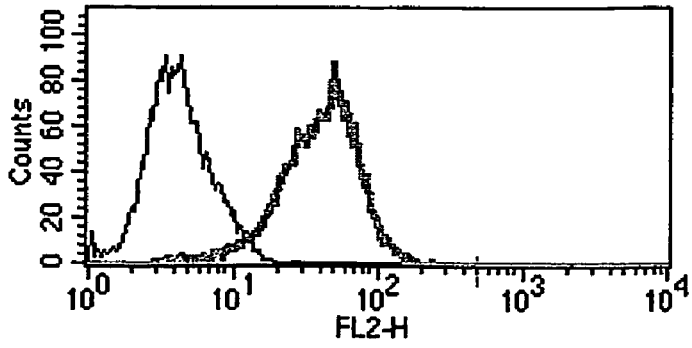

FIGURE 3
FIGURE 3(i)
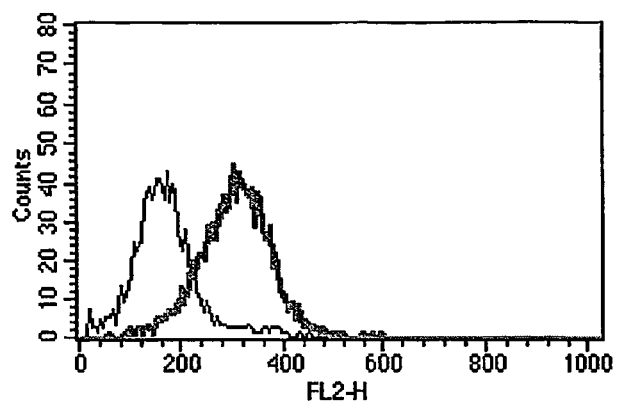
FIGURE 3(ii)
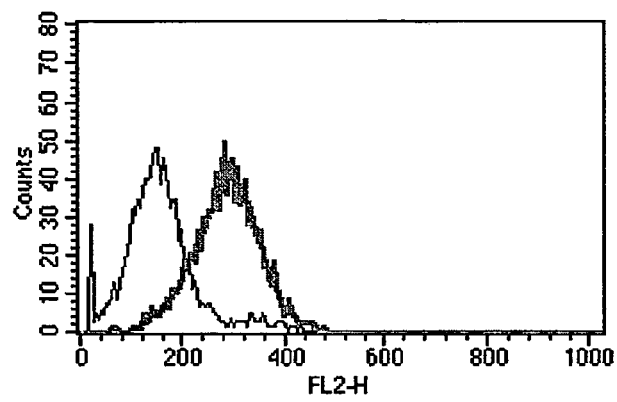
FIGURE 3(iii)
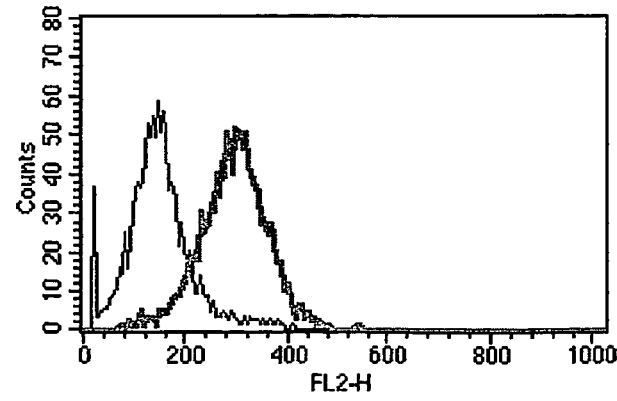
FIGURE 3(iv)
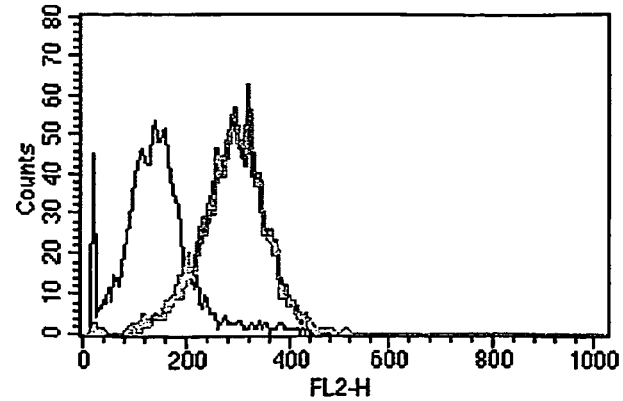

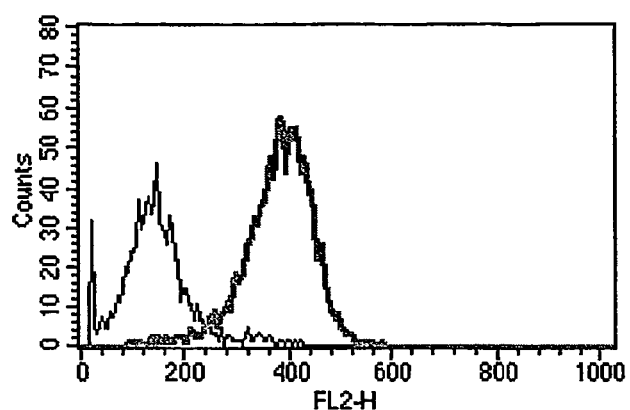
FIGURE 3(v)
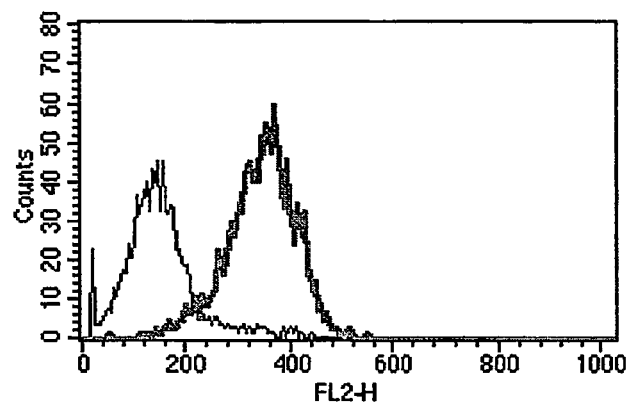
FIGURE 3(vi)
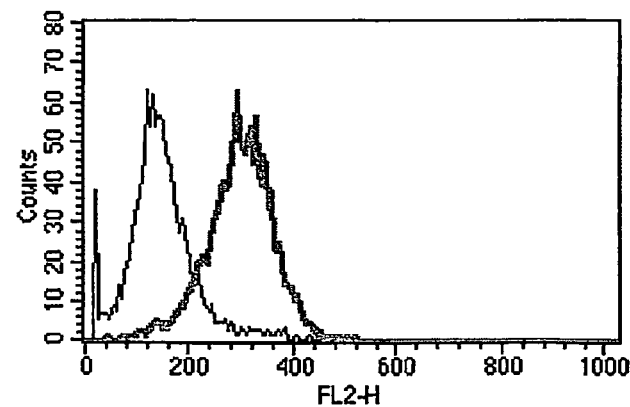
FIGURE 3(vii)
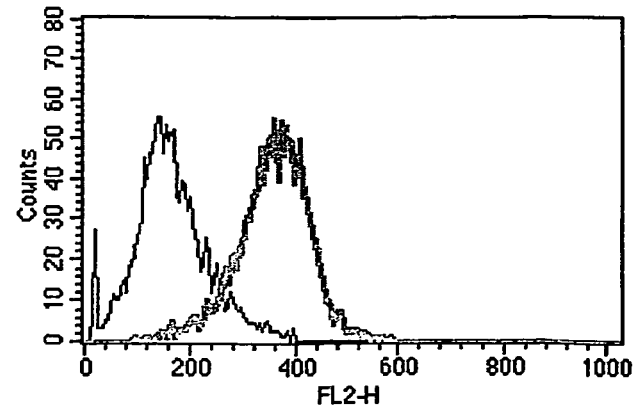
FIGURE 3(viii)

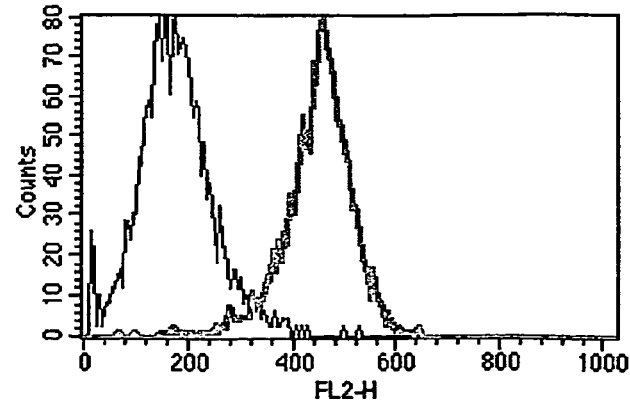
FIGURE 3(xii)

FIGURE 3(xiii)
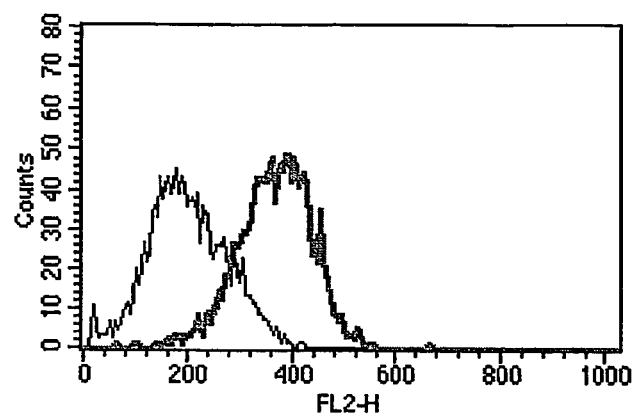
FIGURE 3(xiv)
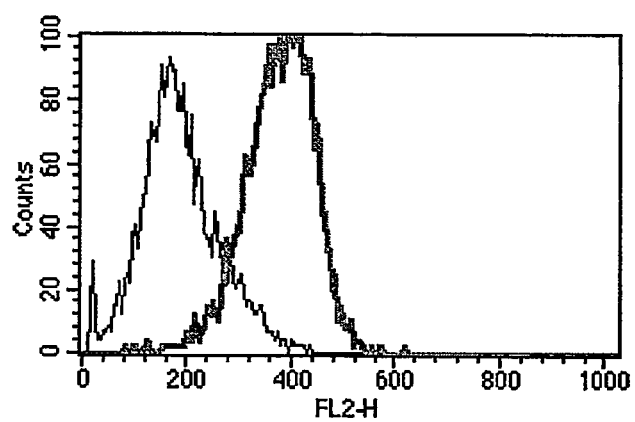
FIGURE 3(xv)
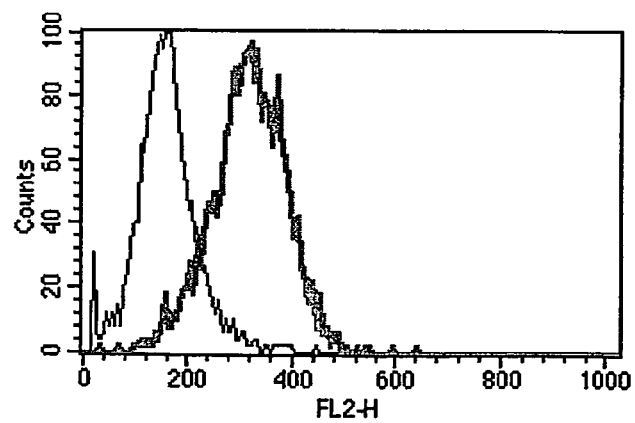
FIGURE 3(xvi)
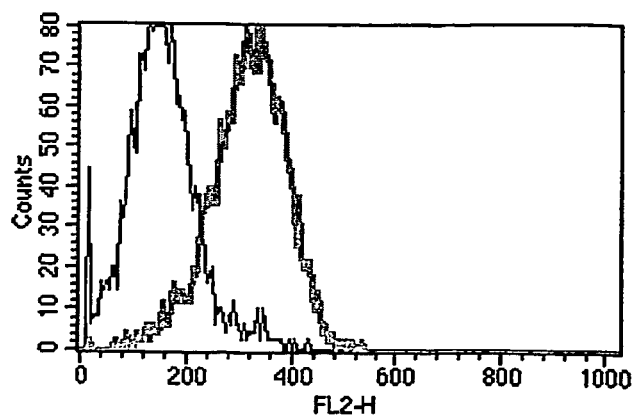

FIGURE 3(xvii) 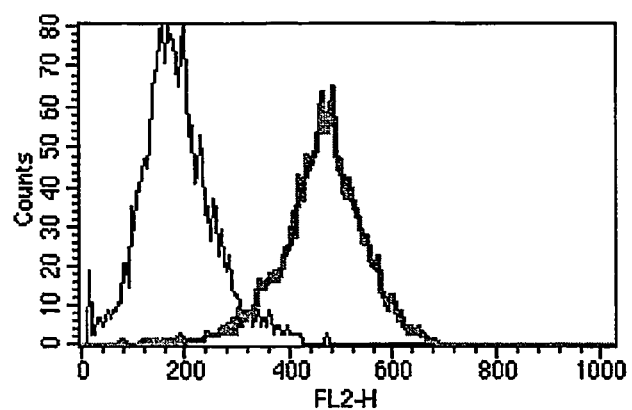
FIGURE 3(xviii) 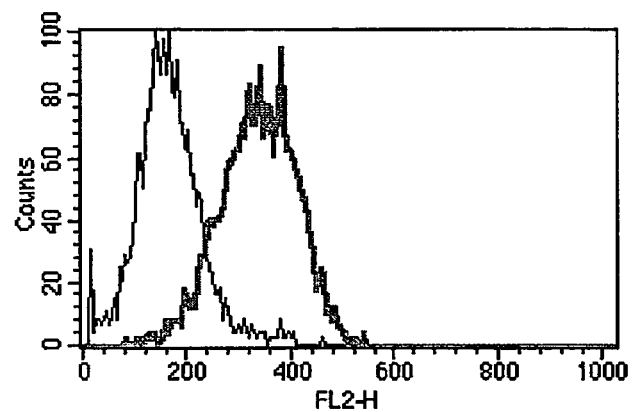
FIGURE 3(xix) 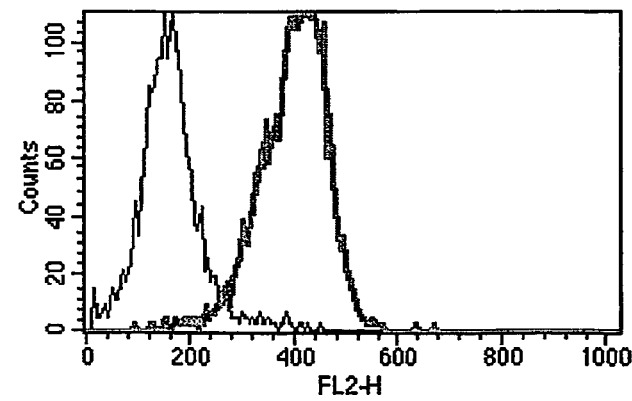

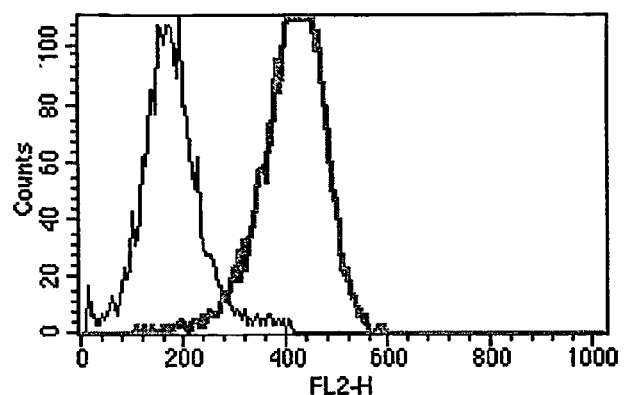
FIGURE 3(xxi)
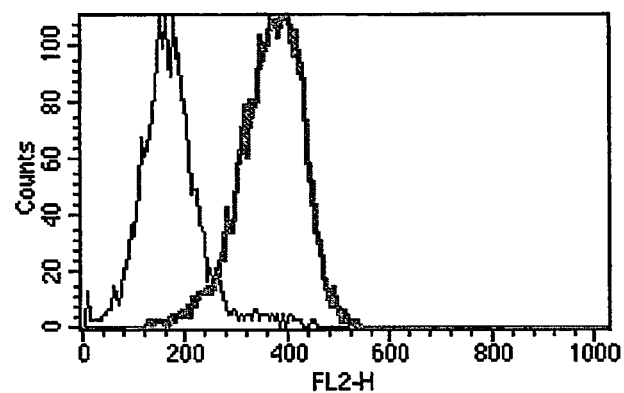
FIGURE 3(xxii)
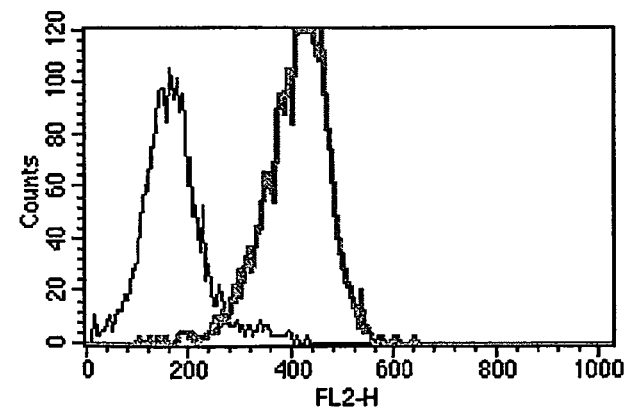
FIGURE 3(xxiii)
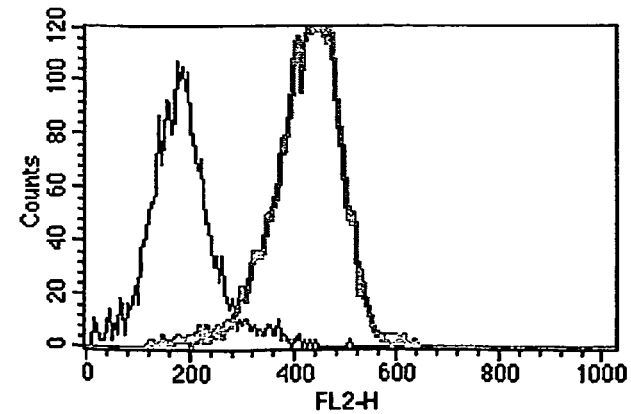
FIGURE 3(xxiv)

FIGURE 3(xxv)
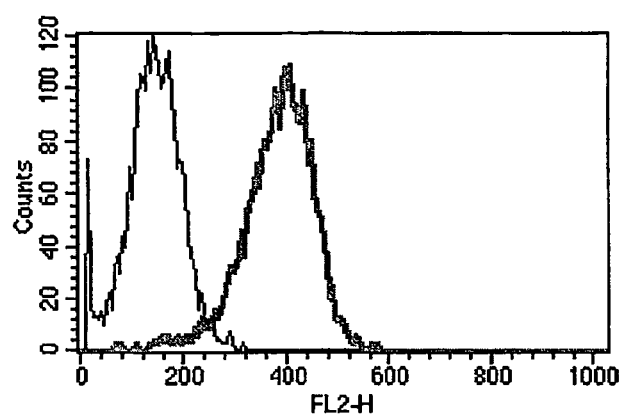
FIGURE 3(xxvi)
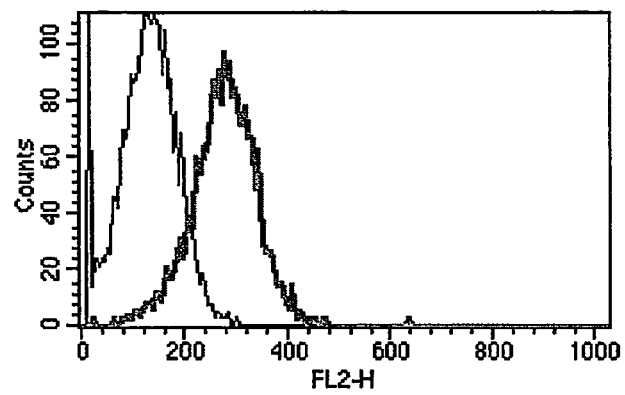
FIGURE 3(xxvii)
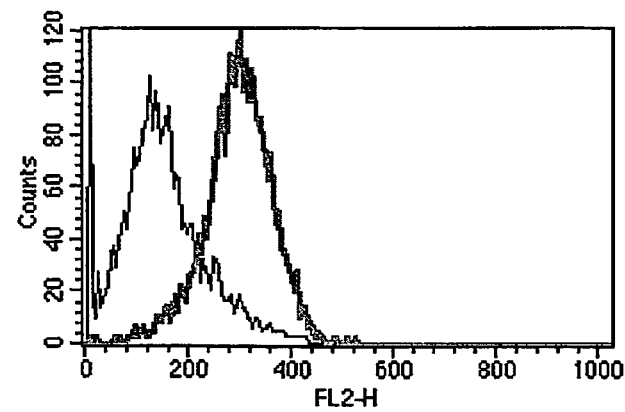
FIGURE 3(xxviii)
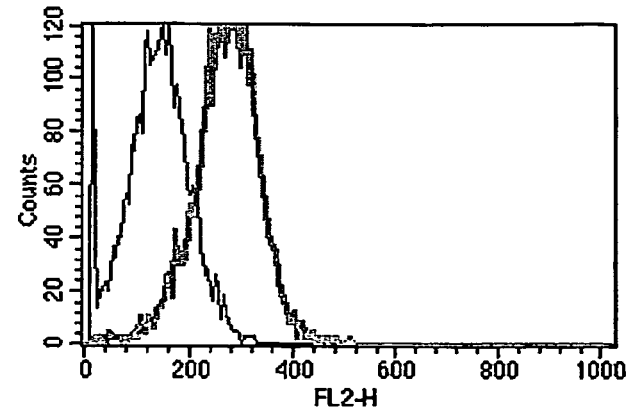

FIGURE 3(xxix)
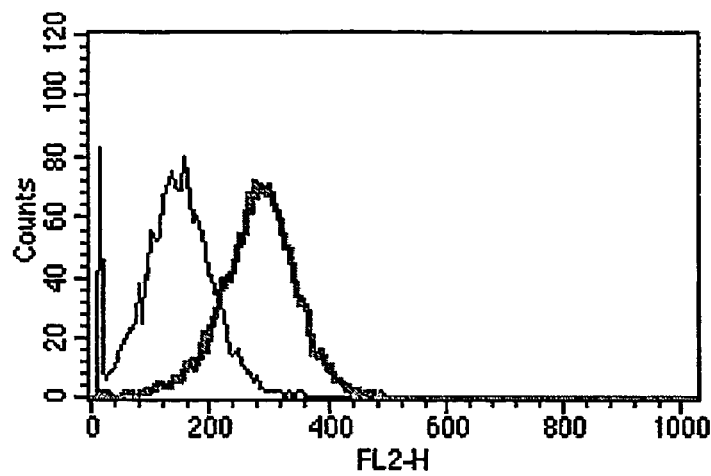
FIGURE 3(xxx)
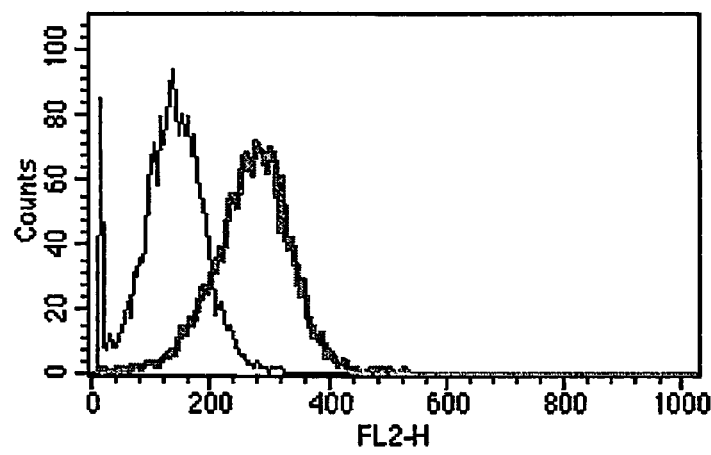
FIGURE 3(xxxi)
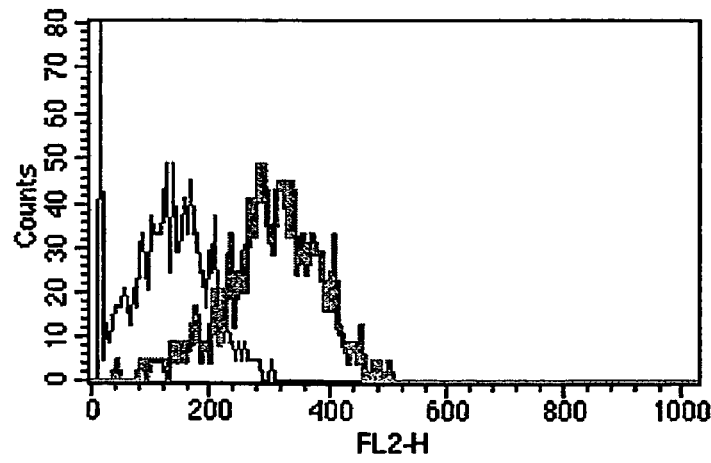

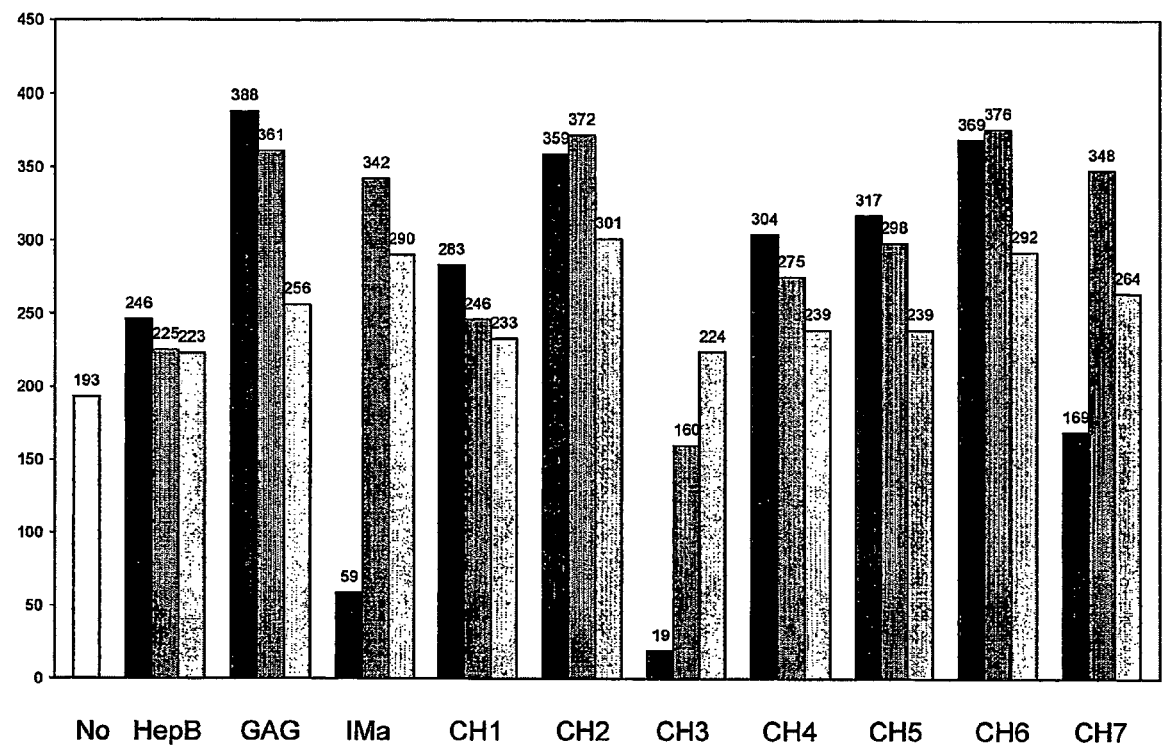
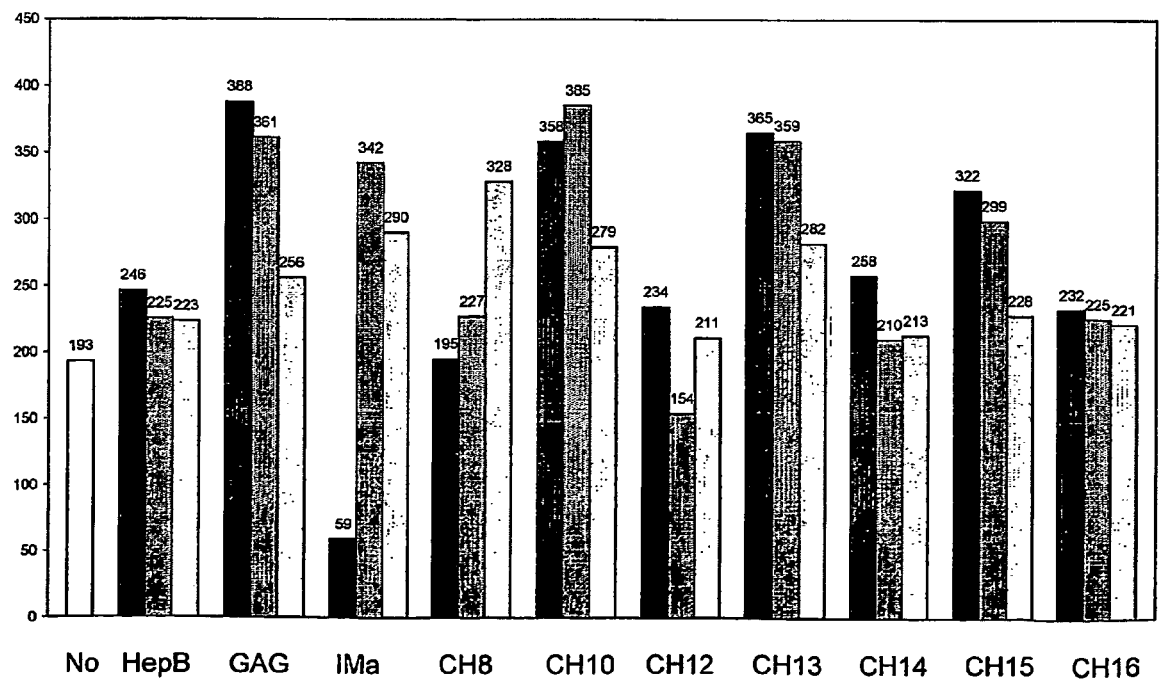

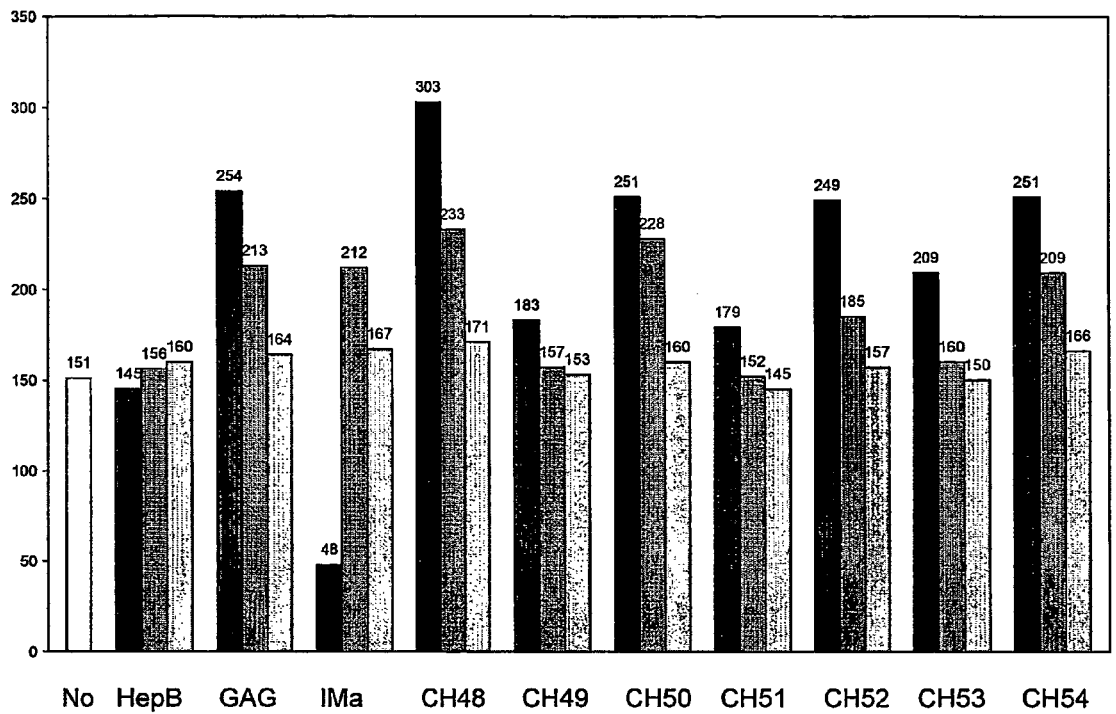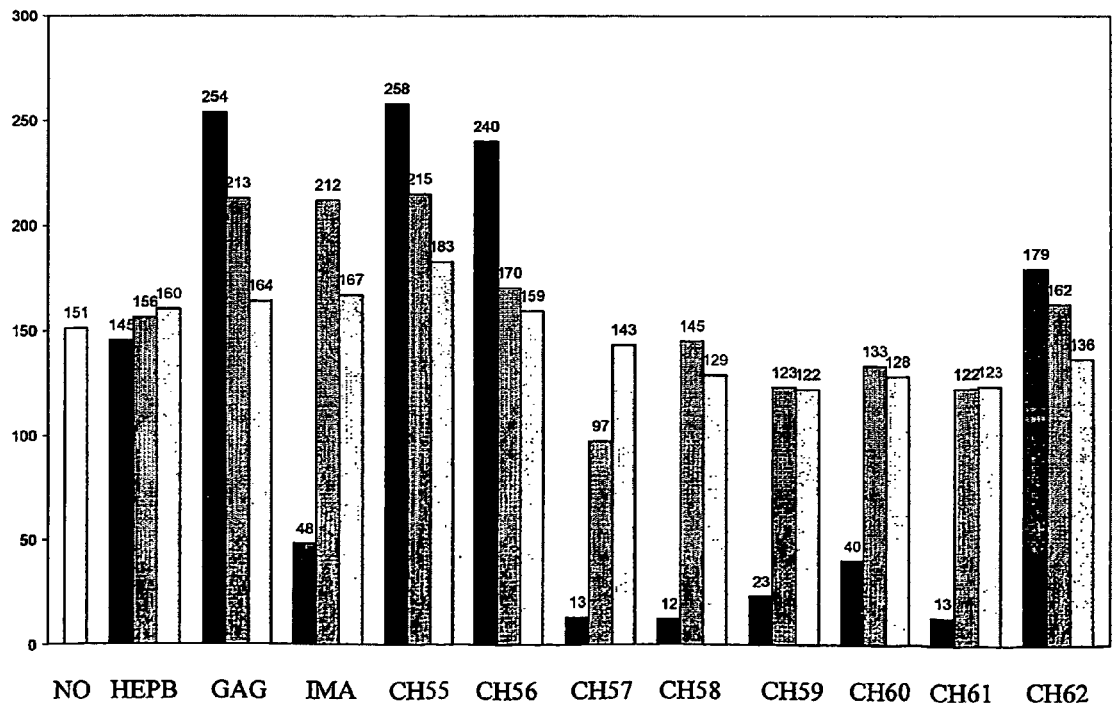

SEQUENCE LISTING

<160> NUMBER OF SEQ ID NOS: 181

<210> SEQ ID NO 1
<211> LENGTH: 9
<212> TYPE: PRT
<213> ORGANISM: Chlamydia pneumoniae

<400> SEQUENCE: 1

Gln Leu Leu Asp Glu Gly Lys Glu Leu 1               5

<210> SEQ ID NO 2
<211> LENGTH: 9
<212> TYPE: PRT
<213> ORGANISM: Chlamydia pneumoniae

<400> SEQUENCE: 2

Ile Leu Leu Asn Glu Val Pro Tyr Val
1               5

<210> SEQ ID NO 3
<211> LENGTH: 9
<212> TYPE: PRT
<213> ORGANISM: Chlamydia pneumoniae

<400> SEQUENCE: 3

Val Leu Asn Leu Phe Phe Ser Ala Leu
1               5

<210> SEQ ID NO 4
<211> LENGTH: 9
<212> TYPE: PRT
<213> ORGANISM: Chlamydia pneumoniae

<400> SEQUENCE: 4

Gln Leu Leu Glu Ser Leu Ala Pro Leu
1               5

<210> SEQ ID NO 5
<211> LENGTH: 9
<212> TYPE: PRT
<213> ORGANISM: Chlamydia pneumoniae

<400> SEQUENCE: 5

Ser Ile Leu Glu Leu Leu Gln Phe Val
1               5

<210> SEQ ID NO 6
<211> LENGTH: 9
<212> TYPE: PRT
<213> ORGANISM: Chlamydia pneumoniae

<400> SEQUENCE: 6

Tyr Leu Leu Glu Glu Ile Tyr Thr Val
1               5

<210> SEQ ID NO 7
<211> LENGTH: 9
<212> TYPE: PRT
<213> ORGANISM: Chlamydia pneumoniae

<400> SEQUENCE: 7

Tyr Met Asp Asn Asn Leu Phe Tyr Val
1               5

<210> SEQ ID NO 8
<211> LENGTH: 9
<212> TYPE: PRT
<213> ORGANISM: Chlamydia pneumoniae

<400> SEQUENCE: 8

Phe Leu Thr Leu Ala Trp Trp Phe Ile
1               5

```
<210> SEQ ID NO 9
<211> LENGTH: 9
<212> TYPE: PRT
<213> ORGANISM: Chlamydia pneumoniae

<400> SEQUENCE: 9

Gly Leu Thr Glu Glu Ile Asp Tyr Val
1               5

<210> SEQ ID NO 10
<211> LENGTH: 9
<212> TYPE: PRT
<213> ORGANISM: Chlamydia pneumoniae

<400> SEQUENCE: 10

Asn Leu Ala Gly Gly Ile Leu Ser Val
1               5

<210> SEQ ID NO 11
<211> LENGTH: 9
<212> TYPE: PRT
<213> ORGANISM: Chlamydia pneumoniae

<400> SEQUENCE: 11

Tyr Val Phe Asp Arg Ile Leu Lys Val
1               5

<210> SEQ ID NO 12
<211> LENGTH: 9
<212> TYPE: PRT
<213> ORGANISM: Chlamydia pneumoniae

<400> SEQUENCE: 12

Phe Val Ser Lys Phe Trp Phe Ser Leu
1               5

<210> SEQ ID NO 13
<211> LENGTH: 9
<212> TYPE: PRT
<213> ORGANISM: Chlamydia pneumoniae

<400> SEQUENCE: 13

Tyr Leu Thr Ser Tyr Ser Pro Tyr Val
1               5

<210> SEQ ID NO 14
<211> LENGTH: 9
<212> TYPE: PRT
<213> ORGANISM: Chlamydia pneumoniae

<400> SEQUENCE: 14

Ser Ile Thr Val Phe Arg Trp Leu Val
1               5

<210> SEQ ID NO 15
<211> LENGTH: 9
<212> TYPE: PRT
<213> ORGANISM: Chlamydia pneumoniae

<400> SEQUENCE: 15

Ile Leu Gln Glu Ala Glu Gln Met Val
1               5

<210> SEQ ID NO 16
```

```
<211> LENGTH: 9
<212> TYPE: PRT
<213> ORGANISM: Chlamydia pneumoniae

<400> SEQUENCE: 16

Tyr Leu Ile Val Phe Val Leu Thr Ile
1               5

<210> SEQ ID NO 17
<211> LENGTH: 9
<212> TYPE: PRT
<213> ORGANISM: Chlamydia pneumoniae

<400> SEQUENCE: 17

Val Met Leu Phe Ile Gly Leu Gly Val
1               5

<210> SEQ ID NO 18
<211> LENGTH: 9
<212> TYPE: PRT
<213> ORGANISM: Chlamydia pneumoniae

<400> SEQUENCE: 18

Ala Leu Met Leu Leu Asn Asn Tyr Val
1               5

<210> SEQ ID NO 19
<211> LENGTH: 9
<212> TYPE: PRT
<213> ORGANISM: Chlamydia pneumoniae

<400> SEQUENCE: 19

Thr Leu Trp Gly Ser Phe Val Asp Val
1               5

<210> SEQ ID NO 20
<211> LENGTH: 9
<212> TYPE: PRT
<213> ORGANISM: Chlamydia pneumoniae

<400> SEQUENCE: 20

Trp Leu Phe Asp Leu Arg Phe Ser Val
1               5

<210> SEQ ID NO 21
<211> LENGTH: 9
<212> TYPE: PRT
<213> ORGANISM: Chlamydia pneumoniae

<400> SEQUENCE: 21

Leu Ile Gln Glu Thr Leu Leu Phe Val
1               5

<210> SEQ ID NO 22
<211> LENGTH: 9
<212> TYPE: PRT
<213> ORGANISM: Chlamydia pneumoniae

<400> SEQUENCE: 22

Lys Leu Phe Thr Pro Phe Phe Thr Thr
1               5

<210> SEQ ID NO 23
<211> LENGTH: 9
<212> TYPE: PRT
```

-continued

<213> ORGANISM: Chlamydia pneumoniae

<400> SEQUENCE: 23

Arg Leu Leu Glu Ile Ile Trp Gly Val
1               5

<210> SEQ ID NO 24
<211> LENGTH: 9
<212> TYPE: PRT
<213> ORGANISM: Chlamydia pneumoniae

<400> SEQUENCE: 24

Tyr Leu Met Gln Lys Leu Gln Asn Val
1               5

<210> SEQ ID NO 25
<211> LENGTH: 9
<212> TYPE: PRT
<213> ORGANISM: Chlamydia pneumoniae

<400> SEQUENCE: 25

Phe Leu Gln Arg Gly Glu Ser Phe Val
1               5

<210> SEQ ID NO 26
<211> LENGTH: 9
<212> TYPE: PRT
<213> ORGANISM: Chlamydia pneumoniae

<400> SEQUENCE: 26

Trp Leu Leu Arg Asp Asp Trp Leu Leu
1               5

<210> SEQ ID NO 27
<211> LENGTH: 9
<212> TYPE: PRT
<213> ORGANISM: Chlamydia pneumoniae

<400> SEQUENCE: 27

Lys Leu Trp Glu Trp Leu Gly Tyr Leu
1               5

<210> SEQ ID NO 28
<211> LENGTH: 9
<212> TYPE: PRT
<213> ORGANISM: Chlamydia pneumoniae

<400> SEQUENCE: 28

Val Leu Phe Leu Leu Ile Arg Ser Val
1               5

<210> SEQ ID NO 29
<211> LENGTH: 9
<212> TYPE: PRT
<213> ORGANISM: Chlamydia pneumoniae

<400> SEQUENCE: 29

Lys Leu Leu Lys Asp His Phe Asp Leu
1               5

<210> SEQ ID NO 30
<211> LENGTH: 9
<212> TYPE: PRT
<213> ORGANISM: Chlamydia pneumoniae

```
<400> SEQUENCE: 30

Ile Leu Ser Phe Leu Pro Trp Leu Val
1               5

<210> SEQ ID NO 31
<211> LENGTH: 9
<212> TYPE: PRT
<213> ORGANISM: Chlamydia pneumoniae

<400> SEQUENCE: 31

Phe Leu Phe Gln Leu Gly Met Gln Ile
1               5

<210> SEQ ID NO 32
<211> LENGTH: 9
<212> TYPE: PRT
<213> ORGANISM: Chlamydia pneumoniae

<400> SEQUENCE: 32

Tyr Leu Leu Asp Phe Arg Trp Pro Leu
1               5

<210> SEQ ID NO 33
<211> LENGTH: 9
<212> TYPE: PRT
<213> ORGANISM: Chlamydia pneumoniae

<400> SEQUENCE: 33

Asn Leu Leu Lys Arg Trp Gln Phe Val
1               5

<210> SEQ ID NO 34
<211> LENGTH: 9
<212> TYPE: PRT
<213> ORGANISM: Chlamydia pneumoniae

<400> SEQUENCE: 34

Phe Leu Leu Arg His Leu Ser Ser Val
1               5

<210> SEQ ID NO 35
<211> LENGTH: 9
<212> TYPE: PRT
<213> ORGANISM: Chlamydia pneumoniae

<400> SEQUENCE: 35

Lys Leu Leu Ala Phe Pro Ala Phe Ala
1               5

<210> SEQ ID NO 36
<211> LENGTH: 9
<212> TYPE: PRT
<213> ORGANISM: Chlamydia pneumoniae

<400> SEQUENCE: 36

Lys Leu Ser Glu Gln Leu Glu Ala Leu
1               5

<210> SEQ ID NO 37
<211> LENGTH: 9
<212> TYPE: PRT
<213> ORGANISM: Chlamydia pneumoniae

<400> SEQUENCE: 37
```

```
Lys Val Leu Leu Gly Gln Glu Trp Val
1               5
```

<210> SEQ ID NO 38
<211> LENGTH: 9
<212> TYPE: PRT
<213> ORGANISM: Chlamydia pneumoniae
<400> SEQUENCE: 38

```
Asn Leu Ala Glu Gln Val Thr Ala Leu
1               5
```

<210> SEQ ID NO 39
<211> LENGTH: 9
<212> TYPE: PRT
<213> ORGANISM: Chlamydia pneumoniae
<400> SEQUENCE: 39

```
Tyr Val Val Gly Phe Ile Ile Phe Leu
1               5
```

<210> SEQ ID NO 40
<211> LENGTH: 9
<212> TYPE: PRT
<213> ORGANISM: Chlamydia pneumoniae
<400> SEQUENCE: 40

```
Trp Met Met Gly Val Val Leu Met Ile
1               5
```

<210> SEQ ID NO 41
<211> LENGTH: 9
<212> TYPE: PRT
<213> ORGANISM: Chlamydia pneumoniae
<400> SEQUENCE: 41

```
Asn Leu Ser Ile Ser Val Phe Leu Leu
1               5
```

<210> SEQ ID NO 42
<211> LENGTH: 9
<212> TYPE: PRT
<213> ORGANISM: Chlamydia pneumoniae
<400> SEQUENCE: 42

```
Val Ile Gln Ala Phe Gly Asp Phe Val
1               5
```

<210> SEQ ID NO 43
<211> LENGTH: 9
<212> TYPE: PRT
<213> ORGANISM: Chlamydia pneumoniae
<400> SEQUENCE: 43

```
Tyr Leu Ala Leu Asp Pro Asp Ser Val
1               5
```

<210> SEQ ID NO 44
<211> LENGTH: 9
<212> TYPE: PRT
<213> ORGANISM: Chlamydia pneumoniae
<400> SEQUENCE: 44

```
Lys Met Ser His Phe Gln Gln Ala Leu
1               5
```

<210> SEQ ID NO 45
<211> LENGTH: 9
<212> TYPE: PRT
<213> ORGANISM: Chlamydia pneumoniae

<400> SEQUENCE: 45

Ser Leu Cys Ala Gln Ser Ser Tyr Val
1               5

<210> SEQ ID NO 46
<211> LENGTH: 9
<212> TYPE: PRT
<213> ORGANISM: Chlamydia pneumoniae

<400> SEQUENCE: 46

Asn Leu Ser Arg Gln Ala Phe Phe Ala
1               5

<210> SEQ ID NO 47
<211> LENGTH: 9
<212> TYPE: PRT
<213> ORGANISM: Chlamydia pneumoniae

<400> SEQUENCE: 47

Ser Leu Leu Glu Glu His Pro Val Val
1               5

<210> SEQ ID NO 48
<211> LENGTH: 9
<212> TYPE: PRT
<213> ORGANISM: Chlamydia pneumoniae

<400> SEQUENCE: 48

Asn Leu Trp Ser His Tyr Thr Asp Leu
1               5

<210> SEQ ID NO 49
<211> LENGTH: 9
<212> TYPE: PRT
<213> ORGANISM: Chlamydia pneumoniae

<400> SEQUENCE: 49

Ala Leu Trp Lys Glu Asn Gln Ala Leu
1               5

<210> SEQ ID NO 50
<211> LENGTH: 9
<212> TYPE: PRT
<213> ORGANISM: Chlamydia pneumoniae

<400> SEQUENCE: 50

Ala Leu Trp Gly His Asn Val Leu Leu
1               5

<210> SEQ ID NO 51
<211> LENGTH: 9
<212> TYPE: PRT
<213> ORGANISM: Chlamydia pneumoniae

<400> SEQUENCE: 51

Trp Leu Val Phe Phe Asn Pro Phe Val
1               5

```
<210> SEQ ID NO 52
<211> LENGTH: 9
<212> TYPE: PRT
<213> ORGANISM: Chlamydia pneumoniae

<400> SEQUENCE: 52

Val Met Leu Ile Phe Glu Lys Lys Val
1               5

<210> SEQ ID NO 53
<211> LENGTH: 9
<212> TYPE: PRT
<213> ORGANISM: Chlamydia pneumoniae

<400> SEQUENCE: 53

Val Gln Leu Ala Tyr Val Phe Asp Val
1               5

<210> SEQ ID NO 54
<211> LENGTH: 9
<212> TYPE: PRT
<213> ORGANISM: Chlamydia pneumoniae

<400> SEQUENCE: 54

Ile Ala Leu Leu Val Ile Phe Phe Val
1               5

<210> SEQ ID NO 55
<211> LENGTH: 9
<212> TYPE: PRT
<213> ORGANISM: Chlamydia pneumoniae

<400> SEQUENCE: 55

Leu Leu Leu Thr Leu Gly Tyr Ala Val
1               5

<210> SEQ ID NO 56
<211> LENGTH: 9
<212> TYPE: PRT
<213> ORGANISM: Chlamydia pneumoniae

<400> SEQUENCE: 56

Leu Leu Met Leu Ala Ile Ser Leu Val
1               5

<210> SEQ ID NO 57
<211> LENGTH: 9
<212> TYPE: PRT
<213> ORGANISM: Chlamydia pneumoniae

<400> SEQUENCE: 57

Leu Leu Leu Ile Phe Asn Asn Tyr Leu
1               5

<210> SEQ ID NO 58
<211> LENGTH: 9
<212> TYPE: PRT
<213> ORGANISM: Chlamydia trachomatis

<400> SEQUENCE: 58

Gln Leu Leu Glu Gly Leu Asp Glu Leu
1               5

<210> SEQ ID NO 59
<211> LENGTH: 9
```

```
<212> TYPE: PRT
<213> ORGANISM: Chlamydia trachomatis

<400> SEQUENCE: 59

Val Leu Leu Glu Glu Ile Tyr Thr Val
1               5

<210> SEQ ID NO 60
<211> LENGTH: 9
<212> TYPE: PRT
<213> ORGANISM: Chlamydia trachomatis

<400> SEQUENCE: 60

Phe Val Phe Asp Arg Val Leu Lys Thr
1               5

<210> SEQ ID NO 61
<211> LENGTH: 9
<212> TYPE: PRT
<213> ORGANISM: Chlamydia trachomatis

<400> SEQUENCE: 61

Trp Leu Ala Asp Leu Arg Ile Ser Met
1               5

<210> SEQ ID NO 62
<211> LENGTH: 9
<212> TYPE: PRT
<213> ORGANISM: Chlamydia trachomatis

<400> SEQUENCE: 62

Leu Ile Gln Glu Leu Pro Leu Lys Val
1               5

<210> SEQ ID NO 63
<211> LENGTH: 9
<212> TYPE: PRT
<213> ORGANISM: Chlamydia trachomatis

<400> SEQUENCE: 63

Lys Leu Phe Ile Pro Phe Phe Thr Thr
1               5

<210> SEQ ID NO 64
<211> LENGTH: 9
<212> TYPE: PRT
<213> ORGANISM: Chlamydia trachomatis

<400> SEQUENCE: 64

Leu Leu Leu Arg Asp Asp Ile Lys Leu
1               5

<210> SEQ ID NO 65
<211> LENGTH: 9
<212> TYPE: PRT
<213> ORGANISM: Chlamydia trachomatis

<400> SEQUENCE: 65

Phe Leu Leu Arg Ala Pro Trp Leu Leu
1               5

<210> SEQ ID NO 66
<211> LENGTH: 9
<212> TYPE: PRT
<213> ORGANISM: Chlamydia trachomatis
```

```
<400> SEQUENCE: 66

Lys Leu Leu Asn Asp Arg Phe Pro Leu
1               5

<210> SEQ ID NO 67
<211> LENGTH: 9
<212> TYPE: PRT
<213> ORGANISM: Chlamydia trachomatis

<400> SEQUENCE: 67

Ile Leu Ser Ser Leu Tyr Ser Leu Val
1               5

<210> SEQ ID NO 68
<211> LENGTH: 9
<212> TYPE: PRT
<213> ORGANISM: Chlamydia trachomatis

<400> SEQUENCE: 68

Ile Leu Ser Leu Leu Pro Met Ile Val
1               5

<210> SEQ ID NO 69
<211> LENGTH: 9
<212> TYPE: PRT
<213> ORGANISM: Chlamydia trachomatis

<400> SEQUENCE: 69

Arg Leu Leu Lys Arg Lys Gln Phe Val
1               5

<210> SEQ ID NO 70
<211> LENGTH: 9
<212> TYPE: PRT
<213> ORGANISM: Chlamydia trachomatis

<400> SEQUENCE: 70

Val Leu Leu Arg Asn Leu Ser Ala Val
1               5

<210> SEQ ID NO 71
<211> LENGTH: 9
<212> TYPE: PRT
<213> ORGANISM: Chlamydia trachomatis

<400> SEQUENCE: 71

Ile Leu Leu Arg His Gly Gln Ser Val
1               5

<210> SEQ ID NO 72
<211> LENGTH: 9
<212> TYPE: PRT
<213> ORGANISM: Chlamydia trachomatis

<400> SEQUENCE: 72

Val Leu Leu Ala Leu Ile Ala Phe Ala
1               5

<210> SEQ ID NO 73
<211> LENGTH: 9
<212> TYPE: PRT
<213> ORGANISM: Chlamydia trachomatis

<400> SEQUENCE: 73
```

```
Arg Leu Ser Lys Gln Leu Glu Asn Leu
1               5
```

<210> SEQ ID NO 74
<211> LENGTH: 9
<212> TYPE: PRT
<213> ORGANISM: Chlamydia trachomatis

<400> SEQUENCE: 74

```
Lys Leu Ser Glu Gly Leu Lys Val Leu
1               5
```

<210> SEQ ID NO 75
<211> LENGTH: 9
<212> TYPE: PRT
<213> ORGANISM: Chlamydia trachomatis

<400> SEQUENCE: 75

```
Asn Leu Ser Tyr Pro Leu Glu Ala Leu
1               5
```

<210> SEQ ID NO 76
<211> LENGTH: 9
<212> TYPE: PRT
<213> ORGANISM: Chlamydia trachomatis

<400> SEQUENCE: 76

```
Lys Val Leu Ser Gly Asp Glu Ser Val
1               5
```

<210> SEQ ID NO 77
<211> LENGTH: 9
<212> TYPE: PRT
<213> ORGANISM: Chlamydia trachomatis

<400> SEQUENCE: 77

```
Asn Leu Ala Glu Arg Val Leu Asp Leu
1               5
```

<210> SEQ ID NO 78
<211> LENGTH: 9
<212> TYPE: PRT
<213> ORGANISM: Chlamydia trachomatis

<400> SEQUENCE: 78

```
Trp Met Leu Gly Val Val Leu Met Ile
1               5
```

<210> SEQ ID NO 79
<211> LENGTH: 9
<212> TYPE: PRT
<213> ORGANISM: Chlamydia trachomatis

<400> SEQUENCE: 79

```
Asn Leu Trp Gly Cys Tyr Thr Glu Leu
1               5
```

<210> SEQ ID NO 80
<211> LENGTH: 9
<212> TYPE: PRT
<213> ORGANISM: Chlamydia trachomatis

<400> SEQUENCE: 80

```
Ala Leu Trp Ile Asn Asn Gln Pro Leu
```

-continued

<210> SEQ ID NO 81
<211> LENGTH: 9
<212> TYPE: PRT
<213> ORGANISM: Chlamydia trachomatis

<400> SEQUENCE: 81

Met Leu Trp Gly Val Met Val Leu Leu
1               5

<210> SEQ ID NO 82
<211> LENGTH: 9
<212> TYPE: PRT
<213> ORGANISM: Chlamydia trachomatis

<400> SEQUENCE: 82

Lys Leu Ala Gly Phe Pro Leu Ser Val
1               5

<210> SEQ ID NO 83
<211> LENGTH: 360
<212> TYPE: PRT
<213> ORGANISM: Chlamydia pneumoniae

<400> SEQUENCE: 83

Met Gly Glu Lys Thr Glu Lys Ala Thr Pro Lys Arg Leu Arg Asp Ala
1               5                   10                  15

Arg Lys Lys Gly Gln Val Ala Lys Ser Gln Asp Phe Pro Ser Ala Val
            20                  25                  30

Thr Phe Ile Val Ser Met Phe Thr Ala Phe Ser Leu Ser Thr Phe Phe
        35                  40                  45

Phe Lys His Leu Gly Gly Phe Leu Val Ser Met Leu Ser Gln Ala Pro
    50                  55                  60

Thr Arg His Asp Pro Val Ile Thr Leu Phe Tyr Leu Lys Asn Cys Leu
65                  70                  75                  80

Met Leu Ile Leu Thr Ala Ser Leu Pro Leu Leu Gly Ala Val Ala Val
                85                  90                  95

Val Gly Val Ile Val Gly Phe Leu Ile Val Gly Pro Thr Phe Ser Thr
            100                 105                 110

Glu Val Phe Lys Pro Asp Ile Lys Lys Phe Asn Pro Ile Glu Asn Ile
        115                 120                 125

Lys Gln Lys Phe Lys Ile Lys Thr Leu Ile Glu Leu Ile Lys Ser Ile
    130                 135                 140

Leu Lys Ile Phe Gly Ala Ala Leu Ile Leu Tyr Ile Thr Leu Lys Ser
145                 150                 155                 160

Lys Val Ser Leu Ile Ile Glu Thr Ala Gly Val Ser Pro Ile Ile Thr
                165                 170                 175

Ala Gln Ile Phe Lys Glu Ile Phe Tyr Lys Ala Val Thr Ser Ile Gly
            180                 185                 190

Ile Phe Phe Leu Ile Val Ala Ile Leu Asp Leu Val Tyr Gln Arg His
        195                 200                 205

Asn Phe Ala Lys Glu Leu Lys Met Glu Lys Phe Glu Val Lys Gln Glu
    210                 215                 220

Phe Lys Asp Thr Glu Gly Asn Pro Glu Ile Lys Gly Arg Arg Gln
225                 230                 235                 240

Ile Ala Gln Glu Ile Ala Tyr Glu Asp Ser Ser Gln Val Lys His
                245                 250                 255

```
Ala Ser Thr Val Val Ser Asn Pro Lys Asp Ile Ala Val Ala Ile Gly
            260                 265                 270

Tyr Met Pro Glu Lys Tyr Lys Ala Pro Trp Ile Ile Ala Met Gly Ile
            275                 280                 285

Asn Leu Arg Ala Lys Arg Ile Leu Asp Glu Ala Glu Lys Tyr Gly Ile
            290                 295                 300

Pro Ile Met Arg Asn Val Pro Leu Ala His Gln Leu Leu Asp Glu Gly
305                 310                 315                 320

Lys Glu Leu Lys Phe Ile Pro Glu Ser Thr Tyr Glu Ala Ile Gly Glu
            325                 330                 335

Ile Leu Leu Tyr Ile Thr Ser Leu Asn Ala Gln Asn Pro Asn Asn Lys
            340                 345                 350

Asn Thr Asn Gln Pro Asp His Leu
            355                 360

<210> SEQ ID NO 84
<211> LENGTH: 710
<212> TYPE: PRT
<213> ORGANISM: Chlamydia pneumoniae

<400> SEQUENCE: 84

Met Asn Lys Leu Leu Asn Phe Val Ser Arg Thr Leu Gly Gly Asp Thr
1               5                   10                  15

Ala Leu Asn Met Ile Asn Lys Ser Ser Asp Leu Ile Leu Ala Leu Trp
            20                  25                  30

Met Met Gly Val Val Leu Met Ile Ile Pro Leu Pro Pro Pro Ile
            35                  40                  45

Val Asp Leu Met Ile Thr Ile Asn Leu Ser Ile Ser Val Phe Leu Leu
        50                  55                  60

Met Val Ala Leu Tyr Ile Pro Ser Ala Leu Gln Leu Ser Val Phe Pro
65                  70                  75                  80

Ser Leu Leu Leu Ile Thr Thr Met Phe Arg Leu Gly Ile Asn Ile Ser
            85                  90                  95

Ser Ser Arg Gln Ile Leu Leu Lys Ala Tyr Ala Gly His Val Ile Gln
            100                 105                 110

Ala Phe Gly Asp Phe Val Val Gly Gly Asn Tyr Val Val Gly Phe Ile
            115                 120                 125

Ile Phe Leu Ile Ile Thr Ile Ile Gln Phe Ile Val Val Thr Lys Gly
            130                 135                 140

Ala Glu Arg Val Ala Glu Val Ala Ala Arg Phe Arg Leu Asp Ala Met
145                 150                 155                 160

Pro Gly Lys Gln Met Ala Ile Asp Ala Asp Leu Arg Ala Gly Met Ile
            165                 170                 175

Asp Ala Thr Gln Ala Arg Asp Lys Arg Ala Gln Ile Gln Lys Glu Ser
            180                 185                 190

Glu Leu Tyr Gly Ala Met Asp Gly Ala Met Lys Phe Ile Lys Gly Asp
            195                 200                 205

Val Ile Ala Gly Ile Val Ile Ser Leu Ile Asn Ile Val Gly Gly Leu
            210                 215                 220

Thr Ile Gly Val Ala Met His Gly Met Asp Leu Ala Gln Ala Ala His
225                 230                 235                 240

Val Tyr Thr Leu Leu Ser Ile Gly Asp Gly Leu Val Ser Gln Ile Pro
            245                 250                 255

Ser Leu Leu Ile Ala Leu Thr Ala Gly Ile Val Thr Thr Arg Val Ser
```

```
                 260                 265                 270
Ser Asp Lys Asn Thr Asn Leu Gly Lys Glu Ile Ser Thr Gln Leu Val
            275                 280                 285
Lys Glu Pro Arg Ala Leu Leu Leu Ala Gly Ala Ala Thr Leu Gly Val
        290                 295                 300
Gly Phe Phe Lys Gly Phe Pro Leu Trp Ser Phe Ser Ile Leu Ala Leu
305                 310                 315                 320
Ile Phe Val Ala Leu Gly Ile Leu Leu Leu Thr Lys Lys Ser Ala Ala
                325                 330                 335
Gly Lys Lys Gly Gly Gly Ser Gly Ala Ser Thr Thr Val Gly Ala Ala
            340                 345                 350
Gly Asp Gly Ala Ala Thr Val Gly Asp Asn Pro Asp Asp Tyr Ser Leu
        355                 360                 365
Thr Leu Pro Val Ile Leu Glu Leu Gly Lys Asp Leu Ser Lys Leu Ile
370                 375                 380
Gln His Lys Thr Lys Ser Gly Gln Ser Phe Val Asp Asp Met Ile Pro
385                 390                 395                 400
Lys Met Arg Gln Ala Leu Tyr Gln Asp Ile Gly Ile Arg Tyr Pro Gly
                405                 410                 415
Ile His Val Arg Thr Asp Ser Pro Ser Leu Glu Gly Tyr Asp Tyr Met
            420                 425                 430
Ile Leu Leu Asn Glu Val Pro Tyr Val Arg Gly Lys Ile Pro Pro His
        435                 440                 445
His Val Leu Thr Asn Glu Val Glu Asp Asn Leu Ser Arg Tyr Asn Leu
    450                 455                 460
Pro Phe Ile Thr Tyr Lys Asn Ala Ala Gly Leu Pro Ser Ala Trp Val
465                 470                 475                 480
Ser Glu Asp Ala Lys Ala Ile Leu Glu Lys Ala Ile Lys Tyr Trp
                485                 490                 495
Thr Pro Leu Glu Val Ile Ile Leu His Leu Ser Tyr Phe Phe His Lys
            500                 505                 510
Ser Ser Gln Glu Phe Leu Gly Ile Gln Glu Val Arg Ser Met Ile Glu
        515                 520                 525
Phe Met Glu Arg Ser Phe Pro Asp Leu Val Lys Glu Val Thr Arg Leu
    530                 535                 540
Ile Pro Leu Gln Lys Leu Thr Glu Ile Phe Lys Arg Leu Val Gln Glu
545                 550                 555                 560
Gln Ile Ser Ile Lys Asp Leu Arg Thr Ile Leu Glu Ser Leu Ser Glu
                565                 570                 575
Trp Ala Gln Thr Glu Lys Asp Thr Val Leu Leu Thr Glu Tyr Val Arg
            580                 585                 590
Ser Ser Leu Lys Leu Tyr Ile Ser Phe Lys Phe Ser Gln Gly Gln Ser
        595                 600                 605
Ala Ile Ser Val Tyr Leu Leu Asp Pro Glu Ile Glu Glu Met Ile Arg
    610                 615                 620
Gly Ala Ile Lys Gln Thr Ser Ala Gly Ser Tyr Leu Ala Leu Asp Pro
625                 630                 635                 640
Asp Ser Val Asn Leu Ile Leu Lys Ser Met Arg Asn Thr Ile Thr Pro
                645                 650                 655
Thr Pro Ala Gly Gly Gln Pro Val Leu Leu Thr Ala Ile Asp Val
            660                 665                 670
Arg Arg Tyr Val Arg Lys Leu Ile Glu Thr Glu Phe Pro Asp Ile Ala
        675                 680                 685
```

```
Val Ile Ser Tyr Gln Glu Ile Leu Pro Glu Ile Arg Ile Gln Pro Leu
    690                 695                 700

Gly Arg Ile Gln Ile Phe
705                 710

<210> SEQ ID NO 85
<211> LENGTH: 399
<212> TYPE: PRT
<213> ORGANISM: Chlamydia pneumoniae

<400> SEQUENCE: 85

Met Ala Ala Ser Gly Gly Thr Gly Gly Leu Gly Gly Thr Gln Gly Val
1               5                   10                  15

Asn Leu Ala Ala Val Glu Ala Ala Ala Lys Ala Asp Ala Ala Glu
            20                  25                  30

Val Val Ala Ser Gln Glu Gly Ser Glu Met Asn Met Ile Gln Gln Ser
        35                  40                  45

Gln Asp Leu Thr Asn Pro Ala Ala Thr Arg Thr Lys Lys Lys Glu
    50                  55                  60

Glu Lys Phe Gln Thr Leu Glu Ser Arg Lys Gly Glu Ala Gly Lys
65                  70                  75                  80

Ala Glu Lys Lys Ser Glu Ser Thr Glu Glu Lys Pro Asp Thr Asp Leu
                85                  90                  95

Ala Asp Lys Tyr Ala Ser Gly Asn Ser Glu Ile Ser Gly Gln Glu Leu
            100                 105                 110

Arg Gly Leu Arg Asp Ala Ile Gly Asp Ala Ser Pro Glu Asp Ile
        115                 120                 125

Leu Ala Leu Val Gln Glu Lys Ile Lys Asp Pro Ala Leu Gln Ser Thr
    130                 135                 140

Ala Leu Asp Tyr Leu Val Gln Thr Thr Pro Ser Gln Gly Lys Leu
145                 150                 155                 160

Lys Glu Ala Leu Ile Gln Ala Arg Asn Thr His Thr Glu Gln Phe Gly
                165                 170                 175

Arg Thr Ala Ile Gly Ala Lys Asn Ile Leu Phe Ala Ser Gln Glu Tyr
            180                 185                 190

Ala Asp Gln Leu Asn Val Ser Pro Ser Gly Leu Arg Ser Leu Tyr Leu
        195                 200                 205

Glu Val Thr Gly Asp Thr His Thr Cys Asp Gln Leu Leu Ser Met Leu
    210                 215                 220

Gln Asp Arg Tyr Thr Tyr Gln Asp Met Ala Ile Val Ser Ser Phe Leu
225                 230                 235                 240

Met Lys Gly Met Ala Thr Glu Leu Lys Arg Gln Gly Pro Tyr Val Pro
                245                 250                 255

Ser Ala Gln Leu Gln Val Leu Met Thr Glu Thr Arg Asn Leu Gln Ala
            260                 265                 270

Val Leu Thr Ser Tyr Asp Tyr Phe Glu Ser Arg Val Pro Ile Leu Leu
        275                 280                 285

Asp Ser Leu Lys Ala Glu Gly Ile Gln Thr Pro Ser Asp Leu Asn Phe
    290                 295                 300

Val Lys Val Ala Glu Ser Tyr His Lys Ile Ile Asn Asp Lys Phe Pro
305                 310                 315                 320

Thr Ala Ser Lys Val Glu Arg Glu Val Arg Asn Leu Ile Gly Asp Asp
                325                 330                 335

Val Asp Ser Val Thr Gly Val Leu Asn Leu Phe Phe Ser Ala Leu Arg
```

-continued

```
                340                 345                 350
Gln Thr Ser Ser Arg Leu Phe Ser Ala Asp Lys Arg Gln Gln Leu
        355                 360                 365

Gly Ala Met Ile Ala Asn Ala Leu Asp Ala Val Asn Ile Asn Asn Glu
    370                 375                 380

Asp Tyr Pro Lys Ala Ser Asp Phe Pro Lys Pro Tyr Pro Trp Ser
385                 390                 395

<210> SEQ ID NO 86
<211> LENGTH: 147
<212> TYPE: PRT
<213> ORGANISM: Chlamydia pneumoniae

<400> SEQUENCE: 86

Met Gln Asn Gln Tyr Glu Gln Leu Leu Glu Ser Leu Ala Pro Leu Leu
1               5                   10                  15

Asn Thr Thr Leu Ala Pro Asp Lys Asn Asn Ser Cys Leu Ile Arg Phe
            20                  25                  30

Ser Asp Thr His Val Pro Val Gln Ile Glu Glu Asp Gly Asn Ser Gly
        35                  40                  45

Asp Leu Ala Val Ser Thr Leu Leu Gly Thr Leu Pro Glu Asn Val Phe
    50                  55                  60

Arg Glu Arg Ile Phe Lys Ala Ala Leu Ser Val Asn Gly Ser Phe Gln
65                  70                  75                  80

Ser Ser Ile Lys Gly Ile Leu Gly Tyr Gly Glu Val Thr Gln Gln Leu
                85                  90                  95

Tyr Leu Ser Asp Ile Leu Ser Met Asn Tyr Leu Asn Gly Glu Lys Leu
            100                 105                 110

Phe Glu Tyr Leu Lys Leu Phe Ser Leu His Ala Lys Ile Trp Met Glu
        115                 120                 125

Ser Leu Arg Thr Gly Asn Leu Pro Asp Leu His Val Leu Gly Ile Tyr
    130                 135                 140

Tyr Val Ala
145

<210> SEQ ID NO 87
<211> LENGTH: 919
<212> TYPE: PRT
<213> ORGANISM: Chlamydia pneumoniae

<400> SEQUENCE: 87

Met Lys Thr Val Ile Leu Asn Ile Gly Arg Lys Ile Leu Gln Gly Ile
1               5                   10                  15

Lys Lys Lys Lys Lys Lys Ile Gly Ile Leu Ser Gly Leu Phe Phe Leu
            20                  25                  30

Asp Leu Val Leu Leu Gly Val Ser Ser Gln Arg Pro Thr Glu Thr Ser
        35                  40                  45

Ala Asn Val Lys His Asn Leu Arg Asp Glu Lys Leu Ala Ala Cys Pro
    50                  55                  60

Lys Asn Ser Ala Ala Ser Leu Ser Ala Lys Ser His Thr Lys Lys
65                  70                  75                  80

Thr Thr Pro Gly Ser Ile Pro Ser Lys Val Phe Ser Lys Phe Asp Ala
                85                  90                  95

Thr Gln Asp Lys Thr Phe Gln Lys Thr Ser Gly Ser Ala Phe Pro Ala
            100                 105                 110

Lys Pro Thr Thr Leu Lys Glu Leu Glu Glu Arg Lys Lys Pro Arg Pro
```

-continued

```
            115                 120                 125
Glu Arg Arg Thr Thr Ala Asp Val Lys Arg Ser Pro Arg Phe Leu Pro
            130                 135                 140

Thr Gln Glu Val Glu Glu Pro Val Pro Ala Ala Ser Lys Glu Gln Leu
145                 150                 155                 160

Asp Ser Ile Gln Val Trp Glu Glu Lys Gln Asn Tyr Ala Arg Arg Ala
                    165                 170                 175

Val Asn Ala Ile Asn Leu Ser Ile Lys Lys Gln Leu Glu Glu Gln Thr
                180                 185                 190

Ser Thr Val Thr Glu Lys Asp Val Gln Pro Lys Thr Gln Ala Thr Pro
                195                 200                 205

His Ala Ser Lys Lys Asn Val Ala Ser Pro Ser Thr Ser Met Pro Gly
            210                 215                 220

Ile Glu Lys Ala Ala Thr Thr Val Ala Val Pro Gln Asp Lys Ser Glu
225                 230                 235                 240

Glu Glu Lys Val Lys Glu Arg Leu Thr Lys Arg Glu Leu Thr Cys Glu
                    245                 250                 255

Asp Leu Lys Asp Asn Gly Tyr Thr Val Asn Phe Glu Asp Ile Ser Ile
                260                 265                 270

Leu Glu Leu Leu Gln Phe Val Ser Lys Ile Ser Gly Thr Asn Phe Val
                275                 280                 285

Phe Asp Ser Asn Asp Leu Gln Phe Asn Val Thr Ile Val Ser His Asp
            290                 295                 300

Pro Thr Ser Val Asp Asp Leu Ser Thr Ile Leu Leu Gln Val Leu Lys
305                 310                 315                 320

Met His Asp Leu Lys Val Val Glu Gln Gly Asn Asn Val Leu Ile Tyr
                    325                 330                 335

Arg Asn Pro His Leu Ser Lys Leu Ser Thr Val Val Thr Asp Ser Ser
                340                 345                 350

Leu Lys Glu Thr Cys Glu Ala Val Val Val Thr Arg Val Phe Arg Leu
                355                 360                 365

Tyr Ser Val Ser Pro Ser Ala Ala Val Asn Ile Ile Gln Pro Leu Leu
            370                 375                 380

Ser His Asp Ala Ile Val Ser Ala Ser Glu Ala Thr Arg His Val Ile
385                 390                 395                 400

Ile Ser Asp Ile Ala Gly Asn Val Asp Lys Val Ser Asp Leu Leu Ala
                    405                 410                 415

Ala Leu Asp Cys Pro Gly Thr Ser Val Asp Met Thr Glu Tyr Glu Val
                420                 425                 430

Lys Tyr Ala Asn Pro Ala Ala Leu Val Ser Tyr Cys Gln Asp Val Leu
                435                 440                 445

Gly Thr Leu Ala Glu Asp Asp Ala Phe Gln Met Phe Ile Gln Pro Gly
            450                 455                 460

Thr Asn Lys Ile Phe Val Ser Ser Pro Arg Leu Ala Asn Lys Ala
465                 470                 475                 480

Glu Gln Leu Leu Lys Ser Leu Asp Val Pro Glu Met Ala His Thr Leu
                    485                 490                 495

Asp Asp Pro Ala Ser Thr Ala Leu Ala Leu Gly Gly Thr Gly Thr Thr
                500                 505                 510

Ser Pro Lys Ser Leu Arg Phe Phe Met Tyr Lys Leu Lys Tyr Gln Asn
                515                 520                 525

Gly Glu Val Ile Ala Asn Ala Leu Gln Asp Ile Gly Tyr Asn Leu Tyr
530                 535                 540
```

```
Val Thr Thr Ala Met Asp Glu Asp Phe Ile Asn Thr Leu Asn Ser Ile
545                 550                 555                 560

Gln Trp Leu Glu Val Asn Asn Ser Ile Val Ile Ile Gly Asn Gln Gly
                565                 570                 575

Asn Val Asp Arg Val Ile Gly Leu Leu Asn Gly Leu Asp Leu Pro Pro
            580                 585                 590

Lys Gln Val Tyr Ile Glu Val Leu Ile Leu Asp Thr Ser Leu Glu Lys
                595                 600                 605

Ser Trp Asp Phe Gly Val Gln Trp Val Ala Leu Gly Asp Glu Gln Ser
    610                 615                 620

Lys Val Ala Tyr Ala Ser Gly Leu Leu Asn Asn Thr Gly Ile Ala Thr
625                 630                 635                 640

Pro Thr Lys Ala Thr Val Pro Pro Gly Thr Pro Asn Pro Gly Ser Ile
                645                 650                 655

Pro Leu Pro Thr Pro Gly Gln Leu Thr Gly Phe Ser Asp Met Leu Asn
            660                 665                 670

Ser Ser Ser Ala Phe Gly Leu Gly Ile Ile Gly Asn Val Leu Ser His
                675                 680                 685

Lys Gly Lys Ser Phe Leu Thr Leu Gly Gly Leu Leu Ser Ala Leu Asp
690                 695                 700

Gln Asp Gly Asp Thr Val Ile Val Leu Asn Pro Arg Ile Met Ala Gln
705                 710                 715                 720

Asp Thr Gln Gln Ala Ser Phe Phe Val Gly Gln Thr Val Pro Tyr Gln
                725                 730                 735

Thr Thr Asn Thr Ile Ile Gln Glu Thr Gly Thr Val Thr Gln Asn Ile
            740                 745                 750

Asp Tyr Glu Asp Ile Gly Val Asn Leu Val Val Thr Ser Thr Val Ala
            755                 760                 765

Pro Asn Asn Val Val Thr Leu Gln Ile Glu Gln Thr Ile Ser Glu Leu
        770                 775                 780

His Ser Ala Ser Gly Ser Leu Thr Pro Val Thr Asp Lys Thr Tyr Ala
785                 790                 795                 800

Ala Thr Arg Leu Gln Ile Pro Asp Gly Cys Phe Leu Val Met Ser Gly
                805                 810                 815

His Ile Arg Asp Lys Thr Thr Lys Val Val Ser Gly Val Pro Leu Leu
            820                 825                 830

Asn Ser Ile Pro Leu Ile Arg Gly Leu Phe Ser Arg Thr Ile Asp Gln
        835                 840                 845

Arg Gln Lys Arg Asn Ile Met Met Phe Ile Lys Pro Lys Val Ile Ser
850                 855                 860

Ser Phe Glu Glu Gly Thr Arg Val Thr Asn Lys Glu Gly Tyr Arg Tyr
865                 870                 875                 880

Asn Trp Glu Ala Asp Glu Gly Ser Met Gln Val Ala Pro Arg His Ala
                885                 890                 895

Pro Glu Cys Gln Gly Pro Pro Ser Leu Gln Ala Glu Ser Asp Phe Lys
            900                 905                 910

Ile Ile Glu Ile Glu Ala Gln
        915

<210> SEQ ID NO 88
<211> LENGTH: 231
<212> TYPE: PRT
<213> ORGANISM: Chlamydia pneumoniae
```

<400> SEQUENCE: 88

```
Met Ser Lys Pro Ser Pro Arg Asn Ala Asn Gln Pro Gln Lys Pro Ser
1               5                   10                  15

Ala Ser Phe Asn Lys Lys Thr Arg Ser Arg Leu Ala Glu Leu Ala Ala
            20                  25                  30

Gln Lys Lys Ala Lys Ala Asp Asp Leu Glu Gln Val His Pro Val Pro
        35                  40                  45

Thr Glu Glu Glu Ile Lys Lys Ala Leu Gly Asn Ile Phe Glu Gly Leu
    50                  55                  60

Ser Asn Gly Leu Asp Leu Gln Gln Ile Leu Gly Leu Ser Asp Tyr Leu
65                  70                  75                  80

Leu Glu Glu Ile Tyr Thr Val Ala Tyr Thr Phe Tyr Ser Gln Gly Lys
                85                  90                  95

Tyr Asn Glu Ala Val Gly Leu Phe Gln Leu Ala Ala Ala Gln Pro
            100                 105                 110

Gln Asn Tyr Lys Tyr Met Leu Gly Leu Ser Ser Cys Tyr His Gln Leu
        115                 120                 125

His Leu Tyr Asn Glu Ala Ala Phe Gly Phe Phe Leu Ala Phe Asp Ala
    130                 135                 140

Gln Pro Asp Asn Pro Ile Pro Pro Tyr Tyr Ile Ala Asp Ser Leu Leu
145                 150                 155                 160

Lys Leu Gln Gln Pro Glu Glu Ser Asn Asn Phe Leu Asp Val Thr Met
                165                 170                 175

Asp Ile Cys Gly Asn Asn Pro Glu Phe Lys Ile Leu Lys Glu Arg Cys
            180                 185                 190

Gln Ile Met Lys Gln Ser Ile Glu Lys Gln Met Ala Gly Glu Thr Lys
        195                 200                 205

Lys Ala Pro Thr Lys Lys Pro Ala Gly Lys Ser Lys Thr Thr Thr Asn
    210                 215                 220

Lys Lys Ser Gly Lys Lys Arg
225                 230
```

<210> SEQ ID NO 89
<211> LENGTH: 289
<212> TYPE: PRT
<213> ORGANISM: Chlamydia pneumoniae

<400> SEQUENCE: 89

```
Met Gly Ile Ser Leu Pro Glu Leu Phe Ser Asn Leu Gly Ser Ala Tyr
1               5                   10                  15

Leu Asp Tyr Ile Phe Gln His Pro Pro Ala Tyr Val Trp Ser Val Phe
            20                  25                  30

Leu Leu Leu Leu Ala Arg Leu Leu Pro Ile Phe Ala Val Ala Pro Phe
        35                  40                  45

Leu Gly Ala Lys Leu Phe Pro Ser Pro Ile Lys Ile Gly Ile Ser Leu
    50                  55                  60

Ser Trp Leu Ala Ile Ile Phe Pro Lys Val Leu Ala Asp Thr Gln Ile
65                  70                  75                  80

Thr Asn Tyr Met Asp Asn Asn Leu Phe Tyr Val Leu Val Lys Glu
                85                  90                  95

Met Ile Ile Gly Ile Val Ile Gly Phe Val Leu Ala Phe Pro Phe Tyr
            100                 105                 110

Ala Ala Gln Ser Ala Gly Ser Phe Ile Thr Asn Gln Gln Gly Ile Gln
        115                 120                 125
```

```
Gly Leu Glu Gly Ala Thr Ser Leu Ile Ser Ile Glu Gln Thr Ser Pro
            130                 135                 140

His Gly Ile Leu Tyr His Tyr Phe Val Thr Ile Ile Phe Trp Leu Val
145                 150                 155                 160

Gly Gly His Arg Ile Val Ile Ser Leu Leu Gln Thr Leu Glu Val
                165                 170                 175

Ile Pro Ile His Ser Phe Phe Pro Ala Glu Met Met Ser Leu Ser Ala
                180                 185                 190

Pro Ile Trp Ile Thr Met Ile Lys Met Cys Gln Leu Cys Leu Val Met
            195                 200                 205

Thr Ile Gln Leu Ser Ala Pro Ala Leu Ala Met Leu Met Ser Asp
210                 215                 220

Leu Phe Leu Gly Ile Ile Asn Arg Met Ala Pro Gln Val Gln Val Ile
225                 230                 235                 240

Tyr Leu Leu Ser Ala Leu Lys Ala Phe Met Gly Leu Leu Phe Leu Thr
                245                 250                 255

Leu Ala Trp Trp Phe Ile Ile Lys Gln Ile Asp Tyr Phe Thr Leu Ala
            260                 265                 270

Trp Phe Lys Glu Val Pro Ile Met Leu Leu Gly Ser Asn Pro Gln Val
        275                 280                 285

Leu

<210> SEQ ID NO 90
<211> LENGTH: 335
<212> TYPE: PRT
<213> ORGANISM: Chlamydia pneumoniae

<400> SEQUENCE: 90

Met Val Arg Arg Ser Ile Ser Phe Cys Leu Phe Phe Leu Met Thr Leu
1               5                   10                  15

Leu Cys Cys Thr Ser Cys Asn Ser Arg Ser Leu Ile Val His Gly Leu
                20                  25                  30

Pro Gly Arg Glu Ala Asn Glu Ile Val Val Leu Leu Val Ser Lys Gly
            35                  40                  45

Val Ala Ala Gln Lys Leu Pro Gln Ala Ala Ala Thr Ala Gly Ala
    50                  55                  60

Ala Thr Glu Gln Met Trp Asp Ile Ala Val Pro Ser Ala Gln Ile Thr
65                  70                  75                  80

Glu Ala Leu Ala Ile Leu Asn Gln Ala Gly Leu Pro Arg Met Lys Gly
                85                  90                  95

Thr Ser Leu Leu Asp Leu Phe Ala Lys Gln Gly Leu Val Pro Ser Glu
            100                 105                 110

Leu Gln Glu Lys Ile Arg Tyr Gln Glu Gly Leu Ser Glu Gln Met Ala
        115                 120                 125

Ser Thr Ile Arg Lys Met Asp Gly Val Val Asp Ala Ser Val Gln Ile
    130                 135                 140

Ser Phe Thr Thr Glu Asn Glu Asp Asn Leu Pro Leu Thr Ala Ser Val
145                 150                 155                 160

Tyr Ile Lys His Arg Gly Val Leu Asp Asn Pro Asn Ser Ile Met Val
                165                 170                 175

Ser Lys Ile Lys Arg Leu Ile Ala Ser Ala Val Pro Gly Leu Val Pro
            180                 185                 190

Glu Asn Val Ser Val Val Ser Asp Arg Ala Ala Tyr Ser Asp Ile Thr
        195                 200                 205
```

```
Ile Asn Gly Pro Trp Gly Leu Thr Glu Glu Ile Asp Tyr Val Ser Val
    210                 215                 220

Trp Gly Ile Ile Leu Ala Lys Ser Ser Leu Thr Lys Phe Arg Leu Ile
225                 230                 235                 240

Phe Tyr Val Leu Ile Leu Ile Leu Phe Val Ile Ser Cys Gly Leu Leu
                245                 250                 255

Trp Val Ile Trp Lys Thr His Thr Leu Ile Met Thr Met Gly Gly Thr
            260                 265                 270

Lys Gly Phe Phe Asn Pro Thr Pro Tyr Thr Lys Asn Ala Leu Glu Ala
                275                 280                 285

Lys Lys Ala Glu Gly Ala Ala Asp Lys Glu Lys Glu Asp Ala
290                 295                 300

Asp Ser Gln Gly Glu Ser Lys Asn Ala Glu Thr Ser Asp Lys Asp Ser
305                 310                 315                 320

Ser Asp Lys Asp Ala Pro Glu Gly Ser Asn Glu Ile Glu Gly Ala
                325                 330                 335

<210> SEQ ID NO 91
<211> LENGTH: 172
<212> TYPE: PRT
<213> ORGANISM: Chlamydia pneumoniae

<400> SEQUENCE: 91

Met Ser His Leu Asn Tyr Leu Leu Glu Lys Ile Ala Ala Ser Ser Lys
1               5                   10                  15

Glu Asp Phe Pro Phe Pro Asp Asp Leu Glu Ser Tyr Leu Glu Gly Tyr
            20                  25                  30

Val Pro Asp Lys Asn Ile Ala Leu Asp Thr Tyr Gln Lys Ile Phe Lys
        35                  40                  45

Ile Ser Ser Glu Asp Leu Glu Lys Val Tyr Lys Glu Gly Tyr His Ala
    50                  55                  60

Tyr Leu Asp Lys Asp Tyr Ala Lys Ser Ile Thr Val Phe Arg Trp Leu
65                  70                  75                  80

Val Phe Phe Asn Pro Phe Val Ser Lys Phe Trp Phe Ser Leu Gly Ala
                85                  90                  95

Ser Leu His Met Ser Glu Gln Tyr Ser Gln Ala Leu His Ala Tyr Gly
            100                 105                 110

Val Thr Ala Val Leu Arg Asp Lys Asp Pro Tyr Pro His Tyr Tyr Ala
        115                 120                 125

Tyr Ile Cys Tyr Thr Leu Thr Asn Glu His Glu Ala Glu Lys Ala
    130                 135                 140

Leu Glu Met Ala Trp Val Arg Ala Gln His Lys Pro Leu Tyr Asn Glu
145                 150                 155                 160

Leu Lys Glu Glu Ile Leu Asp Ile Arg Lys His Lys
                165                 170

<210> SEQ ID NO 92
<211> LENGTH: 389
<212> TYPE: PRT
<213> ORGANISM: Chlamydia pneumoniae

<400> SEQUENCE: 92

Met Lys Lys Leu Leu Lys Ser Ala Leu Leu Ser Ala Ala Phe Ala Gly
1               5                   10                  15

Ser Val Gly Ser Leu Gln Ala Leu Pro Val Gly Asn Pro Ser Asp Pro
            20                  25                  30
```

```
Ser Leu Leu Ile Asp Gly Thr Ile Trp Glu Gly Ala Ala Gly Asp Pro
         35                  40                  45

Cys Asp Pro Cys Ala Thr Trp Cys Asp Ala Ile Ser Leu Arg Ala Gly
 50                  55                  60

Phe Tyr Gly Asp Tyr Val Phe Asp Arg Ile Leu Lys Val Asp Ala Pro
 65                  70                  75                  80

Lys Thr Phe Ser Met Gly Ala Lys Pro Thr Gly Ser Ala Ala Ala Asn
                 85                  90                  95

Tyr Thr Thr Ala Val Asp Arg Pro Asn Pro Ala Tyr Asn Lys His Leu
            100                 105                 110

His Asp Ala Glu Trp Phe Thr Asn Ala Gly Phe Ile Ala Leu Asn Ile
        115                 120                 125

Trp Asp Arg Phe Asp Val Phe Cys Thr Leu Gly Ala Ser Asn Gly Tyr
    130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                165                 170                 175

Asn Gly Val Val Glu Leu Tyr Thr Asp Thr Ser Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Lys Pro Lys Val Glu Glu Leu Asn Val
    210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr His Glu Trp Gln Val Gly Ala
            260                 265                 270

Ser Leu Ser Tyr Arg Leu Asn Ser Leu Val Pro Tyr Ile Gly Val Gln
        275                 280                 285

Trp Ser Arg Ala Thr Phe Asp Ala Asp Asn Ile Arg Ile Ala Gln Pro
    290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
            340                 345                 350

Cys Gly Val Thr Val Gly Ala Thr Leu Val Asp Ala Asp Lys Trp Ser
        355                 360                 365

Leu Thr Ala Glu Ala Arg Leu Ile Asn Glu Arg Ala Ala His Val Ser
    370                 375                 380

Gly Gln Phe Arg Phe
385

<210> SEQ ID NO 93
<211> LENGTH: 426
<212> TYPE: PRT
<213> ORGANISM: Chlamydia pneumoniae

<400> SEQUENCE: 93

Met Thr Leu Ile Phe Val Ile Ile Ile Val Trp Cys Asn Ala Phe Leu
 1               5                  10                  15
```

-continued

```
Ile Lys Leu Cys Val Ile Met Gly Leu Gln Ser Arg Leu Gln His Cys
         20                  25                  30
Ile Glu Val Ser Gln Asn Ser Asn Phe Asp Ser Gln Val Lys Gln Phe
             35                  40                  45
Ile Tyr Ala Cys Gln Asp Lys Thr Leu Arg Gln Ser Val Leu Lys Ile
 50                  55                  60
Phe Arg Tyr His Pro Leu Leu Lys Ile His Asp Ile Ala Arg Ala Val
 65                  70                  75                  80
Tyr Leu Leu Met Ala Leu Glu Glu Gly Glu Asp Leu Gly Leu Ser Phe
                 85                  90                  95
Leu Asn Val Gln Gln Tyr Pro Ser Gly Ala Val Glu Leu Phe Ser Cys
            100                 105                 110
Gly Gly Phe Pro Trp Lys Gly Leu Pro Tyr Pro Ala Glu His Ala Glu
            115                 120                 125
Phe Gly Leu Leu Leu Leu Gln Ile Ala Glu Phe Tyr Glu Glu Ser Gln
            130                 135                 140
Ala Tyr Val Ser Lys Met Ser His Phe Gln Gln Ala Leu Phe Asp His
145                 150                 155                 160
Gln Gly Ser Val Phe Pro Ser Leu Trp Ser Gln Glu Asn Ser Arg Leu
                165                 170                 175
Leu Lys Glu Lys Thr Thr Leu Ser Gln Ser Phe Leu Phe Gln Leu Gly
                180                 185                 190
Met Gln Ile His Pro Glu Tyr Ser Leu Glu Asp Pro Ala Leu Gly Phe
                195                 200                 205
Trp Met Gln Arg Thr Arg Ser Ser Ser Ala Phe Val Ala Ala Ser Gly
210                 215                 220
Cys Gln Ser Ser Leu Gly Ala Tyr Ser Ser Gly Asp Val Gly Val Ile
225                 230                 235                 240
Ala Tyr Gly Pro Cys Ser Gly Asp Ile Ser Asp Cys Tyr Tyr Phe Gly
                245                 250                 255
Cys Cys Gly Ile Ala Lys Glu Phe Val Cys Gln Lys Ser His Gln Thr
            260                 265                 270
Thr Glu Ile Ser Phe Leu Thr Ser Thr Gly Lys Pro His Pro Arg Asn
            275                 280                 285
Thr Gly Phe Ser Tyr Leu Arg Asp Ser Tyr Val His Leu Pro Ile Arg
            290                 295                 300
Cys Lys Ile Thr Ile Ser Asp Lys Gln Tyr Arg Val His Ala Ala Leu
305                 310                 315                 320
Ala Glu Ala Thr Ser Ala Met Thr Phe Ser Ile Phe Cys Lys Gly Lys
                325                 330                 335
Asn Cys Gln Val Val Asp Gly Pro Arg Leu Arg Ser Cys Ser Leu Asp
            340                 345                 350
Ser Tyr Lys Gly Pro Gly Asn Asp Ile Met Ile Leu Gly Glu Asn Asp
            355                 360                 365
Ala Ile Asn Ile Val Ser Ala Ser Pro Tyr Met Glu Ile Phe Ala Leu
 370                 375                 380
Gln Gly Lys Glu Lys Phe Trp Asn Ala Asp Phe Leu Ile Asn Ile Pro
385                 390                 395                 400
Tyr Lys Glu Glu Gly Val Met Leu Ile Phe Glu Lys Lys Val Thr Ser
                405                 410                 415
Glu Lys Gly Arg Phe Phe Thr Lys Met Asn
            420                 425
```

<210> SEQ ID NO 94
<211> LENGTH: 1407
<212> TYPE: PRT
<213> ORGANISM: Chlamydia pneumoniae

<400> SEQUENCE: 94

```
Met Lys Tyr Ser Leu Pro Trp Leu Leu Thr Ser Ser Ala Leu Val Phe
1               5                   10                  15

Ser Leu His Pro Leu Met Ala Ala Asn Thr Asp Leu Ser Ser Ser Asp
            20                  25                  30

Asn Tyr Glu Asn Gly Ser Ser Gly Ser Ala Ala Phe Thr Ala Lys Glu
        35                  40                  45

Thr Ser Asp Ala Ser Gly Thr Thr Tyr Thr Leu Thr Ser Asp Val Ser
    50                  55                  60

Ile Thr Asn Val Ser Ala Ile Thr Pro Ala Asp Lys Ser Cys Phe Thr
65                  70                  75                  80

Asn Thr Gly Gly Ala Leu Ser Phe Val Gly Ala Asp His Ser Leu Val
                85                  90                  95

Leu Gln Thr Ile Ala Leu Thr His Asp Gly Ala Ala Ile Asn Asn Thr
            100                 105                 110

Asn Thr Ala Leu Ser Phe Ser Gly Phe Ser Ser Leu Leu Ile Asp Ser
        115                 120                 125

Ala Pro Ala Thr Gly Thr Ser Gly Gly Lys Gly Ala Ile Cys Val Thr
    130                 135                 140

Asn Thr Glu Gly Gly Thr Ala Thr Phe Thr Asp Asn Ala Ser Val Thr
145                 150                 155                 160

Leu Gln Lys Asn Thr Ser Glu Lys Asp Gly Ala Ala Val Ser Ala Tyr
                165                 170                 175

Ser Ile Asp Leu Ala Lys Thr Thr Ala Ala Leu Leu Asp Gln Asn
            180                 185                 190

Thr Ser Thr Lys Asn Gly Gly Ala Leu Cys Ser Thr Ala Asn Thr Thr
        195                 200                 205

Val Gln Gly Asn Ser Gly Thr Val Thr Phe Ser Ser Asn Thr Ala Thr
    210                 215                 220

Asp Lys Gly Gly Gly Ile Tyr Ser Lys Glu Lys Asp Ser Thr Leu Asp
225                 230                 235                 240

Ala Asn Thr Gly Val Val Thr Phe Lys Ser Asn Thr Ala Lys Thr Gly
                245                 250                 255

Gly Ala Trp Ser Ser Asp Asp Asn Leu Ala Leu Thr Gly Asn Thr Gln
            260                 265                 270

Val Leu Phe Gln Glu Asn Lys Thr Thr Gly Ser Ala Ala Gln Ala Asn
        275                 280                 285

Asn Pro Glu Gly Cys Gly Gly Ala Ile Cys Cys Tyr Leu Ala Thr Ala
    290                 295                 300

Thr Asp Lys Thr Gly Leu Ala Ile Ser Gln Asn Gln Glu Met Ser Phe
305                 310                 315                 320

Thr Ser Asn Thr Thr Thr Ala Asn Gly Gly Ala Ile Tyr Ala Thr Lys
                325                 330                 335

Cys Thr Leu Asp Gly Asn Thr Thr Leu Thr Phe Asp Gln Asn Thr Ala
            340                 345                 350

Thr Ala Gly Cys Gly Gly Ala Ile Tyr Thr Glu Thr Glu Asp Phe Ser
        355                 360                 365

Leu Lys Gly Ser Thr Gly Thr Val Thr Phe Ser Thr Asn Thr Ala Lys
    370                 375                 380
```

```
Thr Gly Gly Ala Leu Tyr Ser Lys Gly Asn Ser Ser Leu Thr Gly Asn
385                 390                 395                 400

Thr Asn Leu Leu Phe Ser Gly Asn Lys Ala Thr Gly Pro Ser Asn Ser
            405                 410                 415

Ser Ala Asn Gln Glu Gly Cys Gly Gly Ala Ile Leu Ala Phe Ile Asp
                420                 425                 430

Ser Gly Ser Val Ser Asp Lys Thr Gly Leu Ser Ile Ala Asn Asn Gln
            435                 440                 445

Glu Val Ser Leu Thr Ser Asn Ala Ala Thr Val Ser Gly Gly Ala Ile
450                 455                 460

Tyr Ala Thr Lys Cys Thr Leu Thr Gly Asn Gly Ser Leu Thr Phe Asp
465                 470                 475                 480

Gly Asn Thr Ala Gly Thr Ser Gly Gly Ala Ile Tyr Thr Glu Thr Glu
                485                 490                 495

Asp Phe Thr Leu Thr Gly Ser Thr Gly Thr Val Thr Phe Ser Thr Asn
                500                 505                 510

Thr Ala Lys Thr Gly Gly Ala Leu Tyr Ser Lys Gly Asn Asn Ser Leu
            515                 520                 525

Ser Gly Asn Thr Asn Leu Leu Phe Ser Gly Asn Lys Ala Thr Gly Pro
            530                 535                 540

Ser Asn Ser Ser Ala Asn Gln Glu Gly Cys Gly Gly Ala Ile Leu Ser
545                 550                 555                 560

Phe Leu Glu Ser Ala Ser Val Ser Thr Lys Lys Gly Leu Trp Ile Glu
                565                 570                 575

Asp Asn Glu Asn Val Ser Leu Ser Gly Asn Thr Ala Thr Val Ser Gly
                580                 585                 590

Gly Ala Ile Tyr Ala Thr Lys Cys Ala Leu His Gly Asn Thr Thr Leu
            595                 600                 605

Thr Phe Asp Gly Asn Thr Ala Glu Thr Ala Gly Gly Ala Ile Tyr Thr
            610                 615                 620

Glu Thr Glu Asp Phe Thr Leu Thr Gly Ser Thr Gly Thr Val Thr Phe
625                 630                 635                 640

Ser Thr Asn Thr Ala Lys Thr Ala Gly Ala Leu His Thr Lys Gly Asn
                645                 650                 655

Thr Ser Phe Thr Lys Asn Lys Ala Leu Val Phe Ser Gly Asn Ser Ala
            660                 665                 670

Thr Ala Thr Ala Thr Thr Thr Asp Gln Glu Gly Cys Gly Gly Ala
            675                 680                 685

Ile Leu Cys Asn Ile Ser Glu Ser Asp Ile Ala Thr Lys Ser Leu Thr
690                 695                 700

Leu Thr Glu Asn Glu Ser Leu Ser Phe Ile Asn Asn Thr Ala Lys Arg
705                 710                 715                 720

Ser Gly Gly Gly Ile Tyr Ala Pro Lys Cys Val Ile Ser Gly Ser Glu
                725                 730                 735

Ser Ile Asn Phe Asp Gly Asn Thr Ala Glu Thr Ser Gly Gly Ala Ile
            740                 745                 750

Tyr Ser Lys Asn Leu Ser Ile Thr Ala Asn Gly Pro Val Ser Phe Thr
            755                 760                 765

Asn Asn Ser Gly Gly Lys Gly Gly Ala Ile Tyr Ile Ala Asp Ser Gly
            770                 775                 780

Glu Leu Ser Leu Glu Ala Ile Asp Gly Asp Ile Thr Phe Ser Gly Asn
785                 790                 795                 800
```

-continued

Arg Ala Thr Glu Gly Thr Ser Thr Pro Asn Ser Ile His Leu Gly Ala
                805                 810                 815

Gly Ala Lys Ile Thr Lys Leu Ala Ala Pro Gly His Thr Ile Tyr
            820                 825                 830

Phe Tyr Asp Pro Ile Thr Met Glu Ala Pro Ala Ser Gly Gly Thr Ile
            835                 840                 845

Glu Glu Leu Val Ile Asn Pro Val Val Lys Ala Ile Val Pro Pro Pro
850                 855                 860

Gln Pro Lys Asn Gly Pro Ile Ala Ser Val Pro Val Pro Val Ala
865                 870                 875                 880

Pro Ala Asn Pro Asn Thr Gly Thr Ile Val Phe Ser Ser Gly Lys Leu
                885                 890                 895

Pro Ser Gln Asp Ala Ser Ile Pro Ala Asn Thr Thr Thr Ile Leu Asn
            900                 905                 910

Gln Lys Ile Asn Leu Ala Gly Gly Asn Val Val Leu Lys Glu Gly Ala
            915                 920                 925

Thr Leu Gln Val Tyr Ser Phe Thr Gln Gln Pro Asp Ser Thr Val Phe
930                 935                 940

Met Asp Ala Gly Thr Thr Leu Glu Thr Thr Thr Thr Asn Asn Thr Asp
945                 950                 955                 960

Gly Ser Ile Asp Leu Lys Asn Leu Ser Val Asn Leu Asp Ala Leu Asp
                965                 970                 975

Gly Lys Arg Met Ile Thr Ile Ala Val Asn Ser Thr Ser Gly Gly Leu
            980                 985                 990

Lys Ile Ser Gly Asp Leu Lys Phe His Asn Asn Glu Gly Ser Phe Tyr
            995                 1000                1005

Asp Asn Pro Gly Leu Lys Ala Asn Leu Asn Leu Pro Phe Leu Asp Leu
    1010                1015                1020

Ser Ser Thr Ser Gly Thr Val Asn Leu Asp Asp Phe Asn Pro Ile Pro
1025                1030                1035                1040

Ser Ser Met Ala Ala Pro Asp Tyr Gly Tyr Gln Gly Ser Trp Thr Leu
            1045                1050                1055

Val Pro Lys Val Gly Ala Gly Lys Val Thr Leu Val Ala Glu Trp
            1060                1065                1070

Gln Ala Leu Gly Tyr Thr Pro Lys Pro Glu Leu Arg Ala Thr Leu Val
            1075                1080                1085

Pro Asn Ser Leu Trp Asn Ala Tyr Val Asn Ile His Ser Ile Gln Gln
    1090                1095                1100

Glu Ile Ala Thr Ala Met Ser Asp Ala Pro Ser His Pro Gly Ile Trp
1105                1110                1115                1120

Ile Gly Gly Ile Gly Asn Ala Phe His Gln Asp Lys Gln Lys Glu Asn
                1125                1130                1135

Ala Gly Phe Arg Leu Ile Ser Arg Gly Tyr Ile Val Gly Gly Ser Met
            1140                1145                1150

Thr Thr Pro Gln Glu Tyr Thr Phe Ala Val Ala Phe Ser Gln Leu Phe
        1155                1160                1165

Gly Lys Ser Lys Asp Tyr Val Val Ser Asp Ile Lys Ser Gln Val Tyr
            1170                1175                1180

Ala Gly Ser Leu Cys Ala Gln Ser Ser Tyr Val Ile Pro Leu His Ser
1185                1190                1195                1200

Ser Leu Arg Arg His Val Leu Ser Lys Val Leu Pro Glu Leu Pro Gly
            1205                1210                1215

Glu Thr Pro Leu Val Leu His Gly Gln Val Ser Tyr Gly Arg Asn His

-continued

```
                1220              1225              1230
His Asn Met Thr Thr Lys Leu Ala Asn Asn Thr Gln Gly Lys Ser Asp
        1235              1240              1245

Trp Asp Ser His Ser Phe Ala Val Glu Val Gly Gly Ser Leu Pro Val
    1250              1255              1260

Asp Leu Asn Tyr Arg Tyr Leu Thr Ser Tyr Ser Pro Tyr Val Lys Leu
1265              1270              1275              1280

Gln Val Val Ser Val Asn Gln Lys Gly Phe Gln Glu Val Ala Ala Asp
                1285              1290              1295

Pro Arg Ile Phe Asp Ala Ser His Leu Val Asn Val Ser Ile Pro Met
        1300              1305              1310

Gly Leu Thr Phe Lys His Glu Ser Ala Lys Pro Pro Ser Ala Leu Leu
    1315              1320              1325

Leu Thr Leu Gly Tyr Ala Val Asp Ala Tyr Arg Asp His Pro His Cys
1330              1335              1340

Leu Thr Ser Leu Thr Asn Gly Thr Ser Trp Ser Thr Phe Ala Thr Asn
1345              1350              1355              1360

Leu Ser Arg Gln Ala Phe Phe Ala Glu Ala Ser Gly His Leu Lys Leu
            1365              1370              1375

Leu His Gly Leu Asp Cys Phe Ala Ser Gly Ser Cys Glu Leu Arg Ser
        1380              1385              1390

Ser Ser Arg Ser Tyr Asn Ala Asn Cys Gly Thr Arg Tyr Ser Phe
            1395              1400              1405

<210> SEQ ID NO 95
<211> LENGTH: 1609
<212> TYPE: PRT
<213> ORGANISM: Chlamydia pneumoniae

<400> SEQUENCE: 95

Met Val Ala Lys Lys Thr Val Arg Ser Tyr Arg Ser Ser Phe Ser His
1               5                   10                  15

Ser Val Ile Val Ala Ile Leu Ser Ala Gly Ile Ala Phe Glu Ala His
                20                  25                  30

Ser Leu His Ser Ser Glu Leu Asp Leu Gly Val Phe Asn Lys Gln Phe
            35                  40                  45

Glu Glu His Ser Ala His Val Glu Glu Ala Gln Thr Ser Val Leu Lys
        50                  55                  60

Gly Ser Asp Pro Val Asn Pro Ser Gln Lys Glu Ser Glu Lys Val Leu
65                  70                  75                  80

Tyr Thr Gln Val Pro Leu Thr Gln Gly Ser Ser Gly Glu Ser Leu Asp
                85                  90                  95

Leu Ala Asp Ala Asn Phe Leu Glu His Phe Gln His Leu Phe Glu Glu
                100                 105                 110

Thr Thr Val Phe Gly Ile Asp Gln Lys Leu Val Trp Ser Asp Leu Asp
            115                 120                 125

Thr Arg Asn Phe Ser Gln Pro Thr Gln Glu Pro Asp Thr Ser Asn Ala
        130                 135                 140

Val Ser Glu Lys Ile Ser Ser Asp Thr Lys Glu Asn Arg Lys Asp Leu
145                 150                 155                 160

Glu Thr Glu Asp Pro Ser Lys Lys Ser Gly Leu Lys Glu Val Ser Ser
                165                 170                 175

Asp Leu Pro Lys Ser Pro Glu Thr Ala Val Ala Ala Ile Ser Glu Asp
                180                 185                 190
```

```
Leu Glu Ile Ser Glu Asn Ile Ser Ala Arg Asp Pro Leu Gln Gly Leu
            195                 200                 205

Ala Phe Phe Tyr Lys Asn Thr Ser Ser Gln Ser Ile Ser Glu Lys Asp
    210                 215                 220

Ser Ser Phe Gln Gly Ile Ile Phe Ser Gly Ser Ala Asn Ser Gly
225                 230                 235                 240

Leu Gly Phe Glu Asn Leu Lys Ala Pro Lys Ser Gly Ala Ala Val Tyr
                245                 250                 255

Ser Asp Arg Asp Ile Val Phe Glu Asn Leu Val Lys Gly Leu Ser Phe
            260                 265                 270

Ile Ser Cys Glu Ser Leu Glu Asp Gly Ser Ala Ala Gly Val Asn Ile
        275                 280                 285

Val Val Thr His Cys Gly Asp Val Thr Leu Thr Asp Cys Ala Thr Gly
    290                 295                 300

Leu Asp Leu Glu Ala Leu Arg Leu Val Lys Asp Phe Ser Arg Gly Gly
305                 310                 315                 320

Ala Val Phe Thr Ala Arg Asn His Glu Val Gln Asn Asn Leu Ala Gly
                325                 330                 335

Gly Ile Leu Ser Val Val Gly Asn Lys Gly Ala Ile Val Val Glu Lys
            340                 345                 350

Asn Ser Ala Glu Lys Ser Asn Gly Gly Ala Phe Ala Cys Gly Ser Phe
        355                 360                 365

Val Tyr Ser Asn Asn Glu Asn Thr Ala Leu Trp Lys Glu Asn Gln Ala
    370                 375                 380

Leu Ser Gly Gly Ala Ile Ser Ser Ala Ser Asp Ile Asp Ile Gln Gly
385                 390                 395                 400

Asn Cys Ser Ala Ile Glu Phe Ser Gly Asn Gln Ser Leu Ile Ala Leu
                405                 410                 415

Gly Glu His Ile Gly Leu Thr Asp Phe Val Gly Gly Ala Leu Ala
            420                 425                 430

Ala Gln Gly Thr Leu Thr Leu Arg Asn Asn Ala Val Val Gln Cys Val
        435                 440                 445

Lys Asn Thr Ser Lys Thr His Gly Gly Ala Ile Leu Ala Gly Thr Val
    450                 455                 460

Asp Leu Asn Glu Thr Ile Ser Glu Val Ala Phe Lys Gln Asn Thr Ala
465                 470                 475                 480

Ala Leu Thr Gly Gly Ala Leu Ser Ala Asn Asp Lys Val Ile Ile Ala
                485                 490                 495

Asn Asn Phe Gly Glu Ile Leu Phe Glu Gln Asn Glu Val Arg Asn His
            500                 505                 510

Gly Gly Ala Ile Tyr Cys Gly Cys Arg Ser Asn Pro Lys Leu Glu Gln
        515                 520                 525

Lys Asp Ser Gly Glu Asn Ile Asn Ile Gly Asn Ser Gly Ala Ile
    530                 535                 540

Thr Phe Leu Lys Asn Lys Ala Ser Val Leu Glu Val Met Thr Gln Ala
545                 550                 555                 560

Glu Asp Tyr Ala Gly Gly Ala Leu Trp Gly His Asn Val Leu Leu
                565                 570                 575

Asp Ser Asn Ser Gly Asn Ile Gln Phe Ile Gly Asn Ile Gly Gly Ser
            580                 585                 590

Thr Phe Trp Ile Gly Glu Tyr Val Gly Gly Gly Ala Ile Leu Ser Thr
        595                 600                 605

Asp Arg Val Thr Ile Ser Asn Asn Ser Gly Asp Val Val Phe Lys Gly
```

-continued

```
            610                 615                 620
Asn Lys Gly Gln Cys Leu Ala Gln Lys Tyr Val Ala Pro Gln Glu Thr
625                 630                 635                 640

Ala Pro Val Glu Ser Asp Ala Ser Ser Thr Asn Lys Asp Glu Lys Ser
                    645                 650                 655

Leu Asn Ala Cys Ser His Gly Asp His Tyr Pro Pro Lys Thr Val Glu
                    660                 665                 670

Glu Val Pro Pro Ser Leu Leu Glu Glu His Pro Val Val Ser Ser
                675                 680                 685

Thr Asp Ile Arg Gly Gly Ala Ile Leu Ala Gln His Ile Phe Ile
690                 695                 700

Thr Asp Asn Thr Gly Asn Leu Arg Phe Ser Gly Asn Leu Gly Gly
705                 710                 715                 720

Glu Glu Ser Ser Thr Val Gly Asp Leu Ala Ile Val Gly Gly Ala
                725                 730                 735

Leu Leu Ser Thr Asn Glu Val Asn Val Cys Ser Asn Gln Asn Val Val
                740                 745                 750

Phe Ser Asp Asn Val Thr Ser Asn Gly Cys Asp Ser Gly Gly Ala Ile
755                 760                 765

Leu Ala Lys Lys Val Asp Ile Ser Ala Asn His Ser Val Glu Phe Val
770                 775                 780

Ser Asn Gly Ser Gly Lys Phe Gly Gly Ala Val Cys Ala Leu Asn Glu
785                 790                 795                 800

Ser Val Asn Ile Thr Asp Asn Gly Ser Ala Val Ser Phe Ser Lys Asn
                805                 810                 815

Arg Thr Arg Leu Gly Gly Ala Gly Val Ala Ala Pro Gln Gly Ser Val
                820                 825                 830

Thr Ile Cys Gly Asn Gln Gly Asn Ile Ala Phe Lys Glu Asn Phe Val
                835                 840                 845

Phe Gly Ser Glu Asn Gln Arg Ser Gly Gly Gly Ala Ile Ile Ala Asn
850                 855                 860

Ser Ser Val Asn Ile Gln Asp Asn Ala Gly Asp Ile Leu Phe Val Ser
865                 870                 875                 880

Asn Ser Thr Gly Ser Tyr Gly Gly Ala Ile Phe Val Gly Ser Leu Val
                885                 890                 895

Ala Ser Glu Gly Ser Asn Pro Arg Thr Leu Thr Ile Thr Gly Asn Ser
                900                 905                 910

Gly Asp Ile Leu Phe Ala Lys Asn Ser Thr Gln Thr Ala Ala Ser Leu
                915                 920                 925

Ser Glu Lys Asp Ser Phe Gly Gly Gly Ala Ile Tyr Thr Gln Asn Leu
930                 935                 940

Lys Ile Val Lys Asn Ala Gly Asn Val Ser Phe Tyr Gly Asn Arg Ala
945                 950                 955                 960

Pro Ser Gly Ala Gly Val Gln Ile Ala Asp Gly Gly Thr Val Cys Leu
                965                 970                 975

Glu Ala Phe Gly Gly Asp Ile Leu Phe Glu Gly Asn Ile Asn Phe Asp
                980                 985                 990

Gly Ser Phe Asn Ala Ile His Leu Cys Gly Asn Asp Ser Lys Ile Val
                995                 1000                1005

Glu Leu Ser Ala Val Gln Asp Lys Asn Ile Ile Phe Gln Asp Ala Ile
                1010                1015                1020

Thr Tyr Glu Glu Asn Thr Ile Arg Gly Leu Pro Asp Lys Asp Val Ser
1025                1030                1035                1040
```

```
Pro Leu Ser Ala Pro Ser Leu Ile Phe Asn Ser Lys Pro Gln Asp Asp
            1045                1050                1055

Ser Ala Gln His His Glu Gly Thr Ile Arg Phe Ser Arg Gly Val Ser
            1060                1065                1070

Lys Ile Pro Gln Ile Ala Ala Ile Gln Glu Gly Thr Leu Ala Leu Ser
            1075                1080                1085

Gln Asn Ala Glu Leu Trp Leu Ala Gly Leu Lys Gln Glu Thr Gly Ser
            1090                1095                1100

Ser Ile Val Leu Ser Ala Gly Ser Ile Leu Arg Ile Phe Asp Ser Gln
1105                1110                1115                1120

Val Asp Ser Ser Ala Pro Leu Pro Thr Glu Asn Lys Glu Glu Thr Leu
            1125                1130                1135

Val Ser Ala Gly Val Gln Ile Asn Met Ser Ser Pro Thr Pro Asn Lys
            1140                1145                1150

Asp Lys Ala Val Asp Thr Pro Val Leu Ala Asp Ile Ile Ser Ile Thr
            1155                1160                1165

Val Asp Leu Ser Ser Phe Val Pro Glu Gln Asp Gly Thr Leu Pro Leu
            1170                1175                1180

Pro Pro Glu Ile Ile Ile Pro Lys Gly Thr Lys Leu His Ser Asn Ala
1185                1190                1195                1200

Ile Asp Leu Lys Ile Ile Asp Pro Thr Asn Val Gly Tyr Glu Asn His
            1205                1210                1215

Ala Leu Leu Ser Ser His Lys Asp Ile Pro Leu Ile Ser Leu Lys Thr
            1220                1225                1230

Ala Glu Gly Met Thr Gly Thr Pro Thr Ala Asp Ala Ser Leu Ser Asn
            1235                1240                1245

Ile Lys Ile Asp Val Ser Leu Pro Ser Ile Thr Pro Ala Thr Tyr Gly
            1250                1255                1260

His Thr Gly Val Trp Ser Glu Ser Lys Met Glu Asp Gly Arg Leu Val
1265                1270                1275                1280

Val Gly Trp Gln Pro Thr Gly Tyr Lys Leu Asn Pro Glu Lys Gln Gly
            1285                1290                1295

Ala Leu Val Leu Asn Asn Leu Trp Ser His Tyr Thr Asp Leu Arg Ala
            1300                1305                1310

Leu Lys Gln Glu Ile Phe Ala His His Thr Ile Ala Gln Arg Met Glu
            1315                1320                1325

Leu Asp Phe Ser Thr Asn Val Trp Gly Ser Gly Leu Gly Val Val Glu
            1330                1335                1340

Asp Cys Gln Asn Ile Gly Glu Phe Asp Gly Phe Lys His His Leu Thr
1345                1350                1355                1360

Gly Tyr Ala Leu Gly Leu Asp Thr Gln Leu Val Glu Asp Phe Leu Ile
            1365                1370                1375

Gly Gly Cys Phe Ser Gln Phe Phe Gly Lys Thr Glu Ser Gln Ser Tyr
            1380                1385                1390

Lys Ala Lys Asn Asp Val Lys Ser Tyr Met Gly Ala Ala Tyr Ala Gly
            1395                1400                1405

Ile Leu Ala Gly Pro Trp Leu Ile Lys Gly Ala Phe Val Tyr Gly Asn
            1410                1415                1420

Ile Asn Asn Asp Leu Thr Thr Asp Tyr Gly Thr Leu Gly Ile Ser Thr
1425                1430                1435                1440

Gly Ser Trp Ile Gly Lys Gly Phe Ile Ala Gly Thr Ser Ile Asp Tyr
            1445                1450                1455
```

```
Arg Tyr Ile Val Asn Pro Arg Phe Ile Ser Ala Ile Val Ser Thr
            1460                1465                1470

Val Val Pro Phe Val Glu Ala Glu Tyr Val Arg Ile Asp Leu Pro Glu
        1475                1480                1485

Ile Ser Glu Gln Gly Lys Glu Val Arg Thr Phe Gln Lys Thr Arg Phe
    1490                1495                1500

Glu Asn Val Ala Ile Pro Phe Gly Phe Ala Leu Glu His Ala Tyr Ser
1505                1510                1515                1520

Arg Gly Ser Arg Ala Glu Val Asn Ser Val Gln Leu Ala Tyr Val Phe
                1525                1530                1535

Asp Val Tyr Arg Lys Gly Pro Val Ser Leu Ile Thr Leu Lys Asp Ala
            1540                1545                1550

Ala Tyr Ser Trp Lys Ser Tyr Gly Val Asp Ile Pro Cys Lys Ala Trp
        1555                1560                1565

Lys Ala Arg Leu Ser Asn Asn Thr Glu Trp Asn Ser Tyr Leu Ser Thr
    1570                1575                1580

Tyr Leu Ala Phe Asn Tyr Glu Trp Arg Glu Asp Leu Ile Ala Tyr Asp
1585                1590                1595                1600

Phe Asn Gly Gly Ile Arg Ile Ile Phe
                1605

<210> SEQ ID NO 96
<211> LENGTH: 651
<212> TYPE: PRT
<213> ORGANISM: Chlamydia pneumoniae

<400> SEQUENCE: 96

Met Val Asn Pro Ile Gly Pro Gly Pro Ile Asp Glu Thr Glu Arg Thr
1               5                   10                  15

Pro Pro Ala Asp Leu Ser Ala Gln Gly Leu Glu Ala Ser Ala Ala Asn
            20                  25                  30

Lys Ser Ala Glu Ala Gln Arg Ile Ala Gly Ala Glu Ala Lys Pro Lys
        35                  40                  45

Glu Ser Lys Thr Asp Ser Val Glu Arg Trp Ser Ile Leu Arg Ser Ala
    50                  55                  60

Val Asn Ala Leu Met Ser Leu Ala Asp Lys Leu Gly Ile Ala Ser Ser
65                  70                  75                  80

Asn Ser Ser Ser Thr Ser Arg Ser Ala Asp Val Asp Ser Thr Thr
                85                  90                  95

Ala Thr Ala Pro Thr Pro Pro Pro Thr Phe Asp Asp Tyr Lys Thr
            100                 105                 110

Gln Ala Gln Thr Ala Tyr Asp Thr Ile Phe Thr Ser Thr Ser Leu Ala
        115                 120                 125

Asp Ile Gln Ala Ala Leu Val Ser Leu Gln Asp Ala Val Thr Asn Ile
130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Leu Leu Gln Ser Val
        195                 200                 205

Ala Asn Asn Asn Lys Ala Ala Glu Leu Leu Lys Glu Met Gln Asp Asn
210                 215                 220
```

-continued

```
Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
            245                 250                 255

Arg Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
            275                 280                 285

Ile Ala Thr Ala Lys Thr Gln Ile Ala Glu Ala Gln Lys Lys Phe Pro
            290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
            325                 330                 335

Pro Gly Thr Thr Val Gly Gly Ser Lys Gln Gln Gly Ser Ser Ile Gly
            340                 345                 350

Ser Ile Arg Val Ser Met Leu Leu Asp Asp Ala Glu Asn Glu Thr Ala
            355                 360                 365

Ser Ile Leu Met Ser Gly Phe Arg Gln Met Ile His Met Phe Asn Thr
370                 375                 380

Glu Asn Pro Asp Ser Gln Ala Ala Gln Gln Glu Leu Ala Ala Gln Ala
385                 390                 395                 400

Arg Ala Ala Lys Ala Ala Gly Asp Asp Ser Ala Ala Ala Leu Ala
            405                 410                 415

Asp Ala Gln Lys Ala Leu Glu Ala Ala Leu Gly Lys Ala Gly Gln Gln
            420                 425                 430

Gln Gly Ile Leu Asn Ala Leu Gly Gln Ile Ala Ser Ala Ala Val Val
            435                 440                 445

Ser Ala Gly Val Pro Pro Ala Ala Ala Ser Ser Ile Gly Ser Ser Val
            450                 455                 460

Lys Gln Leu Tyr Lys Thr Ser Lys Ser Thr Gly Ser Asp Tyr Lys Thr
465                 470                 475                 480

Gln Ile Ser Ala Gly Tyr Asp Ala Tyr Lys Ser Ile Asn Asp Ala Tyr
            485                 490                 495

Gly Arg Ala Arg Asn Asp Ala Thr Arg Asp Val Ile Asn Asn Val Ser
            500                 505                 510

Thr Pro Ala Leu Thr Arg Ser Val Pro Arg Ala Arg Thr Glu Ala Arg
            515                 520                 525

Gly Pro Glu Lys Thr Asp Gln Ala Leu Ala Arg Val Ile Ser Gly Asn
530                 535                 540

Ser Arg Thr Leu Gly Asp Val Tyr Ser Gln Val Ser Ala Leu Gln Ser
545                 550                 555                 560

Val Met Gln Ile Ile Gln Ser Asn Pro Gln Ala Asn Asn Glu Glu Ile
            565                 570                 575

Arg Gln Lys Leu Thr Ser Ala Val Thr Lys Pro Pro Gln Phe Gly Tyr
            580                 585                 590

Pro Tyr Val Gln Leu Ser Asn Asp Ser Thr Gln Lys Phe Ile Ala Lys
            595                 600                 605

Leu Glu Ser Leu Phe Ala Glu Gly Ser Arg Thr Ala Ala Glu Ile Lys
            610                 615                 620

Ala Leu Ser Phe Glu Thr Asn Ser Leu Phe Ile Gln Gln Val Leu Val
625                 630                 635                 640
```

Asn Ile Gly Ser Leu Tyr Ser Gly Tyr Leu Gln
            645                 650

<210> SEQ ID NO 97
<211> LENGTH: 390
<212> TYPE: PRT
<213> ORGANISM: Chlamydia pneumoniae

<400> SEQUENCE: 97

Met Ser Ser Pro Val Asn Asn Thr Pro Ser Ala Pro Asn Ile Pro Ile
1               5                   10                  15

Pro Ala Pro Thr Thr Pro Gly Ile Pro Thr Thr Lys Pro Arg Ser Ser
            20                  25                  30

Phe Ile Glu Lys Val Ile Ile Val Ala Lys Tyr Ile Leu Phe Ala Ile
        35                  40                  45

Ala Ala Thr Ser Gly Ala Leu Gly Thr Ile Leu Gly Leu Ser Gly Ala
    50                  55                  60

Leu Thr Pro Gly Ile Gly Ile Ala Leu Leu Val Ile Phe Phe Val Ser
65                  70                  75                  80

Met Val Leu Leu Gly Leu Ile Leu Lys Asp Ser Ile Ser Gly Gly Glu
                85                  90                  95

Glu Arg Arg Leu Arg Glu Glu Val Ser Arg Phe Thr Ser Glu Asn Gln
            100                 105                 110

Arg Leu Thr Val Ile Thr Thr Thr Leu Glu Thr Glu Val Lys Asp Leu
        115                 120                 125

Lys Ala Ala Lys Asp Gln Leu Thr Leu Glu Ile Glu Ala Phe Arg Asn
    130                 135                 140

Glu Asn Gly Asn Leu Lys Thr Thr Ala Glu Asp Leu Glu Glu Gln Val
145                 150                 155                 160

Ser Lys Leu Ser Glu Gln Leu Glu Ala Leu Glu Arg Ile Asn Gln Leu
                165                 170                 175

Ile Gln Ala Asn Ala Gly Asp Ala Gln Glu Ile Ser Ser Glu Leu Lys
            180                 185                 190

Lys Leu Ile Ser Gly Trp Asp Ser Lys Val Val Glu Gln Ile Asn Thr
        195                 200                 205

Ser Ile Gln Ala Leu Lys Val Leu Leu Gly Gln Glu Trp Val Gln Glu
    210                 215                 220

Ala Gln Thr His Val Lys Ala Met Gln Glu Gln Ile Gln Ala Leu Gln
225                 230                 235                 240

Ala Glu Ile Leu Gly Met His Asn Gln Ser Thr Ala Leu Gln Lys Ser
                245                 250                 255

Val Glu Asn Leu Leu Val Gln Asp Gln Ala Leu Thr Arg Val Val Gly
            260                 265                 270

Glu Leu Leu Glu Ser Glu Asn Lys Leu Ser Gln Ala Cys Ser Ala Leu
        275                 280                 285

Arg Gln Glu Ile Glu Lys Leu Ala Gln His Glu Thr Ser Leu Gln Gln
    290                 295                 300

Arg Ile Asp Ala Met Leu Ala Gln Glu Gln Asn Leu Ala Glu Gln Val
305                 310                 315                 320

Thr Ala Leu Glu Lys Met Lys Gln Glu Ala Gln Lys Ala Glu Ser Glu
                325                 330                 335

Phe Ile Ala Cys Val Arg Asp Arg Thr Phe Gly Arg Arg Glu Thr Pro
            340                 345                 350

Pro Pro Thr Thr Pro Val Val Glu Gly Asp Glu Ser Gln Glu Glu Asp
        355                 360                 365

Glu Gly Gly Thr Pro Pro Val Ser Gln Pro Ser Ser Pro Val Asp Arg
            370                 375                 380

Ala Thr Gly Asp Gly Gln
385                 390

<210> SEQ ID NO 98
<211> LENGTH: 922
<212> TYPE: PRT
<213> ORGANISM: Chlamydia pneumoniae

<400> SEQUENCE: 98

Met Arg Phe Ser Leu Cys Gly Phe Pro Leu Val Phe Ser Phe Thr Leu
1               5                   10                  15

Leu Ser Val Phe Asp Thr Ser Leu Ser Ala Thr Thr Ile Ser Leu Thr
            20                  25                  30

Pro Glu Asp Ser Phe His Gly Asp Ser Gln Asn Ala Glu Arg Ser Tyr
        35                  40                  45

Asn Val Gln Ala Gly Asp Val Tyr Ser Leu Thr Gly Asp Val Ser Ile
    50                  55                  60

Ser Asn Val Asp Asn Ser Ala Leu Asn Lys Ala Cys Phe Asn Val Thr
65                  70                  75                  80

Ser Gly Ser Val Thr Phe Ala Gly Asn His His Gly Leu Tyr Phe Asn
                85                  90                  95

Asn Ile Ser Ser Gly Thr Thr Lys Glu Gly Ala Val Leu Cys Cys Gln
            100                 105                 110

Asp Pro Gln Ala Thr Ala Arg Phe Ser Gly Phe Ser Thr Leu Ser Phe
        115                 120                 125

Ile Gln Ser Pro Gly Asp Ile Lys Glu Gln Gly Cys Leu Tyr Ser Lys
    130                 135                 140

Asn Ala Leu Met Leu Leu Asn Asn Tyr Val Val Arg Phe Glu Gln Asn
145                 150                 155                 160

Gln Ser Lys Thr Lys Gly Gly Ala Ile Ser Gly Ala Asn Val Thr Ile
                165                 170                 175

Val Gly Asn Tyr Asp Ser Val Ser Phe Tyr Gln Asn Ala Ala Thr Phe
            180                 185                 190

Gly Gly Ala Ile His Ser Ser Gly Pro Leu Gln Ile Ala Val Asn Gln
        195                 200                 205

Ala Glu Ile Arg Phe Ala Gln Asn Thr Ala Lys Asn Gly Ser Gly Gly
    210                 215                 220

Ala Leu Tyr Ser Asp Gly Asp Ile Asp Ile Asp Gln Asn Ala Tyr Val
225                 230                 235                 240

Leu Phe Arg Glu Asn Glu Ala Leu Thr Thr Ala Ile Gly Lys Gly Gly
                245                 250                 255

Ala Val Cys Cys Leu Pro Thr Ser Gly Ser Thr Pro Val Pro Ile
            260                 265                 270

Val Thr Phe Ser Asp Asn Lys Gln Leu Val Phe Glu Arg Asn His Ser
        275                 280                 285

Ile Met Gly Gly Gly Ala Ile Tyr Ala Arg Lys Leu Ser Ile Ser Ser
    290                 295                 300

Gly Gly Pro Thr Leu Phe Ile Asn Asn Ile Ser Tyr Ala Asn Ser Gln
305                 310                 315                 320

Asn Leu Gly Gly Ala Ile Ala Ile Asp Thr Gly Gly Glu Ile Ser Leu
                325                 330                 335

Ser Ala Glu Lys Gly Thr Ile Thr Phe Gln Gly Asn Arg Thr Ser Leu

-continued

```
                340                 345                 350
Pro Phe Leu Asn Gly Ile His Leu Leu Gln Asn Ala Lys Phe Leu Lys
            355                 360                 365
Leu Gln Ala Arg Asn Gly Tyr Ser Ile Glu Phe Tyr Asp Pro Ile Thr
370                 375                 380
Ser Glu Ala Asp Gly Ser Thr Gln Leu Asn Ile Asn Gly Asp Pro Lys
385                 390                 395                 400
Asn Lys Glu Tyr Thr Gly Thr Ile Leu Phe Ser Gly Glu Lys Ser Leu
                405                 410                 415
Ala Asn Asp Pro Arg Asp Phe Lys Ser Thr Ile Pro Gln Asn Val Asn
            420                 425                 430
Leu Ser Ala Gly Tyr Leu Val Ile Lys Glu Gly Ala Glu Val Thr Val
            435                 440                 445
Ser Lys Phe Thr Gln Ser Pro Gly Ser His Leu Val Leu Asp Leu Gly
            450                 455                 460
Thr Lys Leu Ile Ala Ser Lys Glu Asp Ile Ala Ile Thr Gly Leu Ala
465                 470                 475                 480
Ile Asp Ile Asp Ser Leu Ser Ser Ser Thr Ala Ala Val Ile Lys
                485                 490                 495
Ala Asn Thr Ala Asn Lys Gln Ile Ser Val Thr Asp Ser Ile Glu Leu
            500                 505                 510
Ile Ser Pro Thr Gly Asn Ala Tyr Glu Asp Leu Arg Met Arg Asn Ser
            515                 520                 525
Gln Thr Phe Pro Leu Leu Ser Leu Glu Pro Gly Ala Gly Gly Ser Val
            530                 535                 540
Thr Val Thr Ala Gly Asp Phe Leu Pro Val Ser Pro His Tyr Gly Phe
545                 550                 555                 560
Gln Gly Asn Trp Lys Leu Ala Trp Thr Gly Thr Gly Asn Lys Val Gly
                565                 570                 575
Glu Phe Phe Trp Asp Lys Ile Asn Tyr Lys Pro Arg Pro Glu Lys Glu
            580                 585                 590
Gly Asn Leu Val Pro Asn Ile Leu Trp Gly Asn Ala Val Asp Val Arg
            595                 600                 605
Ser Leu Met Gln Val Gln Glu Thr His Ala Ser Ser Leu Gln Thr Asp
            610                 615                 620
Arg Gly Leu Trp Ile Asp Gly Ile Gly Asn Phe Phe His Val Ser Ala
625                 630                 635                 640
Ser Glu Asp Asn Ile Arg Tyr Arg His Asn Ser Gly Gly Tyr Val Leu
                645                 650                 655
Ser Val Asn Asn Glu Ile Thr Pro Lys His Tyr Thr Ser Met Ala Phe
            660                 665                 670
Ser Gln Leu Phe Ser Arg Asp Lys Asp Tyr Ala Val Ser Asn Asn Glu
            675                 680                 685
Tyr Arg Met Tyr Leu Gly Ser Tyr Leu Tyr Gln Tyr Thr Thr Ser Leu
            690                 695                 700
Gly Asn Ile Phe Arg Tyr Ala Ser Arg Asn Pro Asn Val Asn Val Gly
705                 710                 715                 720
Ile Leu Ser Arg Arg Phe Leu Gln Asn Pro Leu Met Ile Phe His Phe
                725                 730                 735
Leu Cys Ala Tyr Gly His Ala Thr Asn Asp Met Lys Thr Asp Tyr Ala
            740                 745                 750
Asn Phe Pro Met Val Lys Asn Ser Trp Arg Asn Asn Cys Trp Ala Ile
            755                 760                 765
```

```
Glu Cys Gly Gly Ser Met Pro Leu Leu Val Phe Glu Asn Gly Arg Leu
    770                 775                 780

Phe Gln Gly Ala Ile Pro Phe Met Lys Leu Gln Leu Val Tyr Ala Tyr
785                 790                 795                 800

Gln Gly Asp Phe Lys Glu Thr Thr Ala Asp Gly Arg Arg Phe Ser Asn
                805                 810                 815

Gly Ser Leu Thr Ser Ile Ser Val Pro Leu Gly Ile Arg Phe Glu Lys
            820                 825                 830

Leu Ala Leu Ser Gln Asp Val Leu Tyr Asp Phe Ser Phe Ser Tyr Ile
            835                 840                 845

Pro Asp Ile Phe Arg Lys Asp Pro Ser Cys Glu Ala Ala Leu Val Ile
850                 855                 860

Ser Gly Asp Ser Trp Leu Val Pro Ala Ala His Val Ser Arg His Ala
865                 870                 875                 880

Phe Val Gly Ser Gly Thr Gly Arg Tyr His Phe Asn Asp Tyr Thr Glu
                885                 890                 895

Leu Leu Cys Arg Gly Ser Ile Glu Cys Arg Pro His Ala Arg Asn Tyr
            900                 905                 910

Asn Ile Asn Cys Gly Ser Lys Phe Arg Phe
            915                 920

<210> SEQ ID NO 99
<211> LENGTH: 928
<212> TYPE: PRT
<213> ORGANISM: Chlamydia pneumoniae

<400> SEQUENCE: 99

Met Lys Ser Ser Leu His Trp Phe Leu Ile Ser Ser Ser Leu Ala Leu
1               5                   10                  15

Pro Leu Ser Leu Asn Phe Ser Ala Phe Ala Ala Val Val Glu Ile Asn
                20                  25                  30

Leu Gly Pro Thr Asn Ser Phe Ser Gly Pro Gly Thr Tyr Thr Pro Pro
            35                  40                  45

Ala Gln Thr Thr Asn Ala Asp Gly Thr Ile Tyr Asn Leu Thr Gly Asp
        50                  55                  60

Val Ser Ile Thr Asn Ala Gly Ser Pro Thr Ala Leu Thr Ala Ser Cys
65                  70                  75                  80

Phe Lys Glu Thr Thr Gly Asn Leu Ser Phe Gln Gly His Gly Tyr Gln
                85                  90                  95

Phe Leu Leu Gln Asn Ile Asp Ala Gly Ala Asn Cys Thr Phe Thr Asn
                100                 105                 110

Thr Ala Ala Asn Lys Leu Leu Ser Phe Ser Gly Phe Ser Tyr Leu Ser
            115                 120                 125

Leu Ile Gln Thr Thr Asn Ala Thr Thr Gly Thr Gly Ala Ile Lys Ser
130                 135                 140

Thr Gly Ala Cys Ser Ile Gln Ser Asn Tyr Ser Cys Tyr Phe Gly Gln
145                 150                 155                 160

Asn Phe Ser Asn Asp Asn Gly Gly Ala Leu Gln Gly Ser Ser Ile Ser
                165                 170                 175

Leu Ser Leu Asn Pro Asn Leu Thr Phe Ala Lys Asn Lys Ala Thr Gln
            180                 185                 190

Lys Gly Gly Ala Leu Tyr Ser Thr Gly Gly Ile Thr Ile Asn Asn Thr
        195                 200                 205

Leu Asn Ser Ala Ser Phe Ser Glu Asn Thr Ala Ala Asn Asn Gly Gly
```

-continued

```
                210                 215                 220
Ala Ile Tyr Thr Glu Ala Ser Ser Phe Ile Ser Ser Asn Lys Ala Ile
225                 230                 235                 240

Ser Phe Ile Asn Asn Ser Val Thr Ala Thr Ser Ala Thr Gly Gly Ala
                245                 250                 255

Ile Tyr Cys Ser Ser Thr Ser Ala Pro Lys Pro Val Leu Thr Leu Ser
                260                 265                 270

Asp Asn Gly Glu Leu Asn Phe Ile Gly Asn Thr Ala Ile Thr Ser Gly
                275                 280                 285

Gly Ala Ile Tyr Thr Asp Asn Leu Val Leu Ser Gly Gly Pro Thr
290                 295                 300

Leu Phe Lys Asn Asn Ser Ala Ile Asp Thr Ala Ala Pro Leu Gly Gly
305                 310                 315                 320

Ala Ile Ala Ile Ala Asp Ser Gly Ser Leu Ser Leu Ser Ala Leu Gly
                325                 330                 335

Gly Asp Ile Thr Phe Glu Gly Asn Thr Val Val Lys Gly Ala Ser Ser
                340                 345                 350

Ser Gln Thr Thr Thr Arg Asn Ser Ile Asn Ile Gly Asn Thr Asn Ala
                355                 360                 365

Lys Ile Val Gln Leu Arg Ala Ser Gln Gly Asn Thr Ile Tyr Phe Tyr
                370                 375                 380

Asp Pro Ile Thr Thr Ser Ile Thr Ala Ala Leu Ser Asp Ala Leu Asn
385                 390                 395                 400

Leu Asn Gly Pro Asp Leu Ala Gly Asn Pro Ala Tyr Gln Gly Thr Ile
                405                 410                 415

Val Phe Ser Gly Glu Lys Leu Ser Glu Ala Glu Ala Ala Glu Ala Asp
                420                 425                 430

Asn Leu Lys Ser Thr Ile Gln Gln Pro Leu Thr Leu Ala Gly Gly Gln
                435                 440                 445

Leu Ser Leu Lys Ser Gly Val Thr Leu Val Ala Lys Ser Phe Ser Gln
                450                 455                 460

Ser Pro Gly Ser Thr Leu Leu Met Asp Ala Gly Thr Thr Leu Glu Thr
465                 470                 475                 480

Ala Asp Gly Ile Thr Ile Asn Asn Leu Val Leu Asn Val Asp Ser Leu
                485                 490                 495

Lys Glu Thr Lys Lys Ala Thr Leu Lys Ala Thr Gln Ala Ser Gln Thr
                500                 505                 510

Val Thr Leu Ser Gly Ser Leu Ser Leu Val Asp Pro Ser Gly Asn Val
                515                 520                 525

Tyr Glu Asp Val Ser Trp Asn Asn Pro Gln Val Phe Ser Cys Leu Thr
                530                 535                 540

Leu Thr Ala Asp Asp Pro Ala Asn Ile His Ile Thr Asp Leu Ala Ala
545                 550                 555                 560

Asp Pro Leu Glu Lys Asn Pro Ile His Trp Gly Tyr Gln Gly Asn Trp
                565                 570                 575

Ala Leu Ser Trp Gln Glu Asp Thr Ala Thr Lys Ser Lys Ala Ala Thr
                580                 585                 590

Leu Thr Trp Thr Lys Thr Gly Tyr Asn Pro Asn Pro Glu Arg Arg Gly
                595                 600                 605

Thr Leu Val Ala Asn Thr Leu Trp Gly Ser Phe Val Asp Val Arg Ser
                610                 615                 620

Ile Gln Gln Leu Val Ala Thr Lys Val Arg Gln Ser Gln Glu Thr Arg
625                 630                 635                 640
```

Gly Ile Trp Cys Glu Gly Ile Ser Asn Phe Phe His Lys Asp Ser Thr
            645                 650                 655

Lys Ile Asn Lys Gly Phe Arg His Ile Ser Ala Gly Tyr Val Val Gly
        660                 665                 670

Ala Thr Thr Thr Leu Ala Ser Asp Asn Leu Ile Thr Ala Ala Phe Cys
            675                 680                 685

Gln Leu Phe Gly Lys Asp Arg Asp His Phe Ile Asn Lys Asn Arg Ala
        690                 695                 700

Ser Ala Tyr Ala Ala Ser Leu His Leu Gln His Leu Ala Thr Leu Ser
705                 710                 715                 720

Ser Pro Ser Leu Leu Arg Tyr Leu Pro Gly Ser Glu Ser Glu Gln Pro
                725                 730                 735

Val Leu Phe Asp Ala Gln Ile Ser Tyr Ile Tyr Ser Lys Asn Thr Met
            740                 745                 750

Lys Thr Tyr Tyr Thr Gln Ala Pro Lys Gly Glu Ser Ser Trp Tyr Asn
        755                 760                 765

Asp Gly Cys Ala Leu Glu Leu Ala Ser Ser Leu Pro His Thr Ala Leu
770                 775                 780

Ser His Glu Gly Leu Phe His Ala Tyr Phe Pro Phe Ile Lys Val Glu
785                 790                 795                 800

Ala Ser Tyr Ile His Gln Asp Ser Phe Lys Glu Arg Asn Thr Thr Leu
            805                 810                 815

Val Arg Ser Phe Asp Ser Gly Asp Leu Ile Asn Val Ser Val Pro Ile
        820                 825                 830

Gly Ile Thr Phe Glu Arg Phe Ser Arg Asn Glu Arg Ala Ser Tyr Glu
            835                 840                 845

Ala Thr Val Ile Tyr Val Ala Asp Val Tyr Arg Lys Asn Pro Asp Cys
        850                 855                 860

Thr Thr Ala Leu Leu Ile Asn Asn Thr Ser Trp Lys Thr Thr Gly Thr
865                 870                 875                 880

Asn Leu Ser Arg Gln Ala Gly Ile Gly Arg Ala Gly Ile Phe Tyr Ala
                885                 890                 895

Phe Ser Pro Asn Leu Glu Val Thr Ser Asn Leu Ser Met Glu Ile Arg
            900                 905                 910

Gly Ser Ser Arg Ser Tyr Asn Ala Asp Leu Gly Gly Lys Phe Gln Phe
        915                 920                 925

<210> SEQ ID NO 100
<211> LENGTH: 1723
<212> TYPE: PRT
<213> ORGANISM: Chlamydia pneumoniae

<400> SEQUENCE: 100

Met Lys Trp Leu Pro Ala Thr Ala Val Phe Ala Ala Val Leu Pro Ala
1               5                   10                  15

Leu Thr Ala Phe Gly Asp Pro Ala Ser Val Glu Ile Ser Thr Ser His
            20                  25                  30

Thr Gly Ser Gly Asp Pro Thr Ser Asp Ala Ala Leu Thr Gly Phe Thr
        35                  40                  45

Gln Ser Ser Thr Glu Thr Asp Gly Thr Thr Tyr Thr Ile Val Gly Asp
    50                  55                  60

Ile Thr Phe Ser Thr Phe Thr Asn Ile Pro Val Pro Val Val Thr Pro
65                  70                  75                  80

Asp Ala Asn Asp Ser Ser Ser Asn Ser Ser Lys Gly Gly Ser Ser Ser

-continued

```
                    85                  90                  95
Ser Gly Ala Thr Ser Leu Ile Arg Ser Ser Asn Leu His Ser Asp Phe
            100                 105                 110
Asp Phe Thr Lys Asp Ser Val Leu Asp Leu Tyr His Leu Phe Phe Pro
            115                 120                 125
Ser Ala Ser Asn Thr Leu Asn Pro Ala Leu Leu Ser Ser Ser Ser Ser
            130                 135                 140
Gly Gly Ser Ser Ser Ser Ser Ser Ser Ser Ser Gly Ser Ala Ser
145                 150                 155                 160
Ala Val Val Ala Ala Asp Pro Lys Gly Ala Ala Phe Tyr Ser Asn
            165                 170                 175
Glu Ala Asn Gly Thr Leu Thr Phe Thr Thr Asp Ser Gly Asn Pro Gly
            180                 185                 190
Ser Leu Thr Leu Gln Asn Leu Lys Met Thr Gly Asp Gly Ala Ala Ile
            195                 200                 205
Tyr Ser Lys Gly Pro Leu Val Phe Thr Gly Leu Lys Asn Leu Thr Phe
            210                 215                 220
Thr Gly Asn Glu Ser Gln Lys Ser Gly Gly Ala Ala Tyr Thr Glu Gly
225                 230                 235                 240
Ala Leu Thr Thr Gln Ala Ile Val Glu Ala Val Thr Phe Thr Gly Asn
            245                 250                 255
Thr Ser Ala Gly Gln Gly Gly Ala Ile Tyr Val Lys Glu Ala Thr Leu
            260                 265                 270
Phe Asn Ala Leu Asp Ser Leu Lys Phe Glu Lys Asn Thr Ser Gly Gln
            275                 280                 285
Ala Gly Gly Gly Ile Tyr Thr Glu Ser Thr Leu Thr Ile Ser Asn Ile
            290                 295                 300
Thr Lys Ser Ile Glu Phe Ile Ser Asn Lys Ala Ser Val Pro Ala Pro
305                 310                 315                 320
Ala Pro Glu Pro Thr Ser Pro Ala Pro Ser Ser Leu Ile Asn Ser Thr
            325                 330                 335
Thr Ile Asp Thr Ser Thr Leu Gln Thr Arg Ala Ala Ser Ala Thr Pro
            340                 345                 350
Ala Val Ala Pro Val Ala Ala Val Thr Pro Thr Pro Ile Ser Thr Gln
            355                 360                 365
Glu Thr Ala Gly Asn Gly Gly Ala Ile Tyr Ala Lys Gln Gly Ile Ser
            370                 375                 380
Ile Ser Thr Phe Lys Asp Leu Thr Phe Lys Ser Asn Ser Ala Ser Val
385                 390                 395                 400
Asp Ala Thr Leu Thr Val Asp Ser Ser Thr Ile Gly Glu Ser Gly Gly
            405                 410                 415
Ala Ile Phe Ala Ala Asp Ser Ile Gln Ile Gln Gln Cys Thr Gly Thr
            420                 425                 430
Thr Leu Phe Ser Gly Asn Thr Ala Asn Lys Ser Gly Gly Gly Ile Tyr
            435                 440                 445
Ala Val Gly Gln Val Thr Leu Glu Asp Ile Ala Asn Leu Lys Met Thr
            450                 455                 460
Asn Asn Thr Cys Lys Gly Glu Gly Gly Ala Ile Tyr Thr Lys Lys Ala
465                 470                 475                 480
Leu Thr Ile Asn Asn Gly Ala Ile Leu Thr Thr Phe Ser Gly Asn Thr
            485                 490                 495
Ser Thr Asp Asn Gly Gly Ala Ile Phe Ala Val Gly Gly Ile Thr Leu
            500                 505                 510
```

-continued

```
Ser Asp Leu Val Glu Val Arg Phe Ser Lys Asn Lys Thr Gly Asn Tyr
    515                 520                 525

Ser Ala Pro Ile Thr Lys Ala Ala Ser Asn Thr Ala Pro Val Val Ser
    530                 535                 540

Ser Ser Thr Thr Ala Ala Ser Pro Ala Val Pro Ala Ala Ala Ala Ala
545                 550                 555                 560

Pro Val Thr Asn Ala Ala Lys Gly Gly Ala Leu Tyr Ser Thr Glu Gly
                565                 570                 575

Leu Thr Val Ser Gly Ile Thr Ser Ile Leu Ser Phe Glu Asn Asn Glu
                580                 585                 590

Cys Gln Asn Gln Gly Gly Gly Ala Tyr Val Thr Lys Thr Phe Gln Cys
                595                 600                 605

Ser Asp Ser His Arg Leu Gln Phe Thr Ser Asn Lys Ala Ala Asp Glu
            610                 615                 620

Gly Gly Gly Leu Tyr Cys Gly Asp Asp Val Thr Leu Thr Asn Leu Thr
625                 630                 635                 640

Gly Lys Thr Leu Phe Gln Glu Asn Ser Ser Glu Lys His Gly Gly Gly
                645                 650                 655

Leu Ser Leu Ala Ser Gly Lys Ser Leu Thr Met Thr Ser Leu Glu Ser
                660                 665                 670

Phe Cys Leu Asn Ala Asn Thr Ala Lys Glu Asn Gly Gly Gly Ala Asn
                675                 680                 685

Val Pro Glu Asn Ile Val Leu Thr Phe Thr Tyr Thr Pro Thr Pro Asn
            690                 695                 700

Glu Pro Ala Pro Val Gln Gln Pro Val Tyr Gly Glu Ala Leu Val Thr
705                 710                 715                 720

Gly Asn Thr Ala Thr Lys Ser Gly Gly Ile Tyr Thr Lys Asn Ala
                725                 730                 735

Ala Phe Ser Asn Leu Ser Ser Val Thr Phe Asp Gln Asn Thr Ser Ser
                740                 745                 750

Glu Asn Gly Gly Ala Leu Leu Thr Gln Lys Ala Ala Asp Lys Thr Asp
                755                 760                 765

Cys Ser Phe Thr Tyr Ile Thr Asn Val Asn Ile Thr Asn Asn Thr Ala
            770                 775                 780

Thr Gly Asn Gly Gly Ile Ala Gly Lys Ala His Phe Asp Arg
785                 790                 795                 800

Ile Asp Asn Leu Thr Val Gln Ser Asn Gln Ala Lys Lys Gly Gly Gly
                805                 810                 815

Val Tyr Leu Glu Asp Ala Leu Ile Leu Glu Lys Val Ile Thr Gly Ser
                820                 825                 830

Val Ser Gln Asn Thr Ala Thr Glu Ser Gly Gly Ile Tyr Ala Lys
                835                 840                 845

Asp Ile Gln Leu Gln Ala Leu Pro Gly Ser Phe Thr Ile Thr Asp Asn
    850                 855                 860

Lys Val Glu Thr Ser Leu Thr Thr Ser Thr Asn Leu Tyr Gly Gly Gly
865                 870                 875                 880

Ile Tyr Ser Ser Gly Ala Val Thr Leu Thr Asn Ile Ser Gly Thr Phe
                885                 890                 895

Gly Ile Thr Gly Asn Ser Val Ile Asn Thr Ala Thr Ser Gln Asp Ala
                900                 905                 910

Asp Ile Gln Gly Gly Gly Ile Tyr Ala Thr Thr Ser Leu Ser Ile Asn
                915                 920                 925
```

-continued

```
Gln Cys Asn Thr Pro Ile Leu Phe Ser Asn Asn Ser Ala Ala Thr Lys
    930                 935                 940

Lys Thr Ser Thr Thr Lys Gln Ile Ala Gly Gly Ala Ile Phe Ser Ala
945                 950                 955                 960

Ala Val Thr Ile Glu Asn Asn Ser Gln Pro Ile Ile Phe Leu Asn Asn
            965                 970                 975

Ser Ala Lys Ser Glu Ala Thr Thr Ala Ala Thr Ala Gly Asn Lys Asp
        980                 985                 990

Ser Cys Gly Gly Ala Ile Ala Ala Asn Ser Val Thr Leu Thr Asn Asn
    995                 1000                1005

Pro Glu Ile Thr Phe Lys Gly Asn Tyr Ala Glu Thr Gly Gly Ala Ile
    1010                1015                1020

Gly Cys Ile Asp Leu Thr Asn Gly Ser Pro Arg Lys Val Ser Ile
1025                1030                1035                1040

Ala Asp Asn Gly Ser Val Leu Phe Gln Asp Asn Ser Ala Leu Asn Arg
            1045                1050                1055

Gly Gly Ala Ile Tyr Gly Glu Thr Ile Asp Ile Ser Arg Thr Gly Ala
            1060                1065                1070

Thr Phe Ile Gly Asn Ser Ser Lys His Asp Gly Ser Ala Ile Cys Cys
    1075                1080                1085

Ser Thr Ala Leu Thr Leu Ala Pro Asn Ser Gln Leu Ile Phe Glu Asn
    1090                1095                1100

Asn Lys Val Thr Glu Thr Thr Ala Thr Thr Lys Ala Ser Ile Asn Asn
1105                1110                1115                1120

Leu Gly Ala Ala Ile Tyr Gly Asn Asn Glu Thr Ser Asp Val Thr Ile
            1125                1130                1135

Ser Leu Ser Ala Glu Asn Gly Ser Ile Phe Phe Lys Asn Asn Leu Cys
    1140                1145                1150

Thr Ala Thr Asn Lys Tyr Cys Ser Ile Ala Gly Asn Val Lys Phe Thr
    1155                1160                1165

Ala Ile Glu Ala Ser Ala Gly Lys Ala Ile Ser Phe Tyr Asp Ala Val
    1170                1175                1180

Asn Val Ser Thr Lys Glu Thr Asn Ala Gln Glu Leu Lys Leu Asn Glu
1185                1190                1195                1200

Lys Ala Thr Ser Thr Gly Thr Ile Leu Phe Ser Gly Glu Leu His Glu
            1205                1210                1215

Asn Lys Ser Tyr Ile Pro Gln Lys Val Thr Phe Ala His Gly Asn Leu
    1220                1225                1230

Ile Leu Gly Lys Asn Ala Glu Leu Ser Val Val Ser Phe Thr Gln Ser
    1235                1240                1245

Pro Gly Thr Thr Ile Thr Met Gly Pro Gly Ser Val Leu Ser Asn His
    1250                1255                1260

Ser Lys Glu Ala Gly Gly Ile Ala Ile Asn Asn Val Ile Ile Asp Phe
1265                1270                1275                1280

Ser Glu Ile Val Pro Thr Lys Asp Asn Ala Thr Val Ala Pro Pro Thr
            1285                1290                1295

Leu Lys Leu Val Ser Arg Thr Asn Ala Asp Ser Lys Asp Lys Ile Asp
            1300                1305                1310

Ile Thr Gly Thr Val Thr Leu Leu Asp Pro Asn Gly Asn Leu Tyr Gln
    1315                1320                1325

Asn Ser Tyr Leu Gly Glu Asp Arg Asp Ile Thr Leu Phe Asn Ile Asp
    1330                1335                1340

Asn Ser Ala Ser Gly Ala Val Thr Ala Thr Asn Val Thr Leu Gln Gly
```

```
                1345                1350                1355                1360
Asn Leu Gly Ala Lys Lys Gly Tyr Leu Gly Thr Trp Asn Leu Asp Pro
            1365                1370                1375
Asn Ser Ser Gly Ser Lys Ile Ile Leu Lys Trp Thr Phe Asp Lys Tyr
            1380                1385                1390
Leu Arg Trp Pro Tyr Ile Pro Arg Asp Asn His Phe Tyr Ile Asn Ser
            1395                1400                1405
Ile Trp Gly Ala Gln Asn Ser Leu Val Thr Val Lys Gln Gly Ile Leu
            1410                1415                1420
Gly Asn Met Leu Asn Asn Ala Arg Phe Glu Asp Pro Ala Phe Asn Asn
1425                1430                1435                1440
Phe Trp Ala Ser Ala Ile Gly Ser Phe Leu Arg Lys Glu Val Ser Arg
                1445                1450                1455
Asn Ser Asp Ser Phe Thr Tyr His Gly Arg Gly Tyr Thr Ala Ala Val
            1460                1465                1470
Asp Ala Lys Pro Arg Gln Glu Phe Ile Leu Gly Ala Ala Phe Ser Gln
            1475                1480                1485
Val Phe Gly His Ala Glu Ser Glu Tyr His Leu Asp Asn Tyr Lys His
            1490                1495                1500
Lys Gly Ser Gly His Ser Thr Gln Ala Ser Leu Tyr Ala Gly Asn Ile
1505                1510                1515                1520
Phe Tyr Phe Pro Ala Ile Arg Ser Arg Pro Ile Leu Phe Gln Gly Val
            1525                1530                1535
Ala Thr Tyr Gly Tyr Met Gln His Asp Thr Thr Thr Tyr Tyr Pro Ser
            1540                1545                1550
Ile Glu Glu Lys Asn Met Ala Asn Trp Asp Ser Ile Ala Trp Leu Phe
            1555                1560                1565
Asp Leu Arg Phe Ser Val Asp Leu Lys Glu Pro Gln Pro His Ser Thr
            1570                1575                1580
Ala Arg Leu Thr Phe Tyr Thr Glu Ala Glu Tyr Thr Arg Ile Arg Gln
1585                1590                1595                1600
Glu Lys Phe Thr Glu Leu Asp Tyr Asp Pro Arg Ser Phe Ser Ala Cys
            1605                1610                1615
Ser Tyr Gly Asn Leu Ala Ile Pro Thr Gly Phe Ser Val Asp Gly Ala
            1620                1625                1630
Leu Ala Trp Arg Glu Ile Ile Leu Tyr Asn Lys Val Ser Ala Ala Tyr
            1635                1640                1645
Leu Pro Val Ile Leu Arg Asn Asn Pro Lys Ala Thr Tyr Glu Val Leu
            1650                1655                1660
Ser Thr Lys Glu Lys Gly Asn Val Val Asn Val Leu Pro Thr Arg Asn
1665                1670                1675                1680
Ala Ala Arg Ala Glu Val Ser Ser Gln Ile Tyr Leu Gly Ser Tyr Trp
                1685                1690                1695
Thr Leu Tyr Gly Thr Tyr Thr Ile Asp Ala Ser Met Asn Thr Leu Val
            1700                1705                1710
Gln Met Ala Asn Gly Gly Ile Arg Phe Val Phe
            1715                1720

<210> SEQ ID NO 101
<211> LENGTH: 568
<212> TYPE: PRT
<213> ORGANISM: Chlamydia pneumoniae

<400> SEQUENCE: 101
```

Met Gly Leu Phe His Leu Thr Leu Phe Gly Leu Leu Cys Ser Leu
1               5                   10                  15

Pro Ile Ser Leu Val Ala Lys Phe Pro Glu Ser Val Gly His Lys Ile
            20                  25                  30

Leu Tyr Ile Ser Thr Gln Ser Thr Gln Gln Ala Leu Ala Thr Tyr Leu
                35                  40                  45

Glu Ala Leu Asp Ala Tyr Gly Asp His Asp Phe Phe Val Leu Arg Lys
50                      55                  60

Ile Gly Glu Asp Tyr Leu Lys Gln Ser Ile His Ser Ser Asp Pro Gln
65                  70                  75                  80

Thr Arg Lys Ser Thr Ile Ile Gly Ala Gly Leu Ala Gly Ser Ser Glu
                85                  90                  95

Ala Leu Asp Val Leu Ser Gln Ala Met Glu Thr Ala Asp Pro Leu Gln
            100                 105                 110

Gln Leu Leu Val Leu Ser Ala Val Ser Gly His Leu Gly Lys Thr Ser
            115                 120                 125

Asp Asp Leu Leu Phe Lys Ala Leu Ala Ser Pro Tyr Pro Val Ile Arg
130                 135                 140

Leu Glu Ala Ala Tyr Arg Leu Ala Asn Leu Lys Asn Thr Lys Val Ile
145                 150                 155                 160

Asp His Leu His Ser Phe Ile His Lys Leu Pro Glu Glu Ile Gln Cys
                165                 170                 175

Leu Ser Ala Ala Ile Phe Leu Arg Leu Glu Thr Glu Glu Ser Asp Ala
            180                 185                 190

Tyr Ile Arg Asp Leu Leu Ala Ala Lys Lys Ser Ala Ile Arg Ser Ala
            195                 200                 205

Thr Ala Leu Gln Ile Gly Glu Tyr Gln Gln Lys Arg Phe Leu Pro Thr
210                 215                 220

Leu Arg Asn Leu Leu Thr Ser Ala Ser Pro Gln Asp Gln Glu Ala Ile
225                 230                 235                 240

Leu Tyr Ala Leu Gly Lys Leu Lys Asp Gly Gln Ser Tyr Tyr Asn Ile
            245                 250                 255

Lys Lys Gln Leu Gln Lys Pro Asp Val Asp Val Thr Leu Ala Ala Ala
            260                 265                 270

Gln Ala Leu Ile Ala Leu Gly Lys Glu Glu Asp Ala Leu Pro Val Ile
            275                 280                 285

Lys Lys Gln Ala Leu Glu Glu Arg Pro Arg Ala Leu Tyr Ala Leu Arg
290                 295                 300

His Leu Pro Ser Glu Ile Gly Ile Pro Ile Ala Leu Pro Ile Phe Leu
305                 310                 315                 320

Lys Thr Lys Asn Ser Glu Ala Lys Leu Asn Val Ala Leu Ala Leu Leu
            325                 330                 335

Glu Leu Gly Cys Asp Thr Pro Lys Leu Leu Glu Tyr Ile Thr Glu Arg
            340                 345                 350

Leu Val Gln Pro His Tyr Asn Glu Thr Leu Ala Leu Ser Phe Ser Lys
            355                 360                 365

Gly Arg Thr Leu Gln Asn Trp Lys Arg Val Asn Ile Ile Val Pro Gln
            370                 375                 380

Asp Pro Gln Glu Arg Glu Arg Leu Leu Ser Thr Thr Arg Gly Leu Glu
385                 390                 395                 400

Glu Gln Ile Leu Thr Phe Leu Phe Arg Leu Pro Lys Glu Ala Tyr Leu
            405                 410                 415

Pro Cys Ile Tyr Lys Leu Leu Ala Ser Gln Lys Thr Gln Leu Ala Thr

```
                      420                 425                 430
Thr Ala Ile Ser Phe Leu Ser His Thr Ser His Gln Glu Ala Leu Asp
            435                 440                 445

Leu Leu Phe Gln Ala Ala Lys Leu Pro Gly Glu Pro Ile Ile Arg Ala
450                 455                 460

Tyr Ala Asp Leu Ala Ile Tyr Asn Leu Thr Lys Asp Pro Glu Lys Lys
465                 470                 475                 480

Arg Ser Leu His Asp Tyr Ala Lys Lys Leu Ile Gln Glu Thr Leu Leu
                485                 490                 495

Phe Val Asp Thr Glu Asn Gln Arg Pro His Pro Ser Met Pro Tyr Leu
            500                 505                 510

Arg Tyr Gln Val Thr Pro Glu Ser Arg Thr Lys Leu Met Leu Asp Ile
        515                 520                 525

Leu Glu Thr Leu Ala Thr Ser Lys Ser Glu Asp Ile Arg Leu Leu
530                 535                 540

Ile Gln Leu Met Thr Glu Gly Asp Ala Lys Asn Phe Pro Val Leu Ala
545                 550                 555                 560

Gly Leu Leu Ile Lys Ile Val Glu
                565

<210> SEQ ID NO 102
<211> LENGTH: 364
<212> TYPE: PRT
<213> ORGANISM: Chlamydia pneumoniae

<400> SEQUENCE: 102

Met Asn Val Pro Asp Ser Lys Asn Leu His Pro Pro Ala Tyr Glu Leu
1               5                   10                  15

Leu Glu Ile Lys Ala Arg Ile Thr Gln Ser Tyr Lys Glu Ala Ser Ala
            20                  25                  30

Ile Leu Thr Ala Ile Pro Asp Gly Ile Leu Leu Ser Glu Thr Gly
        35                  40                  45

His Phe Leu Ile Cys Asn Ser Gln Ala Arg Glu Ile Leu Gly Ile Asp
    50                  55                  60

Glu Asn Leu Glu Ile Leu Asn Arg Ser Phe Thr Asp Val Leu Pro Asp
65                  70                  75                  80

Thr Cys Leu Gly Phe Ser Ile Gln Glu Ala Leu Glu Ser Leu Lys Val
                85                  90                  95

Pro Lys Thr Leu Arg Leu Ser Leu Cys Lys Glu Ser Lys Glu Lys Glu
            100                 105                 110

Val Glu Leu Phe Ile Arg Lys Asn Glu Ile Ser Gly Tyr Leu Phe Ile
        115                 120                 125

Gln Ile Arg Asp Arg Ser Asp Tyr Lys Gln Leu Glu Asn Ala Ile Glu
    130                 135                 140

Arg Tyr Lys Asn Ile Ala Glu Leu Gly Lys Met Thr Ala Thr Leu Ala
145                 150                 155                 160

His Glu Ile Arg Asn Pro Leu Ser Gly Ile Val Gly Phe Ala Ser Ile
                165                 170                 175

Leu Lys Lys Glu Ile Ser Ser Pro Arg His Gln Arg Met Leu Ser Ser
            180                 185                 190

Ile Ile Ser Gly Thr Arg Ser Leu Asn Asn Leu Val Ser Ser Met Leu
        195                 200                 205

Glu Tyr Thr Lys Ser Gln Pro Leu Asn Leu Lys Ile Ile Asn Leu Gln
    210                 215                 220
```

```
Asp Phe Phe Ser Ser Leu Ile Pro Leu Leu Ser Val Ser Phe Pro Asn
225                 230                 235                 240

Cys Lys Phe Val Arg Glu Gly Ala Gln Pro Leu Phe Arg Ser Ile Asp
                245                 250                 255

Pro Asp Arg Met Asn Ser Val Val Trp Asn Leu Val Lys Asn Ala Val
            260                 265                 270

Glu Thr Gly Asn Ser Pro Ile Thr Leu Thr Leu His Thr Ser Gly Asp
        275                 280                 285

Ile Ser Val Thr Asn Pro Gly Thr Ile Pro Ser Glu Ile Met Asp Lys
    290                 295                 300

Leu Phe Thr Pro Phe Phe Thr Thr Lys Arg Glu Gly Asn Gly Leu Gly
305                 310                 315                 320

Leu Ala Glu Ala Gln Lys Ile Ile Arg Leu His Gly Gly Asp Ile Gln
                325                 330                 335

Leu Lys Thr Ser Asp Ser Ala Val Ser Phe Phe Ile Ile Ile Pro Glu
            340                 345                 350

Leu Leu Ala Ala Leu Pro Lys Glu Arg Ala Ala Ser
            355                 360

<210> SEQ ID NO 103
<211> LENGTH: 373
<212> TYPE: PRT
<213> ORGANISM: Chlamydia pneumoniae

<400> SEQUENCE: 103

Met Ser Ile Ala Ile Ala Arg Glu Gln Tyr Ala Ala Ile Leu Asp Met
1               5                   10                  15

His Pro Lys Pro Ser Ile Ala Met Phe Ser Ser Glu Gln Ala Arg Thr
            20                  25                  30

Ser Trp Glu Lys Arg Gln Ala His Pro Tyr Leu Tyr Arg Leu Leu Glu
        35                  40                  45

Ile Ile Trp Gly Val Val Lys Phe Leu Leu Gly Leu Ile Phe Phe Ile
    50                  55                  60

Pro Leu Gly Leu Phe Trp Val Leu Gln Lys Ile Cys Gln Asn Phe Ile
65                  70                  75                  80

Leu Leu Gly Ala Gly Gly Trp Ile Phe Arg Pro Ile Cys Arg Asp Ser
                85                  90                  95

Asn Leu Leu Arg Gln Ala Tyr Ala Ala Arg Leu Phe Ser Ala Ser Phe
            100                 105                 110

Gln Asp His Val Ser Ser Val Arg Arg Val Cys Leu Gln Tyr Asp Glu
        115                 120                 125

Val Phe Ile Asp Gly Leu Glu Leu Arg Leu Pro Asn Ala Lys Pro Asp
    130                 135                 140

Arg Trp Met Leu Ile Ser Asn Gly Asn Ser Asp Cys Leu Glu Tyr Arg
145                 150                 155                 160

Thr Val Leu Gln Gly Glu Lys Asp Trp Ile Phe Arg Ile Ala Glu Glu
                165                 170                 175

Ser Gln Ser Asn Ile Leu Ile Phe Asn Tyr Pro Gly Val Met Lys Ser
            180                 185                 190

Gln Gly Asn Ile Thr Arg Asn Asn Val Val Lys Ser Tyr Gln Ala Cys
        195                 200                 205

Val Arg Tyr Leu Arg Asp Glu Pro Ala Gly Pro Gln Ala Arg Gln Ile
    210                 215                 220

Val Ala Tyr Gly Tyr Ser Leu Gly Ala Ser Val Gln Ala Glu Ala Leu
225                 230                 235                 240
```

-continued

Ser Lys Glu Ile Ala Asp Gly Ser Asp Ser Val Arg Trp Phe Val Val
              245                 250                 255

Lys Asp Arg Gly Ala Arg Ser Thr Gly Ala Val Ala Lys Gln Phe Ile
              260                 265                 270

Gly Ser Leu Gly Val Trp Leu Ala Asn Leu Thr His Trp Asn Ile Asn
              275                 280                 285

Ser Glu Lys Arg Ser Lys Asp Leu His Cys Pro Glu Leu Phe Ile Tyr
              290                 295                 300

Gly Lys Asp Ser Gln Gly Asn Leu Ile Gly Asp Gly Leu Phe Lys Lys
305                 310                 315                 320

Glu Thr Cys Phe Ala Ala Pro Phe Leu Asp Pro Lys Asn Leu Glu Glu
              325                 330                 335

Cys Ser Gly Lys Lys Ile Pro Val Ala Gln Thr Gly Leu Arg His Asp
              340                 345                 350

His Ile Leu Ser Asp Asp Val Ile Lys Glu Val Ala Gly His Ile Gln
              355                 360                 365

Arg His Phe Asp Asn
    370

<210> SEQ ID NO 104
<211> LENGTH: 980
<212> TYPE: PRT
<213> ORGANISM: Chlamydia pneumoniae

<400> SEQUENCE: 104

Met Tyr Ser Cys Tyr Ser Lys Gly Ile Ser His Asn Tyr Leu Leu His
1               5                   10                  15

Pro Met Ser Arg Leu Asp Ile Phe Val Phe Asp Ser Leu Ile Ala Asn
              20                  25                  30

Gln Asp Gln Asn Leu Leu Glu Glu Ile Phe Cys Ser Glu Asp Thr Val
              35                  40                  45

Leu Phe Lys Ala Tyr Arg Thr Thr Ala Leu Gln Ser Pro Leu Ala Ala
    50                  55                  60

Lys Asn Leu Asn Ile Ala Arg Lys Val Ala Asn Tyr Ile Leu Ala Asp
65                  70                  75                  80

Asn Gly Glu Ile Asp Thr Val Lys Leu Val Glu Ala Ile His His Leu
              85                  90                  95

Ser Gln Cys Thr Tyr Pro Leu Gly Pro His Arg His Asn Glu Ala Gln
              100                 105                 110

Asp Arg Glu His Leu Leu Lys Met Leu Lys Ala Leu Lys Glu Asn Pro
              115                 120                 125

Lys Leu Lys Glu Ser Ile Lys Thr Leu Phe Val Pro Ser Tyr Ser Thr
    130                 135                 140

Ile Gln Asn Leu Ile Arg His Thr Leu Ala Leu Asn Pro Gln Thr Ile
145                 150                 155                 160

Leu Ser Thr Ile His Val Arg Gln Ala Ala Leu Thr Ala Leu Phe Thr
              165                 170                 175

Tyr Leu Arg Gln Asp Val Gly Ser Cys Phe Ala Thr Ala Pro Ala Ile
              180                 185                 190

Leu Ile His Gln Glu Tyr Pro Glu Arg Phe Leu Lys Asp Leu Asn Asp
              195                 200                 205

Leu Ile Ser Ser Gly Lys Leu Ser Arg Ile Val Asn Gln Arg Glu Ile
    210                 215                 220

Ala Val Pro Ile Asn Leu Ser Gly Cys Ile Gly Glu Leu Phe Lys Pro

```
                225                 230                 235                 240
Leu Arg Ile Leu Asp Leu Tyr Pro Asp Pro Leu Val Lys Leu Ser Ser
                245                 250                 255
Ser Pro Gly Leu Lys Lys Ala Phe Ser Ala Ala Asn Leu Ile Glu Thr
            260                 265                 270
Leu Gly Asp Ser Glu Ala Gln Ile Gln Gln Leu Leu Ser His Gln Tyr
            275                 280                 285
Leu Met Gln Lys Leu Gln Asn Val His Glu Thr Leu Thr Ala Asn Asp
        290                 295                 300
Ile Ile Lys Ser Thr Leu Leu His Tyr Gln Leu Gln Glu Ser Thr
305                 310                 315                 320
Val Arg Ala Ile Phe Phe Lys Glu Gly Leu Phe Ser Lys Glu Gln Val
                325                 330                 335
Ala Phe Ser Thr Gln His Pro Arg Glu Leu Ser Glu Ile Gln Arg Val
            340                 345                 350
Tyr His Tyr Leu His Ala Tyr Glu Glu Ala Lys Ser Ala Phe Ile His
            355                 360                 365
Asp Thr Gln Asn Pro Leu Leu Lys Ala Trp Glu Tyr Thr Leu Ala Thr
        370                 375                 380
Leu Ala Asp Ala Ser Gln Pro Thr Ile Ser Asn His Ile Arg Leu Ala
385                 390                 395                 400
Leu Gly Trp Lys Ser Glu Asp Pro His Ser Leu Val Ser Leu Val Thr
                405                 410                 415
His Phe Val Glu Glu Glu Val Glu Asn Ile Arg Ile Leu Val Gln Gln
                420                 425                 430
Cys Glu Gln Thr Tyr His Glu Ala Arg Ser Gln Leu Glu Tyr Ile Glu
            435                 440                 445
Gly Arg Met Arg Asn Pro Leu Asn Asn Gln Asp Ser Gln Ile Leu Thr
            450                 455                 460
Met Asp His Met Arg Phe Arg Gln Glu Leu Asn Lys Ala Leu Tyr Glu
465                 470                 475                 480
Trp Asp Ser Ala Gln Glu Lys Ala Lys Lys Phe Leu His Leu Pro Glu
                485                 490                 495
Phe Leu Leu Ser Phe Tyr Thr Lys Gln Ile Pro Leu Tyr Phe Arg Ser
            500                 505                 510
Ser Tyr Asp Ala Phe Ile Gln Glu Phe Ala His Leu Tyr Ala Asn Ala
            515                 520                 525
Pro Ala Gly Phe Arg Ile Leu Phe Thr His Gly Arg Thr His Pro Asn
        530                 535                 540
Thr Trp Ser Pro Ile Tyr Ser Ile Asn Glu Phe Ile Arg Phe Leu Ser
545                 550                 555                 560
Glu Phe Phe Thr Ser Thr Glu Ser Glu Leu Leu Gly Lys His Ala Val
                565                 570                 575
Ile Asn Leu Glu Lys Glu Thr Ser Arg Leu Val His Asn Ile Thr Ala
                580                 585                 590
Met Leu His Thr Asp Val Phe Gln Glu Ala Leu Leu Thr Arg Ile Leu
            595                 600                 605
Glu Ala Tyr Gln Leu Pro Val Pro Ser Ile Leu Asn His Leu Asp
            610                 615                 620
Gln Leu Ser Gln Thr Pro Trp Val Tyr Val Ser Gly Gly Thr Val Asp
625                 630                 635                 640
Thr Leu Leu Leu Asp Tyr Phe Glu Ser Ser Glu Pro Leu Thr Leu Thr
                645                 650                 655
```

-continued

Glu Lys His Pro Glu Asn Pro His Glu Leu Ala Ala Phe Tyr Ala Asp
            660                 665                 670

Ala Leu Lys Asp Leu Pro Thr Gly Ile Lys Ser Tyr Leu Glu Glu Gly
        675                 680                 685

Ser His Ser Leu Leu Ser Ser Ser Pro Thr His Val Phe Ser Ile Ile
    690                 695                 700

Ala Gly Ser Pro Leu Phe Arg Glu Ala Trp Asp Asn Asp Trp Tyr Ser
705                 710                 715                 720

Tyr Thr Trp Leu Arg Asp Val Trp Val Lys Gln His Gln Asp Phe Leu
                725                 730                 735

Gln Asp Thr Ile Leu Pro Gln Leu Ser Ile Tyr Ala Phe Ile Glu Asn
            740                 745                 750

Phe Cys Asn Lys Tyr Ala Leu Gln His Val Val His Asp Phe His Asp
        755                 760                 765

Phe Cys Ser Asp His Ser Leu Thr Leu Pro Glu Leu Tyr Asp Lys Gly
    770                 775                 780

Ser Arg Phe Leu Ser Ser Leu Phe Thr Lys Asp Lys Thr Val Ala Leu
785                 790                 795                 800

Ile Tyr Ile Arg Arg Leu Leu Tyr Leu Met Val Arg Glu Val Pro Tyr
                805                 810                 815

Val Ser Glu Gln Gln Leu Pro Glu Val Leu Asp Asn Val Ser Ser Tyr
            820                 825                 830

Leu Gly Ile Ser Ser Arg Ile Thr Tyr Glu Lys Phe Arg Ser Leu Ile
        835                 840                 845

Glu Glu Thr Ile Pro Lys Met Thr Leu Leu Ser Ser Ala Asp Leu Arg
    850                 855                 860

His Ile Tyr Lys Gly Leu Leu Met Gln Ser Tyr Gln Lys Ile Tyr Thr
865                 870                 875                 880

Glu Glu Asp Thr Tyr Leu Arg Leu Thr Thr Ala Met Arg His His Asn
                885                 890                 895

Leu Ala Tyr Pro Ala Pro Leu Leu Phe Ala Asp Ser Asn Trp Pro Ser
            900                 905                 910

Ile Tyr Phe Gly Phe Ile Leu Asn Pro Gly Thr Thr Glu Ile Asp Leu
        915                 920                 925

Trp Lys Phe Asn Tyr Ala Gly Leu Gln Gly Pro Leu Asp Asn Ile
    930                 935                 940

Gln Glu Leu Phe Ala Thr Ser Arg Pro Trp Thr Leu Tyr Ala Asn Pro
945                 950                 955                 960

Ile Asp Tyr Gly Met Pro Pro Pro Gly Tyr Arg Ser Arg Leu Pro
                965                 970                 975

Lys Glu Phe Phe
            980

<210> SEQ ID NO 105
<211> LENGTH: 604
<212> TYPE: PRT
<213> ORGANISM: Chlamydia pneumoniae

<400> SEQUENCE: 105

Met Lys His Thr Phe Thr Lys Arg Val Leu Phe Phe Phe Leu Val
1               5                   10                  15

Ile Pro Ile Pro Leu Leu Leu Asn Leu Met Val Val Gly Phe Phe Ser
            20                  25                  30

Phe Ser Ala Ala Lys Ala Asn Leu Val Gln Val Leu His Thr Arg Ala

-continued

```
                35                  40                  45
Thr Asn Leu Ser Ile Glu Phe Glu Lys Lys Leu Thr Ile His Lys Leu
 50                  55                  60
Phe Leu Asp Arg Leu Ala Asn Thr Leu Ala Leu Lys Ser Tyr Ala Ser
 65                  70                  75                  80
Pro Ser Ala Glu Pro Tyr Ala Gln Ala Tyr Asn Glu Met Met Ala Leu
                 85                  90                  95
Ser Asn Thr Asp Phe Ser Leu Cys Leu Ile Asp Pro Phe Asp Gly Ser
                100                 105                 110
Val Arg Thr Lys Asn Pro Gly Asp Pro Phe Ile Arg Tyr Leu Lys Gln
                115                 120                 125
His Pro Glu Met Lys Lys Lys Leu Ser Ala Ala Val Gly Lys Ala Phe
                130                 135                 140
Leu Leu Thr Ile Pro Gly Lys Pro Leu Leu His Tyr Leu Ile Leu Val
145                 150                 155                 160
Glu Asp Val Ala Ser Trp Asp Ser Thr Thr Thr Ser Gly Leu Leu Val
                165                 170                 175
Ser Phe Tyr Pro Met Ser Phe Leu Gln Lys Asp Leu Phe Gln Ser Leu
                180                 185                 190
His Ile Thr Lys Gly Asn Ile Cys Leu Val Asn Lys Tyr Gly Glu Val
                195                 200                 205
Leu Phe Cys Ala Gln Asp Ser Glu Ser Phe Val Phe Ser Leu Asp
                210                 215                 220
Leu Pro Asn Leu Pro Gln Phe Gln Ala Arg Ser Pro Ser Ala Ile Glu
225                 230                 235                 240
Ile Glu Lys Ala Ser Gly Ile Leu Gly Gly Glu Asn Leu Ile Thr Val
                245                 250                 255
Ser Ile Asn Lys Lys Arg Tyr Leu Gly Leu Val Leu Asn Lys Ile Pro
                260                 265                 270
Ile Gln Gly Thr Tyr Thr Leu Ser Leu Val Pro Val Ser Asp Leu Ile
                275                 280                 285
Gln Ser Ala Leu Lys Val Pro Leu Asn Ile Cys Phe Phe Tyr Val Leu
                290                 295                 300
Ala Phe Leu Leu Met Trp Trp Ile Phe Ser Lys Ile Asn Thr Lys Leu
305                 310                 315                 320
Asn Lys Pro Leu Gln Glu Leu Thr Phe Cys Met Glu Ala Ala Trp Arg
                325                 330                 335
Gly Asn His Asn Val Arg Phe Gly Pro Gln Pro Tyr Gly Tyr Glu Phe
                340                 345                 350
Asn Glu Leu Gly Asn Ile Phe Asn Cys Thr Leu Leu Leu Leu Leu Asn
                355                 360                 365
Ser Ile Glu Lys Ala Asp Ile Asp Tyr His Ser Gly Glu Lys Leu Gln
                370                 375                 380
Lys Glu Leu Gly Ile Leu Ser Ser Leu Gln Ser Ala Leu Leu Ser Pro
385                 390                 395                 400
Asp Phe Pro Thr Phe Pro Lys Val Thr Phe Ser Ser Gln His Leu Arg
                405                 410                 415
Arg Arg Gln Leu Ser Gly His Phe Asn Gly Trp Thr Val Gln Asp Gly
                420                 425                 430
Gly Asp Thr Leu Leu Gly Ile Ile Gly Leu Ala Gly Asp Ile Gly Leu
                435                 440                 445
Pro Ser Tyr Leu Tyr Ala Leu Ser Ala Arg Ser Leu Phe Leu Ala Tyr
450                 455                 460
```

Ala Ser Ser Asp Val Ser Leu Gln Lys Ile Ser Lys Asp Thr Ala Asp
465                 470                 475                 480

Ser Phe Ser Lys Thr Thr Glu Gly Asn Glu Ala Val Val Ala Met Thr
            485                 490                 495

Phe Ile Lys Tyr Val Glu Lys Asp Arg Ser Leu Glu Leu Leu Ser Leu
                500                 505                 510

Ser Glu Gly Ala Pro Thr Met Phe Leu Gln Arg Gly Glu Ser Phe Val
            515                 520                 525

Arg Leu Pro Leu Glu Thr His Gln Ala Leu Gln Pro Gly Asp Arg Leu
        530                 535                 540

Ile Cys Leu Thr Gly Gly Glu Asp Ile Leu Lys Tyr Phe Ser Gln Leu
545                 550                 555                 560

Pro Ile Glu Glu Leu Leu Lys Asp Pro Leu Asn Pro Leu Asn Thr Glu
                565                 570                 575

Asn Leu Ile Asp Ser Leu Thr Met Met Leu Asn Asn Glu Thr Glu His
            580                 585                 590

Ser Ala Asp Gly Thr Leu Thr Ile Leu Ser Phe Ser
        595                 600

<210> SEQ ID NO 106
<211> LENGTH: 435
<212> TYPE: PRT
<213> ORGANISM: Chlamydia pneumoniae

<400> SEQUENCE: 106

Met Trp Leu Asp Arg Tyr Ala Asp Lys Phe Ile Leu Arg Glu Lys Glu
1               5                   10                  15

Glu Lys Met Glu Arg His Glu Leu Phe His Ala Thr Met Val Arg Lys
            20                  25                  30

Ala Ser Gly His Ala Tyr Ala Lys Ala Lys Ala Phe Glu Lys Glu
        35                  40                  45

Arg Ser Asn Glu Asn Gln Arg Lys Val Lys Asp Val Glu Lys Trp Leu
    50                  55                  60

Ser Lys Gly Leu Ala Glu Phe Arg Asn Gln Ser Arg Arg Ala Arg
65                  70                  75                  80

Glu Arg Leu Arg Glu Leu Gln Thr Leu Tyr Pro Glu Val Ser Val Glu
                85                  90                  95

Glu Arg Val Leu Glu Arg Gln Arg Thr Lys Lys Val Asn Leu Glu Asn
            100                 105                 110

Leu Tyr Ala Asp Ile Glu Lys Lys Tyr His His Cys Val Arg Glu Gln
        115                 120                 125

Glu His Tyr Trp Lys Glu Val Glu Asn Lys Glu Ala Glu Tyr Arg Glu
    130                 135                 140

Asn Gly Glu Lys Val Leu Ser Ala Glu Val Ser Glu Cys Leu Gln
145                 150                 155                 160

Arg Leu Glu Asp Cys Leu Glu Thr Trp Ser Lys Lys Leu Thr Lys Ala
                165                 170                 175

Glu Glu Ser Val Phe Glu Met Lys Phe Asp Ala Thr Glu Lys Leu Gly
            180                 185                 190

Asn Lys Val Leu Ser Asp Val Thr Asn Arg Leu Glu Ile Leu Cys Glu
        195                 200                 205

Asp Ala Glu Glu Met Ile Phe Arg Ile Glu Glu Ile Glu Met Thr Leu
    210                 215                 220

Arg Met Val Glu Leu Pro Leu Leu Phe Met Lys Asn Thr Phe Glu Lys

```
                225                 230                 235                 240
Ala Ser Leu Gln Tyr Asn Ser Cys Lys Glu Met Leu Ala Lys Val Glu
                245                 250                 255

Pro Gln Cys Lys Glu Ser Pro Thr Tyr Arg Ser Ser Gln Glu Arg Leu
            260                 265                 270

Glu Arg Leu Asn Gln Asp Leu Gln Thr Ala Tyr Thr Asn Cys Gln Glu
        275                 280                 285

Arg Leu Gln Gly Phe Ser Asp Leu Glu Ser Lys Val Arg Thr Cys Arg
    290                 295                 300

Asp His Leu Arg Glu Gln Met Lys His Phe Glu Val Gln Gly Leu Asn
305                 310                 315                 320

Phe Ile Asn Glu Glu Leu Leu Trp Val Gly Ala Glu Leu Phe Thr Gln
                325                 330                 335

Ala Arg Leu Asp Leu Val Ala Thr Val Pro Tyr Met Glu Phe Tyr Leu
            340                 345                 350

Gln Tyr His Asn Ile Lys Arg Glu Lys Val Arg Ser Gln Trp Met Ala
        355                 360                 365

Lys Thr Glu Arg Tyr Arg Glu Ile Arg Gln Ala Phe Gln Gly Val Met
    370                 375                 380

Lys Glu Asp Leu Leu Ala Glu Asp Thr Ile Leu Lys Glu Glu Asp Tyr
385                 390                 395                 400

Trp Leu Leu Arg Asp Asp Trp Leu Leu Arg Asp Glu Arg Lys Asn Arg
                405                 410                 415

Gln Arg Arg Leu Ile Cys Asn Lys Ile Ala Ala Ala Gln Gln Arg Val
            420                 425                 430

Lys Gly Phe
        435

<210> SEQ ID NO 107
<211> LENGTH: 449
<212> TYPE: PRT
<213> ORGANISM: Chlamydia pneumoniae

<400> SEQUENCE: 107

Met Leu Leu Leu Ile Ser Gly Ala Leu Phe Leu Thr Leu Gly Ile Pro
1               5                   10                  15

Gly Leu Thr Ala Gly Val Ser Phe Gly Leu Gly Ile Gly Leu Ser Ala
            20                  25                  30

Leu Gly Gly Val Leu Val Val Ser Gly Leu Leu Cys Leu Leu Val Lys
        35                  40                  45

Arg Glu Val Ser Lys Val Cys Pro Glu Glu Ile Pro Ala Val Gln Pro
    50                  55                  60

Glu Glu Thr Pro Glu Gly Val Pro Val Thr Pro Phe Glu Lys Pro Ala
65                  70                  75                  80

Leu Asp Glu Ala Gln Lys Glu Gln Lys Thr Gln Lys Ile Leu Asp Gln
                85                  90                  95

Leu Pro Gln Glu Leu Asp Gln Leu Asp Arg Tyr Ile Gln Glu Ala Phe
            100                 105                 110

Ala Cys Leu Gly Pro Leu Lys Asp Leu Lys Tyr Glu Asp Gln Gly Phe
        115                 120                 125

Leu Gln Asp Val Lys Glu Glu Phe Gln Val Phe Asp Phe Val Gln Lys
    130                 135                 140

Asp Met Ile Ala Glu Phe Val Glu Leu Gln Gln Ile Leu Cys Gln Glu
145                 150                 155                 160
```

```
Gly Arg Leu Leu Glu Phe Val Ile Asn Gln Thr Arg Tyr Ile Gly Arg
            165                 170                 175

Asp Leu Phe Lys Arg Glu Asp Ser Leu Tyr Lys Leu Trp Glu Trp Leu
        180                 185                 190

Gly Tyr Leu Pro Ser Gly Asp Val Arg Gly Glu Arg Leu Lys Lys Ser
            195                 200                 205

Ala Arg Glu Val Val Asp Arg Phe Met Arg Thr Thr Cys Asn Ile Arg
210                 215                 220

Lys Ile Ala Met Thr Phe Asp Arg His Val Tyr Ser Val Ala Lys Thr
225                 230                 235                 240

Ala Phe Glu Lys Ala Phe Gly Ala Leu Glu Thr Cys Val Tyr Glu Ser
                245                 250                 255

Met Arg Glu Ser Tyr Arg Glu Ala Phe Cys Glu Tyr Glu Lys Ala Lys
            260                 265                 270

Leu Leu Gly Asp Glu Glu Lys Ser Ala His Ala Glu Gln Arg Phe Gln
        275                 280                 285

Asp Ile Lys Asn Arg Trp Glu Asp Val Lys Asp Ala Phe Phe Trp Val
    290                 295                 300

Lys Glu Asp Gly Lys Ile Glu Ile Asp Ala Ile Gly Asn Ser Cys
305                 310                 315                 320

Lys Trp Ser Glu Arg Tyr Glu His Arg Ile Thr Arg Ala Arg Trp
                325                 330                 335

Tyr Lys Val Ala Glu His Gln Leu Phe Asn Ala Thr Met Arg Val Lys
            340                 345                 350

Asp Ser Leu Arg Glu His Asn Glu Ala Arg Val Ala Phe Glu Lys Glu
        355                 360                 365

Arg Ser Lys Glu Asn Gln Arg Gln Val Gln Lys Lys Glu Lys Arg
    370                 375                 380

Leu Arg Asp Leu Lys Glu Leu His Asp Gln Glu Leu Pro Arg Ala Gln
385                 390                 395                 400

Glu Arg Leu Arg Glu Leu Gln Ala Leu Tyr Pro Glu Ile Ala Val Ser
                405                 410                 415

Val Val Glu Ala Arg Arg Glu Val Ala Ser Asp Leu Glu Lys Ala His
            420                 425                 430

Glu Ser Ile Asp Lys His Tyr Gln Ser Cys Val Arg Glu Gln Glu Leu
        435                 440                 445

Tyr

<210> SEQ ID NO 108
<211> LENGTH: 344
<212> TYPE: PRT
<213> ORGANISM: Chlamydia pneumoniae

<400> SEQUENCE: 108

Met Glu Asn Ala Met Ser Ser Phe Val Tyr Asn Gly Pro Ser Trp
1               5                   10                  15

Ile Leu Lys Thr Ser Val Ala Gln Glu Val Phe Lys Lys His Gly Lys
            20                  25                  30

Gly Ile Gln Val Leu Leu Ser Thr Ser Val Met Leu Phe Ile Gly Leu
        35                  40                  45

Gly Val Cys Ala Phe Ile Phe Pro Gln Tyr Leu Ile Val Phe Val Leu
    50                  55                  60

Thr Ile Ala Leu Leu Met Leu Ala Ile Ser Leu Val Leu Phe Leu Leu
65                  70                  75                  80
```

```
Ile Arg Ser Val Arg Ser Ser Met Val Asp Arg Leu Trp Cys Ser Glu
            85                  90                  95

Lys Gly Tyr Ala Leu His Gln His Glu Asn Gly Pro Phe Leu Asp Val
            100                 105                 110

Lys Arg Val Gln Gln Ile Leu Leu Arg Ser Pro Tyr Ile Lys Val Arg
            115                 120                 125

Ala Leu Trp Pro Ser Gly Asp Ile Pro Glu Asp Pro Ser Gln Ala Ala
            130                 135                 140

Val Leu Leu Leu Ser Pro Trp Thr Phe Phe Ser Ser Val Asp Val Glu
145                 150                 155                 160

Ala Leu Leu Pro Ser Pro Gln Glu Lys Glu Gly Lys Tyr Ile Asp Pro
                165                 170                 175

Val Leu Pro Lys Leu Ser Arg Ile Glu Arg Val Ser Leu Leu Val Phe
            180                 185                 190

Leu Ser Ala Phe Thr Leu Asp Asp Leu Asn Glu Gln Gly Val Asn Pro
            195                 200                 205

Leu Met Asn Asn Glu Glu Phe Leu Phe Phe Ile Asn Lys Lys Ala Arg
            210                 215                 220

Glu His Gly Ile Gln Asp Leu Lys His Glu Ile Met Ser Ser Leu Glu
225                 230                 235                 240

Lys Thr Gly Val Pro Leu Asp Pro Ser Met Ser Phe Gln Val Ser Gln
            245                 250                 255

Ala Met Phe Ser Val Tyr Arg Tyr Leu Arg Gln Arg Asp Leu Thr Thr
            260                 265                 270

Ser Glu Leu Arg Cys Phe His Leu Leu Ser Cys Phe Lys Gly Asp Val
            275                 280                 285

Val His Cys Leu Ala Ser Phe Glu Asn Pro Lys Asp Leu Ala Asp Ser
            290                 295                 300

Asp Phe Leu Glu Ala Cys Lys Asn Val Glu Trp Gly Glu Phe Ile Ser
305                 310                 315                 320

Ala Cys Glu Lys Ala Leu Leu Lys Asn Pro Gln Gly Ile Ser Ile Lys
            325                 330                 335

Asp Leu Lys Gln Phe Leu Val Arg
            340

<210> SEQ ID NO 109
<211> LENGTH: 325
<212> TYPE: PRT
<213> ORGANISM: Chlamydia pneumoniae

<400> SEQUENCE: 109

Met Ile Glu Phe Ala Phe Val Pro His Thr Ser Val Thr Ala Asp Arg
1               5                   10                  15

Ile Glu Asp Arg Met Ala Cys Arg Met Asn Lys Leu Ser Thr Leu Ala
            20                  25                  30

Ile Thr Ser Leu Cys Val Leu Ile Ser Ser Val Cys Ile Met Ile Gly
            35                  40                  45

Ile Leu Cys Ile Ser Gly Thr Val Gly Thr Tyr Ala Phe Val Val Gly
            50                  55                  60

Ile Ile Phe Ser Val Leu Ala Leu Val Ala Cys Val Phe Phe Leu Tyr
65                  70                  75                  80

Phe Phe Tyr Phe Ser Ser Glu Glu Phe Lys Cys Ala Ser Ser Gln Glu
            85                  90                  95

Phe Arg Phe Leu Pro Ile Pro Ala Val Val Ser Ala Leu Arg Ser Tyr
            100                 105                 110
```

Glu Tyr Ile Ser Gln Asp Ala Ile Asn Asp Val Ile Lys Asp Thr Met
            115                 120                 125

Gln Leu Ser Thr Leu Ser Ser Leu Leu Asp Pro Glu Ala Phe Phe Leu
        130                 135                 140

Glu Phe Pro Tyr Phe Asn Ser Leu Ile Val Asn His Ser Met Lys Glu
145                 150                 155                 160

Ala Asp Arg Leu Ser Arg Glu Ala Phe Leu Ile Leu Gly Glu Ile
                165                 170                 175

Thr Trp Lys Asp Cys Glu Thr Lys Ile Leu Pro Trp Leu Lys Asp Pro
            180                 185                 190

Asn Ile Thr Pro Asp Asp Phe Trp Lys Leu Lys Asp His Phe Asp
            195                 200                 205

Leu Lys Asp Phe Lys Lys Arg Ile Ala Thr Trp Ile Arg Lys Ala Tyr
    210                 215                 220

Pro Glu Ile Arg Leu Pro Lys Lys His Cys Leu Asp Lys Ser Ile Tyr
225                 230                 235                 240

Lys Gly Cys Cys Lys Phe Leu Leu Leu Ser Glu Asn Asp Val Gln Tyr
                245                 250                 255

Gln Arg Leu Leu His Lys Val Cys Tyr Phe Ser Gly Glu Phe Pro Ala
            260                 265                 270

Met Val Leu Gly Leu Gly Ser Glu Val Pro Met Val Leu Gly Leu Pro
        275                 280                 285

Lys Val Pro Lys Asp Leu Thr Trp Glu Met Phe Met Glu Asn Met Pro
290                 295                 300

Val Leu Leu Gln Ser Lys Arg Glu Gly His Trp Lys Ile Ser Leu Glu
305                 310                 315                 320

Asp Val Ala Ser Leu
            325

<210> SEQ ID NO 110
<211> LENGTH: 264
<212> TYPE: PRT
<213> ORGANISM: Chlamydia pneumoniae

<400> SEQUENCE: 110

Met Lys Asn Val Gly Ser Glu Cys Ser Gln Pro Leu Val Met Glu Leu
1               5                   10                  15

Asn Thr Gln Pro Leu Arg Asn Leu Cys Glu Ser Arg Leu Val Lys Ile
            20                  25                  30

Thr Ser Phe Val Ile Ala Leu Leu Ala Leu Val Gly Gly Ile Thr Leu
        35                  40                  45

Thr Ala Leu Ala Gly Ala Gly Ile Leu Ser Phe Leu Pro Trp Leu Val
    50                  55                  60

Leu Gly Ile Val Leu Val Leu Cys Ala Leu Phe Leu Leu Phe Ser
65                  70                  75                  80

Tyr Lys Phe Cys Pro Ile Lys Glu Leu Gly Val Val Tyr Asn Thr Asp
                85                  90                  95

Ser Gln Ile His Gln Trp Phe Lys Gln Arg Asn Lys Asp Leu Glu
            100                 105                 110

Lys Ala Thr Glu Asn Pro Glu Leu Phe Gly Glu Asn Arg Ala Glu Asp
        115                 120                 125

Asn Asn Arg Ser Ala Arg Ser Gln Val Lys Glu Thr Leu Arg Asp Cys
    130                 135                 140

Asp Gly Asn Val Leu Lys Lys Ile Tyr Glu Arg Asn Leu Asp Val Leu

```
                145                 150                 155                 160
Leu Phe Met Asn Trp Val Pro Lys Thr Met Asp Asp Val Asp Pro Val
                    165                 170                 175

Ser Glu Asp Ser Ile Arg Thr Val Ile Ser Cys Tyr Lys Leu Ile Lys
                180                 185                 190

Ala Cys Lys Pro Glu Phe Arg Ser Leu Ile Ser Glu Leu Leu Arg Ala
            195                 200                 205

Met Gln Ser Gly Leu Gly Leu Leu Ser Arg Cys Ser Arg Tyr Gln Glu
        210                 215                 220

Arg Ala Lys Thr Val Ser His Lys Asp Ala Pro Leu Phe Cys Pro Thr
225                 230                 235                 240

His Ser Tyr Tyr Arg Asp Gly Tyr Leu Thr Pro Leu Arg Ala Gly Pro
                245                 250                 255

Arg Tyr Ile Ile Asn Arg Ala Ile
                260

<210> SEQ ID NO 111
<211> LENGTH: 334
<212> TYPE: PRT
<213> ORGANISM: Chlamydia pneumoniae

<400> SEQUENCE: 111

Met Ser Tyr Asp Thr Leu Phe Lys Asn Leu Glu Lys Glu Asp Ser Val
1               5                   10                  15

His Lys Ile Cys Asn Glu Ile Phe Ala Leu Val Pro Arg Leu Asn Thr
            20                  25                  30

Ile Ala Cys Thr Glu Ala Ile Ile Lys Asn Leu Pro Lys Ala Asp Ile
        35                  40                  45

His Val His Leu Pro Gly Thr Ile Thr Pro Gln Leu Ala Trp Ile Leu
    50                  55                  60

Gly Val Lys Asn Gly Phe Leu Lys Trp Ser Tyr Asn Ser Trp Thr Asn
65                  70                  75                  80

His Arg Leu Leu Ser Pro Lys Asn Pro His Lys Gln Tyr Ser Asn Ile
                85                  90                  95

Phe Arg Asn Phe Gln Asp Ile Cys His Glu Lys Asp Pro Asp Leu Ser
            100                 105                 110

Val Leu Gln Tyr Asn Ile Leu Asn Tyr Asp Phe Asn Ser Phe Asp Arg
        115                 120                 125

Val Met Ala Thr Val Gln Gly His Arg Phe Pro Pro Gly Gly Ile Gln
    130                 135                 140

Asn Glu Glu Asp Leu Leu Leu Ile Phe Asn Asn Tyr Leu Gln Gln Cys
145                 150                 155                 160

Leu Asp Asp Thr Ile Val Tyr Thr Glu Val Gln Gln Asn Ile Arg Leu
                165                 170                 175

Ala His Val Leu Tyr Pro Ser Leu Pro Glu Lys His Ala Arg Met Lys
            180                 185                 190

Phe Tyr Gln Ile Leu Tyr Arg Ala Ser Gln Thr Phe Ser Lys His Gly
        195                 200                 205

Ile Thr Leu Arg Phe Leu Asn Cys Phe Asn Lys Thr Phe Ala Pro Gln
    210                 215                 220

Ile Asn Thr Gln Glu Pro Ala Gln Glu Ala Val Gln Trp Leu Gln Glu
225                 230                 235                 240

Val Asp Ser Thr Phe Pro Gly Leu Phe Val Gly Ile Gln Ser Ala Gly
                245                 250                 255
```

```
Ser Glu Ser Ala Pro Gly Ala Cys Pro Lys Arg Leu Ala Ser Gly Tyr
            260                 265                 270

Arg Asn Ala Tyr Asp Ser Gly Phe Gly Cys Glu Ala His Ala Gly Glu
            275                 280                 285

Gly Ile Glu Thr Arg Thr Ile Phe Ser Ser Ala Lys Val Asn Pro Glu
            290                 295                 300

Gly Leu Ile Glu Ile Thr Arg Val Thr Phe Ser Ser Leu Lys Arg Lys
305                 310                 315                 320

Gln Pro Ser Ser Leu Pro Ile Arg Val Thr Cys Gln Leu Gly
            325                 330

<210> SEQ ID NO 112
<211> LENGTH: 315
<212> TYPE: PRT
<213> ORGANISM: Chlamydia pneumoniae

<400> SEQUENCE: 112

Met Leu Val Glu Leu Glu Ala Leu Lys Arg Glu Phe Ala His Leu Lys
1               5                   10                  15

Asp Gln Lys Pro Thr Ser Asp Gln Glu Ile Thr Ser Leu Tyr Gln Cys
            20                  25                  30

Leu Asp His Leu Glu Phe Val Leu Gly Leu Gly Gln Asp Lys Phe
            35                  40                  45

Leu Lys Ala Thr Glu Asp Glu Asp Val Leu Phe Glu Ser Gln Lys Ala
            50                  55                  60

Ile Asp Ala Trp Asn Ala Leu Leu Thr Lys Ala Arg Asp Val Leu Gly
65                  70                  75                  80

Leu Gly Asp Ile Gly Ala Ile Tyr Gln Thr Ile Glu Phe Leu Gly Ala
                    85                  90                  95

Tyr Leu Ser Lys Val Asn Arg Arg Ala Phe Cys Ile Ala Ser Glu Ile
            100                 105                 110

His Phe Leu Lys Thr Ala Ile Arg Asp Leu Asn Ala Tyr Tyr Leu Leu
            115                 120                 125

Asp Phe Arg Trp Pro Leu Cys Lys Ile Glu Glu Phe Val Asp Trp Gly
            130                 135                 140

Asn Asp Cys Val Glu Ile Ala Lys Arg Lys Leu Cys Thr Phe Glu Lys
145                 150                 155                 160

Glu Thr Lys Glu Leu Asn Ser Leu Leu Arg Glu Glu His Ala Met
            165                 170                 175

Glu Lys Cys Ser Ile Gln Asp Leu Gln Arg Lys Leu Ser Asp Ile Ile
            180                 185                 190

Ile Glu Leu His Asp Val Ser Leu Phe Cys Phe Ser Lys Thr Pro Ser
            195                 200                 205

Gln Glu Glu Tyr Gln Lys Asp Cys Leu Tyr Gln Ser Arg Leu Arg Tyr
            210                 215                 220

Leu Leu Leu Leu Tyr Glu Tyr Thr Leu Leu Cys Lys Thr Ser Thr Asp
225                 230                 235                 240

Phe Gln Glu Gln Ala Arg Ala Lys Glu Glu Phe Ile Arg Glu Lys Phe
            245                 250                 255

Ser Leu Leu Glu Leu Glu Lys Gly Ile Lys Gln Thr Lys Glu Leu Glu
            260                 265                 270

Phe Ala Ile Ala Lys Ser Lys Leu Glu Arg Gly Cys Leu Val Met Arg
            275                 280                 285

Lys Tyr Glu Ala Ala Ala Lys His Ser Leu Asp Ser Met Phe Glu Glu
            290                 295                 300
```

Glu Thr Val Lys Ser Pro Arg Lys Asp Thr Glu
305                 310                 315

<210> SEQ ID NO 113
<211> LENGTH: 419
<212> TYPE: PRT
<213> ORGANISM: Chlamydia pneumoniae

<400> SEQUENCE: 113

Met Lys Cys Ser Pro Leu Thr Leu Val Pro His Ile Phe Leu Lys Asn
1               5                   10                  15

Asp Cys Glu Cys His Arg Ser Cys Ser Leu Lys Ile Arg Thr Ile Ala
            20                  25                  30

Arg Leu Ile Leu Gly Leu Val Leu Ala Leu Val Ser Ala Leu Ser Phe
        35                  40                  45

Val Phe Leu Ala Ala Pro Ile Ser Tyr Ala Ile Gly Gly Thr Leu Ala
50                  55                  60

Leu Ala Ala Ile Val Ile Leu Ile Ile Thr Leu Val Val Ala Leu Leu
65                  70                  75                  80

Ala Lys Ser Lys Val Leu Pro Ile Pro Asn Glu Leu Gln Lys Ile Ile
                85                  90                  95

Tyr Asn Arg Tyr Pro Lys Glu Val Phe Tyr Phe Val Lys Thr His Ser
            100                 105                 110

Leu Thr Val Asn Glu Leu Lys Ile Phe Ile Asn Cys Trp Lys Ser Gly
        115                 120                 125

Thr Asp Leu Pro Pro Asn Leu His Lys Lys Ala Glu Ala Phe Gly Ile
130                 135                 140

Asp Ile Leu Lys Ser Ile Asp Leu Thr Leu Phe Pro Glu Phe Glu Glu
145                 150                 155                 160

Ile Leu Leu Gln Asn Cys Pro Leu Tyr Trp Leu Ser His Phe Ile Asp
                165                 170                 175

Lys Thr Glu Ser Val Ala Gly Glu Ile Gly Leu Asn Lys Thr Gln Lys
            180                 185                 190

Val Tyr Gly Leu Leu Gly Pro Leu Ala Phe His Lys Gly Tyr Thr Thr
        195                 200                 205

Ile Phe His Ser Tyr Thr Arg Pro Leu Leu Thr Leu Ile Ser Glu Ser
210                 215                 220

Gln Tyr Lys Phe Leu Tyr Ser Lys Ala Ser Lys Asn Gln Trp Asp Ser
225                 230                 235                 240

Pro Ser Val Lys Lys Thr Cys Glu Glu Ile Phe Lys Glu Leu Pro His
                245                 250                 255

Asn Met Ile Phe Arg Lys Asp Val Gln Gly Ile Ser Gln Phe Leu Phe
            260                 265                 270

Leu Phe Phe Ser His Gly Ile Thr Trp Glu Gln Ala Gln Met Ile Gln
        275                 280                 285

Leu Ile Asn Pro Asp Asn Trp Lys Met Leu Cys Gln Phe Asp Lys Ala
290                 295                 300

Gly Gly His Cys Ser Met Ala Thr Phe Gly Phe Leu Asn Thr Glu
305                 310                 315                 320

Thr Asn Met Phe Asp Pro Val Ser Ser Asn Tyr Glu Pro Thr Val Asn
            325                 330                 335

Phe Met Thr Trp Lys Glu Leu Lys Val Leu Glu Lys Val Lys Glu
        340                 345                 350

Ser Pro Met His Pro Ala Ser Ala Leu Val Gln Lys Ile Cys Val Asn

```
              355                 360                 365
Thr Thr His His Gln Asn Leu Leu Lys Arg Trp Gln Phe Val Arg Asn
370                 375                 380

Thr Ser Ser Gln Trp Thr Ser Ser Leu Pro Gln Tyr Ala Phe His Ala
385                 390                 395                 400

Gln Thr Tyr Lys Leu Glu Lys Lys Ile Glu Ser Ser Leu Pro Ile Arg
                405                 410                 415

Ser Ser Leu

<210> SEQ ID NO 114
<211> LENGTH: 433
<212> TYPE: PRT
<213> ORGANISM: Chlamydia pneumoniae

<400> SEQUENCE: 114

Met Ser Met Thr Ile Val Pro His Ala Leu Phe Lys Asn His Cys Glu
1               5                   10                  15

Cys His Ser Thr Phe Pro Leu Ser Ser Arg Thr Ile Val Arg Ile Ala
                20                  25                  30

Ile Ala Ser Leu Phe Cys Ile Gly Ala Leu Ala Ala Leu Gly Cys Leu
            35                  40                  45

Ala Pro Pro Val Ser Tyr Ile Val Gly Ser Val Leu Ala Phe Ile Ala
        50                  55                  60

Phe Val Ile Leu Ser Leu Val Ile Leu Ala Leu Ile Phe Gly Glu Lys
65                  70                  75                  80

Lys Leu Pro Pro Thr Pro Arg Ile Ile Pro Asp Arg Phe Thr His Val
                85                  90                  95

Ile Asp Glu Ala Tyr Gly Leu Ser Ile Ser Ala Phe Val Arg Glu Gln
            100                 105                 110

Gln Val Thr Leu Ala Glu Phe Arg Gln Phe Ser Thr Ala Leu Leu Cys
        115                 120                 125

Asn Ile Ser Pro Glu Glu Lys Ile Lys Gln Leu Pro Ser Glu Leu Arg
130                 135                 140

Ser Lys Val Glu Ser Phe Gly Ile Ser Arg Leu Ala Gly Asp Leu Glu
145                 150                 155                 160

Lys Asn Asn Trp Pro Ile Phe Glu Asp Leu Leu Ser Gln Thr Cys Pro
                165                 170                 175

Leu Tyr Trp Leu Gln Lys Phe Ile Ser Ala Gly Asp Pro Gln Val Cys
            180                 185                 190

Arg Asp Leu Gly Val Pro Arg Glu Cys Tyr Gly Tyr Tyr Trp Leu Gly
        195                 200                 205

Pro Leu Gly Tyr Ser Thr Ala Lys Ala Thr Ile Phe Cys Lys Glu Thr
        210                 215                 220

His His Ile Leu Gln Gln Leu Thr Lys Glu Asp Val Leu Leu Leu Lys
225                 230                 235                 240

Asn Lys Ala Leu Gln Glu Lys Trp Asp Thr Asp Glu Val Lys Ala Ile
                245                 250                 255

Val Glu Arg Ile Tyr Thr Thr Tyr Ala Arg Gly Thr Leu Lys Thr
            260                 265                 270

Glu Ala Gly Gly Leu Thr Lys Glu Thr Ile Ser Lys Glu Leu Leu Leu
        275                 280                 285

Leu Ser Leu His Gly Tyr Ser Phe Asp Gln Leu Gln Leu Ile Thr Gln
        290                 295                 300

Leu Pro Arg Asp Ala Trp Asp Trp Leu Cys Phe Val Asp Asn Ser Thr
```

-continued

```
                305                 310                 315                 320
Ala Tyr Asn Leu Gln Leu Cys Ala Leu Val Gly Ala Leu Ser Ser Gln
                    325                 330                 335

Asn Leu Leu Asp Glu Ser Ser Ile Asp Phe Asp Val Asn Leu Gly Leu
                340                 345                 350

Tyr Val Ile Gln Asp Leu Lys Glu Ala Val Gln Ala Phe Ser Ala Ser
                355                 360                 365

Asp Glu Pro Lys Lys Glu Leu Gly Lys Phe Leu Arg His Leu Ser
            370                 375                 380

Ser Val Ser Lys Arg Leu Glu Ser Val Leu Arg Gln Gly Leu His Arg
385                 390                 395                 400

Ile Ala Leu Glu His Gly Asn Ala Arg Ala Arg Val Tyr Asp Val Asn
                    405                 410                 415

Phe Val Thr Gly Ala Arg Ile His Arg Lys Thr Ser Ile Phe Phe Lys
                420                 425                 430

Asp

<210> SEQ ID NO 115
<211> LENGTH: 435
<212> TYPE: PRT
<213> ORGANISM: Chlamydia pneumoniae

<400> SEQUENCE: 115

Met Phe Ser Arg Trp Ile Thr Leu Phe Leu Leu Phe Ile Ser Leu Thr
1               5                   10                  15

Gly Cys Ser Ser Tyr Ser Ser Lys His Lys Gln Ser Leu Ile Ile Pro
                20                  25                  30

Ile His Asp Asp Pro Val Ala Phe Ser Pro Glu Gln Ala Lys Arg Ala
            35                  40                  45

Met Asp Leu Ser Ile Ala Gln Leu Leu Phe Asp Gly Leu Thr Arg Glu
        50                  55                  60

Thr His Arg Glu Ser Asn Asp Leu Glu Leu Ala Ile Ala Ser Arg Tyr
65                  70                  75                  80

Thr Val Ser Glu Asp Phe Cys Ser Tyr Thr Phe Phe Ile Lys Asp Ser
                85                  90                  95

Ala Leu Trp Ser Asp Gly Thr Pro Ile Thr Ser Glu Asp Ile Arg Asn
                100                 105                 110

Ala Trp Glu Tyr Ala Gln Glu Asn Ser Pro His Ile Gln Ile Phe Gln
            115                 120                 125

Gly Leu Asn Phe Ser Thr Pro Ser Ser Asn Ala Ile Thr Ile His Leu
        130                 135                 140

Asp Ser Pro Asn Pro Asp Phe Pro Lys Leu Leu Ala Phe Pro Ala Phe
145                 150                 155                 160

Ala Ile Phe Lys Pro Glu Asn Pro Lys Leu Phe Ser Gly Pro Tyr Thr
                165                 170                 175

Leu Val Glu Tyr Phe Pro Gly His Asn Ile His Leu Lys Lys Asn Pro
                180                 185                 190

Asn Tyr Tyr Asp Tyr His Cys Val Ser Ile Asn Ser Ile Lys Leu Leu
            195                 200                 205

Ile Ile Pro Asp Ile Tyr Thr Ala Ile His Leu Leu Asn Arg Gly Lys
        210                 215                 220

Val Asp Trp Val Gly Gln Pro Trp His Gln Gly Ile Pro Trp Glu Leu
225                 230                 235                 240

His Lys Gln Ser Gln Tyr His Tyr Tyr Thr Tyr Pro Val Glu Gly Ala
```

```
                   245                 250                 255
Phe Trp Leu Cys Leu Asn Thr Lys Ser Pro His Leu Asn Asp Leu Gln
            260                 265                 270

Asn Arg His Arg Leu Ala Thr Cys Ile Asp Lys Arg Ser Ile Ile Glu
        275                 280                 285

Glu Ala Leu Gln Gly Thr Gln Gln Pro Ala Glu Thr Leu Ser Arg Gly
    290                 295                 300

Ala Pro Gln Pro Asn Gln Tyr Lys Lys Gln Lys Pro Leu Thr Pro Gln
305                 310                 315                 320

Glu Lys Leu Val Leu Thr Tyr Pro Ser Asp Ile Leu Arg Cys Gln Arg
                325                 330                 335

Ile Ala Glu Ile Leu Lys Glu Gln Trp Lys Ala Ala Gly Ile Asp Leu
            340                 345                 350

Ile Leu Glu Gly Leu Glu Tyr His Leu Phe Val Asn Lys Arg Lys Val
        355                 360                 365

Gln Asp Tyr Ala Ile Ala Thr Gln Thr Gly Val Ala Tyr Tyr Pro Gly
    370                 375                 380

Ala Asn Leu Ile Ser Glu Glu Asp Lys Leu Leu Gln Asn Phe Glu Ile
385                 390                 395                 400

Ile Pro Ile Tyr Tyr Leu Ser Tyr Asp Tyr Leu Thr Gln Asp Phe Ile
                405                 410                 415

Glu Gly Val Ile Tyr Asn Ala Ser Gly Ala Val Asp Leu Lys Tyr Thr
            420                 425                 430

Tyr Phe Pro
        435

<210> SEQ ID NO 116
<211> LENGTH: 819
<212> TYPE: PRT
<213> ORGANISM: Chlamydia trachomatis

<400> SEQUENCE: 116

Met Arg Tyr Asp Pro Gly Leu Ile Glu Glu Lys Trp Gln Lys Phe Trp
1               5                   10                  15

Glu Asn Glu Gln Val Phe Lys Ala Glu Glu Asp Glu Thr Lys Thr Lys
            20                  25                  30

Tyr Tyr Val Leu Asp Met Phe Pro Tyr Pro Ser Gly Ala Gly Leu His
        35                  40                  45

Val Gly His Leu Ile Gly Tyr Thr Ala Thr Asp Ile Val Ala Arg Tyr
    50                  55                  60

Lys Arg Ala Gln Gly Phe Ser Val Leu His Pro Met Gly Trp Asp Ser
65                  70                  75                  80

Phe Gly Leu Pro Ala Glu Gln Tyr Ala Ile Arg Thr Gly Thr His Pro
                85                  90                  95

Arg Glu Thr Thr Glu Lys Asn Ile Ala Asn Phe Lys Lys Gln Leu Thr
            100                 105                 110

Ala Met Gly Phe Ser Tyr Asp Glu Ser Arg Glu Phe Ala Thr Ser Asp
        115                 120                 125

Pro Glu Tyr Tyr Lys Trp Thr Gln Lys Leu Phe Leu Ile Leu Tyr Glu
    130                 135                 140

Lys Gly Leu Ala Tyr Met Ala Asp Met Ala Val Asn Tyr Cys Pro Glu
145                 150                 155                 160

Leu Gly Thr Val Leu Ser Asn Glu Glu Ile Glu Asn Gly Phe Ser Val
                165                 170                 175
```

-continued

```
Asp Gly Gly Tyr Pro Val Glu Arg Arg Met Leu Arg Gln Trp Val Leu
                180                 185                 190

Arg Ile Thr Ala Phe Ala Asp Gln Leu Leu Glu Gly Leu Asp Glu Leu
            195                 200                 205

Asp Trp Pro Glu Ser Val Lys Gln Leu Gln Lys Asn Trp Ile Gly Lys
        210                 215                 220

Ser Ser Gly Ala Ser Val Asn Phe Ala Thr Glu His Gly Val Ile Glu
225                 230                 235                 240

Val Phe Thr Thr Arg Pro Asp Thr Leu Ile Gly Val Ser Phe Leu Ala
                245                 250                 255

Leu Ala Pro Glu His Pro Leu Val Asp Leu Leu Thr Ser Asp Glu Gln
            260                 265                 270

Lys Ala Val Val Ala Gln Tyr Ile Lys Glu Thr Gln Ser Lys Ser Glu
        275                 280                 285

Arg Asp Arg Ile Ser Glu Met Lys Thr Lys Ser Gly Val Phe Thr Gly
290                 295                 300

Ser Tyr Ala Lys His Pro Val Thr His Lys Leu Ile Pro Ile Trp Ile
305                 310                 315                 320

Ala Asp Tyr Val Leu Ile Gly Phe Gly Ser Gly Ala Val Met Gly Val
                325                 330                 335

Pro Ala His Asp Glu Arg Asp Leu Leu Phe Ala Glu Gln Phe Asn Leu
            340                 345                 350

Pro Val Val Ser Val Leu Asn Lys Glu Gly Val Cys Ile Asn Ser Cys
        355                 360                 365

Cys Glu Gly Phe His Leu Asp Gly Leu Ser Gly Glu Glu Ala Lys Gln
370                 375                 380

Tyr Val Ile Asn Phe Leu Glu Glu Asn His Leu Gly Ala Ala Lys Ile
385                 390                 395                 400

Ala Tyr Lys Leu Arg Asp Trp Leu Phe Ser Arg Gln Arg Tyr Trp Gly
                405                 410                 415

Glu Pro Ile Pro Ile Ile His Phe Glu Asp Gly Ser Cys Arg Pro Leu
            420                 425                 430

Arg Asp Tyr Glu Leu Pro Leu Leu Pro Glu Ile Gln Asp Tyr Arg
        435                 440                 445

Pro Glu Gly Val Gly Gln Gly Pro Leu Ala Lys Val Arg Glu Trp Val
        450                 455                 460

Gln Val Phe Asp Thr Glu Thr Gln Arg Ala Gly Lys Arg Glu Thr His
465                 470                 475                 480

Thr Met Pro Gln Trp Ala Gly Ser Cys Trp Tyr Tyr Leu Arg Phe Cys
                485                 490                 495

Asp Ala His Asn Ser Ala Ala Pro Trp Ala Lys Glu Lys Glu Gln Tyr
            500                 505                 510

Trp Met Pro Val Asp Leu Tyr Ile Gly Gly Ala Glu His Ala Val Leu
        515                 520                 525

His Leu Leu Tyr Ala Arg Phe Trp His Gln Val Phe Tyr Glu Ala Gly
530                 535                 540

Ile Val Ser Thr Pro Glu Pro Phe Lys Lys Leu Val Asn Gln Gly Leu
545                 550                 555                 560

Val Leu Ala Thr Ser Tyr Arg Ile Pro Gly Lys Gly Tyr Ile Tyr Pro
                565                 570                 575

Glu Ile Ala Lys Glu Glu Asn Gly Lys Trp Val Ala Pro Ser Gly Glu
            580                 585                 590

Glu Leu Asp Val Arg Gln Glu Lys Met Ser Lys Ser Lys Leu Asn Gly
```

-continued

```
            595                 600                 605
Val Asp Pro Gln Ile Leu Ile Asp Glu Phe Gly Ala Asp Ala Val Arg
610                 615                 620

Met Tyr Ala Met Phe Ser Gly Pro Leu Asp Lys Asn Lys Leu Trp Ser
625                 630                 635                 640

Asn Gln Gly Val Ala Gly Cys Arg Arg Phe Leu Asn Arg Phe Tyr Glu
                645                 650                 655

Met Val Ser Ser Asp Arg Val Lys Glu Asp Asn Asn Phe Glu Gly Leu
                660                 665                 670

Ser Leu Ala His Lys Leu Val Gln Arg Val Thr Asp Ala Ile Glu Lys
                675                 680                 685

Leu Ser Leu Asn Thr Ile Pro Ser Ser Phe Met Glu Phe Ile Asn Asp
690                 695                 700

Phe Val Lys Leu Ala Val Tyr Pro Lys Ser Ala Val Glu Met Ala Val
705                 710                 715                 720

Arg Ala Leu Ala Pro Ile Ala Pro His Ile Ser Glu Glu Leu Trp Val
                725                 730                 735

Leu Leu Gly Asn Ser Pro Gly Val Gln Lys Ser Gly Trp Pro Ser Val
                740                 745                 750

Leu Pro Glu Tyr Leu Glu Gly Gln Thr Val Thr Ile Val Gln Val
                755                 760                 765

Asn Gly Lys Leu Arg Ala Arg Leu Asp Ile Met Lys Asp Ala Ser Lys
770                 775                 780

Glu Glu Val Leu Ala Leu Ala Arg Glu Ser Ala Ser Lys Tyr Leu Glu
785                 790                 795                 800

Gly Cys Glu Val Lys Lys Ala Ile Phe Val Pro Ala Arg Leu Val Asn
                805                 810                 815

Phe Val Val

<210> SEQ ID NO 117
<211> LENGTH: 232
<212> TYPE: PRT
<213> ORGANISM: Chlamydia trachomatis

<400> SEQUENCE: 117

Met Ser Thr Pro Ser Ser Asn Asn Ser Lys Lys Pro Ser Ala Ser Phe
1               5                   10                  15

Asn Lys Lys Ser Arg Ser Arg Leu Ala Glu Ile Ala Ala Gln Lys Lys
                20                  25                  30

Ala Lys Ala Glu Asp Leu Glu Gln Lys Tyr Pro Val Pro Thr Glu Glu
            35                  40                  45

Glu Thr Lys Gln Val Leu Met Asp Ile Leu Gln Gly Leu Ser Asn Gly
        50                  55                  60

Leu Thr Leu Gln Gln Ile Leu Gly Leu Ser Asp Val Leu Leu Glu Glu
65                  70                  75                  80

Ile Tyr Thr Val Ala Tyr Thr Phe Tyr Ser Gln Gly Lys Tyr Gln Glu
                85                  90                  95

Ala Ile Gly Leu Phe Gln Ile Leu Thr Ala Ser Lys Pro Gln Cys Tyr
            100                 105                 110

Lys Tyr Ile Leu Gly Leu Ser Ser Cys Tyr His Gln Leu Lys Met Tyr
        115                 120                 125

Asp Glu Ala Ala Phe Gly Phe Leu Ala Phe Asp Ala Gln Pro Glu
    130                 135                 140

Asn Pro Ile Pro Pro Tyr Tyr Ile Ala Asp Ser Leu Met Lys Leu Asn
```

-continued

```
             145                 150                 155                 160
Gln Pro Glu Glu Ser Gln Asp Phe Leu Asp Ile Thr Ile Asp Met Cys
                165                 170                 175
Lys Asn Lys Pro Glu Tyr Lys Val Leu Lys Asp Arg Cys Ser Ile Met
            180                 185                 190
Lys Gln Ser Leu Asp Ala Val Leu Lys Lys Glu Lys Ser Ala Lys Gly
        195                 200                 205
Ser Glu Thr Gln Ala Ser Ser Pro Lys Asn Thr Lys Ala Lys Lys Ala
    210                 215                 220
Ala Ser Asn Lys Lys Ala Lys
225                 230

<210> SEQ ID NO 118
<211> LENGTH: 393
<212> TYPE: PRT
<213> ORGANISM: Chlamydia trachomatis

<400> SEQUENCE: 118

Met Lys Lys Leu Leu Lys Ser Val Leu Val Phe Ala Ala Leu Ser Ser
1               5                   10                  15
Ala Ser Ser Leu Gln Ala Leu Pro Val Gly Asn Pro Ala Glu Pro Ser
            20                  25                  30
Leu Met Ile Asp Gly Ile Leu Trp Glu Gly Phe Gly Gly Asp Pro Cys
        35                  40                  45
Asp Pro Cys Ala Thr Trp Cys Asp Ala Ile Ser Met Arg Val Gly Tyr
    50                  55                  60
Tyr Gly Asp Phe Val Phe Asp Arg Val Leu Lys Thr Asp Val Asn Lys
65                  70                  75                  80
Glu Phe Gln Met Gly Ala Lys Pro Thr Thr Asp Thr Gly Asn Ser Ala
                85                  90                  95
Ala Pro Ser Thr Leu Thr Ala Arg Glu Asn Pro Ala Tyr Gly Arg His
            100                 105                 110
Met Gln Asp Ala Glu Met Phe Thr Asn Ala Ala Cys Met Ala Leu Asn
        115                 120                 125
Ile Trp Asp Arg Phe Asp Val Phe Cys Thr Leu Gly Ala Thr Ser Gly
    130                 135                 140
Tyr Leu Lys Gly Asn Ser Ala Ser Phe Asn Leu Val Gly Leu Phe Gly
145                 150                 155                 160
Asp Asn Glu Asn Gln Lys Thr Val Lys Ala Glu Ser Val Pro Asn Met
                165                 170                 175
Ser Phe Asp Gln Ser Val Val Glu Leu Tyr Thr Asp Thr Thr Phe Ala
            180                 185                 190
Trp Ser Val Gly Ala Arg Ala Ala Leu Trp Glu Cys Gly Cys Ala Thr
        195                 200                 205
Leu Gly Ala Ser Phe Gln Tyr Ala Gln Ser Lys Pro Lys Val Glu Glu
    210                 215                 220
Leu Asn Val Leu Cys Asn Ala Ala Glu Phe Thr Ile Asn Lys Pro Lys
225                 230                 235                 240
Gly Tyr Val Gly Lys Glu Phe Pro Leu Asp Leu Thr Ala Gly Thr Asp
                245                 250                 255
Ala Ala Thr Gly Thr Lys Asp Ala Ser Ile Asp Tyr His Glu Trp Gln
            260                 265                 270
Ala Ser Leu Ala Leu Ser Tyr Arg Leu Asn Met Phe Thr Pro Tyr Ile
        275                 280                 285
```

```
Gly Val Lys Trp Ser Arg Ala Ser Phe Asp Ala Asp Thr Ile Arg Ile
            290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
            355                 360                 365

Asp Lys Tyr Ala Val Thr Val Glu Thr Arg Leu Ile Asp Glu Arg Ala
            370                 375                 380

Ala His Val Asn Ala Gln Phe Arg Phe
385                 390

<210> SEQ ID NO 119
<211> LENGTH: 1751
<212> TYPE: PRT
<213> ORGANISM: Chlamydia trachomatis

<400> SEQUENCE: 119

Met Lys Trp Leu Ser Ala Thr Ala Val Phe Ala Ala Val Leu Pro Ser
1               5                   10                  15

Val Ser Gly Phe Cys Phe Pro Glu Pro Lys Glu Leu Asn Phe Ser Arg
            20                  25                  30

Val Gly Thr Ser Ser Ser Thr Phe Thr Glu Thr Val Gly Glu Ala
            35                  40                  45

Gly Ala Glu Tyr Ile Val Ser Gly Asn Ala Ser Phe Thr Lys Phe Thr
        50                  55                  60

Asn Ile Pro Thr Thr Asp Thr Thr Pro Thr Asn Ser Asn Ser Ser
65                  70                  75                  80

Ser Ser Asn Gly Glu Thr Ala Ser Val Ser Glu Asp Ser Asp Ser Thr
                85                  90                  95

Thr Thr Pro Asp Pro Lys Gly Gly Gly Ala Phe Tyr Asn Ala His
            100                 105                 110

Ser Gly Val Leu Ser Phe Met Thr Arg Ser Gly Thr Glu Gly Ser Leu
            115                 120                 125

Thr Leu Ser Glu Ile Lys Ile Thr Gly Glu Gly Gly Ala Ile Phe Ser
130                 135                 140

Gln Gly Glu Leu Leu Phe Thr Asp Leu Thr Gly Leu Thr Ile Gln Asn
145                 150                 155                 160

Asn Leu Ser Gln Leu Ser Gly Gly Ala Ile Phe Gly Glu Ser Thr Ile
                165                 170                 175

Ser Leu Ser Gly Ile Thr Lys Ala Thr Phe Ser Ser Asn Ser Ala Glu
            180                 185                 190

Val Pro Ala Pro Val Lys Lys Pro Thr Glu Pro Lys Ala Gln Thr Ala
            195                 200                 205

Ser Glu Thr Ser Gly Ser Ser Ser Ser Gly Asn Asp Ser Val Ser
            210                 215                 220

Ser Pro Ser Ser Ser Arg Ala Glu Pro Ala Ala Ala Asn Leu Gln Ser
225                 230                 235                 240

His Phe Ile Cys Ala Thr Ala Thr Pro Ala Ala Gln Thr Asp Thr Glu
                245                 250                 255

Thr Ser Thr Pro Ser His Lys Pro Gly Ser Gly Gly Ala Ile Tyr Ala
            260                 265                 270
```

```
Lys Gly Asp Leu Thr Ile Ala Asp Ser Gln Glu Val Leu Phe Ser Ile
            275                 280                 285
Asn Lys Ala Thr Lys Asp Gly Ala Ile Phe Ala Glu Lys Asp Val
        290                 295                 300
Ser Phe Glu Asn Ile Thr Ser Leu Lys Val Gln Thr Asn Gly Ala Glu
305                 310                 315                 320
Glu Lys Gly Gly Ala Ile Tyr Ala Lys Gly Asp Leu Ser Ile Gln Ser
                325                 330                 335
Ser Lys Gln Ser Leu Phe Asn Ser Asn Tyr Ser Lys Gln Gly Gly Gly
            340                 345                 350
Ala Leu Tyr Val Glu Gly Asp Ile Asn Phe Gln Asp Leu Glu Glu Ile
            355                 360                 365
Arg Ile Lys Tyr Asn Lys Ala Gly Thr Phe Glu Thr Lys Lys Ile Thr
            370                 375                 380
Leu Pro Lys Ala Gln Ala Ser Ala Gly Asn Ala Asp Ala Trp Ala Ser
385                 390                 395                 400
Ser Ser Pro Gln Ser Gly Ser Gly Ala Thr Thr Val Ser Asn Ser Gly
                405                 410                 415
Asp Ser Ser Ser Gly Ser Asp Ser Asp Thr Ser Glu Thr Val Pro Ala
                420                 425                 430
Thr Ala Lys Gly Gly Gly Leu Tyr Thr Asp Lys Asn Leu Ser Ile Thr
            435                 440                 445
Asn Ile Thr Gly Ile Ile Glu Ile Ala Asn Asn Lys Ala Thr Asp Val
            450                 455                 460
Gly Gly Gly Ala Tyr Val Lys Gly Thr Leu Thr Cys Glu Asn Ser His
465                 470                 475                 480
Arg Leu Gln Phe Leu Lys Asn Ser Ser Asp Lys Gln Gly Gly Gly Ile
                485                 490                 495
Tyr Gly Glu Asp Asn Ile Thr Leu Ser Asn Leu Thr Gly Lys Thr Leu
                500                 505                 510
Phe Gln Glu Asn Thr Ala Lys Glu Glu Gly Gly Gly Leu Phe Ile Lys
            515                 520                 525
Gly Thr Asp Lys Ala Leu Thr Met Thr Gly Leu Asp Ser Phe Cys Leu
            530                 535                 540
Ile Asn Asn Thr Ser Glu Lys His Gly Gly Gly Ala Phe Val Thr Lys
545                 550                 555                 560
Glu Ile Ser Gln Thr Tyr Thr Ser Asp Val Glu Thr Ile Pro Gly Ile
                565                 570                 575
Thr Pro Val His Gly Glu Thr Val Ile Thr Gly Asn Lys Ser Thr Gly
                580                 585                 590
Gly Asn Gly Gly Gly Val Cys Thr Lys Arg Leu Ala Leu Ser Asn Leu
            595                 600                 605
Gln Ser Ile Ser Ile Ser Gly Asn Ser Ala Ala Glu Asn Gly Gly Gly
            610                 615                 620
Ala His Thr Cys Pro Asp Ser Phe Pro Thr Ala Asp Thr Ala Glu Gln
625                 630                 635                 640
Pro Ala Ala Ala Ser Ala Ala Thr Ser Thr Pro Glu Ser Ala Pro Val
                645                 650                 655
Val Ser Thr Ala Leu Ser Thr Pro Ser Ser Ser Thr Val Ser Ser Leu
            660                 665                 670
Thr Leu Leu Ala Ala Ser Ser Gln Ala Ser Pro Ala Thr Ser Asn Lys
            675                 680                 685
```

-continued

Glu Thr Gln Asp Pro Asn Ala Asp Thr Asp Leu Leu Ile Asp Tyr Val
    690                 695                 700

Val Asp Thr Thr Ile Ser Lys Asn Thr Ala Lys Lys Gly Gly Gly Ile
705                 710                 715                 720

Tyr Ala Lys Lys Ala Lys Met Ser Arg Ile Asp Gln Leu Asn Ile Ser
                725                 730                 735

Glu Asn Ser Ala Thr Glu Ile Gly Gly Ile Cys Cys Lys Glu Ser
            740                 745                 750

Leu Glu Leu Asp Ala Leu Val Ser Leu Ser Val Thr Glu Asn Leu Val
        755                 760                 765

Gly Lys Glu Gly Gly Gly Leu His Ala Lys Thr Val Asn Ile Ser Asn
    770                 775                 780

Leu Lys Ser Gly Phe Ser Phe Ser Asn Asn Lys Ala Asn Ser Ser Ser
785                 790                 795                 800

Thr Gly Val Ala Thr Thr Ala Ser Ala Pro Ala Ala Ala Ala Ser
            805                 810                 815

Leu Gln Ala Ala Ala Ala Val Pro Ser Ser Pro Ala Thr Pro Thr
        820                 825                 830

Tyr Ser Gly Val Val Gly Gly Ala Ile Tyr Gly Glu Lys Val Thr Phe
            835                 840                 845

Ser Gln Cys Ser Gly Thr Cys Gln Phe Ser Gly Asn Gln Ala Ile Asp
    850                 855                 860

Asn Asn Pro Ser Gln Ser Ser Leu Asn Val Gln Gly Gly Ala Ile Tyr
865                 870                 875                 880

Ala Lys Thr Ser Leu Ser Ile Gly Ser Ser Asp Ala Gly Thr Ser Tyr
                885                 890                 895

Ile Phe Ser Gly Asn Ser Val Ser Thr Gly Lys Ser Gln Thr Thr Gly
            900                 905                 910

Gln Ile Ala Gly Gly Ala Ile Tyr Ser Pro Thr Val Thr Leu Asn Cys
        915                 920                 925

Pro Ala Thr Phe Ser Asn Asn Thr Ala Ser Met Ala Thr Pro Lys Thr
    930                 935                 940

Ser Ser Glu Asp Gly Ser Ser Gly Asn Ser Ile Lys Asp Thr Ile Gly
945                 950                 955                 960

Gly Ala Ile Ala Gly Thr Ala Ile Thr Leu Ser Gly Val Ser Arg Phe
                965                 970                 975

Ser Gly Asn Thr Ala Asp Leu Gly Ala Ala Ile Gly Thr Leu Ala Asn
            980                 985                 990

Ala Asn Thr Pro Ser Ala Thr Ser Gly Ser Gln Asn Ser Ile Thr Glu
        995                 1000                1005

Lys Ile Thr Leu Glu Asn Gly Ser Phe Ile Phe Glu Arg Asn Gln Ala
    1010                1015                1020

Asn Lys Arg Gly Ala Ile Tyr Ser Pro Ser Val Ser Ile Lys Gly Asn
1025                1030                1035                1040

Asn Ile Thr Phe Asn Gln Asn Thr Ser Thr His Asp Gly Ser Ala Ile
                1045                1050                1055

Tyr Phe Thr Lys Asp Ala Thr Ile Glu Ser Leu Gly Ser Val Leu Phe
            1060                1065                1070

Thr Gly Asn Asn Val Thr Ala Thr Gln Ala Ser Ser Ala Thr Ser Gly
        1075                1080                1085

Gln Asn Thr Asn Thr Ala Asn Tyr Gly Ala Ala Ile Phe Gly Asp Pro
    1090                1095                1100

Gly Thr Thr Gln Ser Ser Gln Thr Asp Ala Ile Leu Thr Leu Leu Ala

-continued

```
             1105                1110                1115                1120
Ser Ser Gly Asn Ile Thr Phe Ser Asn Asn Ser Leu Gln Asn Asn Gln
                 1125                1130                1135
Gly Asp Thr Pro Ala Ser Lys Phe Cys Ser Ile Ala Gly Tyr Val Lys
             1140                1145                1150
Leu Ser Leu Gln Ala Ala Lys Gly Lys Thr Ile Ser Phe Phe Asp Cys
             1155                1160                1165
Val His Thr Thr Lys Lys Ile Gly Ser Thr Gln Asn Val Tyr Glu
             1170            1175                1180
Thr Leu Asp Ile Asn Lys Glu Glu Asn Ser Asn Pro Tyr Thr Gly Thr
1185                1190                1195                1200
Ile Val Phe Ser Ser Glu Leu His Glu Asn Lys Ser Tyr Ile Pro Gln
                 1205                1210                1215
Asn Ala Ile Leu His Asn Gly Thr Leu Val Leu Lys Glu Lys Thr Glu
                 1220                1225                1230
Leu His Val Val Ser Phe Glu Gln Lys Glu Gly Ser Lys Leu Ile Met
                 1235                1240                1245
Lys Pro Gly Ala Val Leu Ser Asn Gln Asn Ile Ala Asn Gly Ala Leu
             1250                1255                1260
Val Ile Asn Gly Leu Thr Ile Asp Leu Ser Ser Met Gly Thr Pro Gln
1265                1270                1275                1280
Ala Gly Glu Ile Phe Ser Pro Pro Glu Leu Arg Ile Val Ala Thr Thr
                 1285                1290                1295
Ser Ser Ala Ser Gly Gly Ser Gly Val Ser Ser Ile Pro Thr Asn
             1300                1305                1310
Pro Lys Arg Ile Ser Ala Ala Ala Pro Ser Gly Ser Ala Ala Thr Thr
             1315                1320                1325
Pro Thr Met Ser Glu Asn Lys Val Phe Leu Thr Gly Asp Leu Thr Leu
             1330                1335                1340
Ile Asp Pro Asn Gly Asn Phe Tyr Gln Asn Pro Met Leu Gly Ser Asp
1345                1350                1355                1360
Leu Asp Val Pro Leu Ile Lys Leu Pro Thr Asn Thr Ser Asp Val Gln
                 1365                1370                1375
Val Tyr Asp Leu Thr Leu Ser Gly Asp Leu Phe Pro Gln Lys Gly Tyr
             1380                1385                1390
Met Gly Thr Trp Thr Leu Asp Ser Asn Pro Gln Thr Gly Lys Leu Gln
             1395                1400                1405
Ala Arg Trp Thr Phe Asp Thr Tyr Arg Arg Trp Val Tyr Ile Pro Arg
             1410                1415                1420
Asp Asn His Phe Tyr Ala Asn Ser Ile Leu Gly Ser Gln Asn Ser Met
1425                1430                1435                1440
Ile Val Val Lys Gln Gly Leu Ile Asn Asn Met Leu Asn Asn Ala Arg
                 1445                1450                1455
Phe Asp Asp Ile Ala Tyr Asn Asn Phe Trp Val Ser Gly Val Gly Thr
                 1460                1465                1470
Phe Leu Ala Gln Gln Gly Thr Pro Leu Ser Glu Glu Phe Ser Tyr Tyr
             1475                1480                1485
Ser Arg Gly Thr Ser Val Ala Ile Asp Ala Lys Pro Arg Gln Asp Phe
         1490                1495                1500
Ile Leu Gly Ala Ala Phe Ser Lys Met Val Gly Lys Thr Lys Ala Ile
1505                1510                1515                1520
Lys Lys Met His Asn Tyr Phe Lys Gly Ser Glu Tyr Ser Tyr Gln
                 1525                1530                1535
```

-continued

Ala Ser Val Tyr Gly Gly Lys Phe Leu Tyr Phe Leu Leu Asn Lys Gln
                1540                1545                1550

His Gly Trp Ala Leu Pro Phe Leu Ile Gln Gly Val Val Ser Tyr Gly
            1555                1560                1565

His Ile Lys His Asp Thr Thr Thr Leu Tyr Pro Ser Ile His Glu Arg
        1570                1575                1580

Asn Lys Gly Asp Trp Glu Asp Leu Gly Trp Leu Ala Asp Leu Arg Ile
1585                1590                1595                1600

Ser Met Asp Leu Lys Glu Pro Ser Lys Asp Ser Ser Lys Arg Ile Thr
                1605                1610                1615

Val Tyr Gly Glu Leu Glu Tyr Ser Ser Ile Arg Gln Lys Gln Phe Thr
            1620                1625                1630

Glu Ile Asp Tyr Asp Pro Arg His Phe Asp Asp Cys Ala Tyr Arg Asn
        1635                1640                1645

Leu Ser Leu Pro Val Gly Cys Ala Val Glu Gly Ala Ile Met Asn Cys
1650                1655                1660

Asn Ile Leu Met Tyr Asn Lys Leu Ala Leu Ala Tyr Met Pro Ser Ile
1665                1670                1675                1680

Tyr Arg Asn Asn Pro Val Cys Lys Tyr Arg Val Leu Ser Ser Asn Glu
            1685                1690                1695

Ala Gly Gln Val Ile Cys Gly Val Pro Thr Arg Thr Ser Ala Arg Ala
        1700                1705                1710

Glu Tyr Ser Thr Gln Leu Tyr Leu Gly Pro Phe Trp Thr Leu Tyr Gly
            1715                1720                1725

Asn Tyr Thr Ile Asp Val Gly Met Tyr Thr Leu Ser Gln Met Thr Ser
        1730                1735                1740

Cys Gly Ala Arg Met Ile Phe
1745                1750

<210> SEQ ID NO 120
<211> LENGTH: 820
<212> TYPE: PRT
<213> ORGANISM: Chlamydia trachomatis

<400> SEQUENCE: 120

Met Thr His Lys Leu Thr Pro Met Met Gln Gln Trp His Gln Cys Lys
1               5                   10                  15

Glu Gln Ala Gly Asp Cys Leu Leu Leu Phe Arg Leu Gly Glu Phe Tyr
                20                  25                  30

Glu Ala Phe Phe Asp Asp Ala Leu Ile Leu Ala Gln Asn Leu Asp Ile
            35                  40                  45

Thr Leu Thr Gln Arg Gln Asn Val Pro Met Ser Gly Ile Pro Ala Thr
        50                  55                  60

Cys Leu Asp Gly Tyr Val Asp Arg Leu Val Ser Arg Gly Phe Lys Val
65                  70                  75                  80

Ala Ile Ala Glu Gln Ala Asp Asn Thr Glu Gly Ser Lys Gly Leu Val
                85                  90                  95

Pro Arg Thr Ile Asn Arg Leu Ile Thr Pro Gly Ala Leu Leu Ser Ser
                100                 105                 110

Ser Leu Leu Pro Glu Lys Ala Asn Asn Tyr Val Leu Ala Ile Asn Gln
            115                 120                 125

Val Gly Ser Leu Tyr Gly Leu Ser Cys Leu Asp Leu Ser Ile Gly Thr
        130                 135                 140

Phe Leu Val Ala Glu Tyr Asp Asn Thr Lys Asp Leu Ile Glu Ala Ile

-continued

```
            145                 150                 155                 160
Cys Arg Leu Ala Pro Thr Glu Leu Leu Ser His Ala Lys Phe Tyr Gln
                165                 170                 175
Lys Asn Glu Ala Val Ile Lys Gln Leu Gln Gln His Leu Arg Ile Thr
            180                 185                 190
Leu Ser Glu Tyr Val Ser Trp Ala Phe Glu Tyr Gln Ser Ala Thr Lys
        195                 200                 205
Lys Leu Tyr Thr Cys Phe Gln Val Ser Ser Leu Asp Gly Phe Gly Leu
210                 215                 220
Gln Gly Leu Val Pro Ala Ile Asn Ala Gly Ala Leu Leu Ser Tyr
225                 230                 235                 240
Ile Gln Asp Lys Leu Leu Pro Ile Ser His Leu Ser Ile Pro Lys
                245                 250                 255
Ile Tyr Gly Gln Gln Lys His Leu Leu Ile Asp Lys Ala Ser Gln Thr
                260                 265                 270
Asn Leu Glu Leu Leu Ser Pro Ile His Gly His Gly Lys Gly Ser
            275                 280                 285
Leu Leu Gln Val Met Glu Arg Thr Ser Thr Pro Met Gly Gly Arg Leu
        290                 295                 300
Leu Arg Asn Thr Leu Ile Asn Pro Phe Tyr Asp Leu Lys Glu Ile Thr
305                 310                 315                 320
Leu Arg Gln Asp Ser Val Glu Phe Phe Leu Gln Ala Asp Leu Arg
                325                 330                 335
Lys Ile Leu Lys Arg Gln Leu Ser Cys Val Arg Asp Leu Glu Arg Leu
            340                 345                 350
Ala Thr Lys Ile Ser Thr Ser Leu Ala Thr Pro Lys Asp Ile Gly Thr
        355                 360                 365
Leu Arg Asp Ser Leu Leu Ser Cys Thr His Ile Ala Asp Asn Leu Gln
    370                 375                 380
Asn Cys Ala Leu Pro Glu Phe Leu Glu Asn Lys Phe Leu Ile Ala Pro
385                 390                 395                 400
Pro Leu Cys Ser Leu Ile Lys Thr Leu Ser Thr Glu Leu Ile Gln Glu
                405                 410                 415
Leu Pro Leu Lys Val Ser Glu Gly Asn Ile Phe Ala Asn His Tyr His
            420                 425                 430
Pro Asp Leu Leu Arg Leu Arg Asn Ile Lys Glu Asn Ser Lys Ser Trp
        435                 440                 445
Ile Leu Glu Tyr Gln Glu Arg Ile Arg Asn Glu Thr Gly Ile Lys Lys
    450                 455                 460
Leu Lys Val Cys Tyr Ala Gln Ala Leu Gly Tyr Tyr Ile Glu Val Ala
465                 470                 475                 480
Ser Asn Leu Ala Pro Gln Leu Pro Lys Glu Phe Ile Arg Arg Gln Ser
                485                 490                 495
Arg Leu His Ala Glu Arg Phe Thr Thr Gln Glu Leu Gln Gln Phe Gln
            500                 505                 510
Asp Glu Val Phe Ser Val Glu Asp Lys Leu Gln Thr Leu Glu Thr Lys
        515                 520                 525
Leu Phe Lys Glu Leu Cys Phe Tyr Ile Val Glu His Arg Asp Leu Ile
    530                 535                 540
Leu Lys Leu Ser Thr Ala Val Ala Asp Leu Asp Tyr Val Val Ser Leu
545                 550                 555                 560
Ala Glu Leu Ala Ala Glu Tyr Asp Tyr Arg Arg Pro Leu Val Asp His
                565                 570                 575
```

```
Ser Asp Ala Leu Ser Ile Thr Lys Gly Met His Pro Val Ala Leu Thr
            580                 585                 590

Leu Leu Asp Lys Gly Thr Phe Ile Pro Asn Asp Thr Val Met His Ser
        595                 600                 605

Ala Gln Thr Arg Met Ile Leu Leu Thr Gly Pro Asn Met Ala Gly Lys
    610                 615                 620

Ser Thr Tyr Ile Arg Gln Ile Ala Leu Leu Val Ile Met Ala Gln Met
625                 630                 635                 640

Gly Ser Phe Ile Pro Ala Arg Ser Ala His Ile Gly Ile Val Asp Lys
                645                 650                 655

Ile Phe Thr Arg Ile Gly Ala Gly Asp Asn Leu Ser Lys Gly Met Ser
                660                 665                 670

Thr Phe Met Val Glu Met Ala Glu Thr Ala Asn Ile Leu His Asn Ala
                675                 680                 685

Thr Asp Arg Ser Leu Val Ile Leu Asp Glu Ile Gly Arg Gly Thr Ser
            690                 695                 700

Thr Tyr Asp Gly Leu Ala Ile Ala Gln Ala Val Val Glu Phe Leu Leu
705                 710                 715                 720

Phe Thr Asp Gly Lys Lys Ala Lys Thr Leu Phe Ala Thr His Tyr Lys
                725                 730                 735

Glu Leu Thr Glu Leu Glu Met His Cys Gln His Val Glu Asn Phe His
                740                 745                 750

Ala Met Val Lys Glu Asn Ser Gly Gln Pro Ile Phe Met Tyr Glu Ile
                755                 760                 765

Val Lys Gly His Ser Lys Lys Ser Phe Gly Ile His Val Ala Lys Leu
            770                 775                 780

Ala Gly Phe Pro Leu Ser Val Val Ser Arg Ala Gln Gln Ile Leu His
785                 790                 795                 800

Gln Phe Glu Gly Pro Asp Leu Arg Pro Glu Pro Glu Lys Ala Gln Gln
                805                 810                 815

Leu Val Met Phe
            820

<210> SEQ ID NO 121
<211> LENGTH: 352
<212> TYPE: PRT
<213> ORGANISM: Chlamydia trachomatis

<400> SEQUENCE: 121

Met Pro Lys Ile Asp Thr Cys Asp Ser Cys Val Ser Asn Thr Glu Leu
1               5                   10                  15

Leu Ala Ile Arg Thr Arg Val Thr Gln Ser Tyr Asn Glu Ala Gln Thr
            20                  25                  30

Ile Leu Ser Ser Ile Pro Asp Gly Ile Phe Leu Leu Ser Glu Ser Gly
        35                  40                  45

Glu Ile Leu Ile Cys Asn Pro Gln Ala Arg Ala Ile Leu Gly Ile Pro
    50                  55                  60

Glu Asp Ile Gln Leu Val Thr Arg Met Phe His Asp Phe Phe Pro Asp
65                  70                  75                  80

Thr Phe Phe Gly Phe Ser Val Gln Glu Ala Leu Glu Lys Glu Val Pro
                85                  90                  95

Pro Lys Thr Ile Arg Leu Thr Leu Ser Gln Glu Leu Ser Gln Lys Glu
            100                 105                 110

Val Glu Val Phe Val Arg Lys Asn Ile Ser His Asp Phe Leu Phe Leu
```

```
                115                 120                 125
Leu Ile Arg Asp Arg Ser Asp Tyr Arg Gln Leu Glu Gln Ala Ile Glu
        130                 135                 140

Lys Tyr Arg Ser Ile Ser Glu Leu Gly Lys Ile Ala Ala Thr Leu Ala
145                 150                 155                 160

His Glu Ile Arg Asn Pro Leu Thr Ser Ile Ser Gly Phe Ala Thr Leu
                165                 170                 175

Leu Lys Glu Glu Leu Ser Ser Glu Arg His Gln Arg Met Leu Asn Val
        180                 185                 190

Ile Ile Glu Gly Thr Arg Ser Leu Asn Ser Leu Val Ser Ser Met Leu
            195                 200                 205

Glu Tyr Thr Lys Ile Gln Pro Leu Asn Leu Arg Ser Ile Asp Leu Gln
        210                 215                 220

Asp Phe Phe Ser Ser Leu Ile Pro Glu Leu Ser Leu Thr Phe Pro Ser
225                 230                 235                 240

Cys Thr Phe Arg Arg Thr Ile Leu Ser Pro Ile Gln Arg Ser Ile Asp
                245                 250                 255

Pro Asp Arg Leu Arg Cys Val Ile Trp Asn Leu Val Lys Asn Ala Val
        260                 265                 270

Glu Ala Ser Asp Glu Glu Ile Phe Leu Glu Leu His Glu Lys Gly Phe
    275                 280                 285

Ser Val Ile Asn Thr Gly Thr Leu Pro Pro Asn Ile Gln Glu Lys Leu
        290                 295                 300

Phe Ile Pro Phe Phe Thr Thr Lys Pro Gln Gly Asn Gly Leu Gly Leu
305                 310                 315                 320

Ala Glu Ala His Lys Ile Met Arg Leu His Gly Gly Asp Leu Val Val
                325                 330                 335

Ser Thr Gln Asp Asn Arg Thr Thr Phe Thr Ile Leu Trp Thr Pro Ala
        340                 345                 350

<210> SEQ ID NO 122
<211> LENGTH: 434
<212> TYPE: PRT
<213> ORGANISM: Chlamydia trachomatis

<400> SEQUENCE: 122

Met Lys Lys Thr Ser Val Ile Asp Thr Ser Val Leu Ile Tyr Asp Pro
1               5                   10                  15

Lys Ala Leu Ser Ser Phe Ser Asn Thr Arg Ile Ile Pro Phe Thr
            20                  25                  30

Val Ile Glu Glu Leu Glu Ser Cys Ala Lys Phe Arg Asp Glu Ser Gly
        35                  40                  45

Lys Asn Ala Ser Arg Ala Leu Gly Asn Ile Arg Val Leu Leu Glu Gln
    50                  55                  60

Ser Glu Arg Pro Ser Ser Gly Gln Ile Leu Leu Lys Asn Gly Ser Glu
65                  70                  75                  80

Leu Cys Ile Glu Val Ser Pro Leu Val Asn Leu Ser Asn His Lys Lys
                85                  90                  95

Gln Lys Lys His Leu Thr Leu Glu Leu Leu Gln Ile Ile Ser Gln Arg
            100                 105                 110

Glu Ser Val Val Phe Val Thr Lys Ser Leu Gly Arg Arg Val His Ala
        115                 120                 125

Glu Ala Leu Gly Ile Glu Ala Lys Asp Tyr Glu Asn Lys Cys Val Ser
    130                 135                 140
```

```
Phe Gln Ser Leu Tyr Arg Gly His Arg Lys Leu Lys Val Ala Asn Ser
145                 150                 155                 160

Thr Ile Glu Tyr Phe Tyr Lys Asp Gly Ser Ile Ala Phe Pro Ser Asp
                165                 170                 175

Leu Ser Pro Leu Pro Ser Pro Asn Glu Tyr Phe Phe Leu Ser Gly Asp
            180                 185                 190

Ser Asp Asn Tyr Ser Ala Val Gly Arg Tyr Ser Ser Lys Asp Asn Lys
        195                 200                 205

Ile Leu Ser Leu Lys Pro Ala Pro Glu Lys Ile Trp Gly Val Lys Pro
    210                 215                 220

Leu Asn Ile Glu Gln Arg Cys Ala Leu Asp Leu Leu Arg Asp Asp
225                 230                 235                 240

Ile Lys Leu Val Thr Leu Met Gly Gln Ala Gly Ser Gly Lys Thr Ile
                245                 250                 255

Leu Ala Leu Ala Ala Ala Met Tyr Gln Val Phe Glu Lys Pro Lys Tyr
            260                 265                 270

Asn Lys Leu Leu Val Ser Arg Pro Ile Ile Pro Met Gly Lys Asp Ile
        275                 280                 285

Gly Phe Leu Pro Gly Ile Lys Glu Ala Lys Leu Met His Trp Met Gln
290                 295                 300

Pro Ile Tyr Asp Asn Met Glu Phe Leu Phe Asp Val Asn Asn Met Gly
305                 310                 315                 320

Asp Phe Ser Glu Thr Leu His Ser Leu Met Glu Thr Lys Lys Leu Glu
                325                 330                 335

Met Glu Ala Leu Thr Tyr Ile Arg Gly Arg Ser Leu Pro Lys Val Phe
            340                 345                 350

Met Ile Ile Asp Glu Ala Gln Asn Leu Thr Pro His Glu Ile Lys Thr
        355                 360                 365

Ile Ile Ser Arg Ala Gly Lys Gly Thr Lys Ile Val Leu Thr Gly Asp
    370                 375                 380

Pro Thr Gln Ile Asp Ser Leu Tyr Phe Asp Glu Asn Ser Asn Gly Leu
385                 390                 395                 400

Thr Tyr Leu Val Gly Lys Phe His His Leu Pro Leu Tyr Gly His Met
                405                 410                 415

Phe Met Thr Arg Thr Glu Arg Ser Glu Leu Ala Ala Ala Ala Thr
            420                 425                 430

Ile Leu

<210> SEQ ID NO 123
<211> LENGTH: 470
<212> TYPE: PRT
<213> ORGANISM: Chlamydia trachomatis

<400> SEQUENCE: 123

Met Asp Ser Lys Thr Ser His Leu Asp Asp Glu Leu Cys Phe Lys Leu
1               5                   10                  15

Glu Glu Ala Phe Asp Thr Leu Thr Ala Gly Glu His Ser Gln Asp Leu
                20                  25                  30

Thr Ser Ile Val Ser Val Tyr Asn Pro Ile Asp Leu Ala Tyr Ala Val
            35                  40                  45

Ser Cys Leu Pro Ser Asp Ser Arg Ser Ile Leu Tyr Lys Asn Leu Asp
        50                  55                  60

Ser Ile Ala Ser Lys Ile Ala Phe Ile Ile Asn Thr Asp Ser Ala Ser
65                  70                  75                  80
```

-continued

```
Arg Trp Ala Ile Phe Arg Asn Leu Ser Asp Gly Glu Ile Cys Ala Leu
                85                  90                  95
Ile Glu Gln Met Pro Pro Asp Glu Ala Ile Trp Val Leu Asp Asp Ile
            100                 105                 110
Pro Asp Arg Arg Tyr Arg Ile Leu Asp Leu Ile Asp Val Lys Lys
        115                 120                 125
Ala Leu Lys Ile Arg Asp Leu Gln Lys His Gly Arg Asn Thr Ala Gly
    130                 135                 140
Arg Leu Met Thr Asn Glu Phe Phe Ala Phe Leu Met Glu Thr Thr Val
145                 150                 155                 160
Lys Glu Val Ala Thr Cys Ile Arg Asn Asn Pro Gly Ile Asp Leu Thr
                165                 170                 175
Arg Leu Val Phe Val Leu Asp Phe Lys Gly Glu Leu Gln Gly Phe Val
            180                 185                 190
Thr Asp Arg Ser Leu Ile Ile Ala Ser Pro Glu Met Pro Leu Lys Gln
        195                 200                 205
Ile Met Arg Pro Ile Glu His Lys Val Leu Ala Asp Thr Thr Arg Glu
    210                 215                 220
Glu Val Val Asp Leu Val Glu Arg Tyr Lys Val Ala Val Leu Pro Val
225                 230                 235                 240
Val Asp Glu Glu Asn Phe Leu Ile Gly Ala Ile Thr Tyr Glu Asp Val
                245                 250                 255
Val Glu Thr Ile Glu Asp Ile Ala Asp Glu Thr Ile Ala Arg Met Ala
            260                 265                 270
Gly Thr Thr Glu Asp Val Gly Tyr His Asp Cys His Val Val Gln Arg
        275                 280                 285
Phe Leu Leu Arg Ala Pro Trp Leu Leu Ile Thr Leu Cys Ala Gly Leu
    290                 295                 300
Val Ser Ala Ser Val Met Ala Tyr Phe Gln Lys Ile Ala Pro Thr Leu
305                 310                 315                 320
Leu Ala Met Val Ile Phe Phe Ile Pro Leu Val Asn Gly Leu Ser Gly
                325                 330                 335
Asn Val Gly Val Gln Cys Ser Thr Ile Leu Val Arg Ser Met Ala Thr
            340                 345                 350
Gly Thr Leu Ser Phe Gly Arg Arg Glu Thr Ile Leu Lys Glu Met
        355                 360                 365
Ser Ile Gly Leu Leu Thr Gly Val Ala Leu Gly Ile Leu Cys Gly Leu
    370                 375                 380
Val Val Cys Cys Met Gly Cys Leu Gly Leu Gly Leu Phe Ala Thr Gly
385                 390                 395                 400
Gly Val Gln Leu Gly Val Thr Val Ser Val Gly Ile Leu Gly Ala Ser
                405                 410                 415
Leu Thr Ala Thr Thr Leu Gly Val Leu Ser Pro Phe Phe Ala Lys
            420                 425                 430
Ile Gly Val Asp Pro Ala Leu Ala Ser Gly Pro Ile Val Thr Ala Leu
        435                 440                 445
Asn Asp Ile Met Ser Met Val Ile Phe Leu Leu Ile Thr Gly Thr Leu
    450                 455                 460
Asn Val Leu Phe Phe Lys
465                 470

<210> SEQ ID NO 124
<211> LENGTH: 934
<212> TYPE: PRT
```

<213> ORGANISM: Chlamydia trachomatis

<400> SEQUENCE: 124

Met Gln Arg Tyr Glu Leu Ile Arg Leu Ile Gly Lys Gly Gly Met Gly
1 5 10 15

Glu Val Tyr Leu Ala His Asp Lys Ala Cys Ser Arg Arg Val Ala Leu
20 25 30

Lys Arg Ile Arg Glu Asp Leu Ser Gly Asn Ala Leu Leu Arg Gln Arg
35 40 45

Phe Leu Arg Glu Ala Lys Ile Ala Ala Asp Leu Ile His Pro Gly Ile
50 55 60

Val Pro Val Tyr Ser Ile Cys Ser Asp Gly Glu Ala Val Tyr Tyr Thr
65 70 75 80

Met Pro Tyr Ile Glu Gly Phe Ser Leu Lys Ser Leu Leu Lys Ser Val
85 90 95

Trp Gln Lys Glu Val Leu Ser Lys Glu Leu Glu Glu Lys Thr Ser Val
100 105 110

Lys Ser Phe Leu Pro Ile Phe Asp Lys Ile Cys Ala Thr Val Glu Tyr
115 120 125

Ile His Ser Lys Gly Val Leu His Arg Asp Leu Lys Pro Asp Asn Ile
130 135 140

Leu Leu Gly Leu Phe Gly Glu Val Val Ile Ile Asp Trp Gly Ala Ala
145 150 155 160

Ile Phe Lys His Ala Lys Glu Leu Lys Leu Glu Gln Asp Asp Glu Ala
165 170 175

Ala Val Ser Phe Asp Glu Arg Asn Ile Cys Tyr Ser Ser Met Thr Ile
180 185 190

Pro Gly Lys Ile Val Gly Thr Pro Asp Tyr Met Ala Pro Glu Ser Leu
195 200 205

Leu Gly Val Glu Ala Ser Glu Lys Thr Asp Ile Tyr Ala Leu Gly Leu
210 215 220

Ile Leu Tyr Gln Met Leu Thr Leu Ala Phe Pro Tyr Arg Arg Lys Lys
225 230 235 240

Gly Arg Lys Leu Ser Tyr Arg Asp Val Val Leu Pro Pro Ile Glu Met
245 250 255

Ser Pro Tyr Arg Glu Ile Pro Pro Ser Leu Ser Gln Ile Ala Met Lys
260 265 270

Ala Ile Ala Ile Asn Pro Ala Asp Arg Phe Ser Ser Ile Gln Glu Leu
275 280 285

Arg Gln Ala Leu Gln Pro Tyr Leu Gln Gly Asp Pro Glu Trp Thr Val
290 295 300

Lys Ala Thr Leu Met Ala Lys Glu Lys Ser Cys Trp Lys Tyr Tyr Asp
305 310 315 320

Pro Ile Leu Leu Ser Arg Tyr Phe Pro Val Leu Ala Ser Ser Pro Ala
325 330 335

Gln Trp Tyr Asn Phe Met Leu Ser Glu Val Glu Ile Ser Ala Ser Thr
340 345 350

Arg Val Glu Tyr Thr Val Thr Lys Ser Ala Val His Glu Gly Met Gly
355 360 365

Ile Leu Phe Leu Pro Ser Lys Glu Ala Glu Arg Gly Glu Phe Tyr Cys
370 375 380

Gly Tyr Gly Leu Trp Phe Ser Val Gln Asn His Glu Leu Thr Val Ser
385 390 395 400

```
Leu Ile Lys Asn Gly Ile Glu Ile Gln Lys Lys Ser Gln Glu Met Ile
                405                 410                 415
Ser Gln Gln Ser Arg Phe Ala Ile Leu Ile Glu Lys Ser Asp Asn Arg
            420                 425                 430
Ile Ala Val Phe Val Glu Gln Ala Leu Phe Ile Leu His Ile Asp Tyr
                435                 440                 445
Leu Pro Ser Leu Gly Asn Arg Leu Gly Val Ile Gln Asp Leu Gln
    450                 455                 460
Gly Met Ser Asn Ile Ala Ile Ser Glu Ser Ile Gly Ala Leu Arg Val
465                 470                 475                 480
Ser Cys Leu Ala Val Pro Asp Ala Phe Leu Ser Glu Lys Leu Tyr Asp
                485                 490                 495
Gln Ala Ala Ile Phe Tyr Arg Lys Ile Arg Asp Ser Phe Pro Gly Arg
                500                 505                 510
Lys Glu Ser Tyr Glu Ala Gln Phe Arg Leu Gly Val Thr Leu Leu Thr
            515                 520                 525
Gln Ile Glu Glu Gln Gly Gly Asp Leu Thr Gln Ala Leu Ser Ser Phe
    530                 535                 540
Asp Tyr Leu His Gly Gly Ala Gly Ala Pro Leu Glu Tyr Leu Gly Lys
545                 550                 555                 560
Ala Leu Val Tyr Gln Arg Asn Gly Ser Phe Val Glu Glu Ile Arg Cys
                565                 570                 575
Leu Leu Phe Ala Leu Lys Arg Tyr Ser Gln His Pro Glu Ile Pro Arg
                580                 585                 590
Leu Glu Asp His Leu Cys Phe Arg Leu Tyr Asp Ser Leu His Lys His
            595                 600                 605
Arg Ser Glu Ala Leu Val Phe Met Leu Leu Ile Leu Trp Ile Ala Pro
    610                 615                 620
Glu Lys Ile Ser Val Arg Glu Glu Arg Phe Leu Arg Ile Ile Tyr
625                 630                 635                 640
His Lys Gln Gln Ala Thr Leu Phe Cys Gln Val Asp Lys Ala Pro Leu
                645                 650                 655
Gln Phe Arg Ser Ser Lys Met Glu Leu Phe Leu Ser Phe Trp Thr Gly
                660                 665                 670
Phe Ser Leu Phe Leu Pro Glu Leu Phe Arg Arg Ala Gly Gly Leu Arg
            675                 680                 685
Asp Tyr Gln Ala Leu Ala Asp Ile Phe Tyr Val Ala Gly Val Ser Gly
    690                 695                 700
Asn Arg Glu Ala Phe Met Gln Phe Ser Thr Ala Leu Ala Asn Val Ser
705                 710                 715                 720
Asp Glu Ile Thr Phe Pro Glu Ser Leu His Asn Gln Lys Val Ala Glu
                725                 730                 735
Leu Met Phe Phe Val Lys Gly Val Glu Ala Leu Arg Asn Lys Asp Tyr
                740                 745                 750
Gln Lys Ala Lys Lys Leu Leu Trp Lys Thr Pro Phe Thr Leu Gln Leu
            755                 760                 765
Tyr Ala Leu Asp Met Phe His Ile Gln Ala Phe Leu Asp Glu Ile
    770                 775                 780
Glu Ser Phe Ile Asp Leu Leu Gln Ala Ile Tyr Asp Pro Ala Ser Glu
785                 790                 795                 800
Glu Glu Arg Asp His Ile Leu Val Tyr Ile Ile Gln Thr His Leu Trp
                805                 810                 815
Asn Arg Asp Leu Glu Arg Ala Tyr Lys Leu Leu Asn Asp Arg Phe Pro
```

-continued

```
                820                 825                 830

Leu Asp Glu Glu Leu Ala Glu Tyr Ser Glu Ala Phe Ile Leu Trp Gly
        835                 840                 845

Cys Tyr Leu Ala Leu Thr Gly Asp Arg Val Val Lys Ala His Phe
    850                 855                 860

Ser Arg Cys Arg Tyr Lys Tyr Gly Lys Ser Ala Leu Ile Gly Lys Cys
865                 870                 875                 880

Val Asp Gly Asp Ile Phe Asp Tyr Leu Asp Asn Leu Val Trp Trp Glu
                885                 890                 895

Lys Lys Met Thr Leu Phe Gln Ser Tyr Phe Leu Leu Arg Cys Leu Asn
        900                 905                 910

Glu Ser Pro Arg Arg Tyr Glu Lys Tyr Arg Gln Ala Tyr Leu Ser Met
        915                 920                 925

Glu Asn Asn Phe Phe Asp
    930

<210> SEQ ID NO 125
<211> LENGTH: 1036
<212> TYPE: PRT
<213> ORGANISM: Chlamydia trachomatis

<400> SEQUENCE: 125

Met Asp Asn Glu Asp Lys Ile Ser Ile Ser Ala Lys Glu Glu Lys Ile
1               5                   10                  15

Leu Ser Phe Trp Lys Glu Gln Asp Ile Phe Gln Lys Thr Leu Asp Asn
            20                  25                  30

Arg Glu Gly Cys Pro Thr Phe Ser Phe Tyr Asp Gly Pro Pro Phe Ala
        35                  40                  45

Thr Gly Leu Pro His Tyr Gly His Leu Leu Ala Gly Thr Ile Lys Asp
    50                  55                  60

Val Val Cys Arg Tyr Ala Ser Met Asp Gly His Tyr Val Pro Arg Arg
65                  70                  75                  80

Phe Gly Trp Asp Cys His Gly Val Pro Val Glu Tyr Glu Val Glu Lys
                85                  90                  95

Ser Leu Gly Leu Thr Glu Pro Gly Ala Ile Glu Arg Phe Gly Val Ala
            100                 105                 110

Asn Phe Asn Glu Glu Cys Arg Lys Ile Val Phe Arg Tyr Ala Asp Glu
        115                 120                 125

Trp Lys Tyr Phe Val Asp Arg Ile Gly Arg Trp Val Asp Phe Ser Ala
    130                 135                 140

Thr Trp Arg Thr Met Asp Leu Ser Phe Met Glu Ser Val Trp Trp Val
145                 150                 155                 160

Phe Arg Ser Leu Tyr Asp Gln Gly Leu Val Tyr Glu Gly Thr Lys Val
                165                 170                 175

Val Pro Phe Ser Thr Lys Leu Gly Thr Pro Leu Ser Asn Phe Glu Ala
            180                 185                 190

Gly Gln Asn Tyr Lys Glu Val Asp Asp Pro Ser Val Val Lys Phe
        195                 200                 205

Ala Leu Gln Asp Asn Gln Gly Phe Leu Leu Ala Trp Thr Thr Thr Pro
    210                 215                 220

Trp Thr Leu Val Ser Asn Met Ala Leu Ala Val His Pro Glu Leu Thr
225                 230                 235                 240

Tyr Val Arg Ile Lys Asp Lys Glu Ser Gly Asp Glu Tyr Ile Leu Gly
                245                 250                 255
```

-continued

```
Gln Glu Ser Leu Pro Arg Trp Phe Pro Asp Arg Glu Ser Tyr Glu Trp
            260                 265                 270
Ile Gly Gln Leu Ser Gly Lys Ser Leu Val Gly Gln Ser Tyr Glu Pro
            275                 280                 285
Leu Phe Pro Tyr Phe Gln Asp Lys Lys Glu Leu Glu Ala Phe Arg Ile
            290                 295                 300
Leu Pro Ala Asp Phe Ile Glu Glu Ser Glu Gly Thr Gly Ile Val His
305                 310                 315                 320
Met Ala Pro Ala Phe Gly Glu Ala Asp Phe Phe Ala Cys Gln Glu His
                325                 330                 335
Asn Val Pro Leu Val Cys Pro Val Asp Asn Gln Gly Cys Tyr Thr Ala
            340                 345                 350
Glu Val Lys Asp Phe Val Gly Glu Tyr Ile Lys Ser Ala Asp Lys Gly
            355                 360                 365
Ile Ala Arg Arg Leu Lys Asn Glu Asn Lys Leu Phe Tyr Gln Gly Thr
            370                 375                 380
Val Arg His Arg Tyr Pro Phe Cys Trp Arg Thr Asp Ser Pro Leu Ile
385                 390                 395                 400
Tyr Lys Ala Val Asn Ser Trp Phe Val Ala Val Glu Lys Val Lys Ser
                405                 410                 415
Lys Met Leu Lys Ala Asn Glu Ser Ile His Trp Thr Pro Glu His Ile
            420                 425                 430
Lys Gln Gly Arg Phe Gly Lys Trp Leu Glu Gly Ala Arg Asp Trp Ala
            435                 440                 445
Ile Ser Arg Asn Arg Tyr Trp Gly Thr Pro Ile Pro Ile Trp Arg Ser
            450                 455                 460
Asp Asp Gly Glu Leu Leu Val Ile Gly Ser Ile Gln Glu Leu Glu Ala
465                 470                 475                 480
Leu Ser Gly Gln Lys Ile Val Asp Leu His Arg His Phe Ile Asp Glu
                485                 490                 495
Ile Glu Ile Asn Gln Asn Gly Lys Ser Phe Arg Arg Ile Pro Tyr Val
            500                 505                 510
Phe Asp Cys Trp Phe Asp Ser Gly Ala Met Pro Tyr Ala Gln Asn His
            515                 520                 525
Tyr Pro Phe Glu Arg Ala Glu Glu Thr Glu Ala Cys Phe Pro Ala Asp
            530                 535                 540
Phe Ile Ala Glu Gly Leu Asp Gln Thr Arg Gly Trp Phe Tyr Thr Leu
545                 550                 555                 560
Thr Val Ile Ala Ala Ala Leu Phe Asp Gln Pro Ala Phe Lys Asn Val
                565                 570                 575
Ile Val Asn Gly Ile Ile Leu Ala Glu Asp Gly Asn Lys Met Ser Lys
            580                 585                 590
Arg Leu Asn Asn Tyr Pro Ser Pro Lys Met Ile Met Asp Ala Tyr Gly
            595                 600                 605
Ala Asp Ala Leu Arg Leu Tyr Leu Leu Asn Ser Val Val Val Lys Ala
            610                 615                 620
Glu Asp Leu Arg Phe Ser Asp Lys Gly Val Glu Ser Val Leu Lys Gln
625                 630                 635                 640
Val Leu Leu Pro Leu Ser Asn Ala Leu Ala Phe Tyr Lys Thr Tyr Ala
                645                 650                 655
Glu Leu Tyr Gly Phe Asp Pro Lys Glu Thr Asp Asn Ile Glu Leu Ala
            660                 665                 670
Glu Ile Asp Arg Trp Ile Leu Ser Ser Leu Tyr Ser Leu Val Gly Lys
```

```
                    675                 680                 685
Thr Arg Glu Ser Met Ser Gln Tyr Asp Leu His Ala Val Asn Pro
            690                 695                 700
Phe Val Asp Phe Ile Glu Asp Leu Thr Asn Trp Tyr Ile Arg Arg Ser
705                 710                 715                 720
Arg Arg Arg Phe Trp Asp Ala Glu Asp Ser Ala Asp Arg Arg Ala Ala
                725                 730                 735
Phe Ser Thr Leu Tyr Glu Val Leu Val Val Phe Ser Lys Val Ile Ala
            740                 745                 750
Pro Phe Ile Pro Phe Ile Ala Glu Asp Met Tyr Gln Gln Leu Arg Gly
            755                 760                 765
Glu Thr Asp Pro Glu Ser Val His Leu Cys Asp Phe Pro His Val Val
    770                 775                 780
Leu Glu Lys Ile Leu Pro Asp Leu Glu Arg Lys Met Gln Asp Ile Arg
785                 790                 795                 800
Glu Ile Val Ala Leu Gly His Ser Leu Arg Lys Glu His Lys Leu Lys
                805                 810                 815
Val Arg Gln Pro Leu Gln Asn Val Tyr Ile Val Gly Ser Lys Glu Arg
            820                 825                 830
Lys Glu Ala Leu Ala Gln Val Gly Ser Leu Ile Gly Glu Glu Leu Asn
835                 840                 845
Val Lys Asp Val His Phe Cys Ser Glu Thr Pro Glu Tyr Val Thr Thr
    850                 855                 860
Leu Ile Lys Pro Asn Phe Arg Thr Leu Gly Lys Val Gly Asn Arg
865                 870                 875                 880
Leu Pro Glu Ile Gln Arg Ala Leu Ala Gly Leu Pro Gln Glu Gln Ile
                885                 890                 895
Gln Ala Phe Met His Lys Gly Gln Met Val Val Ser Leu Gly Glu Glu
            900                 905                 910
Thr Ile Ser Leu Asp Lys Glu Asp Ile Thr Val Ser Trp Ala Ser Ala
            915                 920                 925
Glu Gly Phe Val Ala Arg Ser Ser Ala Ser Phe Val Ala Val Leu Asp
        930                 935                 940
Cys Gln Leu Thr Glu Pro Leu Ile Met Glu Gly Ile Ala Arg Glu Leu
945                 950                 955                 960
Val Asn Lys Ile Asn Thr Met Arg Arg Asn Arg Lys Leu His Val Ser
                965                 970                 975
Asp Arg Ile Ala Ile Arg Leu His Ala Pro Val Ile Val Gln Glu Ala
            980                 985                 990
Phe Ala Leu His Lys Glu Tyr Ile Cys Glu Glu Thr Leu Thr Thr Ser
        995                 1000                1005
Val Ser Val Ile Asp Tyr Lys Glu Gly Glu Trp Asp Ile Asn Gly
    1010                1015                1020
His Ala Val Ser Phe Val Leu Glu Arg Val Glu Arg
1025                1030                1035

<210> SEQ ID NO 126
<211> LENGTH: 492
<212> TYPE: PRT
<213> ORGANISM: Chlamydia trachomatis

<400> SEQUENCE: 126

Met Leu Arg Tyr Ile Leu Lys Arg Leu Leu Leu Ile Pro Leu Thr Leu
1               5                   10                  15
```

-continued

```
Phe Ala Ile Ile Ser Val Asn Phe Val Ile Leu Asn Ala Ala Pro Gly
             20                  25                  30

Asp Leu Leu Glu Glu His Ser Met Asp Ala Gln Gly Glu Ala Gly Arg
         35                  40                  45

Ser Asp Lys Val Arg Thr Tyr Lys Gly Pro Asp Arg Tyr Leu Gln Phe
 50                  55                  60

Arg Glu His Tyr Gly Leu Thr Leu Pro Ile Phe Phe Asn Thr Arg Pro
 65                  70                  75                  80

Gln Ile Ser Arg Ser Glu Leu Arg Ala Gly Ile Gln Glu Ile Ile Asp
                 85                  90                  95

Gly Thr Ile His Lys Lys Ser Lys Thr Gly Ser Ile Thr Asn Ile Lys
                100                 105                 110

Val Tyr Trp Gly Asp Cys Ala Lys Phe Ile Met Pro Ala Leu Leu Ala
            115                 120                 125

Glu Ala Glu Asp Ser Ser Lys Glu Asp Ile Tyr Arg His Val Ala Ala
        130                 135                 140

Asp Leu Phe Ile Arg Gly Gly Ile Arg Gln Gly Ile Val Gly Ala Arg
145                 150                 155                 160

Leu Leu Glu Glu Gln Arg Glu Tyr Asn Gln Lys Val Ser Lys Ser Asn
                165                 170                 175

Ala Glu Leu Val Arg Leu Leu Asn Glu Asp Asn Ile Glu Val Lys Val
            180                 185                 190

Ala Ala Leu Gln Glu Trp Val Glu Gln Gly Gly Arg Gly Gln Leu
        195                 200                 205

Met Arg Arg Asp Leu Trp Arg Ile Phe Phe Leu Glu Thr Arg Phe Ala
210                 215                 220

Lys Tyr Leu Ser Arg Ile Val Arg Leu Asp Phe Gly Thr Leu Arg Asn
225                 230                 235                 240

Asp Cys His Lys Thr Val Val Ser Glu Val Ile Lys Arg Leu Gly Ser
                245                 250                 255

Ser Leu Ile Leu Ser Leu Leu Pro Met Ile Val Phe Ile Leu Cys
            260                 265                 270

Gln Val Phe Gly Met Ile Met Ala Val Asn Lys Asn His Trp Ile Asp
        275                 280                 285

His Leu Leu Asn Phe Leu Phe Leu Ile Leu Phe Ser Ile Pro Val Phe
            290                 295                 300

Val Ala Val Pro Trp Ile Ile Asp Asn Phe Val Leu Asn Lys Thr Val
305                 310                 315                 320

Pro Phe Thr Ser Ile Ser Met Pro Tyr Ser Gly Leu Cys Ser Ser Pro
                325                 330                 335

Glu Ile Phe Lys Glu Met Thr Ser Phe Glu Lys Leu Thr Asp Ile Val
            340                 345                 350

Leu His Ser Phe Leu Pro Phe Cys Ala Val Ser Tyr Gly Ala Phe Ala
        355                 360                 365

Ala Gln Ser Arg Leu Ser Arg Ala Val Phe Leu Glu Val Leu Gly Glu
    370                 375                 380

Asp His Ile Ser Ala Leu Arg Ala Arg Gly Ile Ser Gln Tyr Asp Ile
385                 390                 395                 400

Leu Val Arg His Val Gly Lys Asn Ser Ala Ala Thr Leu Ile Thr Ser
                405                 410                 415

Leu Ala Ser Ser Leu Ser Ala Leu Leu Gly Gly Ala Leu Val Val Glu
            420                 425                 430

Thr Leu Phe Asp Ile Asp Gly Phe Gly Lys Phe Phe Tyr Gln Ala Ile
```

```
                435                 440                 445
Leu Asn Arg Asp His Asn Val Val Met Phe Ser Val Ile Met Gly Ser
    450                 455                 460

Val Ile Ser Leu Ile Gly Tyr Leu Ile Gly Asp Ile Cys Tyr Val Leu
465                 470                 475                 480

Leu Asp Pro Arg Val Gln Leu Glu Glu Arg Lys Val
                485                 490

<210> SEQ ID NO 127
<211> LENGTH: 120
<212> TYPE: PRT
<213> ORGANISM: Chlamydia trachomatis

<400> SEQUENCE: 127

Met Ser Arg Leu Thr Leu Pro Lys Asn Ala Arg Leu Leu Lys Arg Lys
1               5                   10                  15

Gln Phe Val Tyr Val Gln Arg Asn Gly Arg Cys Cys Arg Ala Asp Gln
            20                  25                  30

Val Thr Leu Arg Val Val Pro Ser Arg His Ser Asn Thr Arg Lys Val
        35                  40                  45

Gly Ile Thr Val Ser Lys Lys Phe Gly Lys Ala His Gln Arg Asn Arg
    50                  55                  60

Phe Lys Arg Ile Val Arg Glu Ala Phe Arg His Val Arg Pro Asn Leu
65                  70                  75                  80

Pro Gly Cys Gln Val Val Ile Ser Pro Arg Gly Asn Ser Gln Pro Asp
                85                  90                  95

Phe Leu Lys Leu Ser Glu Glu Leu Leu Gln Arg Ile Pro Glu Ala Leu
            100                 105                 110

Pro Leu Ala Ser Ser Ser Arg Cys
        115                 120

<210> SEQ ID NO 128
<211> LENGTH: 167
<212> TYPE: PRT
<213> ORGANISM: Chlamydia trachomatis

<400> SEQUENCE: 128

Met Ile Cys Cys Asp Lys Val Leu Ser Ser Val Gln Ser Met Pro Val
1               5                   10                  15

Ile Asp Lys Cys Ser Val Thr Lys Cys Leu Gln Thr Ala Lys Gln Ala
            20                  25                  30

Ala Val Leu Ala Leu Ser Leu Phe Ala Val Phe Ala Ser Gly Ser Leu
        35                  40                  45

Ser Ile Leu Ser Ala Ala Val Leu Phe Ser Gly Thr Ala Ala Val Leu
    50                  55                  60

Pro Tyr Leu Leu Ile Leu Thr Thr Ala Leu Leu Gly Phe Val Cys Ala
65                  70                  75                  80

Val Ile Val Leu Leu Arg Asn Leu Ser Ala Val Val Gln Ser Cys Lys
                85                  90                  95

Lys Arg Ser Pro Glu Glu Ile Glu Gly Ala Ala Arg Pro Ser Asp Gln
            100                 105                 110

Gln Glu Ser Gly Gly Arg Leu Ser Glu Glu Ser Ala Ser Pro Gln Ala
        115                 120                 125

Ser Pro Thr Ser Ser Thr Phe Gly Leu Glu Ser Ala Leu Arg Ser Ile
    130                 135                 140

Gly Asp Ser Val Ser Gly Ala Phe Asp Asp Ile Asn Lys Asp Asn Ser
```

```
                 145                 150                 155                 160
Arg Ser Arg Ser His Ser Phe
                165

<210> SEQ ID NO 129
<211> LENGTH: 226
<212> TYPE: PRT
<213> ORGANISM: Chlamydia trachomatis

<400> SEQUENCE: 129

Met Thr Leu Leu Ile Leu Leu Arg His Gly Gln Ser Val Trp Asn Gln
1               5                   10                  15

Lys Asn Leu Phe Thr Gly Trp Val Asp Ile Pro Leu Ser Gln Gln Gly
            20                  25                  30

Ile Gln Glu Ala Ile Ala Ala Gly Glu Ser Ile Lys His Leu Pro Ile
        35                  40                  45

Asp Cys Ile Phe Thr Ser Thr Leu Val Arg Ser Leu Ile Thr Ala Leu
    50                  55                  60

Leu Ala Met Thr Asn His Ser Ser Gln Lys Val Pro Tyr Ile Val His
65                  70                  75                  80

Glu Glu Arg Pro Asp Met Ser Arg Ile His Ser Gln Lys Glu Met Glu
                85                  90                  95

Gln Met Ile Pro Leu Phe Gln Ser Ala Leu Asn Glu Arg Met Tyr
            100                 105                 110

Gly Glu Leu Gln Gly Lys Asn Lys Gln Glu Val Ala Ala Gln Phe Gly
        115                 120                 125

Glu Glu Gln Val Lys Leu Trp Arg Arg Ser Tyr Arg Ile Ala Pro Pro
    130                 135                 140

Gln Gly Glu Ser Leu Phe Asp Thr Gly Gln Arg Thr Leu Pro Tyr Phe
145                 150                 155                 160

Gln Glu Arg Ile Phe Pro Leu Leu Gln Gln Gly Lys Asn Ile Phe Ile
                165                 170                 175

Ser Ala His Gly Asn Ser Leu Arg Ser Leu Ile Met Asp Leu Glu Lys
            180                 185                 190

Leu Ser Glu Glu Gln Val Leu Ser Leu Glu Leu Pro Thr Gly Gln Pro
        195                 200                 205

Ile Val Tyr Glu Trp Thr Gly Gln Lys Phe Thr Lys His Ala Pro Ser
    210                 215                 220

Leu Gly
225

<210> SEQ ID NO 130
<211> LENGTH: 446
<212> TYPE: PRT
<213> ORGANISM: Chlamydia trachomatis

<400> SEQUENCE: 130

Met Ser Ala Glu Ile Leu Ala Arg Val Gln Phe Ala Leu Phe Ile Gly
1               5                   10                  15

Phe His Tyr Leu Phe Val Pro Ile Ser Leu Gly Leu Ser Met Met Ile
            20                  25                  30

Val Leu Met Glu Gly Leu Tyr Leu Phe Thr Lys Lys Ser Ile Tyr Lys
        35                  40                  45

Gln Leu Thr Trp Phe Trp Ile Arg Ile Phe Thr Leu Thr Phe Val Val
    50                  55                  60

Gly Val Val Thr Gly Leu Met Gln Ile Phe Ser Phe Gly Ala Asn Trp
```

-continued

```
                65                  70                  75                  80
Ser Arg Phe Ala Glu Tyr Thr Gly Asn Val Phe Gly Met Phe Leu Gly
                    85                  90                  95

Ser Glu Gly Met Phe Ala Phe Phe Leu Glu Ser Gly Phe Leu Gly Val
                   100                 105                 110

Leu Leu Phe Gly Arg Tyr Lys Val Ser Lys Lys Met His Phe Phe Ser
                   115                 120                 125

Ala Cys Met Val Ala Leu Gly Ala His Met Ser Ala Phe Trp Ile Val
            130                 135                 140

Cys Ala Asn Ser Trp Met Gln Thr Pro Ser Gly Tyr Glu Met Val Met
145                 150                 155                 160

Arg Asn Gly Met Leu Val Pro Gln Met Thr Ser Phe Trp Ala Ala Val
                165                 170                 175

Leu Ser Pro Ser Ala Leu Gln Arg Phe Thr His Val Val Leu Gly Ala
                180                 185                 190

Trp Leu Ser Gly Ile Phe Leu Val Leu Ser Val Ser Ala His Tyr Leu
                195                 200                 205

Arg Lys Glu Arg His Lys Asp Phe Ala Asn Gln Gly Leu Lys Ile Ser
            210                 215                 220

Met Phe Cys Ala Phe Leu Val Leu Ala Leu Gln Leu Trp Ser Ala Asp
225                 230                 235                 240

Val Thr Ala Arg Gly Val Ala Lys His Gln Pro Ala Lys Leu Ala Ala
                245                 250                 255

Phe Glu Gly Val Phe Lys Thr Gln Gly His Thr Pro Ile Tyr Leu Leu
                260                 265                 270

Gly Ile Val Asp Met Lys Lys Glu Arg Val Ile Gly Ile Pro Ile Pro
                275                 280                 285

Ser Gly Leu Ser Leu Leu Val His Arg Asn Ala Lys Thr Pro Val Thr
            290                 295                 300

Gly Leu Asp Gln Phe Pro Lys Asp Glu Trp Pro Asn Val Ala Phe Val
305                 310                 315                 320

Phe Gln Thr Tyr His Leu Met Val Met Leu Trp Gly Val Met Val Leu
                325                 330                 335

Leu Ala Leu Ile Ala Phe Ala Val Tyr Lys Lys Lys Ser Trp Ser Cys
                340                 345                 350

Lys Lys Gly Ile Leu Trp Ile Leu Ser Phe Ser Val Leu Cys Pro Glu
            355                 360                 365

Leu Cys Asn Glu Ile Gly Trp Ile Ser Thr Glu Val Gly Arg Gln Pro
            370                 375                 380

Trp Val Val Tyr Gly Leu Leu Lys Thr Lys Asp Ala Thr Ser Pro Ile
385                 390                 395                 400

Val Asn Ala Gly Gln Ile Trp Gln Ser Leu Ile Leu Phe Ser Ile Ile
                405                 410                 415

Phe Ile Cys Leu Leu Ser Val Phe Val Ser Leu Leu Lys Lys Ile
                420                 425                 430

Gly Glu Gly Pro Asp Glu Gln Asp Leu Ile Glu Val Asp Leu
            435                 440                 445

<210> SEQ ID NO 131
<211> LENGTH: 359
<212> TYPE: PRT
<213> ORGANISM: Chlamydia trachomatis

<400> SEQUENCE: 131
```

Met Glu Ile Lys Val Leu Glu Cys Leu Lys Arg Leu Glu Glu Val Glu
1               5                   10                  15

Lys Gln Ile Ser Asp Pro Asn Ile Phe Ser Asn Pro Lys Glu Tyr Ser
            20                  25                  30

Ser Leu Ser Lys Glu His Ala Arg Leu Ser Ile Lys Asn Ala His
        35                  40                  45

Glu Ser Leu Val Ala Thr Lys Lys Ile Leu Gln Asp Asp Lys Leu Ala
    50                  55                  60

Leu Ser Thr Glu Lys Asp Pro Glu Ile Val Ala Met Leu Glu Glu Gly
65                  70                  75                  80

Val Leu Val Gly Glu Ala Val Glu Arg Leu Ser Lys Gln Leu Glu
                85                  90                  95

Asn Leu Leu Ile Pro Pro Asp Pro Asp Asp Leu Ser Val Ile Met
            100                 105                 110

Glu Leu Arg Ala Gly Thr Gly Gly Asp Glu Ala Ala Leu Phe Val Gly
        115                 120                 125

Asp Cys Val Arg Met Tyr His Leu Tyr Ala Ala Ser Lys Gly Trp Gln
    130                 135                 140

Cys Glu Val Leu Ser Thr Ser Glu Ser Asp Leu Gly Gly Tyr Lys Glu
145                 150                 155                 160

Tyr Val Met Gly Ile Ser Gly Ala Ser Val Lys Arg Phe Leu Gln Tyr
                165                 170                 175

Glu Ala Gly Thr His Arg Val Gln Arg Val Pro Glu Thr Glu Thr Gln
        180                 185                 190

Gly Arg Val His Thr Ser Ala Val Thr Val Ala Val Leu Pro Glu Pro
    195                 200                 205

Ala Glu Asp Asp Glu Glu Val Phe Ile Asp Glu Lys Asp Leu Arg Ile
    210                 215                 220

Asp Thr Phe Arg Ser Ser Gly Ala Gly Gly Gln His Val Asn Val Thr
225                 230                 235                 240

Asp Ser Ala Val Arg Ile Thr His Ile Pro Ser Gly Val Val Val Thr
                245                 250                 255

Cys Gln Asp Glu Arg Ser Gln His Lys Asn Lys Ala Lys Ala Met Arg
        260                 265                 270

Val Leu Lys Ala Arg Ile Arg Asp Ala Glu Val Gln Lys Arg Ala Gln
    275                 280                 285

Glu Ala Ser Ala Met Arg Ser Ala Gln Val Gly Ser Gly Asp Arg Ser
    290                 295                 300

Glu Arg Ile Arg Thr Tyr Asn Phe Pro Gln Asn Arg Val Thr Asp His
305                 310                 315                 320

Arg Ile Gly Leu Thr Leu Tyr Asn Leu Asp Arg Val Met Glu Gly Glu
                325                 330                 335

Leu Asp Met Ile Thr Thr Ala Leu Val Thr His Val His Arg Gln Leu
        340                 345                 350

Phe Gly His Glu Glu Thr Ala
    355

<210> SEQ ID NO 132
<211> LENGTH: 649
<212> TYPE: PRT
<213> ORGANISM: Chlamydia trachomatis

<400> SEQUENCE: 132

Met Arg Val Asp Val Asp Lys Tyr Leu Phe Ile Gly Arg Glu Lys Ser
1               5                   10                  15

-continued

```
Glu Phe Phe Ser Ala Cys Arg Glu Ile Gly Ala Val Glu Phe Leu Ser
            20                  25                  30

Lys Ser Lys Leu Lys Asp Ser Glu Lys Val Arg Lys Leu Ser Glu Gly
            35                  40                  45

Leu Lys Val Leu Asn Leu Leu Thr Lys Ser Cys Ser Pro Ala Asp Leu
 50                  55                  60

Val Ser Thr Lys Ser Gly Tyr Leu Val Thr Glu Gln Leu Leu Gln Glu
 65                  70                  75                  80

Ile Phe Asp Leu Asn Gln Glu Ile Thr Thr Leu Thr Glu Ser Leu Lys
                    85                  90                  95

Ala Leu Gly Lys Glu Ile Val Arg Val Lys Pro Leu Gly Asp Phe Ser
                100                 105                 110

Ser Glu Glu Ile Arg Glu Leu Thr Leu Lys Thr Gly Leu Ala Val Arg
            115                 120                 125

Phe Leu Tyr Lys Arg His Ile Glu Gly Ala Pro Leu Glu Val Glu Glu
130                 135                 140

Glu Asn Val Phe Tyr Leu Ala Thr Ala Tyr Asn Tyr Asp Tyr Tyr Ala
145                 150                 155                 160

Val Ile Gly Ile Val Ser Leu Ser Lys Asp Ile Phe Thr Glu Ile Glu
                165                 170                 175

Ala Pro Arg Ser Val Asn Glu Leu Arg Glu Glu Gly His Leu Gln
            180                 185                 190

Ala Leu Leu Arg Lys Lys Lys Ala Arg Val Cys Glu Leu Tyr Ala Tyr
            195                 200                 205

Arg Glu Asp Leu Leu Glu Ala Leu Cys Glu Gln Cys Asn Glu Gln Ser
210                 215                 220

Leu Gln His Ala Glu Val Ser Ala Glu Asp Leu Phe Asp Asp Lys Val
225                 230                 235                 240

Phe Ser Ala Leu Gly Trp Val Ile Val Asp Arg Leu Asp Glu Val Lys
                245                 250                 255

Lys Leu Cys Asp Ser Leu Gly Ile Tyr Leu Glu Arg Val Gln Pro Asp
            260                 265                 270

Pro Asp Glu Val Ile Pro Thr Tyr Leu Glu Asn His Gly Leu Gly Ala
            275                 280                 285

Leu Gly Glu Ser Leu Val Asn Ile Tyr Asp Thr Pro Ala Ser Thr Asp
            290                 295                 300

Lys Asp Pro Ser Leu Trp Val Phe Phe Ser Phe Val Phe Ser
305                 310                 315                 320

Met Ile Ile Asn Asp Ala Gly Tyr Gly Leu Val Phe Leu Ala Thr Ser
                325                 330                 335

Leu Phe Leu Ser Phe Lys Ala Arg Lys Gln Ile Lys Arg Ser Ile Ala
            340                 345                 350

Leu Lys Arg Phe Leu Gln Met Phe Met Ile Leu Gly Leu Gly Cys Val
            355                 360                 365

Cys Trp Gly Gly Ala Thr Thr Ser Phe Phe Gly Val Ser Val Ser Tyr
370                 375                 380

Thr Ser Pro Phe Arg Glu Tyr Ser Leu Thr His Phe Leu Ala Leu Lys
385                 390                 395                 400

Lys Ala Glu Tyr Tyr Leu Lys Glu Arg Pro Lys Gly Tyr Lys Glu Leu
                405                 410                 415

Val His Asp Tyr Pro Ile Leu Lys Glu Lys Thr Pro Lys Glu Phe
                420                 425                 430
```

```
Leu Leu Ala Gln Ser Thr Ser Ser Gly Asp Ser Val Tyr Lys Ala Val
            435                 440                 445

Val Tyr Asp Lys Phe Ile Asp Asn Ile Leu Met Glu Ile Ala Leu Leu
    450                 455                 460

Val Gly Val Val His Leu Ser Leu Gly Met Leu Arg Tyr Cys Arg Gln
465                 470                 475                 480

Arg Tyr Ser Ser Ile Gly Trp Val Ile Phe Met Cys Gly Ala Tyr Met
            485                 490                 495

Tyr Leu Pro Ile Tyr Leu Gln Ala Val Ser Leu Ile His Tyr Ala Leu
            500                 505                 510

His Ile Pro Tyr Glu Leu Gly Leu Val Gly Tyr Val Ala Phe
            515                 520                 525

Ile Gly Leu Gly Val Ala Ile Leu Gly Gly Val Ile Gln Arg Gly Leu
            530                 535                 540

Arg Gly Leu Asp Glu Ile Thr Ala Val Ile Gln Val Phe Ser Asp Val
545                 550                 555                 560

Leu Ser Tyr Leu Arg Leu Tyr Ala Leu Ser Leu Ala Gly Ala Met Val
                565                 570                 575

Gly Asn Thr Val Met Val Met Ser Glu Arg Phe Ser Pro Ala Val Gly
            580                 585                 590

Ile Leu Ile Ile Ile Phe Gly His Thr Val Asn Ile Ala Leu Ser Ile
            595                 600                 605

Met Gly Gly Val Ile His Gly Leu Arg Leu Asn Phe Ile Glu Trp Tyr
            610                 615                 620

His Tyr Ser Phe Asp Gly Gly Lys Leu Leu His Pro Leu Lys Lys
625                 630                 635                 640

Val Ile Cys Gln Lys Ser Gln Asn Leu
                645

<210> SEQ ID NO 133
<211> LENGTH: 229
<212> TYPE: PRT
<213> ORGANISM: Chlamydia trachomatis

<400> SEQUENCE: 133

Met Thr Asp Phe His Asn Lys Pro Asn Ile Gln Ile Met Phe Asp Ser
1               5                   10                  15

Leu Ala Pro Thr Tyr Asp Lys Ile Asn Gly Ile Leu Ser Leu Gly Leu
                20                  25                  30

His Ile Ala Trp Asn Asn Ala Leu Val Ser Leu Gly Glu Thr Asn
            35                  40                  45

His Leu Leu Asp Leu Cys Ala Gly Thr Gly Arg Val Ala Leu Ser Tyr
        50                  55                  60

Val Gln Asn Tyr Pro Arg Ala Ser Ala Thr Leu Val Asp Phe Ser Thr
65                  70                  75                  80

Lys Met Leu Glu Asn Val Gln Lys Arg His Pro Ser Ala Pro Phe Ser
                85                  90                  95

Tyr Ile Thr Ser Asp Val Thr His Leu Pro Leu Pro Asp Asn Thr Phe
            100                 105                 110

Arg Leu Ala Ser Met Ala Tyr Gly Leu Arg Asn Leu Ser Tyr Pro Leu
        115                 120                 125

Glu Ala Leu Arg Glu Val Tyr Arg Val Leu Gln Pro Gly His Leu
    130                 135                 140

Gly Ile Leu Glu Leu Thr Arg Pro Ala Thr Tyr Asn Pro Val Tyr Leu
145                 150                 155                 160
```

```
Leu His Lys Leu Tyr Leu Asn Leu Val Val Pro Ser Val Gly Arg Phe
            165                 170                 175

Tyr Ser Gly Asn Ser Tyr Ala Tyr Ser Tyr Leu Lys Glu Ser Ile Arg
            180                 185                 190

Asp Leu Pro Arg Asp Ala Ala Leu Glu Ala Ile Phe His Ala Ala His
            195                 200                 205

Leu Arg Pro Ile Arg Lys Arg Lys Leu Leu Phe Gly Thr Ala Thr Ile
            210                 215                 220

Trp Ile Leu Glu Lys
225

<210> SEQ ID NO 134
<211> LENGTH: 255
<212> TYPE: PRT
<213> ORGANISM: Chlamydia trachomatis

<400> SEQUENCE: 134

Met Leu His Leu Cys Asp Val His Val Cys Cys Glu Glu Lys Lys Ile
1               5                   10                  15

Leu Glu Gly Leu Ser Leu Ser Ile His Pro Gly Glu Leu His Ile Ile
            20                  25                  30

Met Gly Pro Asn Gly Ala Gly Lys Ser Thr Leu Ala Lys Val Leu Ser
        35                  40                  45

Gly Asp Glu Ser Val Glu Val Ser Ser Gly Thr Met Thr Leu Ala Gly
    50                  55                  60

Gln Asp Leu Leu Glu Leu Ser Pro Glu Glu Arg Ala His Ala Gly Met
65                  70                  75                  80

Phe Ile Ser Phe Gln His Pro Leu Glu Ile Pro Gly Val Asn Asn Arg
                85                  90                  95

Ile Phe Leu Lys Glu Ala Cys Asn Ala Cys Arg Lys Ala Arg Asn Gln
            100                 105                 110

Ala Val Leu Asp Asp Ala Ala Phe Glu Glu Leu Leu Thr Asp Leu Glu
        115                 120                 125

Glu Val Tyr Gly Phe Pro Gly Phe His Phe Phe Ser Asn Arg Asn Val
    130                 135                 140

Asn Glu Gly Phe Ser Gly Gly Glu Lys Lys Lys Asn Glu Leu Trp Gln
145                 150                 155                 160

Met Leu Ala Leu Glu Pro Lys Met Val Val Leu Asp Glu Pro Asp Ser
                165                 170                 175

Gly Leu Asp Val Asp Ala Leu Lys Gly Ile Cys Ser Val Leu Gln Arg
            180                 185                 190

Tyr Arg Gln Gln His Pro Glu Thr Ala Phe Cys Ile Ile Thr His Asn
        195                 200                 205

Pro Arg Leu Gly Asp Leu Leu Gln Pro Asp His Val His Ile Leu Leu
    210                 215                 220

Asn Gly Arg Val Val Phe Ser Gly Asp Met His Leu Met Glu Glu Leu
225                 230                 235                 240

Glu Arg Lys Ser Tyr Gln Glu Leu Leu Asp Val Val Thr Gln Glu
                245                 250                 255

<210> SEQ ID NO 135
<211> LENGTH: 464
<212> TYPE: PRT
<213> ORGANISM: Chlamydia trachomatis

<400> SEQUENCE: 135
```

-continued

```
Met Lys Glu Glu Ser Pro Ala Glu Val Leu Gln Lys Val Lys Glu His
1               5                   10                  15

Lys Arg Arg Glu Gly Pro Leu Ser Leu Glu Lys Glu Val Ser Glu Asp
                20                  25                  30

Ser Ala Val Ala Thr Glu Lys Glu Thr Ser Gln Pro Val Ala Val
            35                  40                  45

Thr Lys Ile Ala Lys Leu Gln Arg Met Gly Ile Asn Glu Leu Asn Val
    50                  55                  60

Leu Ala Arg Gln Tyr Gly Val Lys Asn Val Gly Ser Leu Thr Lys Ser
65                  70                  75                  80

Gln Val Val Phe Glu Ile Val Lys Ala Lys Ser Glu Arg Pro Asp Glu
                85                  90                  95

Phe Leu Ile Gly Glu Gly Val Leu Glu Val Leu Pro Asp Gly Phe Gly
                100                 105                 110

Phe Leu Arg Ser Pro Thr Tyr Asn Tyr Leu Pro Ser Ala Glu Asp Ile
                115                 120                 125

Tyr Val Ser Pro Ala Gln Ile Arg Arg Phe Asp Leu Lys Lys Gly Asp
    130                 135                 140

Thr Ile Val Gly Thr Ile Arg Ser Pro Lys Glu Lys Glu Lys Tyr Phe
145                 150                 155                 160

Ala Leu Leu Lys Val Asp Lys Ile Asn Gly Ser Thr Pro Asp Lys Ala
                165                 170                 175

Lys Glu Arg Val Leu Phe Glu Asn Leu Thr Pro Leu His Pro Asn Glu
                180                 185                 190

Arg Leu Ile Met Glu Met Gly Lys Glu Asn Leu Ala Glu Arg Val Leu
                195                 200                 205

Asp Leu Thr Ala Pro Ile Gly Lys Gly Gln Arg Gly Leu Ile Val Ala
                210                 215                 220

Pro Pro Arg Ser Gly Lys Thr Val Ile Leu Gln Ser Ile Ala His Ala
225                 230                 235                 240

Ile Ala Val Asn Asn Pro Asp Ala Glu Leu Ile Val Leu Leu Ile Asp
                245                 250                 255

Glu Arg Pro Glu Glu Val Thr Asp Met Ile Arg Gln Val Arg Gly Glu
                260                 265                 270

Val Val Ala Ser Thr Phe Asp Glu Gln Pro Asp Arg His Ile Gln Val
                275                 280                 285

Thr Glu Met Val Ile Glu Lys Ala Arg Arg Leu Val Glu His Gly Lys
                290                 295                 300

Asp Val Val Ile Leu Leu Asp Ser Ile Thr Arg Leu Ala Arg Ala Tyr
305                 310                 315                 320

Asn Thr Val Gln Pro His Ser Gly Lys Ile Leu Thr Gly Gly Val Asp
                325                 330                 335

Ala Ser Ala Leu His Lys Pro Arg Phe Phe Gly Ala Ala Arg Asn
                340                 345                 350

Ile Glu Gly Gly Gly Ser Leu Thr Ile Leu Ala Thr Ala Leu Ile Asp
                355                 360                 365

Thr Gly Ser Arg Met Asp Glu Val Ile Phe Glu Glu Phe Lys Gly Thr
                370                 375                 380

Gly Asn Met Glu Leu Val Leu Asp Arg His Leu Ser Asp Arg Arg Ile
385                 390                 395                 400

Tyr Pro Ala Ile Asp Leu Ile Lys Ser Gly Thr Arg Lys Glu Glu Leu
                405                 410                 415
```

Leu Tyr His Pro Gly Glu Leu Glu Lys Ile Arg Leu Phe Arg Gln Ala
                420                 425                 430

Ile Ala Gly Leu Thr Ala Ile Asp Ala Met His Leu Leu Leu Gly Arg
            435                 440                 445

Leu Lys Lys Thr Asn Ser Asn Thr Glu Phe Leu Ser Leu Lys Asp
        450                 455                 460

<210> SEQ ID NO 136
<211> LENGTH: 708
<212> TYPE: PRT
<213> ORGANISM: Chlamydia trachomatis

<400> SEQUENCE: 136

Met Asn Lys Leu Leu Asn Phe Val Ser Arg Thr Phe Gly Gly Asp Ala
1               5                   10                  15

Ala Leu Asn Met Ile Asn Lys Ser Ser Asp Leu Ile Leu Ala Met Trp
            20                  25                  30

Met Leu Gly Val Val Leu Met Ile Ile Leu Pro Leu Pro Pro Ala Met
        35                  40                  45

Val Asp Phe Met Ile Thr Ile Asn Leu Ala Ile Ser Val Phe Leu Leu
    50                  55                  60

Met Val Ala Leu Tyr Ile Pro Ser Ala Leu Gln Leu Ser Val Phe Pro
65                  70                  75                  80

Ser Leu Leu Ile Thr Thr Met Phe Arg Leu Gly Ile Asn Ile Ser
                85                  90                  95

Ser Ser Arg Gln Ile Leu Leu His Ala Tyr Ala Gly His Val Ile Gln
            100                 105                 110

Ala Phe Gly Asp Phe Val Val Gly Gly Asn Tyr Val Val Gly Phe Ile
        115                 120                 125

Ile Phe Leu Ile Ile Thr Ile Ile Gln Phe Ile Val Val Thr Lys Gly
    130                 135                 140

Ala Glu Arg Val Ala Glu Val Ala Ala Arg Phe Arg Leu Asp Ala Met
145                 150                 155                 160

Pro Gly Lys Gln Met Ala Ile Asp Ala Asp Leu Arg Ala Gly Met Ile
                165                 170                 175

Asp Ala Thr Gln Ala Arg Asp Lys Arg Ser Gln Ile Gln Lys Glu Ser
            180                 185                 190

Glu Leu Tyr Gly Ala Met Asp Gly Ala Met Lys Phe Ile Lys Gly Asp
        195                 200                 205

Val Ile Ala Gly Ile Val Ile Ser Leu Ile Asn Ile Val Gly Gly Leu
    210                 215                 220

Val Ile Gly Val Thr Met Lys Gly Met Thr Met Ala Gln Ala Ala His
225                 230                 235                 240

Ile Tyr Thr Leu Ile Thr Ile Gly Asp Gly Leu Val Ser Gln Ile Pro
                245                 250                 255

Ser Leu Leu Ile Ser Leu Thr Ala Gly Ile Val Thr Arg Val Ser
            260                 265                 270

Ser Asp Lys Asp Thr Asn Leu Gly Lys Glu Ile Ser Ser Gln Leu Val
        275                 280                 285

Lys Glu Pro Arg Ala Leu Leu Leu Ser Ala Gly Ala Thr Leu Gly Ile
    290                 295                 300

Gly Phe Phe Lys Gly Phe Pro Leu Trp Ser Phe Ala Leu Met Ala Val
305                 310                 315                 320

Leu Phe Ala Val Leu Gly Ile Leu Leu Ile Thr Lys Lys Asn Ser Pro
                325                 330                 335

```
Gly Lys Lys Gly Gly Ala Ser Ser Thr Thr Val Gly Ala Ala Asp
            340                 345                 350

Gly Ala Ala Ser Gly Glu Asn Ser Asp Asp Tyr Ala Leu Thr Leu
            355                 360                 365

Pro Val Ile Leu Glu Leu Gly Lys Asp Leu Ser Lys Leu Ile Gln Gln
            370                 375                 380

Arg Thr Lys Ser Gly Gln Ser Phe Val Asp Asp Met Ile Pro Lys Met
385                 390                 395                 400

Arg Gln Ala Leu Tyr Gln Asp Ile Gly Ile Arg Tyr Pro Gly Ile His
                405                 410                 415

Val Arg Thr Asp Ser Pro Ser Leu Glu Gly Asn Asp Tyr Met Ile Leu
                420                 425                 430

Leu Asn Glu Val Pro Tyr Val Arg Gly Lys Ile Pro Asn His Val
                435                 440                 445

Leu Thr Asn Glu Val Glu Glu Asn Leu Ser Arg Tyr Asn Leu Pro Phe
            450                 455                 460

Ile Thr Tyr Lys Asn Ala Ala Gly Leu Pro Ser Thr Trp Val Ser Thr
465                 470                 475                 480

Asp Ala Leu Thr Ile Leu Glu Lys Ala Ala Ile Lys Tyr Trp Ser Pro
                485                 490                 495

Leu Glu Val Ile Ile Leu His Leu Ser Tyr Phe Phe His Arg Asn Ser
            500                 505                 510

Gln Glu Phe Leu Gly Ile Gln Glu Val Arg Ser Met Ile Glu Phe Met
            515                 520                 525

Glu Arg Ser Phe Pro Asp Leu Val Lys Glu Val Thr Arg Leu Ile Pro
530                 535                 540

Leu Gln Lys Leu Thr Glu Ile Phe Lys Arg Leu Val Gln Glu Gln Ile
545                 550                 555                 560

Ser Ile Lys Asp Leu Arg Thr Ile Leu Glu Ser Leu Ser Glu Trp Ala
                565                 570                 575

Gln Thr Glu Lys Asp Thr Val Leu Leu Thr Glu Tyr Val Arg Ser Ser
                580                 585                 590

Leu Lys Leu Tyr Ile Ser Phe Lys Phe Ser Gln Gly Gln Ser Ala Ile
            595                 600                 605

Ser Val Tyr Leu Leu Asp Pro Glu Ile Glu Glu Met Ile Arg Gly Ala
            610                 615                 620

Ile Lys Gln Thr Ser Ala Gly Ser Tyr Leu Ala Leu Asp Pro Asp Ser
625                 630                 635                 640

Val Asn Leu Ile Leu Lys Ser Met Arg Met Thr Ile Thr Pro Thr Pro
                645                 650                 655

Pro Gly Gly Gln Pro Pro Val Leu Leu Thr Ala Ile Asp Val Arg Arg
            660                 665                 670

Tyr Val Arg Lys Leu Ile Glu Thr Glu Phe Pro Asp Ile Ala Val Ile
                675                 680                 685

Ser Tyr Gln Glu Val Leu Pro Glu Ile Arg Ile Gln Pro Leu Gly Arg
            690                 695                 700

Ile Gln Ile Phe
705

<210> SEQ ID NO 137
<211> LENGTH: 562
<212> TYPE: PRT
<213> ORGANISM: Chlamydia trachomatis
```

<400> SEQUENCE: 137

```
Met Asp Ile Pro Glu Gln Gly Ser Asn Thr Pro Glu Val Glu Gln Ala
1               5                   10                  15

Ala Cys Cys Asn Gln Glu Ala Ala Glu Asn Asp Arg Ala Lys Asp Glu
            20                  25                  30

Leu Ser Ser Ser Glu Ile Ser Ala Glu Ala Val Gln Ser Cys Glu Ser
        35                  40                  45

Met Glu Ala Phe Glu Gln Val Val Ala Glu Arg Ser Ser Ile Glu Glu
    50                  55                  60

Lys Ile Leu Phe Ala Leu Glu Gln Met Gly Val Leu Leu Lys Gly Ala
65                  70                  75                  80

Asp Gln Asn Ser Asp Leu Lys Leu Phe Trp Asn Val Arg Lys Phe Cys
                85                  90                  95

Leu Pro Leu Phe Gln Gln Leu Glu Asp Pro Val Gln Arg Ala Asn Leu
            100                 105                 110

Trp Gly Cys Tyr Thr Glu Leu Thr Arg Glu Gly Arg His Ile Lys Thr
        115                 120                 125

Leu Gln Asp Glu Glu Gly Ala Phe Leu Val Gly Gln Ile Glu Leu Ala
    130                 135                 140

Ile Ser Cys Leu Glu Ser Gly Val Gln Gly Phe Phe Ser Lys Thr Glu
145                 150                 155                 160

Lys Glu Glu Ile Ser Glu Asp Arg Ala Ala Leu Glu Ile Pro Ser
                165                 170                 175

Leu Ser Ala His Lys Asp Phe Tyr Leu Ser Thr His Ala Asp Leu Arg
            180                 185                 190

Trp Leu Gly Ser Phe Ser Ser Gln Ile Ile Asn Leu Arg Lys Glu Leu
        195                 200                 205

Met Asn Ile Ser Met Arg Met Arg Leu Lys Ser Gln Phe Phe Gln Lys
    210                 215                 220

Leu Ser Val Leu Gly Asn Lys Val Phe Pro Arg Lys Glu Leu Thr
225                 230                 235                 240

Glu Lys Val Ser Glu Leu Phe Ala Gln Asp Val Glu Ala Phe Val Glu
                245                 250                 255

Arg Tyr Phe Ser Arg Ala Ser Arg Glu Ser Leu Lys Lys Ser Val Phe
            260                 265                 270

Phe Leu Arg Lys Glu Ile Lys Arg Leu Gln Gln Ala Ala Lys Tyr Leu
        275                 280                 285

Ser Ile Ser Ser Gly Val Phe Ser Ser Thr Arg Leu Gly Leu Ser Gln
    290                 295                 300

Cys Trp Asp Gln Leu Lys Gly Leu Glu Lys Glu Ile Arg Gln Glu Gln
305                 310                 315                 320

Ser Arg Leu Ala Ala Thr Ser Ala Glu Asn Met Lys Glu Val Gln Gly
                325                 330                 335

Arg Leu Asp Gln Val Glu Val Leu Leu Gln Glu Asn Glu Glu Val His
            340                 345                 350

Lys Ile Arg Lys Glu Ile Glu Ala Ile Ser Lys His Ile Arg Gly Ile
        355                 360                 365

Ser Leu Val His Asp Asp Val Val Leu Leu Lys Gly Arg Ile Gln Thr
    370                 375                 380

Leu Leu Gly Glu Val Arg Glu Arg Ala Val Ile Glu Lys Glu Met
385                 390                 395                 400

Lys Glu Leu Gln Ala Lys Ala Glu Arg Ala Arg Ala Glu Ala Ile Gln
                405                 410                 415
```

```
Ala Leu Glu Asn Glu Val Gln Ser Phe Cys Asp Gln Cys Asn Glu Gly
            420                 425                 430

Asp Leu Pro Glu Gly Ala Lys Glu Arg Cys Gln Glu Leu Lys Glu Ala
            435                 440                 445

Val Gln Lys Met Ala Tyr Leu Pro Tyr Ala Lys Lys Val Ala Leu Asp
450                 455                 460

Asn Gln Ile Asn Ala Ala Gln Arg Ser Val Leu Ala Arg Leu Glu Glu
465                 470                 475                 480

Gln Met Leu Ala Cys Pro Asp Ala Lys Glu Lys Val Leu Asn Met Arg
                485                 490                 495

Gln Val Leu Glu Gln Arg Met Leu Arg Arg Lys Glu Leu Lys Ala Lys
            500                 505                 510

Phe Glu Cys Asp Lys Lys Leu Leu Gly Gly Ser Gly Leu Asp Phe Asp
            515                 520                 525

Arg Ala Leu Gln Tyr Ser Ala Met Val Glu Asp Arg Lys Ala Leu
            530                 535                 540

Glu Glu Leu Asp Ala Ala Ile Ile Glu Leu Lys Arg Gln Ile Gln Gln
545                 550                 555                 560

Phe Val

<210> SEQ ID NO 138
<211> LENGTH: 213
<212> TYPE: PRT
<213> ORGANISM: Chlamydia trachomatis

<400> SEQUENCE: 138

Met Thr Thr Asn Lys Ser Tyr Leu Thr Tyr Phe Thr Asp Ala Leu Trp
1               5                   10                  15

Ile Asn Asn Gln Pro Leu Ile Ala Ile Leu Gly Ile Cys Ser Ala Leu
            20                  25                  30

Ala Val Thr Thr Thr Val Thr Thr Ala Leu Thr Met Gly Phe Ala Val
            35                  40                  45

Ser Phe Val Thr Gly Cys Ser Ser Phe Val Val Ser Leu Leu Arg Lys
50                  55                  60

Ile Thr Pro Glu Ser Val Arg Met Ile Ala Gln Leu Ile Ile Ser
65                  70                  75                  80

Leu Phe Val Ile Leu Ile Asp Gln Phe Leu Lys Ala Phe Phe Thr
                85                  90                  95

Ile Ser Lys Thr Leu Ser Val Phe Val Gly Leu Ile Ile Thr Asn Cys
            100                 105                 110

Ile Val Met Gly Arg Ala Glu Ser Met Ala Arg His Val Ser Pro Ile
            115                 120                 125

Pro Ala Phe Leu Asp Gly Leu Gly Ser Gly Leu Gly Tyr Gly Trp Val
130                 135                 140

Leu Val Cys Ile Ser Ile Ile Arg Glu Leu Phe Gly Phe Gly Thr Ile
145                 150                 155                 160

Leu Gly Phe Arg Val Ile Pro Glu Ile Leu Tyr Thr Ser Ala Ala His
                165                 170                 175

Pro Asp Gly Tyr Glu Asn Leu Gly Leu Met Val Leu Ala Pro Ser Ala
            180                 185                 190

Phe Phe Leu Leu Gly Ile Met Ile Trp Ile Val Asn Ile Ile Arg Ala
            195                 200                 205

Pro Lys Thr Lys Arg
210
```

<210> SEQ ID NO 139
<211> LENGTH: 360
<212> TYPE: PRT
<213> ORGANISM: Chlamydia trachomatis

<400> SEQUENCE: 139

Met Gly Glu Lys Thr Glu Lys Ala Thr Pro Lys Arg Leu Arg Asp Ala
1               5                   10                  15

Arg Lys Lys Gly Gln Val Ala Lys Ser Gln Asp Phe Pro Ser Ala Ile
            20                  25                  30

Thr Phe Ile Val Ser Met Phe Leu Thr Phe Ser Leu Ala Ser Phe Phe
        35                  40                  45

Ala Lys His Leu Gly Ser Phe Leu Val Ser Ile Phe Lys Thr Ala Pro
    50                  55                  60

Gln Asn His Asp Pro His Leu Ala Val Tyr Tyr Leu Lys Asn Cys Leu
65                  70                  75                  80

Ile Leu Ile Leu Thr Val Ser Leu Pro Leu Leu Gly Ala Val Gly Phe
                85                  90                  95

Val Gly Leu Leu Ile Gly Phe Leu Ile Val Gly Pro Thr Phe Ser Thr
            100                 105                 110

Glu Val Phe Lys Pro Asp Leu Lys Lys Phe Asn Pro Ile Asp Asn Leu
        115                 120                 125

Lys Gln Lys Phe Lys Val Lys Thr Phe Ile Glu Leu Leu Lys Ser Ile
    130                 135                 140

Phe Lys Ile Ser Gly Ala Ala Leu Ile Leu Tyr Ile Val Leu Lys Asn
145                 150                 155                 160

Arg Val Glu Leu Val Ile Glu Thr Ala Gly Ile Pro Pro Leu Val Thr
                165                 170                 175

Ala Gln Val Phe Lys Glu Ile Leu Tyr Lys Ala Val Thr Ser Ile Gly
            180                 185                 190

Ile Phe Phe Leu Val Val Ala Val Ile Asp Leu Val Tyr Gln Arg His
        195                 200                 205

Ser Phe Ala Lys Glu Leu Lys Met Glu Lys Phe Glu Val Lys Gln Glu
    210                 215                 220

Phe Lys Asp Thr Glu Gly Asn Pro Glu Ile Lys Gly Arg Arg Gln
225                 230                 235                 240

Ile Ala Gln Glu Ile Ala Tyr Glu Asp Thr Ser Ser Gln Ile Lys His
                245                 250                 255

Ala Ser Ala Val Val Ser Asn Pro Lys Asp Ile Ala Val Ala Ile Gly
            260                 265                 270

Tyr Met Pro Glu Lys Tyr Lys Ala Pro Trp Ile Ile Ala Met Gly Val
        275                 280                 285

Asn Leu Arg Ala Lys Arg Ile Ile Ala Glu Ala Glu Lys Tyr Gly Val
    290                 295                 300

Pro Ile Met Arg Asn Val Pro Leu Ala His Gln Leu Leu Asp Glu Gly
305                 310                 315                 320

Lys Glu Leu Lys Phe Ile Pro Glu Thr Thr Tyr Glu Ala Val Gly Glu
                325                 330                 335

Ile Leu Leu Tyr Ile Thr Ser Leu Asn Ala Gln Asn Leu Glu Asn Lys
            340                 345                 350

Asn Ile Asn Gln Phe Asp Asn Leu
        355                 360

<210> SEQ ID NO 140
<211> LENGTH: 921
<212> TYPE: PRT
<213> ORGANISM: Chlamydia trachomatis

<400> SEQUENCE: 140

Met Asn Ile Val Thr Ser Lys Ile Gly Ser Lys Ile Leu Arg Ile Ile
1               5                   10                  15

Gln Asn Asn Lys Lys Leu Gly Leu Leu Ser Ala Leu Val Val Leu Asp
            20                  25                  30

Ala Ala Leu Leu Ser Val Asn Ser Arg Ser Glu Gly Leu Ile Gly
        35                  40                  45

Gln Ser Ala Ser Leu Pro Asn Tyr His Glu Thr Glu Gln Gln Ile Ala
    50                  55                  60

Ala Cys Pro Lys Asn Ile Ala Lys Asn Leu Ala Lys Lys Ser Ser Pro
65                  70                  75                  80

Gly Ser Lys Pro Thr Val Gly Ala Ser Phe Pro Ser Gln Pro Val Ser
                85                  90                  95

Val Lys Ala Ala Pro Ala Lys Pro Gln Thr Pro Val Ala Gln Thr Arg
            100                 105                 110

His Phe Lys Lys Ser His Gln Ile Phe Ser Pro Asn Phe Thr Gln Ser
        115                 120                 125

Pro Gln Gln Val Asn Lys Pro Glu Glu Arg Arg Pro Leu Glu Ser
    130                 135                 140

Arg Tyr Leu Gln Gly Ala Val Lys Gln Ala Ala Ala Lys Glu Lys
145                 150                 155                 160

Lys Ala Leu Glu Gln Glu Val Ser Lys Gln Glu Glu Ala Ser Lys
                165                 170                 175

Leu Trp Glu Glu Lys Gln Ser Tyr Ala Arg Arg Ala Val Asn Ala Ile
            180                 185                 190

Asn Phe Ser Val Arg Lys Gln Ile Glu Glu Gln Lys Thr Ile Ser
        195                 200                 205

Asn Pro Gly Asn Asp Gln Thr Leu Pro Arg Lys Lys Asp Pro Gln Thr
    210                 215                 220

Ser Gly Glu Pro Val Ile Gln Thr Val Gln Asp Cys Ser Gln Asp Gln
225                 230                 235                 240

Glu Glu Glu Lys Lys Val Leu Glu Arg Leu Asn Lys Arg Ser Leu Thr
                245                 250                 255

Cys Gln Asp Leu Lys Glu Val Glu Tyr Thr Val Asn Phe Glu Asp Ile
            260                 265                 270

Ser Ile Leu Glu Leu Leu Gln Phe Val Ser Lys Ile Ser Gly Thr Asn
        275                 280                 285

Phe Val Phe Asp Ser Asn Asp Leu Gln Phe Asn Val Thr Ile Val Ser
    290                 295                 300

His Asp Pro Thr Ser Val Asp Asp Leu Ala Thr Ile Leu Leu Gln Val
305                 310                 315                 320

Leu Lys Met His Asp Leu Lys Val Val Glu Gln Gly Asn Asn Val Leu
                325                 330                 335

Ile Tyr Arg Asn Pro Lys Leu Ser Lys Leu Ser Thr Val Val Thr Asp
            340                 345                 350

Gly Ser Ala Lys Asp Thr Cys Glu Ala Val Val Val Thr Arg Val Phe
        355                 360                 365

Arg Leu Tyr Ser Val Ser Pro Ser Ala Ala Val Gly Ile Ile Gln Pro
    370                 375                 380

-continued

```
Leu Leu Ser His Asp Ala Ile Ser Ala Ser Glu Ser Thr Arg His
385                 390                 395                 400

Ile Ile Val Ser Asp Ile Ala Gly Asn Ile Glu Lys Val Arg Glu Leu
            405                 410                 415

Leu Gln Ala Leu Asp Ser Pro Gly Thr Ala Ile Asp Met Ser Glu Tyr
        420                 425                 430

Asp Val Gln Phe Ala Asn Pro Ala Ala Leu Val Ser Tyr Cys Gln Asp
            435                 440                 445

Val Leu Gly Ala Met Ala Glu Glu Ala Phe Gln Ile Phe Ile Gln
        450                 455                 460

Pro Gly Thr Asn Lys Ile Phe Val Ile Ser Ser Pro Arg Leu Thr Ala
465                 470                 475                 480

Lys Thr Ile Gln Leu Leu Glu Ser Leu Asp Ile Pro Glu Met Ala His
                485                 490                 495

Thr Leu Asp Asp Val Thr Ser Pro Ala Ala Leu Gly Ser Ser Gly
            500                 505                 510

Ala Ala Asn Pro Lys Ser Leu Arg Phe Phe Met Tyr Lys Leu Lys Tyr
        515                 520                 525

Gln Asn Gly Ala Ala Ile Ala Gln Ala Ile Gln Asp Ile Gly Tyr Asn
        530                 535                 540

Leu Tyr Val Thr Thr Ala Met Asp Glu Asp Phe Ile Asn Thr Leu Asn
545                 550                 555                 560

Ser Ile Gln Trp Leu Pro Val Asn Asn Ser Ile Val Ile Gly Asn
            565                 570                 575

Gln Ala Asn Val Asp Lys Val Val Ser Leu Leu Asn Gly Leu Asp Leu
        580                 585                 590

Pro Pro Lys Gln Val Tyr Ile Glu Val Leu Ile Leu Glu Thr Ser Leu
        595                 600                 605

Glu Lys Ser Trp Asp Phe Gly Val Gln Trp Ala Ala Leu Gly Asp Glu
        610                 615                 620

Gln Gly Lys Val Ala Tyr Ala Ser Gly Leu Leu Ser Asn Thr Gly Leu
625                 630                 635                 640

Thr Asp Pro Leu Arg Asn Gln Ser Leu Pro Val Ala Pro Asn Pro Gly
                645                 650                 655

Asn Ile Ser Leu Pro Thr Pro Gly Gln Leu Ala Gly Ile Ser Asp Met
            660                 665                 670

Met Tyr Gly Ser Ser Ala Phe Gly Leu Gly Ile Ile Gly Asn Val Leu
        675                 680                 685

Ser His Asn Gly Lys Ser Tyr Leu Thr Leu Gly Gly Leu Leu Ser Ala
        690                 695                 700

Leu Asp Gln Asp Gly Asp Thr Thr Val Val Leu Asn Pro Arg Ile Met
705                 710                 715                 720

Ala Gln Asp Thr Gln Gln Ala Ser Phe Phe Val Gly Gln Thr Ile Pro
                725                 730                 735

Phe Gln Thr Thr Ser Thr Val Ile Gln Glu Thr Gly Ser Val Thr Gln
            740                 745                 750

Asn Ile Glu Tyr Glu Asp Ile Gly Val Asn Leu Val Val Thr Ser Thr
        755                 760                 765

Ile Ala Pro Asn Asn Val Val Thr Leu Gln Ile Glu Gln Thr Ile Ser
        770                 775                 780

Glu Leu His Ser Ala Gln Gly Val Leu Thr Pro Val Thr Asp Lys Thr
785                 790                 795                 800

Phe Ala Ala Thr Arg Leu Gln Val Pro Asp Gly Cys Phe Leu Val Met
```

```
                805                 810                 815
Ser Gly His Ile Arg Asp Lys Leu Thr Lys Ile Val Ser Gly Val Pro
            820                 825                 830

Leu Leu Ser Ser Leu Pro Leu Ile Lys Gly Leu Phe Ser Arg Ser Ile
            835                 840                 845

Asp Gln Arg Gln Lys Arg Asn Ile Met Ile Phe Ile Lys Pro Lys Val
850                 855                 860

Ile Ser Ser Phe Glu Glu Gly Thr Ala Leu Ser Asn Thr Glu Gly Tyr
865                 870                 875                 880

Arg Tyr Asn Trp Glu Ser Glu Arg Gly Ser Leu Glu Val Ala Pro Arg
                885                 890                 895

His Ala Pro Glu Cys Gln His Ile Pro Lys Val Gln Ala Glu Ser Asp
            900                 905                 910

Phe Lys Met Leu Glu Ile Glu Ala Glu
            915                 920

<210> SEQ ID NO 141
<211> LENGTH: 289
<212> TYPE: PRT
<213> ORGANISM: Chlamydia trachomatis

<400> SEQUENCE: 141

Met Ala Thr Leu Pro Glu Val Leu Ser Gly Leu Gly Ser Ser Tyr Ile
1               5                   10                  15

Asp Tyr Ile Phe Gln Lys Pro Ala Asp Tyr Val Trp Thr Val Phe Leu
            20                  25                  30

Leu Leu Ala Ala Arg Ile Leu Ser Met Leu Ser Ile Ile Pro Phe Leu
        35                  40                  45

Gly Ala Lys Leu Phe Pro Ser Pro Ile Lys Ile Gly Ile Ala Leu Ser
    50                  55                  60

Trp Met Gly Leu Leu Pro Gln Val Ile Gln Asp Ser Thr Ile Val
65                  70                  75                  80

His Tyr Gln Asp Leu Asp Ile Phe Tyr Ile Leu Ile Lys Glu Ile
                85                  90                  95

Leu Ile Gly Val Leu Ile Gly Phe Leu Phe Ser Phe Pro Phe Tyr Ala
            100                 105                 110

Ala Gln Ser Ala Gly Ser Phe Ile Thr Asn Gln Gln Gly Ile Gln Gly
        115                 120                 125

Leu Glu Gly Ala Thr Ser Leu Val Ser Ile Glu Gln Thr Ser Pro His
    130                 135                 140

Gly Ile Phe Tyr His Tyr Phe Val Thr Ile Val Phe Trp Leu Ala Gly
145                 150                 155                 160

Gly His Arg Ile Ile Leu Ser Val Leu Leu Gln Ser Leu Glu Ile Ile
                165                 170                 175

Pro Leu His Ala Val Phe Pro Glu Ser Met Met Ser Leu Arg Ala Pro
            180                 185                 190

Met Trp Ile Ala Ile Leu Lys Met Cys Gln Leu Cys Leu Ile Met Thr
        195                 200                 205

Ile Gln Leu Ser Ala Pro Ala Ala Val Ala Met Leu Met Ser Asp Leu
    210                 215                 220

Phe Leu Gly Ile Ile Asn Arg Met Ala Pro Gln Val Gln Val Ile Tyr
225                 230                 235                 240

Leu Leu Ser Ala Leu Lys Ala Phe Met Gly Leu Leu Phe Leu Thr Leu
                245                 250                 255
```

```
Ala Trp Trp Phe Ile Val Lys Gln Ile Asp Tyr Phe Thr Leu Ala Trp
            260                 265                 270

Phe Lys Glu Ile Pro Thr Met Leu Phe Gly Ala His Pro Pro Lys Val
        275                 280                 285

Leu

<210> SEQ ID NO 142
<211> LENGTH: 35
<212> TYPE: DNA
<213> ORGANISM: Artificial Sequence
<220> FEATURE:
<223> OTHER INFORMATION: PCR primer

<400> SEQUENCE: 142
gcactgcatg gctagctggc tggatcgtta tgcag                               35

<210> SEQ ID NO 143
<211> LENGTH: 37
<212> TYPE: DNA
<213> ORGANISM: Artificial Sequence
<220> FEATURE:
<223> OTHER INFORMATION: PCR primer

<400> SEQUENCE: 143
gcactgcatg gctagcgaga atgctatgtc atcatcg                             37

<210> SEQ ID NO 144
<211> LENGTH: 38
<212> TYPE: DNA
<213> ORGANISM: Artificial Sequence
<220> FEATURE:
<223> OTHER INFORMATION: PCR primer

<400> SEQUENCE: 144
gcactgcatg gctagcatcg agtttgcttt tgttcctc                            38

<210> SEQ ID NO 145
<211> LENGTH: 37
<212> TYPE: DNA
<213> ORGANISM: Artificial Sequence
<220> FEATURE:
<223> OTHER INFORMATION: PCR primer

<400> SEQUENCE: 145
gcactgcatg gctagctttt cacgatggat caccctc                             37

<210> SEQ ID NO 146
<211> LENGTH: 35
<212> TYPE: DNA
<213> ORGANISM: Artificial Sequence
<220> FEATURE:
<223> OTHER INFORMATION: PCR primer

<400> SEQUENCE: 146
gcactgcatg gctagcctag tagagttaga ggctc                               35

<210> SEQ ID NO 147
<211> LENGTH: 37
<212> TYPE: DNA
<213> ORGANISM: Artificial Sequence
<220> FEATURE:
<223> OTHER INFORMATION: PCR primer

<400> SEQUENCE: 147
gcactgcatg gctagcggtg aaaaaacaga aaaggcc                             37
```

<210> SEQ ID NO 148
<211> LENGTH: 40
<212> TYPE: DNA
<213> ORGANISM: Artificial Sequence
<220> FEATURE:
<223> OTHER INFORMATION: PCR primer

<400> SEQUENCE: 148
gcactgcatg gctagcaata agctactcaa tttcgtcagc          40

<210> SEQ ID NO 149
<211> LENGTH: 38
<212> TYPE: DNA
<213> ORGANISM: Artificial Sequence
<220> FEATURE:
<223> OTHER INFORMATION: PCR primer

<400> SEQUENCE: 149
gcactgcatg gctagccaaa accaatacga gcaattac            38

<210> SEQ ID NO 150
<211> LENGTH: 33
<212> TYPE: DNA
<213> ORGANISM: Artificial Sequence
<220> FEATURE:
<223> OTHER INFORMATION: PCR primer

<400> SEQUENCE: 150
gcactgcatg gctagcagca tgacgatcgt tcc                 33

<210> SEQ ID NO 151
<211> LENGTH: 44
<212> TYPE: DNA
<213> ORGANISM: Artificial Sequence
<220> FEATURE:
<223> OTHER INFORMATION: PCR primer

<400> SEQUENCE: 151
gcactgcatg gctagcttga ctctaattttt tgttattatt atcg    44

<210> SEQ ID NO 152
<211> LENGTH: 38
<212> TYPE: DNA
<213> ORGANISM: Artificial Sequence
<220> FEATURE:
<223> OTHER INFORMATION: PCR primer

<400> SEQUENCE: 152
gcactgcatg gctagctcaa tagctattgc aagggaac            38

<210> SEQ ID NO 153
<211> LENGTH: 37
<212> TYPE: DNA
<213> ORGANISM: Artificial Sequence
<220> FEATURE:
<223> OTHER INFORMATION: PCR primer

<400> SEQUENCE: 153
gcactgcatg gctagcaaaa aactcttaaa gtcggcg             37

<210> SEQ ID NO 154
<211> LENGTH: 36
<212> TYPE: DNA
<213> ORGANISM: Artificial Sequence
<220> FEATURE:

<223> OTHER INFORMATION: PCR primer

<400> SEQUENCE: 154
gcactgcatg gctagcgtta atcctattgg tccagg                          36

<210> SEQ ID NO 155
<211> LENGTH: 33
<212> TYPE: DNA
<213> ORGANISM: Artificial Sequence
<220> FEATURE:
<223> OTHER INFORMATION: PCR primer

<400> SEQUENCE: 155
gcactgcatg gctagcagca agccctctcc tcg                             33

<210> SEQ ID NO 156
<211> LENGTH: 35
<212> TYPE: DNA
<213> ORGANISM: Artificial Sequence
<220> FEATURE:
<223> OTHER INFORMATION: PCR primer

<400> SEQUENCE: 156
gcactgcatg gctagcggaa tctctctacc agagc                           35

<210> SEQ ID NO 157
<211> LENGTH: 40
<212> TYPE: DNA
<213> ORGANISM: Artificial Sequence
<220> FEATURE:
<223> OTHER INFORMATION: PCR primer

<400> SEQUENCE: 157
gcactgcatg gctagcgttc gtcgatctat ttcttttgc                       40

<210> SEQ ID NO 158
<211> LENGTH: 47
<212> TYPE: DNA
<213> ORGANISM: Artificial Sequence
<220> FEATURE:
<223> OTHER INFORMATION: PCR primer

<400> SEQUENCE: 158
gcactgcatg gctagctcac atttaaatta tttactagaa aaaatcg              47

<210> SEQ ID NO 159
<211> LENGTH: 37
<212> TYPE: DNA
<213> ORGANISM: Artificial Sequence
<220> FEATURE:
<223> OTHER INFORMATION: PCR primer

<400> SEQUENCE: 159
gcactgcatg gctagcaaca agctactcaa ctttgtc                         37

<210> SEQ ID NO 160
<211> LENGTH: 39
<212> TYPE: DNA
<213> ORGANISM: Artificial Sequence
<220> FEATURE:
<223> OTHER INFORMATION: PCR primer

<400> SEQUENCE: 160
gcactgcatg gctagcccaa aaatcgacac ttgtgattc                       39

```
<210> SEQ ID NO 161
<211> LENGTH: 39
<212> TYPE: DNA
<213> ORGANISM: Artificial Sequence
<220> FEATURE:
<223> OTHER INFORMATION: PCR primer

<400> SEQUENCE: 161
gcactgcatg gctagcagca ctccatcttc taataattc                                39

<210> SEQ ID NO 162
<211> LENGTH: 35
<212> TYPE: DNA
<213> ORGANISM: Artificial Sequence
<220> FEATURE:
<223> OTHER INFORMATION: PCR primer

<400> SEQUENCE: 162
gcactgcatg gtcgacttag aagcctttga ctcgc                                    35

<210> SEQ ID NO 163
<211> LENGTH: 40
<212> TYPE: DNA
<213> ORGANISM: Artificial Sequence
<220> FEATURE:
<223> OTHER INFORMATION: PCR primer

<400> SEQUENCE: 163
gcactgcatg gtcgacttac ctcactaaaa attgttttag                               40

<210> SEQ ID NO 164
<211> LENGTH: 38
<212> TYPE: DNA
<213> ORGANISM: Artificial Sequence
<220> FEATURE:
<223> OTHER INFORMATION: PCR primer

<400> SEQUENCE: 164
gcactgcatg gtcgacttaa agagaggcta cgtcttcc                                 38

<210> SEQ ID NO 165
<211> LENGTH: 38
<212> TYPE: DNA
<213> ORGANISM: Artificial Sequence
<220> FEATURE:
<223> OTHER INFORMATION: PCR primer

<400> SEQUENCE: 165
gcactgcatg gtcgacctag gggaaatagg tatatttg                                 38

<210> SEQ ID NO 166
<211> LENGTH: 37
<212> TYPE: DNA
<213> ORGANISM: Artificial Sequence
<220> FEATURE:
<223> OTHER INFORMATION: PCR primer

<400> SEQUENCE: 166
gcactgcatg gtcgacttat tctgtgtctt tccgcgg                                  37

<210> SEQ ID NO 167
<211> LENGTH: 39
<212> TYPE: DNA
<213> ORGANISM: Artificial Sequence
<220> FEATURE:
<223> OTHER INFORMATION: PCR primer
```

<400> SEQUENCE: 167
gcactgcatg gtcgacttat aaatgatcag gttggttag                39

<210> SEQ ID NO 168
<211> LENGTH: 43
<212> TYPE: DNA
<213> ORGANISM: Artificial Sequence
<220> FEATURE:
<223> OTHER INFORMATION: PCR primer

<400> SEQUENCE: 168
gcactgcatg gtcgacttag aaaatctgaa ttcttcctaa agg          43

<210> SEQ ID NO 169
<211> LENGTH: 36
<212> TYPE: DNA
<213> ORGANISM: Artificial Sequence
<220> FEATURE:
<223> OTHER INFORMATION: PCR primer

<400> SEQUENCE: 169
gcactgcatg gtcgactcac gcgacgtagt agattc                  36

<210> SEQ ID NO 170
<211> LENGTH: 39
<212> TYPE: DNA
<213> ORGANISM: Artificial Sequence
<220> FEATURE:
<223> OTHER INFORMATION: PCR primer

<400> SEQUENCE: 170
gcactgcatg gtcgacttag tctttaaaga agatactcg               39

<210> SEQ ID NO 171
<211> LENGTH: 43
<212> TYPE: DNA
<213> ORGANISM: Artificial Sequence
<220> FEATURE:
<223> OTHER INFORMATION: PCR primer

<400> SEQUENCE: 171
gcactgcatg gtcgacttaa ttcatcttcg taaagaatct tcc          43

<210> SEQ ID NO 172
<211> LENGTH: 42
<212> TYPE: DNA
<213> ORGANISM: Artificial Sequence
<220> FEATURE:
<223> OTHER INFORMATION: PCR primer

<400> SEQUENCE: 172
gcactgcatg gtcgactaat tatcgaaatg tctttgaata tg           42

<210> SEQ ID NO 173
<211> LENGTH: 41
<212> TYPE: DNA
<213> ORGANISM: Artificial Sequence
<220> FEATURE:
<223> OTHER INFORMATION: PCR primer

<400> SEQUENCE: 173
gcactgcatg gtcgacttag aatctgaact gaccagatac g            41

<210> SEQ ID NO 174
<211> LENGTH: 40

```
<212> TYPE: DNA
<213> ORGANISM: Artificial Sequence
<220> FEATURE:
<223> OTHER INFORMATION: PCR primer

<400> SEQUENCE: 174
gcactgcatg gtcgacttat tggagataac cagaatatag                              40

<210> SEQ ID NO 175
<211> LENGTH: 38
<212> TYPE: DNA
<213> ORGANISM: Artificial Sequence
<220> FEATURE:
<223> OTHER INFORMATION: PCR primer

<400> SEQUENCE: 175
gcactgcatg gtcgacctaa cgtttctttc cgcttttc                                38

<210> SEQ ID NO 176
<211> LENGTH: 36
<212> TYPE: DNA
<213> ORGANISM: Artificial Sequence
<220> FEATURE:
<223> OTHER INFORMATION: PCR primer

<400> SEQUENCE: 176
gcactgcatg gtcgacttag agtacttgag ggttgg                                  36

<210> SEQ ID NO 177
<211> LENGTH: 39
<212> TYPE: DNA
<213> ORGANISM: Artificial Sequence
<220> FEATURE:
<223> OTHER INFORMATION: PCR primer

<400> SEQUENCE: 177
gcactgcatg gtcgacctaa gcaccctcaa tttcattgc                               39

<210> SEQ ID NO 178
<211> LENGTH: 46
<212> TYPE: DNA
<213> ORGANISM: Artificial Sequence
<220> FEATURE:
<223> OTHER INFORMATION: PCR primer

<400> SEQUENCE: 178
gcactgcatg gtcgacttat ttatgttttc gaatatctag aatttc                       46

<210> SEQ ID NO 179
<211> LENGTH: 42
<212> TYPE: DNA
<213> ORGANISM: Artificial Sequence
<220> FEATURE:
<223> OTHER INFORMATION: PCR primer

<400> SEQUENCE: 179
gcactgcatg acgcgtttag aaaatttgaa ttcttcccaa ag                           42

<210> SEQ ID NO 180
<211> LENGTH: 35
<212> TYPE: DNA
<213> ORGANISM: Artificial Sequence
<220> FEATURE:
<223> OTHER INFORMATION: PCR primer

<400> SEQUENCE: 180
```

-continued

```
gcactgcatg acgcgtttaa gcgggagtcc atagg                    35

<210> SEQ ID NO 181
<211> LENGTH: 42
<212> TYPE: DNA
<213> ORGANISM: Artificial Sequence
<220> FEATURE:
<223> OTHER INFORMATION: PCR primer

<400> SEQUENCE: 181
gcactgcatg acgcgtttac tttgcttttt tcttgttaga ag            42
```

CYTOTOXIC T-CELL EPITOPES FROM *CHLAMYDIA*

This application is a National Stage application of co-pending PCT application PCT/IB03/01161 filed Feb. 13, 2003, which was published in English under PCT Article 21(2) on Aug. 21, 2003, which claims the benefit of Great Britain application Serial No. GB0203403.1 filed Feb. 13, 2002. These applications are incorporated herein by reference in their entireties.

TECHNICAL FIELD

This invention is in the field of cell-mediated immunity, particularly immunity against chlamydial infections, such as those caused by *Chlamydia pneumoniae* and *Chlamydia trachomatis*.

BACKGROUND ART

The *Chlamydia* are obligate intracellular parasites of eukaryotic cells which are responsible for various diseases. They occupy an exclusive eubacterial phylogenic branch, having no close relationship to any other known organisms—they are classified in their own order (*Chlamydiales*) which contains a single family (*Chlamydiaceae*) which in turn contains a single genus (*Chlamydia*). Four species are currently known—*C.trachomatis, C.pneumoniae, C.pecorum* and *C.psittaci*.

The *Chlamydia* undergo a developmental cycle in which two functionally and morphologically different cell types can be recognized: the extracellular elementary body (EB) and the intracellular reticulate body (RB). The developmental cycle is initiated by endocytosis of an EB by a eukaryotic host cell. The bacteria remain within an intracellular vacuole and, shortly after internalization, EBs reorganize and differentiate into RBs, which actively multiply. Late in the cycle, logarithmic growth ceases as RBs begin to restructure into EBs, which are released upon lysis of the host cell.

*Chlamydia pneumoniae* (also known as *Chlamydophila pneumoniae* and, previously, as TWAR) causes infections of the respiratory tract. It has been estimated [1] that it is responsible for up to 10% of all cases of community-acquired pneumonia and 5% of bronchitis and sinusitis cases. Studies have also suggested a role for *C.pneumoniae* in atherosclerosis and coronary heart disease [2].

The human serovariants ("serovars") of *C.trachomatis* are divided into two biovariants ("biovars"). Serovars A-K elicit epithelial infections primarily in the ocular tissue (A-C) or urogenital tract (D-K). Serovars L1, L2 and L3 are the agents of invasive lymphogranuloma venereum. *C.trachomatis* is the leading cause of preventable infectious blindness (ocular trachoma) in the developing world and of sexually transmitted disease ("STD") in the USA. Although antibiotic therapy can be effective, untreated or inadequately treated infections result in hundreds of thousands of cases of pelvic inflammatory disease each year in the USA.

Being intracellular, *Chlamydia* can generally evade antibody-mediated immune responses, and the importance of cell-mediated immune responses (CMI) during infections by obligate intracellular bacteria is being increasingly reported. In this context, induction of CD8+ cytotoxic T lymphocytes (CTLs) which are specific for peptides derived from the Major Outer Membrane protein (MOMP) of *C.trachomatis* has been described [3]. These CTLs are able to kill cervical epithelial cells infected by the pathogen, which suggests that immunisation with suitable CTL epitopes could represent a tool against this and closely related bacteria. Furthermore, activation of CMI responses is believed to be important for protective immunity against *C.pneumoniae* [4, 5, 6].

The identification of peptides derived from *C.pneumoniae* and *C.trachomatis* antigens which are able to bind to different classes of human class I MHC molecules will therefore be useful for the development of a CTL-based vaccine [e.g. references 7 & 8].

Genome sequences of *C.pneumoniae* [9, 10, 11, 12, 13] and *C.trachomatis* [12, 14, 15] are available. Although computer algorithms have been designed to predict T-cell epitopes from amino acid sequences [e.g. 16, 17, 18, 19], their predictions are not particularly accurate. For example, in a study carried out on human papillomavirus type 18 E6 antigen, only 8 out of 18 peptides identified by computer algorithms could actually bind to HLA-A0201 molecules [20].

It is an object of the invention to provide CTL epitopes from *Chlamydia* and to provide materials which can deliver these epitopes for immunisation.

DISCLOSURE OF THE INVENTION

The invention is based on the identification of 57 separate 9 mer cytotoxic T-cell epitopes from *C.pneumoniae* proteins (SEQ IDs 1-57; see Table 1). A preferred subset of these epitopes is SEQ IDs 1, 2, 4, 5, 6,7, 8, 9, 10, 11, 13, 14, 15, 18, 19, 20, 21, 22, 23, 24, 25,26, 27, 29, 30, 32, 33, 34, 35, 36, 37, 38, 40, 43, 45, 47, 48, 49 & 50. A more preferred subset is SEQ IDs 10, 36, 38, 40, 43, 45, 47, 48, 49 & 50.

These 57 epitopes are fragments of 33 proteins (SEQ IDs 83-115) encoded within the genome of *C.pneumoniae* CWL029 [9] and are useful for preparing and investigating vaccines and for diagnostic assays. An empirical approach to epitopes identification showed that computer prediction is not adequate for finding T-cell epitopes within the *C.pneumoniae* genome. For example, of five epitopes predicted in 'low calcium response protein D', the epitope which was empirically shown to be the strongest binder was algorithmically predicted to be the weakest binder.

CTL epitopes from corresponding *C.trachomatis* proteins are shown in Table 3. Some of these are identical to the *C.pneumoniae* epitopes, but those which differ are given as SEQ IDs 58-82. These 25 epitopes are fragments of 26 proteins (SEQ IDs 116-141) encoded within the genome of *C.trachomatis* D/UW-3/CX [14].

T-cell epitopes which are shared by *C.pneumoniae* and *C.trachomatis* are particularly preferred. These can be used where inter-species reactivity is desirable.

New uses for Polypeptides of the Invention

The invention provides a polypeptide for use as an antigen, wherein the polypeptide comprises: (a) an amino acid sequence selected from the group consisting of SEQ IDs 83-141; (b) an amino acid sequence having at least s % sequence identity to an amino acid sequence of (a); or (c) an amino acid sequence comprising both (i) a fragment of at least x amino acids from an amino acid sequence of (a) and (ii) an amino acid sequence selected from the group consisting of SEQ IDs 1-82. Fragments (i) and (ii) may overlap.

The use as an antigen is preferably a use: (1) as a T-cell antigen; (2) for generating a complex between a class I MHC protein (e.g. a class I HLA) and a fragment of said antigen; (3) as an antigen for raising a cell-mediated immune response; and/or (4) as an antigen for raising a CTL response. The use preferably protects or treats disease and/or infection caused by a *Chlamydia* such as *C.pneumoniae* or *C.trachomatis*.

The invention provides the use of a polypeptide in the manufacture of a medicament for immunising a mammal (typically a human) against *C.pneumoniae* or *C.trachomatis* disease and/or infection, wherein the polypeptide is as defined above.

The invention provides a method of raising an immune response in a mammal (typically a human), comprising the step of administering to the mammal a polypeptide as defined above, wherein said immune response is a cell-mediated immune response and, preferably, a CTL response. The immune response is preferably protective or therapeutic.

These uses and methods of the invention are preferably used to prevent or treat a disease or infection caused by a *Chlamydia* (e.g. by *C.pneumoniae* or *C.trachomatis*). Diseases caused by *C.pneumoniae* include pneumonia, cardiovascular diseases, atherosclerosis, bronchitis, pharyngitis, laryngitis, sinusitis, obstructive lung diseases (e.g. asthma and chronic obstructive pulmonary disease), reactive arthritis, otitis media, abdominal aortic aneurysm, erythema nodosum, Reiter syndrome, sarcoidosis and, possibly, CNS diseases such as Alzheimer's disease and multiple sclerosis [1, 21, 22, 23]. Diseases caused by *C.trachomatis* include lymphogranuloma venereum, ocular trachoma, pelvic inflammatory disease, inclusion conjunctivitis, genital trachoma, infant pneumonitis, incipient trachoma, keratitis, papillary hypertrophy, corneal infiltration, vulvovaginitis, mucopurulent rhinitis, salpingitis, cervicitis, cervical follicles, prostatitis, proctitis, urethritis, lymphogranule inguinale, climatic bubo, tropical bubo, and esthiomene.

The uses and methods of the invention preferably elicit a CTL response at the genital mucosa.

The value of x is at least 7 (e.g. at least 8, 9, 10, 11, 12, 13, 14, 15, 16, 17, 18, 19, 20, 21, 22, 23, 24, 25, 30, 35, 40, 45, 50, 60, 70, 75, 80, 90, 100, 150, 200, 250, 300 etc.).

The value of s is preferably at least 50 (e.g. at least 55, 60, 65, 70, 75, 80, 85, 90, 91, 92, 93, 94, 95, 96, 97, 98, 99, 99.5, 99.9 etc.). This includes variants of SEQ IDs 83-141 (e.g. allelic variants, homologs, orthologs, paralogs, mutants etc.) such as those disclosed in references 10 to 13.

Where the polypeptide is not one of SEQ IDs 83-141, it is preferred that it retains sufficient sequence identity to SEQ IDs 83-141 (or to fragments thereof) such that the activity of its T-cell epitope(s) is not inhibited.

Peptides Comprising T-cell Epitopes of the Invention

The invention provides a polypeptide having formula NH$_2$-A-B-C-COOH, wherein: A is a polypeptide sequence consisting of a amino acids; C is a polypeptide sequence consisting of c amino acids; B is a polypeptide selected from the group consisting of SEQ IDs 1-82. The sequence of this polypeptide NH$_2$-A-B-C-COOH is not one of SEQ IDs 83-141.

The value of a is generally at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70,.80, 90, 100, 150, 200, 250, 300, 350, 400, 450, 500 etc.). The value of c is generally at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 450, 500 etc.). The values of a and c (i.e. the lengths of -A- and -C-) are preferably such that the presentation and/or recognition of the T-cell epitope of the invention is permitted or enhanced.

The value of a+c is at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 450, 500 etc.). It is preferred that the value of a+c is at most 1000 (e.g. at most 900, 800, 700, 600, 500, 450, 400, 350, 300, 250, 200, 190, 180, 170, 160, 150, 140, 130, 120, 110, 100, 90, 80, 70, 60, 50, 40, 30, 25, 20, 19, 18, 17, 16, 15, 14, 13, 12, 11, 10, 9, 8, 7, 6, 5, 4, 3, 2).

The amino acid sequence of -A- typically shares less than m% sequence identity to the a amino acids which are N-terminal of sequence -B- in SEQ IDs 83-141, and the amino acid sequence of -C- typically shares less than n % sequence identity to the c amino acids which are C-terminal of sequence -B- in SEQ IDs 83-141. In general, the values of m and n are both 60 or less (e.g. 50, 40, 30, 20, 10 or less). The values of m and n may be the same as or different from each other.

It is preferred that the amino acid sequence of -A- and/or -C- should not interfere with the presentation and/or recognition of the T-cell epitope of the invention.

The amino acid sequence of -A- and/or -C- may comprise a proteolytic cleavage site. This may aid efficient processing and presentation of the epitopes [e.g. reference 24].

The amino acid sequence of -A- and/or -C- may comprise one or more helper T-cell epitopes [e.g. see refs. 25 & 26 for *C.trachomatis* epitopes]. This may assist in the activation of helper T-cells which may in turn assist in the generation of memory and effector T-cell populations.

The amino acid sequence of -A- and/or -C- may comprise a sequence which is known to be suitable for delivery into a cell (i.e. it can deliver the epitope of the invention to a cell). Such sequences are typically able to cross cellular membranes spontaneously. Suitable sequences include, but are not limited to: adenylate cyclase, such as that of *B.pertussis* [27, 28]; the homeodomain of Antennapedia molecule [29] or other 'protein transduction domains' [e.g. 30] such as Tat, VP22 or Pep-1; bacterial exotoxins, such as anthrax toxin, cholera toxin, *E.coli* heat-labile toxin, or their cellular binding domains; heat shock proteins e.g. hsp70 [31, 32], or adjuvant fragments thereof [33]; cell penetrating peptides [34]; and also sequences from proteins which assemble into particles (e.g. virus-like particles [e.g. 35, 36], papillomavirus coat proteins, filamentous phage, etc.). In the latter case, it is preferred that the sequence -B- is situated at a surface-loop of the particle.

The invention also provides a polypeptide having formula NH$_2$-A-(-B-C-)$_n$—COOH, wherein n is an integer of 2 or more (e.g. 2, 3, 4, 5, 6, 7, 8, 9, 10, 11, 12, 13, 14, 15, 16, 17, 18, 19, 20 etc.) and the definitions of A, B and C are as defined above. These polypeptides contain n -B- moieties and -C- moieties. Each -B- moiety may be the same as or different from the others and the value of b may be the same or different for each -B- moiety. Each -C- moiety may be the same as or different from the others and the value of c may be the same or different for each -C- moiety. These polypeptides present multiple T-cell epitopes of the invention and/or multiple copies of the same T-cell epitope of the invention. The sequence NH$_2$-A-(-B-C-)$_n$—COOH is not one of SEQ IDs 83-141.

Polypeptides Including T-cell Epitopes, other than Polypeptides Consisting of SEQ IDs 83-141

The invention provides a polypeptide comprising an amino acid sequence selected from the group consisting of SEQ IDs 1-82, with the proviso that the polypeptide does not consist of an amino acid sequence selected from the group consisting of SEQ IDs 83-141.

This polypeptide is preferably less than y amino acids in length (e.g. less than y-1, y-2, y-3, y-4, y-5, y-6, y-7, y-8, y-9, y-10, y-15, y-20, y-25, y-30 etc.), where y is the length of SEQ ID b. The value of y will vary depending on the value of a, where SEQ ID a (1≦a≦82) is a fragment of SEQ ID b (83≦b≦141).

While the polypeptides of this invention do not include a peptide consisting only of one of the full length sequences of SEQ ID NOs 83-141, the polypeptides of this invention may include portions, fragments or derivatives of these sequences, in combination with the epitopes of SEQ ID NOs 1-82. In addition, the polypeptides of this invention may include polypeptides comprising one or more of the sequences set forth in SEQ ID NOs 83-141, where these sequences are fused with one or more additional protein sequences, including, for instance the sequences set forth in SEQ ID NOs 1-82.

Variants of SEQ IDs 83-141, but Including the T-Cell Epitopes of the Invention

The invention provides a polypeptide, wherein the polypeptide (a) has at least p % sequence identity to an amino acid sequence selected from the group consisting of SEQ IDs 83-141, and (b) comprises an amino acid sequence selected from the group consisting of SEQ IDs 1-82. The value of p is at least 50 (e.g. 60, 70, 80, 85, 90, 95, 97, 98, 99 etc.), but is less than 100 (e.g. is less than 99.9, 99.5, 99, 98, 97, 96, 95, 90, 85, 80, 75, 70 etc.)

This group of polypeptides includes variants of SEQ IDs 83-141 (e.g. allelic variants, homologs, orthologs, paralogs, mutants etc.) such as the corresponding sequences from references 10 to 15, but a T-cell epitope (SEQ IDs 1-57 & 58-82) within the wild-type *C.pneumoniae* (SEQ IDs 83-115) or *C.trachomatis* (SEQ IDs 116-141) sequence is retained without variation.

T-Cell Epitopes of the Invention

The invention provides a polypeptide comprising an amino acid sequence selected from the group consisting of SEQ IDs 1-82. The polypeptide is preferably less than 80 amino acids in length (e.g. less than 75, 70, 65, 60, 55, 50, 45, 40, 35, 30, 29, 28, 27, 26, 25, 24, 23, 22, 21, 20, 19, 18, 17, 16, 15, 14, 13, 12, 11, 10 etc.).

The cell epitopes of the invention have been identified as 9 mers, but it is well-known that shorter peptides can interact with HLA molecules with high affinity (e.g. the 8 mers disclosed in reference 37) and so the invention also provides a polypeptide comprising a 7 or 8 amino acid fragment of an amino acid sequence selected from the group consisting of SEQ IDs 1-82. The polypeptide is preferably less than 80 amino acids in length (e.g. less than 75, 70, 65, 60, 55, 50, 45, 40, 35, 30, 29, 28, 27, 26, 25, 24, 23, 22, 21, 20, 19, 18, 17, 16, 15, 14, 13, 12, 11 etc.). There are three 7 mer fragments and two 8 mer fragments for each of SEQ IDs 1-82. If desired, these 7 mer and 8 mer sequences can be used according to the invention in place of the 9 mer sequences of SEQ IDs 1-82.

Similarly, if desired, 10 mer fragments of SEQ IDs 83-141 (i.e. SEQ IDs 1-82 plus one further C- or N-terminal amino acid from SEQ IDs 83-141) can be used according to the invention in place of the 9 mer sequences of SEQ IDs 1-82.

General Features of Polypeptides of the Invention

Polypeptides of the invention can be prepared in many ways e.g. by chemical synthesis (at least in part), by digesting longer polypeptides using proteases, by translation from RNA, by purification from cell culture (e.g. from recombinant expression), from the organism itself (e.g. isolation from *Chlamydia*), etc.

Polypeptides of the invention can be prepared in various forms (e.g. native, fusions, glycosylated, non-glycosylated etc.).

Polypeptides of the invention may be attached to a solid support.

Polypeptides of the invention may comprise a detectable label (e.g. a radioactive or fluorescent label, or a biotin label).

Polypeptides of the invention may comprise B cell epitopes in addition to T-cell epitopes [38].

Nucleic Acids of the Invention

The invention also provides nucleic acid comprising: (a) a nucleotide sequence which encodes a polypeptide of the invention; (b) a nucleotide sequence which has at least s % sequence identity to a nucleotide sequence of (a); or (c) both (i) a fragment of at least x nucleotides from a nucleotide sequence of (a) and (ii) a nucleotide sequence encoding one or more of SEQ IDs 1-82. Fragments (i) and (ii) may overlap.

The invention provides nucleic acid comprising sequences complementary to those described above (e.g. for antisense or probing purposes).

Nucleic acid according to the invention can be prepared in many ways e.g. by chemical synthesis (at least in part), from genomic or cDNA libraries, from the organism itself etc.

Nucleic acid of the invention can take various forms (e.g. single-stranded, double-stranded, linear, circular, vectors, primers, probes etc.).

The term "nucleic acid" includes DNA, RNA, and also their analogues, such as those containing modified backbones, peptide nucleic acids (PNA), DNA/RNA hybrids etc.

The invention also provides vectors comprising nucleotide sequences of the invention (e.g. expression vectors) and host cells transformed with such vectors.

The value of x is preferably at least 7 (e.g. at least 8, 9, 10, 11, 12, 13, 14, 15, 16, 17, 18, 19, 20, 21, 22, 23, 24, 25, 30, 35, 40, 45, 50, 60, 70, 75, 80, 90, 100, 150, 200, 250, 300 etc.).

The value of s is preferably at least 50 (e.g. at least 55, 60, 65, 70, 75, 80, 85, 90, 91, 92, 93, 94, 95, 96, 97, 98, 99, 99.5, 99.9 etc.).

MHC Proteins

The invention provides a protein complex, wherein the complex comprises (a) a class I MHC protein; and (b) a polypeptide comprising an amino acid sequence selected from the group consisting of SEQ IDs 1-82. The polypeptide is preferably bound to the MHC protein's groove.

The MHC is preferably a human MHC (i.e. a HLA). The HLA may be a HLA-A, HLA-B or HLA-C protein. HLA-A is preferred, with HLA-A2 being particularly preferred.

The MHC is preferably non-covalently associated with $\beta_2$-microglobulin ($\beta_3$m). The MHC preferably includes two internal disulphide bonds.

The protein complex of the invention may be formed in vitro (e.g. by incubating a cell with a polypeptide of the invention) or in vivo (e.g. after administration of a polypeptide of the invention to a subject, followed by cellular processing of the polypeptide and its presentation in the context of a class I MHC protein). The protein complex may be located in vivo.

The invention also provides a cell (e.g. from a vertebrate, such as a mammal) comprising a class I MHC protein and a polypeptide as described above. The cell is preferably a human cell. The MHC protein is preferably located within a membrane in the cell (e.g. the cell membrane or the ER membrane). The cell may be located in vivo or in vitro.

The invention also provides a population of such cells.

T-Cells

The invention provides a cytotoxic T-cell which can bind to a T-cell epitope of the invention. The T-cell will generally have a T-cell receptor which recognises the T-cell epitope when it is presented by a target cell in the context of a class I MHC protein. The cytotoxic T-cell is preferably a memory cell or an effector cell. The cytotoxic T-cell is preferably CD8+. The cytotoxic T-cell may be located in vitro or in vivo. Transfer of such a T-cell into a host may be used to transfer immunity ("adoptive immunotheraphy"). Various methods can be used for obtaining and/or detecting T-cells of the invention, such as those described in reference 39.

The invention also provides a cellular complex, wherein the complex comprises a cytotoxic T-cell, a target cell which expresses a class I MHC protein (e.g. a HLA), and a T-cell epitope of the invention, wherein the target cell displays the T-cell epitope in the context of the class I MHC protein. The complex may be formed and/or located in vitro or in vivo.

The invention also provides a method for activating a naïve T-cell (also referred to as a virgin T-cell) comprising presenting a polypeptide of the invention to said T-cell. The method results in a cytotoxic T-cell. The method preferably involves clonal expansion of the naive T-cell. The method may involve mixing a naïve T-cell with a polypeptide of the invention and an antigen-presenting cell. The method may be performed in vitro or vivo.

The invention also provides a method for killing a target cell, comprising contacting the target cell with a T-cell of the invention. The target cell is preferably infected with a *Chlamydia*. The method may occur in vivo or in vitro.

The population of cells generated from T-cells which bind specifically to epitopes of the invention and which are activated by this interaction will be of two types: effector cells and memory cells. Effector cells are activated by epitopes of the invention to produce cytokines and kill infected cells. A proportion of effector cells can survive as memory cells. Memory cells are longer-lived and can be induced to generate new effector cell populations when the epitope is re-encountered, either by re-administration of epitopes of the invention or by infection by *Chlamydia*. The generation of memory and effector T-cell populations specific for epitopes of the invention may require the participation of helper T-cells which provide factors necessary for their growth and differentiation (e.g. cytokines, such as interleukin-2). The activation of helper T-cells can be achieved through a number of standard approaches. For example the epitope of invention may be joined to one or more helper T-cell epitopes [e.g. refs 25 & 26], or a helper T-cell epitopes could be co-delivered (e.g. by a nucleic acid vector).

The invention may involve the use of "artificial APC" [40] to drive expansion of T cells in vitro.

Compositions for Use According to the Invention

The invention provides a composition comprising (a) a polypeptide and/or a nucleic acid and/or a complex and/or a cell of the invention; and (b) a pharmaceutically acceptable carrier or diluent. The composition will generally be an immunogenic composition, such as a vaccine.

Vaccines of the invention may be prophylactic (i.e. to prevent disease) or therapeutic (i.e. to reduce or eliminate disease symptoms). Vaccines of the invention may be based on polypeptide antigens, but the use of DNA vaccination is preferred [41, 42, 43, 44, 45 etc.] to facilitate intracellular expression of the epitopes. Vaccines of the invention will generally stimulate a specific CTL response via the presentation of the epitopes of the invention by host cells targeted by the vaccine. Effector CTLs generated by this approach are then primed to attack infected cells and produce cytokines and memory CTLs generated in this way provide a pool of cells for subsequent immune responses.

The compositions will generally include an "immunologically effective amount" of the polypeptides and/or nucleic acids of the invention i.e. an amount sufficient to raise a specific CTL response or, more preferably, an amount sufficient to treat, reduce, or prevent *C.pneumoniae* or *C.trachomatis* infection and/or disease symptoms. An immune response can be detected by using the experimental methods disclosed in the examples, or by monitoring symptoms of *C.pneumoniae* or *C.trachomatis* infection. Animal models of infection are available [e.g. p.458 of ref. 1].

The precise effective amount for a given patient will depend upon the patient's age, size, health, the nature and extent of the condition, the precise composition selected for administration, the patient's taxonomic group, the capacity of the patient's immune system, the degree of protection desired, the formulation of the composition, the treating physician's assessment of the medical situation, and other relevant factors. Thus, it is not useful to specify an exact effective amount in advance, but the amount will fall in a relatively broad range that can be determined through routine trials, and is within the judgement of the clinician. For purposes of the present invention, an effective dose will typically be from about 0.01 mg/kg to 50 mg/kg in the individual to which it is administered.

The compositions are formulated with pharmaceutically acceptable carriers or diluents. The term "pharmaceutically acceptable carrier" refers to a carrier for administration of the antigens which does not itself induce the production of antibodies or other immune responses harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of acceptable excipients is available in the well-known *Remington's Pharmaceutical Sciences*.

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles.

Immunogenic compositions (e.g. vaccines) may additionally comprise an adjuvant. For example, the composition may comprise one or more of the following adjuvants: (A) aluminium compounds (e.g. aluminium hydroxide, aluminium phosphate, aluminium hydroxyphosphate, oxyhydroxide, orthophosphate, sulphate etc. [e.g. see chapters 8 & 9 of ref. 46]), or mixtures of different aluminium cmopounds, with the compounds taking any suitable form (e.g. gel, crystalline, amorphous etc.), and with adsorption being preferred; (B) MF59 (5% Squalene, 0.5% Tween 80, and 0.5% Span 85, formulated into submicron particles using a microfluidizer) [see Chapter 10 of ref. 46; see also ref. 47]; (C) liposomes [see Chapters 13 and 14 of ref. 46]; (D) ISCOMs [see Chapter 23 of ref. 46]; (E) SAF, containing 10% Squalane, 0.4% Tween 80, 5% pluronic-block polymer L121, and thr-MDP, either microfluidized into a submicron emulsion or vortexed to generate a larger particle size emulsion [see Chapter 12 of ref. 46]; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 [see Chapter 22 of ref. 46], also known as Stimulon™; (H) ISCOMs, which may be devoid of additional detergent [48]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 46]; (K) microparticles [see above]; (L) monophosphoryl lipid A (MPL) or 3-O-deacylated MPL (3dMPL) [e.g. chapter 21 of ref. 46]; (M) combinations of 3dMPL with, for example, QS21 and/or oil-in-water emulsions [49]; (N) oligonucleotides comprising CpG motifs [50] i.e. containing at least one CG dinucleotide, with 5-methylcytosine optionally being used in place of cytosine; (O) a polyoxyethylene ether or a polyoxyethylene ester [51]; (P) a polyoxyethylene sorbitan ester surfactant in combination with an octoxynol [52] or a polyoxyethylene alkyl ether or ester surfactant in combination with at least one additional non-ionic surfactant such as an octoxynol [53]; (Q) an immunostimulatory oligonucleotide (e.g. a CpG oligonucleotide) and a saponin [54]; (R) an immunostimulant and a particle of metal salt [55]; (S) a saponin and an oil-in-water emulsion [56]; (T) a saponin (e.g. QS21)+3dMPL+IL-12 (optionally+a sterol) [57]; (U) *E.coli* heat-labile enterotoxin ("LT"), or detoxified mutants thereof, such as the K63 or R72 mutants [e.g. Chapter 5 of ref. 58]; (V) cholera toxin ("CT"), or detoxified mutants thereof [e.g. Chapter 5 of ref. 58]; (W) microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone etc.); (X) chitosan [e.g. 59]; and (Y) other substances that act as immunostimulating agents to enhance the effectiveness of the composition [e.g. see Chapter 7 of ref. 46]. Alum (especially aluminium phosphate and/or hydroxide) and MF59 are preferred adjuvants.

Immunogenic compositions may additionally comprise a polypeptide comprising a helper T-cell epitope and/or DNA encoding a polypeptide comprising a helper T-cell epitope.

The compositions are preferably sterile and/or pyrogen-free.

They will typically be buffered between pH 6 and pH 8 (e.g. at around pH 7).

Once formulated, the compositions contemplated by the invention can be (1) administered directly to a subject or (2) delivered ex vivo, to cells derived from the subject (e.g. as in ex vivo gene therapy). Direct delivery of the compositions will generally be accomplished by parenteral injection, e.g. subcutaneously, intraperitoneally, intravenously or intramuscularly, or to the interstitial space of a tissue. Other modes of administration include mucosal administration (e.g. oral, nasal or pulmonary), ocular, suppositories, and transdermal applications, needles, and gene guns or hyposprays. Electric in vivo administration is also useful for delivering T-cell epitopes [60]. Dosage treatment can be a single dose schedule or a multiple dose schedule.

Another method for delivering a polypeptide of the invention is to use a live vector or delivery system e.g. an organism which expresses the polypeptide. An example is an attenuated strain of *Salmonella typhimurium*, which may include a plasmid which encodes the polypeptide. Live attenuated strains of *Chlamydia* could also be used [44].

Methods for the ex vivo delivery and re-implantation of transformed cells into a subject are known in the art [e.g. ref. 61]. Examples of cells useful in ex vivo applications include, for example, stem cells, particularly hematopoetic, lymph cells, macrophages, dendritic cells, or Langerhans cells. Generally, delivery of nucleic acids for both ex vivo and in vitro applications can be accomplished by, for example, dextran-mediated transfection, calcium phosphate precipitation, polybrene-mediated transfection, protoplast fusion, electroporation, encapsulation of the polynucleotide(s) in liposomes, and direct microinjection of the DNA into nuclei, all well known in the art.

Systemic delivery of compositions of the invention can be used, but targeted delivery is preferred. Targeted delivery can avoid CTL responses being raised against non-relevant cells. Typical targets will be cells of the immune system (e.g. T-cells, APCs, dendritic cells, Langerhans cells etc.). Methods for targeted delivery are well known in the art. For instance, delivery may be targeted to receptors on target cells. Receptor-mediated DNA delivery techniques are described in references 62 to 67. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Viral-based vectors for delivery of a desired polynucleotide and expression in a desired cell are well known in the art. Exemplary viral-based vehicles include, but are not limited to, recombinant retroviruses (e.g. references 68 to 78), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (e.g. see refs. 79 to 84). Administration of DNA linked to killed adenovirus [85] can also be employed.

Non-viral delivery vehicles and methods can also be employed, including, but not limited to, polycationic condensed DNA linked or unlinked to killed adenovirus alone [e.g. 85], ligand-linked DNA [86], eukaryotic cell delivery vehicles cells [e.g. refs. 87 to 91] and nucleic charge neutralization or fusion with cell membranes. Naked DNA can also be employed. Exemplary naked DNA introduction methods are described in refs. 92 and 93. Liposomes that can act as gene delivery vehicles are described in refs. 94 to 98. Additional approaches are described in refs. 99 & 100.

Further non-viral delivery suitable for use includes mechanical delivery systems such as the approach described in ref. 100. Moreover, the coding sequence and the product of expression of such can be delivered through deposition of photopolymerized hydrogel materials or use of ionizing radiation [e.g. refs. 101 & 102]. Other conventional methods for gene delivery that can be used for delivery of the coding sequence include, for example, use of hand-held gene transfer particle gun [103] or use of ionizing radiation for activating transferred gene [101 & 102].

Diagnostic Methods

The polypeptides of the invention are also useful for diagnosis of infection by *Chlamydia*. This will typically involve the detection of T-cells which recognise the epitopes of the invention. For example, incubation of a polypeptide of the invention with T-cells from a blood sample will result in the activation and proliferation of specific CTLs in the sample. This activation and proliferation can be assayed for diagnostic purposes.

The invention also provides a method for diagnosing a *Chlamydia* infection in a patient, comprising incubating T-cells from the patient with a polypeptide of the invention and detecting the subsequent presence (infection) or absence (no infection) of T-cell proliferation.

The invention also provides a polypeptide or a T-cell of the invention for use in diagnosis.

Processes for Making Products of the Invention

The invention provides processes for preparing the above products.

The invention provides a process for producing a polypeptide of the invention, comprising the step of culturing a host cell of the invention under conditions which induce the expression of a polypeptide of the invention.

The invention provides a process for producing a polypeptide of the invention, wherein the polypeptide is prepared (at least in part) by chemical synthesis.

The invention provides a process for producing nucleic acid of the invention, wherein the nucleic acid is prepared (at least in part) by chemical synthesis.

The invention provides a process for producing a protein complex of the invention, comprising the step of contacting a class I MRC protein with a polypeptide of the invention, or a fragment thereof.

The invention provides a process for producing a protein complex of the invention, comprising the step administering a polypeptide of the invention, or a fragment thereof, to a subject. The process may comprise the further step of purifying the complex from the subject.

The invention provides a process for producing a composition comprising admixing a polypeptide and/or a nucleic acid of the invention with a pharmaceutically acceptable carrier or diluent.

Other Uses for T-Cell Epitopes of the Invention

As well as being specifically useful for *Chlamydia* immunisation, the T-cell epitopes of the invention can be used as general T-cell epitopes.

For example, the epitopes can be used to remove and/or down-regulate self-proteins as described in reference 104, by inserting the T-cell epitope into the sequence of a self protein, thereby rendering the self protein immunogenic. The modulated self-protein can be used as an auto-vaccine against undesirable proteins in humans or animals, the auto-vaccine being useful against a number of diseases e.g. cancer, chronic inflammatory diseases, rheumatoid arthritis, inflammatory bowel diseases, allergic symptoms, diabetes mellitus etc.

Techniques and Definitions

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and II* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller & M. P. Calos eds. 1987, Cold Spring Harbor Laboratory); Mayer & Walker, eds. (1987), *Immunochemical Methods in Cell and Molecular Biology* (Academic Press, London); Scopes, (1987) *Protein Purification: Principles and Practice,* Second Edition (Springer-Verlag, N.Y.), and *Handbook of Experimental Immunology, Volumes I-IV* (Weir & Blackwell eds 1986).

The term "comprising" means "including" as well as "consisting", so a composition "comprising" X may consist exclusively of X or may include something additional e.g. X+Y.

A composition containing X is "substantially free" from Y when at least 85% by weight of the total X+Y in the composition is X. Preferably, X comprises at least ~90% by weight of the total of X+Y in the composition, more preferably at least ~95% or even 99% by weight.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 105. A preferred alignment program is GCG Gap (Genetics Computer Group, Wisconsin, Suite Version 10.1), preferably using default parameters, which are as follows: open gap=3; extend gap=1.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 105. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in reference 106.

The term "T-cell" refers to lymphocyte cells which mature in the thymus and which express CD3 and a T-cell receptor. It includes naïve cells, memory cells and effector cells. The invention relates to cytotoxic T-cells i.e. T-cells which can cause the lysis of a target cell which displays a T-cell epitope of the invention within a class I MHC molecule. Cytotoxic T-cells are generally CD8+.

The term "T cell epitope" refers to a polypeptide which is recognised by a T-cell receptor. The epitope will generally be recognised by the T-cell receptor when it is displayed in the context of a MHC molecule on the surface of a target cell. The epitope will generally be a fragment of a *Chlamydia* protein. Class I MHC epitopes are usually 8 to 10 amino acids in length. Epitopes of the invention can preferably activate cytotoxic T-cells when presented by class I MHC proteins.

The term "cell-mediated response" refers generally to an immune response which is mediated by the cellular immune system rather than the humoral immune system. The response is provided by the direct action of immune cells (such as effector T lymphocytes) rather than by the production of soluble molecules such as antibodies.

The term "cytotoxic T-cell response" refers to an immune response in which cytotoxic T cells act against host (self) cells which display a T-cell epitope. The T-cell epitope is presented by the host cell in the context of a class I MHC molecule and is recognised by the T-cell receptor on the CTL.

The term "allelic variant" refers to any one of a series of two or more different genes that occupy the same position (locus) on a chromosome.

The term "homolog" refers to a sequence which is related to a reference sequence by having evolved from a common ancestor. For example, all globin genes are homologs.

The term "ortholog" refers to a sequence which is related to a reference sequence by having evolved from a single common ancestral gene. For example, the human and mouse β-globin genes are orthologs.

The term "paralog" refers to a sequence which is related to a reference sequence by having arisen from a common ancestor by duplication and subsequent divergence. For example, the human α-globin and β-globin genes are paralogs.

The term "mutant" refers to a sequence which differs from a reference sequence by having one or more differences (mutations). This may be a substitution, a deletion, or an insertion. The mutant may or may not have a functional effect.

It is preferred that one or more of the differences in allelic variants, homologs, orthologs, paralogs or mutants of the invention, compared to SEQ IDs 83-141, involves a conservative amino acid replacement i.e. replacement of one amino acid with another which has a related side chain.

Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cystine, serine, threonine, tyrosine. Phenylalanine, tryptophan, and tyrosine are sometimes classified jointly as aromatic amino acids. In general, substitution of single amino acids within these families does not have a major effect on the biological activity.

MODES FOR CARRYING OUT THE INVENTION

T-cell Epitope Prediction

Figure 1:
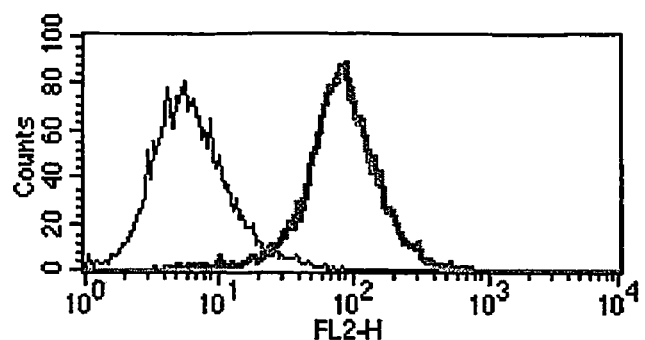
FIG. 1 shows FACS (fluorescence-activated cell sorting) results obtained using HLA-A2-transfected cells, showing binding of specific peptides. The results are also shown in Table 2.
Figure 1X:
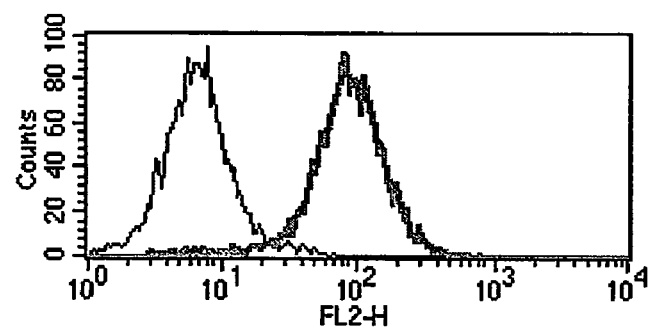
Figure 1:
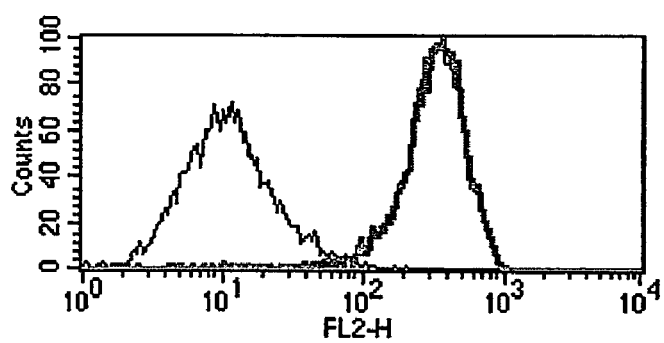

The amino acid sequences of proteins can be analysed by algorithms which aim to predict peptide sequences which can bind to human class I HLA molecules. The computer algorithm BIMAS [17], which ranks potential MHC binders according to the predictive half-time dissociation of peptide/MHC complexes, was used for peptide prediction. In the case of peptides which were predicted to bind to class I HLA-A2, peptides with a BIMAS score higher than 150 were selected. Two known HLA-A2 restricted CTL epitopes were used as positive controls—the HIV-1 p17 gag peptide [107] and the influenza matrix M1 protein peptide FluMP58 [108]. Hepatitis B virus envelope antigen peptide HbenvAg125 was used as a negative control as this does not bind to HLA A2 [109].

Cell Lines Used to Test Peptide Binding to Class I HLA Proteins

Binding of peptides to class I HLA proteins can be tested using the murine T lymphoma cell line RMA-S [110, 111, 112], stably transfected with different HLA genes (RMA-S stably expressing HLA A2 is referred to as 'RMA-S/A2'). This cell line is deficient for the transporter of antigen presentation (TAP) which normally translocates peptides from the cytosol to the lumen of the endoplasmic reticulum, facilitating peptide binding to class I MHC. Consequently, RMA-S cells show a decreased expression of class I molecules at the cell surface, which can be rescued by binding specific high-affinity peptides or by growth at a temperature below 30° C.

Plasmids were transfected into $10^7$ RMA-S cells either by electroporation (250 mV, 500 μF (Bio Rad Gene Pulser™) with 10 μg of either supercoiled or linearised class I DNA) or by Lipofectamine reagent (87 μL; Gibco, using manufacturer's protocols). Transfected cells were selected with 0.5 mg/ml G418 (Gibco) for approximately two weeks. Stably transfected cells were incubated overnight at 26° C. in humidified 5% $CO_2$ atmosphere and HLA expression was monitored by staining the cells with anti-HLA MAbs, followed by reaction with PE-conjugated anti-mouse IgG. HLA A2 expression was evaluated by using the anti-A2 specific BB7.2 monoclonal antibody [113,114].

Fluorescence intensity was analyzed by flow cytometry and HLA highly expressing cells were sorted and directly cloned into 96 well plates by using a FACSVantageSE (Becton Dickinson). HLA expression of expanded clones was tested and clones with highest expression level were sorted once more and recloned into 96 well plates.

Peptide-Binding Assay

To test the binding of peptides to HLA A2 molecules, the following protocol was used. This can be used, with minor adaptations, to test binding to other HLA proteins.

TAP deficient RMA-S/A2 cells ($3-5\times10^5$/well) were seeded in serum-free RPMI medium, supplemented with human β2 microglobulin (3 μg, Sigma), with or without the peptide to be tested (1, 10 or 100 μM). Following overnight incubation at 26° C. in humidified 5% $CO_2$ atmosphere, cells were shifted to 37° C. for 1-2 hours before determining the HLA A2 expression level at the cell surface. HLA A2 expression was monitored by staining the cells with BB7.2, followed by reaction with PE-conjugated anti-mouse IgG. Fluorescence intensity on living cells, which do not incorporate propidium iodide, was analyzed by flow cytometry.

As controls, corresponding samples without peptide and with the different peptide concentrations, were treated only with the anti-mouse secondary antibody. The difference of the mean values between each sample and the corresponding control (ΔMean) quantified the A2 expression level.

Stabilisation of HLA molecules due to peptide binding, was expected to result into a higher HLA specific signal when cells were shifted to 37° C. Consequently, the comparison between the ΔMean of a cell population incubated with a given peptide and the ΔMean of the cell population incubated without any peptide should express the increase of the A2 expression level due to peptide binding.

The peptides selected for binding to HLA A2, in addition to negative (HepB) and positive (GAG and IMa) controls peptides are listed in Table 1.

Figure 2V:
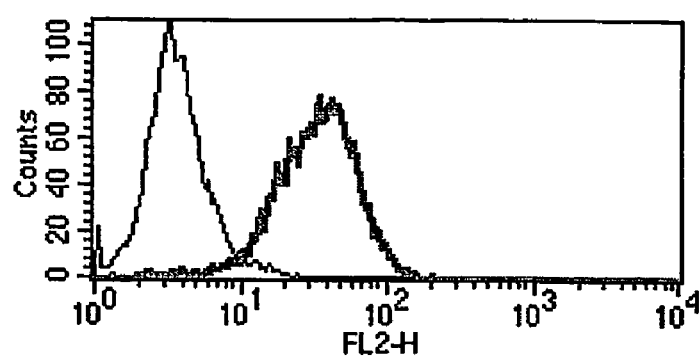
FIG. 2 shows FACS (fluorescence-activated cell sorting) results obtained using HLA-A2-transfected cells, showing binding of specific peptides. The results are also shown in Table 2.
Figure 2:
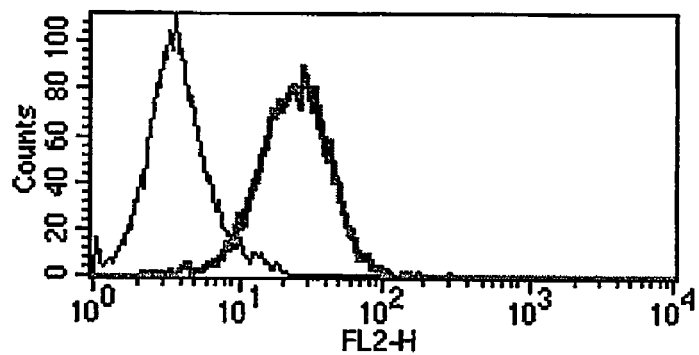
Figure 2:
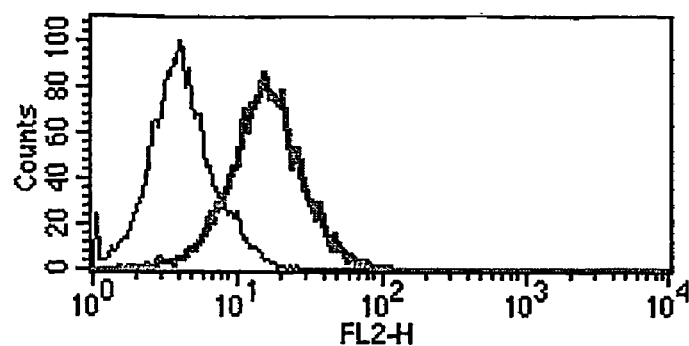
Figure 2X:
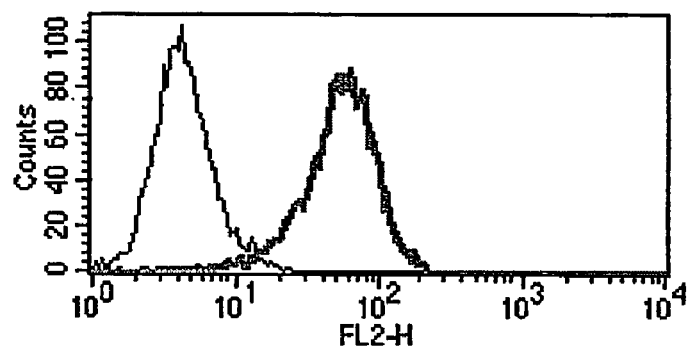
Figure 2:
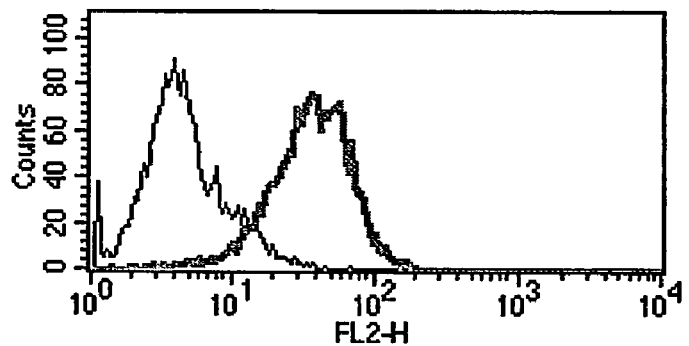
Figure 3:
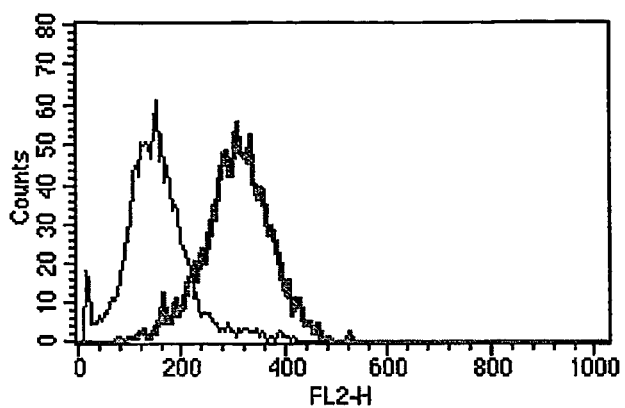
FIG. 3 shows FACS (fluorescence-activated cell sorting) results obtained using HLA-A2-transfected cells, showing binding of specific peptides. The results are also shown in Table 2.
Figure 3X:
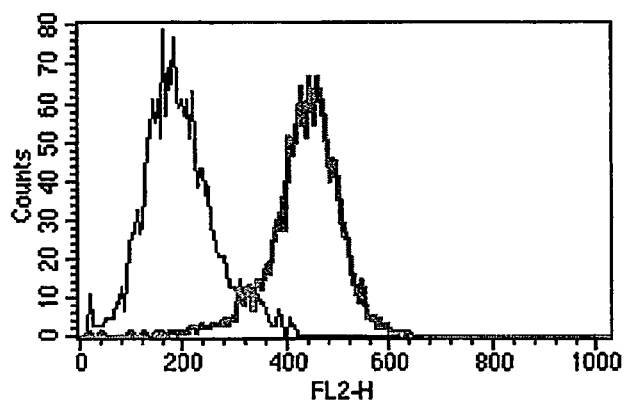
Figure 3:
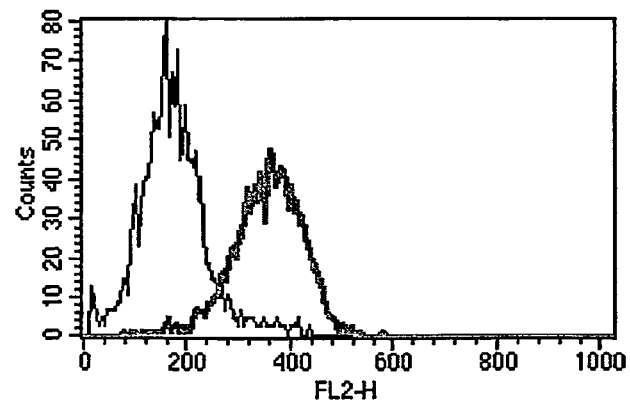
Figure 3:
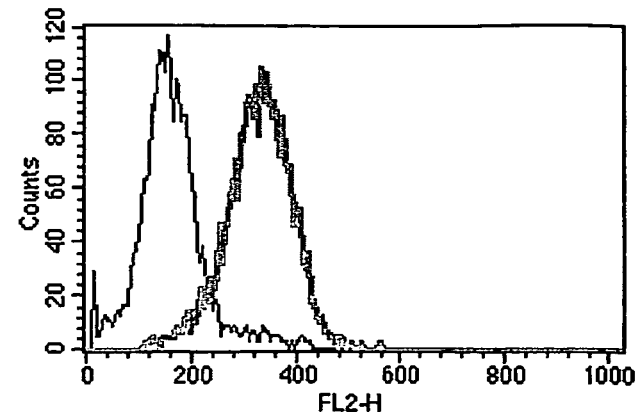
Figure 4C:
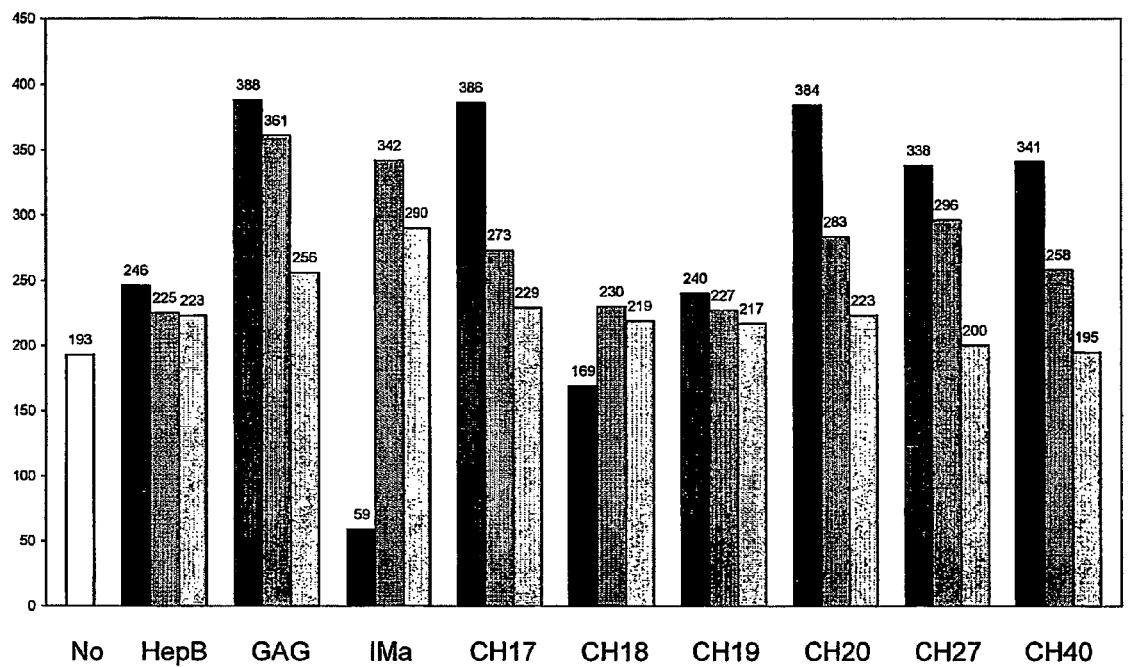
FIG. 4 shows results from FIGS. 1-3 at all three concentrations (100 μM, 10 μM, 1 μM peptide) are represented in FIG. 4, which shows ΔMean values. Values are indicated above bars. Bars are clustered in threes, with the left-most bar being the value obtained with 100 μM peptide, the middle bar being 10 μM peptide, and the right-most bar being 1 μM peptide. The single empty colum at the extreme left shows the relevant peptide-free control.
Figure 4D:
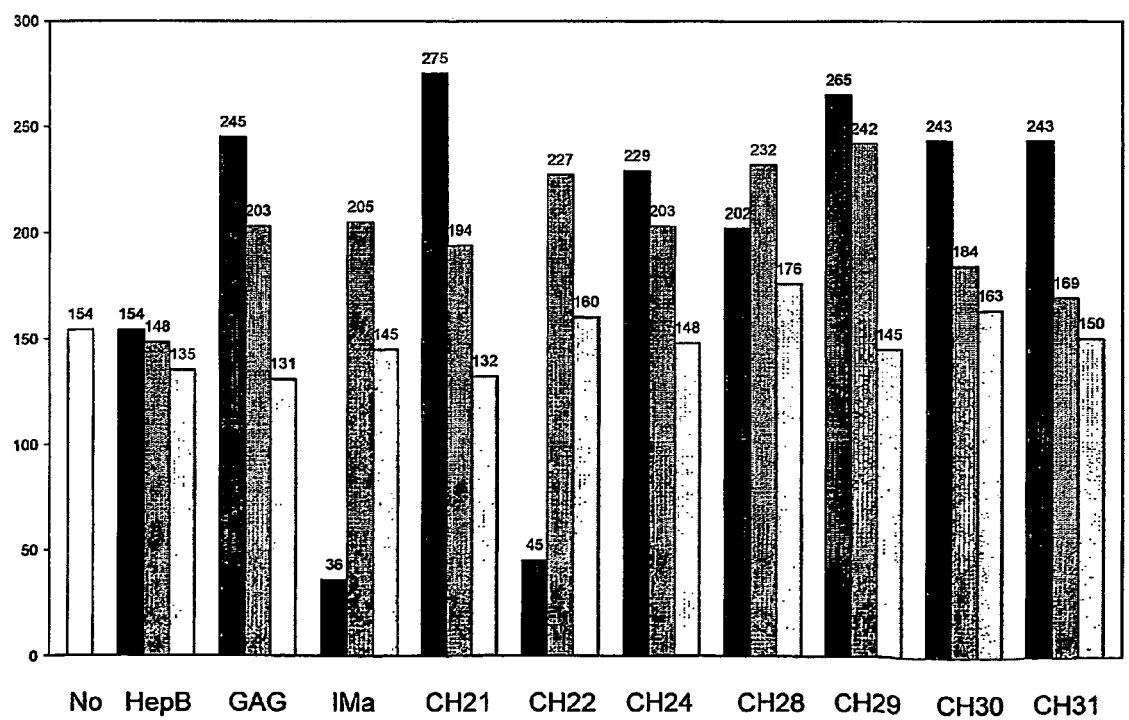
Figure 4E:
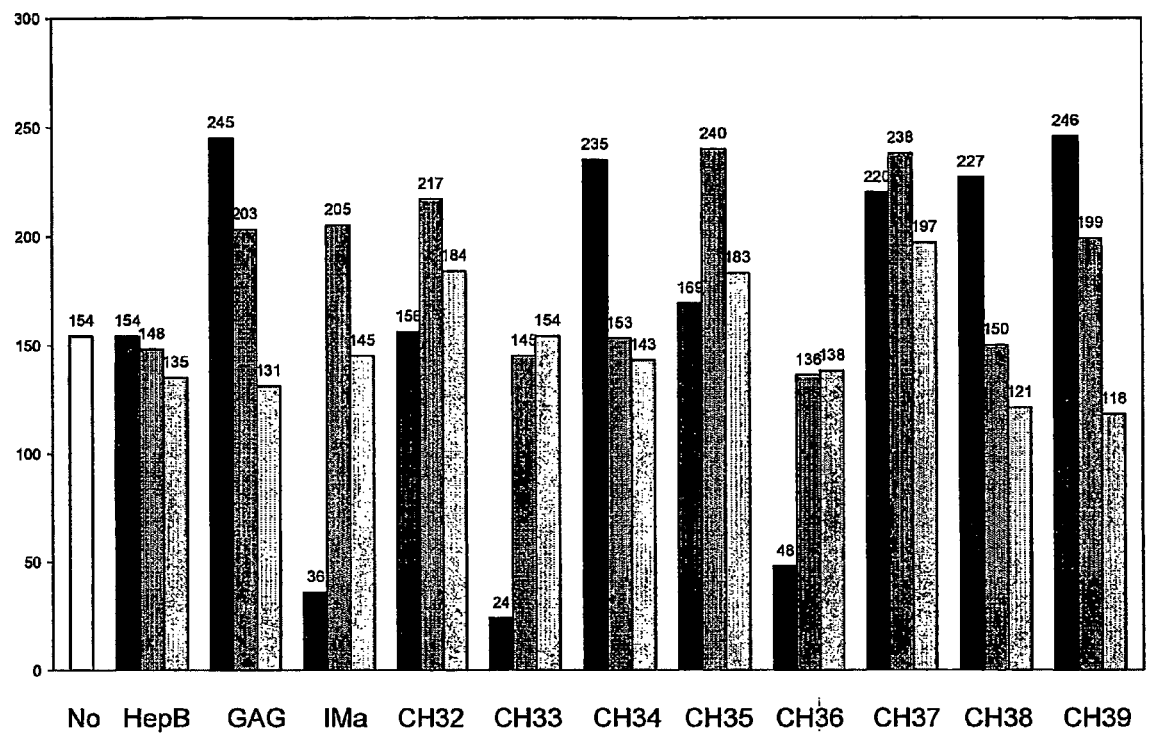
Figure 4F:
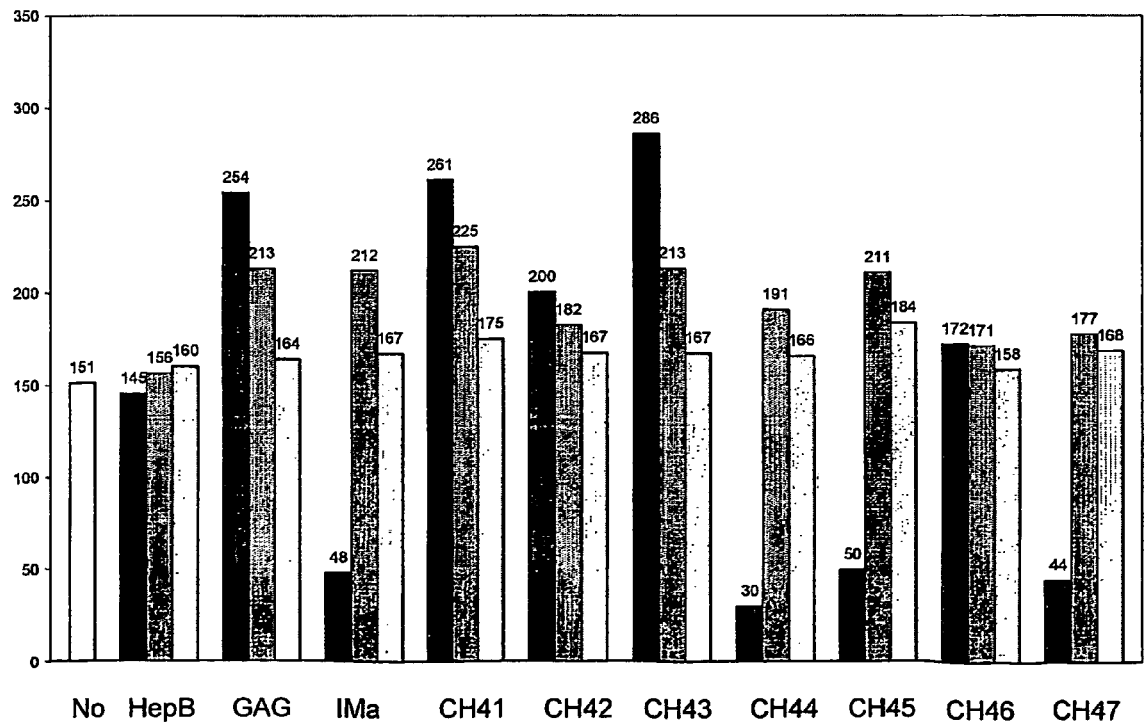

Flow cytometric analysis of RMA-S/A2 cell populations treated with a set of the tested peptides, without (Mean1) and with the anti-A2 specific antibody (Mean2), is shown in FIGS. 1 to 3 (see also Table 2). The experiments were carried out using 100, 10 and 1 μM concentrations for each peptide, but FIGS. 1 to 3 and Table 2 give data only for the concentration which exhibited the highest HLA A2 ΔMean value (i.e. the highest expression level). Graphs of ΔMean values obtained in the same experiments with the peptides at all three concentrations are shown in FIG. 4. For the FIG. 1 experiment, the differences between the highest ΔMean of the GAG and IMa positive control peptides and the highest delta mean of the negative control HepB peptide were 142 and 96 respectively. For the FIG. 2 experiment, the same values were 94 and 52. For the FIG. 3 experiment they were also 94 and 52.

Living cell populations were determined by treating the sample with propidium iodide.

On the basis of these data, at least peptides CH1, CH2, CH4, CH5, CH6, CH7, CH8, CH10, CH13, CH15, CH17, CH20, CH21, CH22, CH24, CH27, CH28, CH29, CH30, CH31, CH32, CH34, CH35, CH37, CH38, CH39, CH40, CH41, CH42, CH43, CH45, CH48, CH50, CH52, CH53, CH54, CH55 and CH56 bind to HLA A2.

Figure 5:
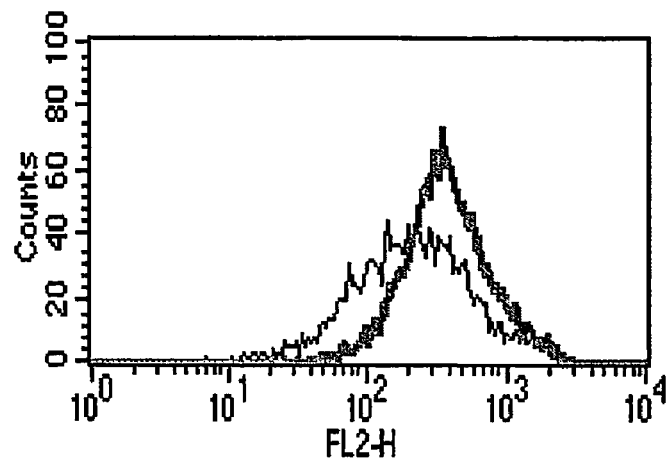
FIG. 5 shows FACS analysis of RMS/A2 cells treated with 100 μM IMa. The Mean1 value was 593 and the Mean2 value was 652, giving a ΔMean of 59.

Very low ΔMean values obtained with high concentrations of some peptides (i.e. IMa, CH3 and CH7) reflect a non-homogeneous cellular distribution of the fluorescent signal most likely due to non-specific effects. An example of such effect is represented in FIG. 5, which shows the flow cytometric results obtained with cells treated with 100 μM IMa.

DNA Immunisation and ELISpot

Full-length *C.pneumoniae* and *C.trachomatis* genes encoding the polypeptides which contain CTL epitopes were amplified by PCR using the primers in Table 4 and cloned into plasmid expression vector pCMVKASF2-120, from which the gp120 sequence had been previously excised by treatment with NheI and SalI restriction enzymes. The chlamydial sequences were thus downstream of the tPA signal sequence.

The plasmids were used for DNA immunisation of transgenic mice expressing the human HLA-A2 gene [115] which express a chimeric class I molecule composed of the α1 and α2 domains of HLA-A2.1 and the α3 transmembrane and cytoplasmic domains of H-2K$^b$.

Mice were immunised at days 0, 21 and 35 by intramuscular injection of 50μg endotoxin-free recombinant plasmid DNA. One week after the third immunisation, the animals were sacrificed, spleens were removed and CD8+ cells were purified by means of CD8α(Ly-2) Microbeads and LS Separation Columns following the technical procedures described by Miltenyi Biotec™. These CD8$^+$ cells were tested by Elispot assay to detect cells which secrete IFN-γ in response to given peptides. The Elispot procedure was as follows:

1. 96-well nitrocellulose plates are coated with 5 μg/ml anti-mouse IFN-γ in 100 μl carbonate buffer, pH 9.2. Cover plate with lid and incubate overnight (o.n.) at 4° C.
2. Discard coating antibody. Rinse plates 3 times with PBS (200 μl per rinse). Shake excess liquid from plate and pat bottom of plate with dry absorbent paper.
3. Add 200 μl blocking solution (PBS-BSA 1%) to each well to saturate remaining binding sites and incubate 2 hours at 37° C. (or o.n. at 4° C.).
4. Discard blocking solution, wash plate 3 times with PBS (200 μl per rinse). Shake excess liquid from plate and pat bottom of plate with dry absorbent paper.
5. Add 100 μl complete medium and incubate 10 minutes at room temperature. Discard liquid and pat bottom of plate with dry absorbent paper.
6. Add cells (5×10$^4$ CD8$^+$ from immunised transgenic mice and 2×10$^5$ irradiated spleen cells from non-immunised transgenic mice) with complete medium supplemented with the tested peptide (5, 10 or 20 μg/ml) and IL-2 (10 units/ml).
7. Incubate 20-24 hours in a humidified 37° C., 5% CO$_2$ incubator.
8. Take off medium, add 200 μl per wash of ice-cold distilled water and incubate on ice for 10 minutes. Then wash ten times in wash buffer (PBS-Tween 0.05%), 200l per wash. Shake excess liquid from plate and pat bottom of plate with dry absorbent paper.
9. To detect IFN-γ spots, add 1 μg/ml biotinylated anti mouse IFN-γ in 100 μl in Elispot dilution buffer (PBS-BSA 1%) and incubate 2 hours at 37° C.
10. Wash plate 3 times with wash buffer (PBS-Tween 0.05%), 200 μl per wash and 3 times with PBS without Tween (200 μl). Shake excess liquid from plate and pat bottom of plate with dry absorbent paper.
11. Add 100 μl 1:2000 dilution of alkaline phosphatase-coupled avidin in PBS-BSA 1% (Sigma). Incubate 1 hour at 37° C.
12. Wash plate 3 times with wash buffer (PBS-Tween 0.05%), 200lil per wash and 3 times with PBS without Tween (200 μl). Shake excess liquid from plate and pat bottom of plate with dry absorbent paper.
13. Spots of IFN-μ secreting cells are visualised by adding 50 μl of the ready-to-use substrate BCIP/NBT (Sigma) dissolved in water. The reaction is stopped after 45 minutes at 37° C. by several washes with distilled water.

Figure 6:
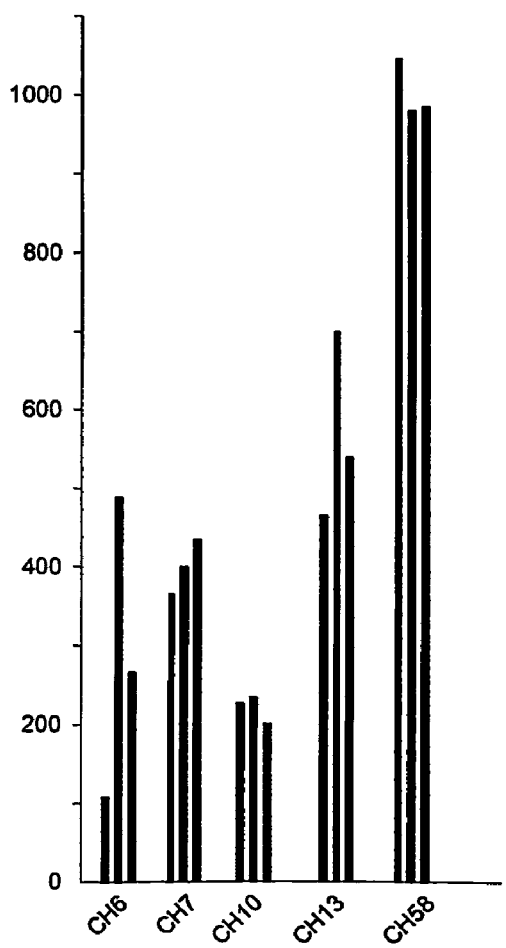
FIG. 6 shows results of Elispot analysis with CH6, CH7, CH10, CH13 and CH58.

The results obtained by testing different peptides at different concentrations with spleen cells of DNA immunised transgenic mice are reported in Table 5 and FIG. 6. Peptides CH6, CH7, CH10, CH13 and CH58 induce a number of IFN-γ secreting CD8$^+$ well above background levels.

Comparison of Computer Prediction with Empirical Results

The empirical results show that computer prediction is not adequate for finding T-cell epitopes. For example, some peptides with high algorithmic scores do not seem to bind (e.g. CH12, CH14, CH16, CH18, CH19, CH33, CH36; i.e. SEQ IDs 51 to 57 are not preferred epxtopes of the invention) and others with low score (e.g. GAG) seem to bind better or as well as others with much higher scores (e.g. CH4 and CH2).

Peptides CH41, CH43, CH48, CH50, CH52, CH54, CH55 and CH56 all show a BIMAS score of <400 but are positive in the binding assay. The results with these peptides thus run contrary to the algorithmic predictions. Indeed, of five epitopes predicted in protein 4376601 (CH44 to CH48; SEQ IDs 41 to 45), the weakest epitope by the algorithmic approach (CH48) was the strongest epitope using the binding assay, with binding comparable to that of the epitope predicted by the algorithm to be the strongest epitope (CH2; SEQ ID 2).

Furthermore, although the percentage of the predicted peptides which are positive in the test with A2 expressing cells is high (74%), this percentage is expected to be lower in the case of peptides which are predicted to bind to other haplotypes, for which fewer data are available which, in turn, will render the prediction less reliable.

CH58 peptide has a BIMAS score of less than 300 and gave negative results in the in vitro binding assay with RMA-S/A2 cells, but was strongly positive in the in vivo IFN-γ CD8+ assay.

It will be understood that the invention has been described by way of example only and modifications may be made whilst remaining within the scope and spirit of the invention.

TABLE 1

*C. pneumoniae* T-cell epitopes of the invention

| Code | SEQ ID | 9mer epitope | Full-length sequence (GenBank) | Annotation for full-length *C. pneumoniae* sequence (taken from GenBank) | 1st residue in full-length sequence |
|---|---|---|---|---|---|
| CH1 | 1 | QLLDEGKEL | 4376600 (SEQ ID 83) | Yop proteins translocation protein U | 315 |
| CH2 | 2 | ILLNEVPYV | 4376601 (SEQ ID 84) | Low calcium response protein D | 433 |
| CH3 | 3 | VLNLFFSAL | 4376602 (SEQ ID 85) | Low calcium response protein E | 343 |
| CH4 | 4 | QLLESLAPL | 4376603 (SEQ ID 86) | Secretion chaperone | 7 |
| CH5 | 5 | SILELLQFV | 4377005 (SEQ ID 87) | Probable Yop proteins translocation protein | 271 |
| CH6 | 6 | YLLEEIYTV | 4377123 (SEQ ID 88) | Low calcium response protein H | 79 |
| CH7 | 7 | YMDNNLFYV | 4377135 (SEQ ID 89) | Yop proteins translocation protein T | 83 |
| CH8 | 8 | FLTLAWWFI | 4377135 (SEQ ID 89) | Yop proteins translocation protein T | 254 |
| CH10 | 9 | GLTEEIDYV | 4377140 (SEQ ID 90) | Yop proteins translocation protein J | 214 |
| CH12 | 51 | WLVFFNPFV | 4377352 (SEQ ID 91) | Low calcium response locus protein H | 79 |
| CH13 | 11 | YVFDRILKV | 4376998 (SEQ ID 92) | Outer membrane protein A | 69 |
| CH14 | 52 | VMLIFEKKV | 4376696 (SEQ ID 93) | CT2 66 hypothetical protein | 406 |
| CH15 | 13 | YLTSYSPYV | 4376727 (SEQ ID 94) | Polymorphic outer membrane protein G/I family | 1270 |
| CH16 | 53 | VQLAYVFDV | 4377287 (SEQ ID 95) | Putative outer membrane protein D family | 1530 |
| CH17 | 15 | ILQEAEQMV | 4377033 (SEQ ID 96) | 76 kDa homolog_1 | 308 |
| CH18 | 54 | IALLVIFFV | 4376456 (SEQ ID 97) | Similar to CT119 IncA | 71 |
| CH19 | 55 | LLLTLGYAV | 4376727 (SEQ ID 94) | Polymorphic outer membrane protein G/I family | 1327 |
| CH20 | 18 | ALMLLNNYV | 4376260 (SEQ ID 98) | Polymorphic outer membrane protein G family | 146 |
| CH21 | 19 | TLWGSFVDV | 4376731 (SEQ ID 99) | Polymorphic outer membrane protein G/I family | 614 |
| CH22 | 20 | WLFDLRFSV | 4376830 (SEQ ID 100) | Polymorphic membrane protein B family | 1566 |
| CH24 | 21 | LIQETLLFV | 4376273 (SEQ ID 101) | Predicted omp | 490 |
| CH27 | 22 | KLFTPFFTT | 4376878 (SEQ ID 102) | 2-component sensor | 304 |
| CH28 | 23 | RLLEIIWGV | 4376854 (SEQ ID 103) | CHLPS 43 kDa protein homolog_1 | 45 |
| CH29 | 24 | YLMQKLQNV | 4377101 (SEQ ID 104) | CT 590 hypothetical protein | 288 |
| CH30 | 25 | FLQRGESFV | 4377102 (SEQ ID 105) | CT 589 hypothetical protein | 520 |
| CH31 | 26 | WLLRDDWLL | 4376265 (SEQ ID 106) | hypothetical | 401 |
| CH32 | 27 | KLWEWLGYL | 4376295 (SEQ ID 107) | hypothetical | 187 |
| CH33 | 56 | LLMLAISLV | 4376395 (SEQ ID 108) | hypothetical | 68 |
| CH34 | 29 | KLLKDHFDL | 4376396 (SEQ ID 109) | hypothetical | 201 |
| CH35 | 30 | ILSFLPWLV | 4376437 (SEQ ID 110) | hypothetical | 56 |
| CH36 | 57 | LLLIFNNYL | 4376439 (SEQ ID 111) | hypothetical | 149 |
| CH37 | 32 | YLLDFRWPL | 4376482 (SEQ ID 112) | hypothetical | 126 |
| CH38 | 33 | NLLKRWQFV | 4376627 (SEQ ID 113) | hypothetical | 374 |
| CH39 | 34 | FLLRHLSSV | 4376630 (SEQ ID 114) | hypothetical | 378 |
| CH40 | 35 | KLLAFPAFA | 4376468 (SEQ ID 115) | Oligopeptide binding protein | 153 |
| CH41 | 36 | KLSEQLEAL | 4376456 (SEQ ID 97) | Similar to CT119 IncA | 162 |
| CH42 | 37 | KVLLGQEWV | 4376456 (SEQ ID 97) | Similar to CT119 IncA | 214 |
| CH43 | 38 | NLAEQVTAL | 4376456 (SEQ ID 97) | Similar to CT119 IncA | 315 |
| CH44 | 39 | YVVGFIIFL | 4376601 (SEQ ID 84) | Low calcium response protein D | 123 |
| CH45 | 40 | WMMGVVLMI | 4376601 (SEQ ID 84) | Low calcium response protein D | 32 |
| CH46 | 41 | NLSISVFLL | 4376601 (SEQ ID 84) | Low calcium response protein D | 56 |
| CH47 | 42 | VIQAFGDFV | 4376601 (SEQ ID 84) | Low calcium response protein D | 110 |
| CH48 | 43 | YLALDPDSV | 4376601 (SEQ ID 84) | Low calcium response protein D | 635 |
| CH49 | 44 | KMSHFQQAL | 4376696 (SEQ ID 93) | CT2 66 hypothetical protein | 149 |
| CH50 | 45 | SLCAQSSYV | 4376727 (SEQ ID 94) | Polymorphic outer membrane protein G/I family | 1187 |
| CH51 | 46 | NLSRQAFFA | 4376727 (SEQ ID 94) | Polymorphic outer membrane protein G/I family | 1360 |
| CH52 | 47 | SLLEEHPVV | 4377287 (SEQ ID 95) | Putative outer membrane protein D family | 678 |
| CH53 | 48 | NLWSHYTDL | 4377287 (SEQ ID 95) | Putative outer membrane protein D family | 1302 |
| CH54 | 49 | ALWKENQAL | 4377287 (SEQ ID 95) | Putative outer membrane protein D family | 377 |
| CH55 | 50 | ALWGHNVLL | 4377287 (SEQ ID 95) | Putative outer membrane protein D family | 568 |
| CH56 | 10 | NLAGGILSV | 4377287 (SEQ ID 95) | Putative outer membrane protein D family | 333 |
| CH57 | 12 | FVSKFWFSL | 4377352 (SEQ ID 91) | Low calcium response locus protein H | 86 |
| CH58 | 14 | SITVFRWLV | 4377352 (SEQ ID 91) | Low calcium response locus protein H | 73 |
| CH59 | 16 | YLIVFVLTI | 4376395 (SEQ ID 108) | Hypothetical | 58 |
| CH60 | 17 | VMLFIGLGV | 4376395 (SEQ ID 108) | Hypothetical | 42 |
| CH61 | 28 | VLFLLIRSV | 4376395 (SEQ ID 108) | Hypothetical | 76 |
| CH62 | 31 | FLFQLGMQI | 4376696 (SEQ ID 93) | CT2 66 hypothetical protein | 397 |

TABLE 2

FACS results for HLA A2 binding assay

| Peptide | BIMAS score | FACS data (Figure number) | Antigen Concentration (μM) | FACS result Mean 1 | Mean 2 | Δ Mean | High - B |
|---|---|---|---|---|---|---|---|
| None | — | 1(i) | — | 187 | 380 | 193 | — |
|  |  | 2(i) | — | 157 | 311 | 154 | — |
|  |  | 3(i) | — | 131 | 282 | 151 | — |
| HepB | — | 1(ii) | 100 | 197 | 138 | 246 | — |
|  |  | 1(iii) | 10 | 201 | 426 | 225 | — |
|  |  | 1(iv) | 1 | 193 | 416 | 223 | — |
|  |  | 2(ii) | 100 | 146 | 300 | 154 | — |
|  |  | 2(iii) | 10 | 147 | 295 | 148 | — |
|  |  | 2(iv) | 1 | 157 | 292 | 135 | — |
|  |  | 3(ii) | 100 | 120 | 265 | 145 | — |
|  |  | 3(iii) | 10 | 118 | 274 | 156 | — |
|  |  | 3(iv) | 1 | 114 | 274 | 160 | — |
| GAG | 157.22 | 1(v) | 100 | 184 | 572 | 388 | — |
|  |  | 1(vi) | 10 | 194 | 555 | 361 | — |
|  |  | 1(vii) | 1 | 187 | 443 | 256 | — |
|  |  | 2(v) | 100 | 142 | 387 | 245 | — |
|  |  | 2(vi) | 10 | 147 | 350 | 203 | — |
|  |  | 2(vii) | 1 | 155 | 286 | 131 | — |
|  |  | 3(v) | 100 | 111 | 365 | 254 | — |
|  |  | 3(vi) | 10 | 114 | 327 | 213 | — |
|  |  | 3(vii) | 1 | 117 | 281 | 164 | — |
| IMa | 550.927 | 1(viii) | 10 | 222 | 564 | 342 | — |
|  |  | 1(ix) | 1 | 197 | 487 | 290 | — |
|  |  | 2(viii) | 10 | 182 | 387 | 205 | — |
|  |  | 2(ix) | 1 | 159 | 304 | 145 | — |
|  |  | 3(viii) | 10 | 131 | 343 | 212 | — |
|  |  | 3(ix) | 1 | 123 | 290 | 167 | — |
| CH1 | 324.06 | 1(x) | 100 | 206 | 489 | 283 | 37 |
| CH2 | 5534.14 | 1(xi) | 10 | 264 | 636 | 372 | 133 |
| CH3 | 262.20 | 1(xii) | 1 | 195 | 419 | 224 | 0 |
| CH4 | 745.35 | 1(xiii) | 100 | 212 | 516 | 304 | 58 |
| CH5 | 1835.22 | 1(xiv) | 10 | 179 | 477 | 298 | 71 |
| CH6 | 11162.99 | 1(xv) | 10 | 198 | 574 | 376 | 130 |
| CH7 | 6781.36 | 1(xvi) | 10 | 203 | 551 | 348 | 102 |
| CH8 | 3365.36 | 1(xvii) | 1 | 204 | 532 | 328 | 82 |
| CH10 | 1767.58 | 1(xviii) | 10 | 202 | 587 | 385 | 139 |
| CH12 | 6686.72 | 1(xix) | 1 | 204 | 415 | 211 | 0 |
| CH13 | 976.76 | 1(xxvii) | 100 | 217 | 582 | 365 | 119 |
| CH14 | 1200.64 | 1(xx) | 100 | 197 | 455 | 258 | 12 |
| CH15 | 1759.66 | 1(xxi) | 100 | 235 | 557 | 322 | 76 |
| CH16 | 591.70 | 1(xxii) | 100 | 201 | 433 | 232 | 0 |
| CH17 | 484.77 | 1(xxiii) | 100 | 185 | 571 | 386 | 140 |
| CH18 | 445.806 | 1(xxiv) | 10 | 198 | 428 | 230 | 0 |
| CH19 | 437.482 | 1(xxv) | 100 | 196 | 436 | 240 | 0 |
| CH20 | 1415.383 | 1(xxvi) | 100 | 194 | 578 | 384 | 138 |
| CH21 | 1096.835 | 2(x) | 100 | 165 | 440 | 275 | 121 |
| CH22 | 28150.17 | 2(xi) | 10 | 163 | 390 | 227 | 73 |
| CH24 | 843.21 | 2(xii) | 100 | 165 | 394 | 229 | 75 |
| CH27 | 1063.467 | 1(xxviii) | 100 | 202 | 540 | 338 | 93 |
| CH28 | 18200.541 | 2(xiii) | 10 | 158 | 390 | 232 | 78 |
| CH29 | 2722.683 | 2(xiv) | 100 | 153 | 418 | 265 | 111 |
| CH30 | 759.666 | 2(xv) | 100 | 155 | 398 | 243 | 89 |
| CH31 | 2726.91 | 2(xvi) | 100 | 165 | 408 | 243 | 89 |
| CH32 | 4184.21 | 2(xvii) | 10 | 161 | 378 | 217 | 63 |
| CH33 | 1006.209 | 2(xviii) | 1 | 164 | 318 | 154 | 0 |
| CH34 | 1604.53 | 2(xix) | 100 | 155 | 390 | 235 | 81 |
| CH35 | 886.788 | 2(xx) | 10 | 171 | 411 | 240 | 86 |
| CH36 | 2808.322 | 2(xxi) | 1 | 163 | 301 | 138 | −16 |
| CH37 | 42485.263 | 2(xxii) | 10 | 164 | 402 | 238 | 84 |
| CH38 | 2406.151 | 2(xxiii) | 100 | 170 | 397 | 227 | 73 |
| CH39 | 2722.683 | 2(xxiv) | 100 | 164 | 410 | 246 | 92 |
| CH40 | 1344.614 | 1(xxix) | 100 | 214 | 555 | 341 | 96 |
| CH41 | 345.482 | 3(x) | 100 | 162 | 423 | 261 | 101 |
| CH42 | 212.396 | 3(xi) | 100 | 136 | 336 | 200 | 40 |
| CH43 | 201.447 | 3(xii) | 100 | 153 | 439 | 286 | 126 |
| CH44 | 413.323 | 3(xiii) | 10 | 150 | 341 | 191 | 31 |
| CH45 | 294.957 | 3(xiv) | 10 | 147 | 358 | 211 | 51 |
| CH46 | 284.974 | 3(xv) | 100 | 131 | 303 | 172 | 12 |
| CH47 | 166.496 | 3(xvi) | 10 | 125 | 302 | 177 | 17 |
| CH48 | 156.77 | 3(xvii) | 100 | 148 | 451 | 303 | 143 |
| CH49 | 205.198 | 3(xviii) | 100 | 134 | 317 | 183 | 23 |
| CH50 | 382.536 | 3(xix) | 100 | 130 | 381 | 251 | 91 |

TABLE 2-continued

FACS results for HLA A2 binding assay

| Peptide | BIMAS score | FACS data (Figure number) | Antigen Concentration (μM) | Mean 1 | Mean 2 | Δ Mean | High - B |
|---|---|---|---|---|---|---|---|
| CH51 | 158.479 | 3(xx) | 100 | 132 | 311 | 179 | 19 |
| CH52 | 432.593 | 3(xxi) | 100 | 147 | 396 | 249 | 89 |
| CH53 | 265.962 | 3(xxii) | 100 | 141 | 350 | 209 | 48 |
| CH54 | 177.308 | 3(xxiii) | 100 | 140 | 391 | 251 | 91 |
| CH55 | 177.308 | 3(xxiv) | 100 | 153 | 411 | 258 | 98 |
| CH56 | 159.970 | 3(xxv) | 100 | 143 | 383 | 240 | 80 |
| CH57 | 322.164 | 3(xxvi) | 1 | 127 | 270 | 143 | −17 |
| CH58 | 272.557 | 3(xxvii) | 10 | 155 | 300 | 145 | −15 |
| CH59 | 419.44 | 3(xxviii) | 10 | 150 | 273 | 123 | −37 |
| CH60 | 315.959 | 3(xxix) | 10 | 148 | 281 | 133 | −27 |
| CH61 | 201.242 | 3(xxx) | 1 | 135 | 258 | 123 | −37 |
| CH62 | 177.566 | 3(xxxi) | 100 | 126 | 305 | 179 | 19 |

'Mean 1' is the mean of the cell population treated with peptide and only the anti-mouse secondary antibody.
'Mean 2' is the mean of the cell population treated with peptide, anti-A2 specific Mab (BB7.2) and anti-mouse secondary antibody.
'ΔMean' is the difference between these two means, reflecting the A2 expression level.
'High - B' is the difference between the ΔMean obtained with the peptide and the highest ΔMean obtained with the HepB negative control peptide in the same experiment.
The FACS data for CH1 to CH62 can be seen in the drawings as indicated in the third column

TABLE 3

C. trachomatis T-cell epitopes of the invention

| Code | SEQ ID | C. pneumoniae epitope | SEQ ID | C. trachomatis epitope(s) | Full-length C. pneumoniae protein | Full-length C. trachomatis protein (GenBank) |
|---|---|---|---|---|---|---|
| CH1 | 1 | QLLDEGKEL | | identical | SEQ ID 83 | 3328487 (SEQ ID 139) |
| CH2 | 2 | ILLNEVPYV | | identical | SEQ ID 84 | 3328486 (SEQ ID 136) |
| CH3 | 3 | VLNLFFSAL | | — | SEQ ID 85 | |
| CH4 | 4 | QLLESLAPL | 58 | QLLEGLDEL | SEQ ID 86 | 3328616 (SEQ ID 116) |
| CH5 | 5 | SILELLQFV | | identical | SEQ ID 87 | 3329125 (SEQ ID 140) |
| CH6 | 6 | YLLEEIYTV | 59 | VLLEEIYTV | SEQ ID 88 | 3329018 (SEQ ID 117) |
| CH7 | 7 | YMDNNLFYV | | — | SEQ ID 89 | |
| CH8 | 8 | FLTLAWWFI | | identical | SEQ ID 89 | 3329005 (SEQ ID 141) |
| CH10 | 9 | GLTEEIDYV | | — | SEQ ID 90 | |
| CH12 | 51 | WLVFFNPFV | | — | SEQ ID 91 | |
| CH13 | 11 | YVFDRILKV | 60 | FVFDRVLKT | SEQ ID 92 | 3329133 (SEQ ID 118) |
| CH14 | 52 | VMLIFEKKV | | — | SEQ ID 93 | |
| CH15 | 13 | YLTSYSPYV | | — | SEQ ID 94 | |
| CH16 | 53 | VQLAYVFDV | | — | SEQ ID 95 | |
| CH17 | 15 | ILQEAEQMV | | — | SEQ ID 96 | |
| CH18 | 54 | IALLVIFFV | | — | SEQ ID 97 | |
| CH19 | 55 | LLLTLGYAV | | — | SEQ ID 94 | |
| CH20 | 18 | ALMLLNNYV | | — | SEQ ID 98 | |
| CH21 | 19 | TLWGSFVDV | | — | SEQ ID 99 | |
| CH22 | 20 | WLFDLRFSV | 61 | WLADLRISM | SEQ ID 100 | 3328841 (SEQ ID 119) |
| CH24 | 21 | LIQETLLFV | 62 | LIQELPLKV | SEQ ID 101 | 3329257 (SEQ ID 120) |
| CH27 | 22 | KLFTPFFTT | 63 | KLFIPFFTT | SEQ ID 102 | 3328901 (SEQ ID 121) |
| CH28 | 23 | RLLEIIWGV | | — | SEQ ID 103 | |
| CH29 | 24 | YLMQKLQNV | | — | SEQ ID 104 | |
| CH30 | 25 | FLQRGESFV | | — | SEQ ID 105 | |
| CH31 | 26 | WLLRDDWLL | 64 | LLLRDDIKL | SEQ ID 106 | 3328404 (SEQ ID 122) |
| | | | 65 | FLLRAPWLL | | 3328600 (SEQ ID 123) |
| CH32 | 27 | KLWEWLGYL | | — | SEQ ID 107 | |
| CH33 | 56 | LLMLAISLV | | — | SEQ ID 108 | |
| CH34 | 29 | KLLKDHFDL | 66 | KLLNDRFPL | SEQ ID 109 | 3328716 (SEQ ID 124) |
| CH35 | 30 | ILSFLPWLV | 67 | ILSSLYSLV | SEQ ID 110 | 3328409 (SEQ ID 125) |
| | | | 68 | ILSLLPMIV | | 3328914 (SEQ ID 126) |
| CH36 | 57 | LLLIFNNYL | | — | SEQ ID 111 | |
| CH37 | 32 | YLLDFRWPL | | — | SEQ ID 112 | |
| CH38 | 33 | NLLKRWQFV | 69 | RLLKRKQFV | SEQ ID 113 | 3329249 (SEQ ID 127) |
| CH39 | 34 | FLLRHLSSV | 70 | VLLRNLSAV | SEQ ID 114 | 3328517 (SEQ ID 128) |
| | | | 71 | ILLRHGQSV | | 3329179 (SEQ ID 129) |
| CH40 | 35 | KLLAFPAFA | 72 | VLLALIAFA | SEQ ID 115 | 3328402 (SEQ ID 130) |
| CH41 | 36 | KLSEQLEAL | 73 | RLSKQLENL | SEQ ID 97 | 3328413 (SEQ ID 131) |
| | | | 74 | KLSEGLKVL | | 3328721 (SEQ ID 132) |
| | | | 75 | NLSYPLEAL | | 3328858 (SEQ ID 133) |
| CH42 | 37 | KVLLGQEWV | 76 | KVLSGDESV | SEQ ID 97 | 3329138 (SEQ ID 134) |
| CH43 | 38 | NLAEQVTAL | 77 | NLAERVLDL | SEQ ID 97 | 3328927 (SEQ ID 135) |

TABLE 3-continued

*C. trachomatis* T-cell epitopes of the invention

| Code | SEQ ID | *C. pneumoniae* epitope | SEQ ID | *C. trachomatis* epitope(s) | Full-length *C. pneumoniae* protein | Full-length *C. trachomatis* protein (GenBank) |
|---|---|---|---|---|---|---|
| CH44 | 39 | YVVGFIIFL | — | | SEQ ID 84 | |
| CH45 | 40 | WMMGVVLMI | 78 | WMLGVVLMI | SEQ ID 84 | 3328486 (SEQ ID 136) |
| CH46 | 41 | NLSISVFLL | — | | SEQ ID 84 | |
| CH47 | 42 | VIQAFGDFV | — | | SEQ ID 84 | |
| CH48 | 43 | YLALDPDSV | | identical | SEQ ID 84 | 3328486 (SEQ ID 136) |
| CH49 | 44 | KMSHFQQAL | — | | SEQ ID 93 | |
| CH50 | 45 | SLCAQSSYV | — | | SEQ ID 94 | |
| CH51 | 46 | NLSRQAFFA | — | | SEQ ID 94 | |
| CH52 | 47 | SLLEEHPVV | — | | SEQ ID 95 | |
| CH53 | 48 | NLWSHYTDL | 79 | NLWGCYTEL | SEQ ID 95 | 3329231 (SEQ ID 137) |
| CH54 | 49 | ALWKENQAL | 80 | ALWINNQPL | SEQ ID 95 | 3328693 (SEQ ID 138) |
| CH55 | 50 | ALWGHNVLL | 81 | MLWGVMVLL | SEQ ID 95 | 3328402 (SEQ ID 130) |
| CH56 | 10 | NLAGGILSV | 82 | KLAGFPLSV | SEQ ID 95 | 3329257 (SEQ ID 120) |
| CH57 | 12 | FVSKFWFSL | — | | SEQ ID 91 | |
| CH58 | 14 | SITVFRWLV | — | | SEQ ID 91 | |
| CH59 | 16 | YLIVFVLTI | — | | SEQ ID 108 | |
| CH60 | 17 | VMLFIGLGV | — | | SEQ ID 108 | |
| CH61 | 28 | VLFLLIRSV | — | | SEQ ID 108 | |
| CH62 | 31 | FLFQLGMQI | — | | SEQ ID 93 | |

TABLE 5

IFN-γ/CD8+ ELISpot assay

| Full-length protein | CH peptide | Dose (μg/ml) | Mean IFN-γ$^{+ve}$ per 10$^6$ CD8$^{+ve}$ cells |
|---|---|---|---|
| 4377123 | 6 | 5 | 106.8 |
| | | 10 | 486.8 |
| | | 20 | 266.6 |
| 4377135 | 7 | 5 | 366 |
| | | 10 | 400 |
| | | 20 | 433 |
| 4377140 | 10 | 5 | 226 |
| | | 10 | 233.3 |
| | | 20 | 200 |
| 4376998 | 13 | 5 | 466.8 |
| | | 10 | 700 |
| | | 20 | 540 |
| 4377352 | 58 | 5 | 1046 |
| | | 10 | 980 |
| | | 20 | 986 |

Values are shown after subtraction of HepB negative controls.

TABLE 4

PCR primers

| Full-length sequence | Forward primer (nulcetides 17-35 of the SEQ ID NOS: indicated | Reverse primer (nucleotides 17-35 of the SEQ ID NOS: indicated | CH peptides in gene |
|---|---|---|---|
| *C. pneumoniae* | | | |
| 4376265 (SEQ ID 106) | TGGCTGGATCG1TATGCAG (SEQ ID NO:142) | TTAGAAGCCTTTGACTCGC (SEQ ID NO:162) | 31 |
| 4376395 (SEQ ID 108) | GAGAATGCTATGTCATCATCG (SEQ ID NO:143) | TTACCTCACTAAAAATTGTTTTAG (SEQ ID NO:163) | 33 59 60 61 |
| 4376396 (SEQ ID 109) | ATCGAGTTTGCTTTTGTTCCTC (SEQ ID NO:144) | TTAAAGAGAGGCTACGTCTTCC (SEQ ID NO:164) | 34 |
| 4376468 (SEQ ID 115) | TTTTCACGATGGATCACCCTC (SEQ ID NO:145) | CTAGGGGAAATAGGTATATTTG (SEQ ID NO:165) | 40 |
| 4376482 (SEQ ID 112) | CTAGTAGAGTTAGAGGCTC (SEQ ID NO:146) | TTATTCTGTGTCTTTCCGCGG (SEQ ID NO:166) | 37 |
| 4376600 (SEQ ID 83) | GGTGAAAAAACAGAAAAGGCC (SEQ ID NO:147) | TTATAAATGATCAGGTTGGTTAG (SEQ ID NO:167) | 1 |
| 4376601 (SEQ ID 84) | AATAAGCTACTCAATTTCGTCAGC (SEQ ID NO:148) | TTAGAAAATCTGAATTCTTCCTAAAGG (SEQ ID NO:168) | 2 44 45 46 47 48 |

TABLE 4-continued

PCR primers

| Full-length sequence | Forward primer (nulcetides 17-35 of the SEQ ID NOS: indicated | Reverse primer (nucleotides 17-35 of the SEQ ID NOS: indicated | CH peptides in gene |
|---|---|---|---|
| 4376603 (SEQ ID 86) | CAAAACCAATACGAGCAATTAC (SEQ ID NO:149) | TCACGCGACGTAGTAGATTC (SEQ ID NO:169) | 4 |
| 4376630 (SEQ ID 114) | AGCATGACGATCGTTCC (SEQ ID NO:150) | TTAGTCTTTAAAGAAGATACTCG (SEQ ID NO:170) | 39 |
| 4376696 (SEQ ID 93) | TTGACTCTAATTTTTGTTATTATTATCG (SEQ ID NO:151) | TTAATTCATCTTCGTAAAGAATCTTCC (SEQ ID NO:171) | 14 49 62 |
| 4376854 (SEQ ID 103) | TCAATAGCTATTGCAAGGGAAC (SEQ ID NO:152) | TAATTATCGAAATGTCTTTGAATATG (SEQ ID NO:172) | 28 |
| 4376998 (SEQ ID 92) | AAAAAACTCTTAAAGTCGGCG (SEQ ID NO:153) | TTAGAACTGAATGACCAGATACG (SEQ ID NO:173) | 13 |
| 4377033 (SEQ ID 96) | GTTAATCCTATTGGTCCAGG (SEQ ID NO:154) | TTATTGGAGATAACCAGAATATAG (SEQ ID NO:174) | 17 |
| 4377123 (SEQ ID 88) | AGCAAGCCCTCTCCTCG (SEQ ID NO:155) | CTAACGTTTCTTTCCGCTTTTC (SEQ ID NO:175) | 6 |
| 4377135 (SEQ ID 89) | GGAATCTCTCTACCAGAGC (SEQ ID NO:156) | TTAGAGTACTTGAGGGTTGG (SEQ ID NO:176) | 7 8 |
| 4377140 (SEQ ID 90) | GTTCGTCGATCTATTTCTTTTGC (SEQ ID NO:157) | CTAACACCCTCAATTTCATTGC (SEQ ID NO:177) | 10 11 |
| 4377352 (SEQ ID 91) | TCACATTTAAATTATTTACTAGAAAAAATCG (SEQ ID NO:158) | TTATTTATGTTTTCGAATATCTAGAATTTC (SEQ ID NO:178) | 12 57 58 |
| C. trachomatis | | | |
| 332846 (SEQ ID 136) | AACAAGCTACTCAACTTTGTC (SEQ ID NO:159) | TTAGAAAATTTGAATTCTTCCCAAAG (SEQ ID NO:179) | 2 45 48 |
| 3328901 (SEQ ID 121) | CCAAAAATCGACACTTGTGATTC (SEQ ID NO:160) | TTAAGCGGGAGTCCATAGG (SEQ ID NO:180) | 27 |
| 3329018 (SEQ ID 117) | AGCACTCCATCTTCTAATAATTC (SEQ ID NO:161) | TTACTTTGCTTTTTTCTTGTTAGAAG (SEQ ID NO:181) | 6 |

Forward primers have formula 5'-gcactgcatggctagc-X-3', where X is the sequence shown in Table 4.

Reverse primers have formula 5'-gcactgcatggtcgac-X-3' (C.pneumoniae) or 5'-gcactgcatgacgcgt-X-3', where X is the sequence shown in Table 4.

Primers were based on available genome sequences cw1029 (C.pneumoniae) and ae001273 (C.trachomatis), with additional NheI and SalI (or MluI) sites at the 5' and 3' ends respectively.

REFERENCES

The Contents of Which are Hereby Incorporated in Full

[1] Kuo et al., Clinical Microbiology 8:451-461 (1995)
[2] Grayston et al., Journal of Infectious Diseases 181: S402-S410 (2000)
[3] Kim et al., Journal of Immunology 162: 6855-6866 (1999)
[4] Surcel et al. Infect hnmun 1993 61:2196-9 (1993)
[5] Bailey et al., Infection and Immunity 63: 389-392 (1995)
[6] Halme et al., Infection and Immunity 68: 7156-7158 (2000)
[7] U.S. patent application 2001041788; see also U.S. Pat. Nos. 6,225,443 and 6,191,259.
[8] U.S. Pat. No. 6,001,372.
[9] Kalman et al. Nat. Genet. 21:385-389 (1999)
[10] International patent application WO99/27105
[11] International patent application WO00/27994
[12] Read et al. (2000) Nucleic Acids Res 28:1397-1406
[13] Shirai et al. (2000) Nucleic Acids Res 28:2311-2314
[14] Stephens et al. (1998) Science 282:754-759
[15] International patent application WO99/28475
[16] D'Amaro et al. Hum. Immunology 43: 13-18 (1995)
[17] Parker et al., Journal of Immunology 152: 163-175 (1994)
[18] SYFPEITHI database (http://www.uni-tuebingen.de/uni/kxi/)
[19] Rammensee et al. Immunogenetics 50(3-4):213-9 (1999)
[20] Yoon et al., Virus Research 54: 23-29 (1998)
[21] Rockey et al. (2000) Infect. Immun. 68:5473-5479.
[22] Yucesan & Sriram Curr Opin Neurol June 2001;14(3): 355-9
[23] Campbell et al. (1998) Emerging Infectious Diseases 4:571-579.
[24] WO01/52614
[25] WO97/06263.
[26] WO094/06827.
[27] Osicka et al. (2000) Infect. Immun. 68:247-256.

[28] Fayolle et al. (2001) *J Virol.* 75:7330-7338.
[29] Chikh et al. (2001) *J. Immunol. Methods* 254:119-135.
[30] Morris et al. (2001) *Nature Biotechnol.* 19:1173-1176.
[31] Suzue & Young (1996) *J Immunol* 156(2):873-9.
[32] Suzue et al. (1997) *PNAS USA* 94(24):13146-51.
[33] Huang et al. (2000) *J. Exp Med* 191(2):403-8.
[34] Wang & Wang (2002) *Nature Biotechnology* 20:149-154.
[35] Liu et al. (2000) *Virology* 273:374-382.
[36] Rueda et al. (1999) *Vaccine* 18:325-332.
[37] Kast et al. (1994) *J. Immunol.* 152:3904-3912.
[38] WO97/06263.
[39] Kim et al. (2000) *J. Immunol.* 165:7285-7292.
[40] Maus et al. (2002) *Nature Biotechnology* 20:143-148.
[41] Strugnell et al. (1997) *Immunol Cell Biol* 75(4):364-369.
[42] Robinson & Torres (1997) *Seminars in Immunol* 9:271-283.
[43] Donnelly et al. (1997) Annu Rev Immunol 15:617-648.
[44] Brunham et al. (2000) *J Infect Dis* 181 Suppl 3:S538-43.
[45] Svanholm et al. (2000) *Scand J Immunol* 51(4):345-53.
[46] *Vaccine design: the subunit and adjuvant approach*, eds. Powell & Newman, Plenum Press 1995 (ISBN 0-306-44867-X).
[47] WO90/14837.
[48] WO00/07621.
[49] European patent applications 0835318, 0735898 and 0761231.
[50] Krieg (2000) *Vaccine* 19:618-622; Krieg (2001) *Curr opin Mol Ther* 2001 3:15-24; WO96/02555, WO98/16247, WO98/18810, WO98/40100, WO98/55495, WO98/37919 and WO98/52581 etc.
[51] WO99/52549.
[52] WO01/21207.
[53] WO01/21152.
[54] WO00/62800.
[55] WO00/23105.
[56] WO99/11241.
[57] WO98/57659.
[58] Del Giudice et al. (1998) *Molecular Aspects of Medicine*, vol. 19, number 1.
[59] WO99/27960.
[60] Uno-Furuta et al. (2001) *Vaccine* 19:2190-2196.
[61] WO 93/14778
[62] Findeis et al., *Trends Biotechnol.* (1993) 11:202
[63] Chiou et al. (1994) *Gene Therapeutics: Methods And Applications Of Direct Gene Transfer.* ed. Wolff
[64] Wu et al., *J. Biol. Chem.* (1988) 263:621
[65] Wu et al., *J. Biol. Chem.* (1994) 269:542
[66] Zenke et al., *Proc. Natl. Acad. Sci. (USA)* (1990) 87:3655
[67] Wu et al., *J. Biol. Chem.* (1991) 266:338
[68] WO 90/07936
[69] WO 94/03622
[70] WO 93/25698
[71] WO 93/25234
[72] U.S. Pat. No. 5,219,740
[73] WO 93/11230
[74] WO 93/10218
[75] U.S. Pat. No. 4,777,127
[76] GB Patent No. 2,200,651
[77] EP-A-0 345 242
[78] WO 91/02805
[79] WO 94/12649
[80] WO 93/03769
[81] WO 93/19191
[82] WO 94/28938
[83] WO 95/11984
[84] WO 95/00655
[85] Curiel, *Hum. Gene Ther.* (1992) 3:147
[86] Wu, *J. Biol. Chem.* (1989) 264:16985
[87] U.S. Pat. No. 5,814,482
[88] WO 95/07994
[89] WO 96/17072
[90] WO 95/30763
[91] WO 97/42338
[92] WO 90/11092
[93] U.S. Pat. No. 5,580,859
[94] U.S. Pat. No. 5,422,120
[95] WO 95/13796
[96] WO 94/23697
[97] WO 91/14445
[98] EP 0524968
[99] Philip, *Mol. Cell Biol.* (1994) 14:2411
[100] Woffendin, *Proc. Natl. Acad. Sci.* (1994) 91:11581
[101] U.S. Pat. No. 5,206,152
[102] WO 92/11033
[103] U.S. Pat. No. 5,149,655
[104] WO95/05849; see also European patent 0752886.
[105] *Current Protocols in Molecular Biology* (F. M. Ausubel et al., eds., 1987) Supplement 30.
[106] Smith and Waterman, Adv. Appl. Math. (1981) 2: 482-489.
[107] Nixon and McMichael, AIDS 5: 1049-1059 (1991)
[108] Bednarek et al., Journal of Immunology 147: 4047 (1991)
[109] Gagliardi et al., Int. Immunology 7: 1741 (1995)
[110] Ljunggren and Karre, Journal of Experimental Medicine 162: 1745-1759 (1985)
[111] Karre et al., Nature 319: 675-678 (1986)
[112] Ljunggren et al., Journal of Immunology 142: 2911-2917 (1989)
[113] Ozato and Sachs, Journal of Imunology 26: 317 (1981)
[114] Parham and Brodsky, Hum. Immunology 3: 277 (1981)
[115] Vitiello et al., J. Exp. Med., 173:1007-1015 (1991)

The invention claimed is:

1. An isolated polypeptide comprising the amino acid sequence SEQ ID NO: 11, wherein the polypeptide is less than 80 amino acids in length.

2. A composition comprising
   (a) an isolated polypeptide according to claim 1; and
   (b) a pharmaceutically acceptable carrier or duluent.

3. The composition of claim 2, wherein the composition is sterile and/or pyrogen-free and/or is buffered between pH 6 and pH 8.

4. A method of raising an immune response in a mammal, comprising the step of administering to the mammal the polypeptide of claim 1 or the composition of claim 2.

* * * * *

UNITED STATES PATENT AND TRADEMARK OFFICE
CERTIFICATE OF CORRECTION

| | | |
|---|---|---|
| PATENT NO. | : 7,754,228 B2 | Page 1 of 1 |
| APPLICATION NO. | : 10/503135 | |
| DATED | : July 13, 2010 | |
| INVENTOR(S) | : Bensi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this
Twenty-second Day of March, 2011

David J. Kappos
*Director of the United States Patent and Trademark Office*